US012655404B2

(12) United States Patent
Scott et al.

(10) Patent No.: US 12,655,404 B2
(45) Date of Patent: Jun. 16, 2026

(54) CRISPR DNA TARGETING ENZYMES AND SYSTEMS

(71) Applicant: ARBOR BIOTECHNOLOGIES, INC., Cambridge, MA (US)

(72) Inventors: David A. Scott, Cambridge, MA (US); David R. Cheng, Boston, MA (US); Winston X. Yan, Boston, MA (US); Tia Marie Ditommaso, Waltham, MA (US)

(73) Assignee: Arbor Biotechnologies, Inc., Cambridge, MA (US)

( * ) Notice: Subject to any disclaimer, the term of this patent is extended or adjusted under 35 U.S.C. 154(b) by 1134 days.

(21) Appl. No.: 17/626,072

(22) PCT Filed: Jul. 10, 2020

(86) PCT No.: PCT/US2020/041714
§ 371 (c)(1),
(2) Date: Jan. 10, 2022

(87) PCT Pub. No.: WO2021/007563
PCT Pub. Date: Jan. 14, 2021

(65) Prior Publication Data
US 2022/0372456 A1     Nov. 24, 2022

Related U.S. Application Data

(60) Provisional application No. 62/895,422, filed on Sep. 3, 2019, provisional application No. 62/895,406, filed on Sep. 3, 2019, provisional application No. 62/873,118, filed on Jul. 11, 2019, provisional application No. 62/873,108, filed on Jul. 11, 2019.

(51) Int. Cl.
| | | |
|---|---|---|
| *C12N 9/22* | (2006.01) | |
| *C12N 15/10* | (2006.01) | |
| *C12N 15/11* | (2006.01) | |
| *C12N 15/90* | (2006.01) | |

(52) U.S. Cl.
CPC ............. *C12N 9/22* (2013.01); *C12N 15/102* (2013.01); *C12N 15/11* (2013.01); *C12N 15/907* (2013.01); *C12N 2310/20* (2017.05)

(58) Field of Classification Search
CPC ........ C12N 9/22; C12N 15/102; C12N 15/11; C12N 15/907; C12N 2310/20; C12N 15/90; C12N 15/1034; C12N 15/113; C40B 40/06; C40B 50/06; C07K 2319/01; C07K 2319/60
See application file for complete search history.

(56) References Cited

U.S. PATENT DOCUMENTS

| | | | |
|---|---|---|---|
| 2018/0155720 A1 | 6/2018 | Donohoue et al. | |
| 2018/0346927 A1 | 12/2018 | Doudna et al. | |
| 2018/0355332 A1 | 12/2018 | Steinberg et al. | |
| 2019/0002875 A1 | 1/2019 | Cheng et al. | |
| 2019/0161743 A1 | 5/2019 | Church et al. | |
| 2021/0324356 A1* | 10/2021 | Doudna | ............... C12N 15/102 |

FOREIGN PATENT DOCUMENTS

| | | | |
|---|---|---|---|
| WO | 2016094867 A1 | 6/2016 | |
| WO | 2019178427 A1 | 9/2019 | |
| WO | 2020181101 A1 | 9/2020 | |
| WO | WO-2020257356 A2 * | 12/2020 | .............. B01L 7/525 |

OTHER PUBLICATIONS

Al-Shayeb et al., "Clades of huge phages from across Earth's ecosystems," Nature (2020) vol. 578, pp. 425-431.
Bernard et al., "Microbial Dark Matter Investigations: How Microbial Studies Transform Biological Knowledge and Empirically Sketch a Logic of Scientific Discovery," Genome Biology and Evolution (2018) vol. 10, Iss. 3, pp. 707-715.
Burstein et al., "New CRISPR-Cas systems from uncultivated microbes," Nature (2016) vol. 542, No. 7640, pp. 237-241.
Crawley et al., "CRISPRdisco: An Automated Pipeline for the Discovery and Analysis of CRISPR-Cas Systems," CRISPR J (2018) vol. No. 2, pp. 171-181.
International Search Report and Written Opinion issued in PCT/US2020/041714, mailed Oct. 29, 2020, 11 pages.
Zhang et al., "Benefits of Genomic Insights and CRISPR-Cas Signatures to Monitor Potential Pathogens across Drinking Water Production and Distribution Systems," Frontiers in Microbiology (2017) vol. 8, Article 2036, 15 pages.

* cited by examiner

*Primary Examiner* — Neil P Hammell
*Assistant Examiner* — Kyle T Rega
(74) *Attorney, Agent, or Firm* — K&L Gates LLP

(57) ABSTRACT

The disclosure describes novel systems, methods, and compositions for the manipulation of nucleic acids in a targeted fashion. The disclosure describes non-naturally occurring, engineered CRISPR systems, components, and methods for targeted modification of nucleic acids. Each system includes one or more protein components and one or more nucleic acid components that together target nucleic acids.

24 Claims, 58 Drawing Sheets

Specification includes a Sequence Listing.

CLUST. | Direct Repeat
200916 | Alignment

CLUST. | Effector A - Functional Domains
200916 |

CLUST.200916: 3300013232 (SEQ ID NO: 1)
with non-coding distribution of targets on pACYC184

CLUST.200916: 3300013232 (SEQ ID NO: 1) with non-coding distribution of targets on ECloni

Fig. 4B

CLUST.200916: 3300013232 (SEQ ID NO: 1)
without non-coding distribution of targets on pACYC184

Fig. 7A

CLUST.200916: 3300013232 (SEQ ID NO: 1) without non-coding distribution of targets on ECIoni CLUST.200916: SRR6837570 (SEQ ID NO: 26)
with non-coding distribution of targets on pACYC184

CLUST.200916: SRR6837570 (SEQ ID NO: 26)
with non-coding distribution of targets on ECloni CLUST.200916: SRR6837570 (SEQ ID NO: 26)
without non-coding distribution of targets on pACYC184

CLUST.200916: SRR6837570 (SEQ ID NO: 26) without non-coding distribution of targets on ECloni

Fig. 13B

CLUST.200916: SRR6837570 (SEQ ID NO: 26)
without non-coding

CLUST.200916: SRR6837575 (SEQ ID NO: 28) with non-coding distribution of targets on pACYC184

Fig. 16A

CLUST.200916: SRR6837575 (SEQ ID NO: 28) with non-coding distribution of targets on ECloni CLUST.200916: SRR6837575 (SEQ ID NO: 28) without non-coding distribution of targets on pACYC184

CLUST.200916: SRR6837575 (SEQ ID NO: 28)
without non-coding distribution of targets on ECloni

Fig. 19B

CLUST.200916: SRR6837577 (SEQ ID NO: 29)
with non-coding distribution of targets on pACYC184

Fig. 22A

CLUST.200916: SRR6837577 (SEQ ID NO: 29) with non-coding distribution of targets on ECloni CLUST.200916: SRR6837577 (SEQ ID NO: 29) without non-coding distribution of targets on pACYC184

CLUST.200916: SRR6837577 (SEQ ID NO: 29)
without non-coding distribution of targets on ECloni CLUST.200916: SRR6837569 (SEQ ID NO: 25)
with non-coding depletion scores 150 depleted targets 2246 non-depleted targets hit threshold normalized output/input reads targets (n)

5'-GTCT...CAGG-[spacer]-3'
5'-CCTG..AGAC-[spacer]-3'

CLUST.200916: SRR6837569 (SEQ ID NO: 25)
with non-coding distribution of targets on pACYC184

Fig. 28A

CLUST.200916: SRR6837569 (SEQ ID NO: 25) with non-coding distribution of targets on ECloni CLUST.200916: SRR6837569 (SEQ ID NO: 25) with non-coding CLUST.200916: SRR6837569 (SEQ ID NO: 25)
without non-coding depletion scores 179 depleted targets 2496 non-depleted targets hit threshold normalized output/input reads targets (n)

5'-GTCT...CAGG-[spacer]-3'
5'-CCTG...AGAC-[spacer]-3'

CLUST.200916: SRR6837569 (SEQ ID NO: 25)
without non-coding distribution of targets on pACYC184

Fig. 31A

CLUST.200916: SRR6837569 (SEQ ID NO: 25) without non-coding distribution of targets on ECloni CLUST.200916: SRR6837569 (SEQ ID NO: 25) without non-coding

Fig. 34E

CRISPR DNA TARGETING ENZYMES AND SYSTEMS

RELATED APPLICATIONS

This application is a U.S. National Phase Application under 35 U.S.C. § 371 of International Application No. PCT/US2020/041714, filed Jul. 10, 2020, which claims priority to U.S. Provisional Application 62/873,108 filed on Jul. 11, 2019, U.S. Provisional Application 62/873,118 filed on Jul. 11, 2019, U.S. Provisional Application 62/895,406 filed on Sep. 3, 2019, and U.S. Provisional Application 62/895,422 filed on Sep. 3, 2019, the entire contents of each of which are hereby incorporated by reference.

SEQUENCE LISTING

The instant application contains a Sequence Listing which has been submitted electronically in ASCII format and is hereby incorporated by reference in its entirety. Said ASCII copy, created on Jul. 10, 2020, is named A2186-7022WO-_SL.txt and is 246,736 bytes in size.

FIELD OF THE INVENTION

The present disclosure relates to systems and methods for genome editing and modulation of gene expression using novel Clustered Regularly Interspaced Short Palindromic Repeats (CRISPR) and CRISPR-associated (Cas) genes.

BACKGROUND

Recent advances in genome sequencing technologies and analyses have yielded significant insight into the genetic underpinnings of biological activities in many diverse areas of nature, ranging from prokaryotic biosynthetic pathways to human pathologies. To fully understand and evaluate the vast quantities of information yielded, equivalent increases in the scale, efficacy, and ease of sequence technologies for genome and epigenome manipulation are needed. These novel technologies will accelerate the development of novel applications in numerous areas, including biotechnology, agriculture, and human therapeutics.

Clustered Regularly Interspaced Short Palindromic Repeats (CRISPR) and CRISPR-associated (Cas) genes, collectively known as CRISPR-Cas or CRISPR/Cas systems, are adaptive immune systems in archaea and bacteria that defend particular species against foreign genetic elements. CRISPR-Cas systems comprise an extremely diverse group of proteins effectors, non-coding elements, and loci architectures, some examples of which have been engineered and adapted to produce important biotechnological advances.

The components of the system involved in host defense include one or more effector proteins capable of modifying a nucleic acid and an RNA guide element that is responsible for targeting the effector protein(s) to a specific sequence on a phage nucleic acid. The RNA guide is composed of a CRISPR RNA (crRNA) and may require an additional trans-activating RNA (tracrRNA) to enable targeted nucleic acid manipulation by the effector protein(s). The crRNA consists of a direct repeat responsible for protein binding to the crRNA and a spacer sequence that is complementary to the desired nucleic acid target sequence. CRISPR systems can be reprogrammed to target alternative DNA or RNA targets by modifying the spacer sequence of the crRNA.

CRISPR-Cas systems can be broadly classified into two classes: Class 1 systems are composed of multiple effector proteins that together form a complex around a crRNA, and Class 2 systems consist of one effector protein that complexes with the RNA guide to target nucleic acid substrates. The single-subunit effector composition of the Class 2 systems provides a simpler component set for engineering and application translation and have thus far been an important source of programmable effectors. Nevertheless, there remains a need for additional programmable effectors and systems for modifying nucleic acids and polynucleotides (i.e., DNA, RNA, or any hybrid, derivative, or modification) beyond the current CRISPR-Cas systems, such as smaller effectors and/or effectors having unique PAM sequence requirements, that enable novel applications through their unique properties.

SUMMARY

This disclosure provides non-naturally-occurring, engineered systems and compositions for novel single-effector Class 2 CRISPR-Cas systems, which were first identified computationally from genomic databases and subsequently engineered and experimentally validated. In particular, identification of the components of these CRISPR-Cas systems allows for their use in non-natural environments, e.g., in bacteria other than those in which the systems were initially discovered or in eukaryotic cells, such as mammalian cells, e.g., human cells. These new effectors are divergent in sequence and function compared to orthologs and homologs of existing Class 2 CRISPR effectors.

In one aspect, the disclosure provides engineered, non-naturally occurring Clustered Regularly Interspaced Short Palindromic Repeat (CRISPR)—Cas systems of CLUST.200916 including: a CRISPR-associated protein, wherein the CRISPR-associated protein includes an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to an amino acid sequence set forth in any one of SEQ ID NOs: 1-29; and an RNA guide including a direct repeat sequence and a spacer sequence capable of hybridizing to a target nucleic acid; wherein the CRISPR-associated protein is capable of binding to the RNA guide and of modifying the target nucleic acid sequence complementary to the spacer sequence. In one aspect, the disclosure provides engineered, non-naturally occurring Clustered Regularly Interspaced Short Palindromic Repeat (CRISPR)—Cas systems of CLUST.200916 including: a CRISPR-associated protein or a nucleic acid encoding the CRISPR-associated protein, wherein the CRISPR-associated protein includes an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to an amino acid sequence set forth in any one of SEQ ID NOs: 1-29; and an RNA guide including a direct repeat sequence and a spacer sequence capable of hybridizing to a target nucleic acid, or a nucleic acid encoding the RNA guide; wherein the CRISPR-associated protein is capable of binding to the RNA guide and of modifying the target nucleic acid sequence complementary to the spacer sequence.

In some embodiments of any of the systems described herein, the CRISPR-associated protein includes at least one (e.g., one, two, or three) RuvC domain or at least one split RuvC domain.

In some embodiments of any of the systems described herein, the direct repeat sequence includes a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to a nucleotide sequence set forth in any one of SEQ ID NOs: 30-45, 77-94, or 122-138.

In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 1, and the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 30, 122, 77, or 78. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 2, and the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 31 or 123. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 3, and the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 31, 123, 79, or 80. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 4, and the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 32 or 124. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 5, and the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 32 or 124. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 6, and the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 33 or 125. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%)

identical to the amino acid sequence of SEQ ID NO: 7, and the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 34 or 126. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 8, and the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 35 or 127. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 9, and the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 35 or 127. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 10, and the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 36 or 128. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 11, and the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 36 or 128. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 12, and the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 37 or 129. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 13, and the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 38 or 130. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 14, and the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 38 or 130. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 15, and the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 38 or 130. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 16, and the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 39 or 131. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 17, and the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 31 or 123. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 18, and the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 40 or 132. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 19, and the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 41 or 133. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 20, and the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 41 or 133. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 21, and the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 39 or 131. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 22, and the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 39, 131, 81, or 82. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 23, and the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 42, 134, 83, or 84. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 24, and the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 43, 135, 85, or 86. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 25, and the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 43, 135, 87, or 88. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 26, and the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 44, 136, 89, or 90. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 27, and the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 45 or 137. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 28, and the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 46, 138, 91, or 92. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 29, and the direct repeat sequence comprises a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the nucleotide sequence of SEQ ID NO: 45, 137, 93, or 94.

In some embodiments of any of the systems described herein, the CRISPR-associated protein is a protein having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identity to an amino acid sequence set forth in SEQ ID NO: 1 (CLUST.200916 3300013232), SEQ ID NO: 26 (CLUST.200916 SRR6837570), SEQ ID NO: 28 (CLUST.200916 SRR6837575), SEQ ID NO: 29 (CLUST.200916 SRR6837577), or SEQ ID NO: 25 (CLUST.200916 SRR6837569).

In some embodiments of any of the systems described herein, the CRISPR-associated protein is capable of recognizing a protospacer adjacent motif (PAM) sequence, wherein the PAM sequence includes a nucleic acid sequence, including a nucleic acid sequence set forth as 5'-TTN-3', 5'-YYN-3', 5'-HHN-3', 5'-YKN-3', or 5'-HBN-3', wherein N is any nucleotide (e.g., A, G, T, or C), Y is C or T, K is G or T, B is G, T, or C, and H is A, C, or T.

In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 1, and the PAM sequence comprises a nucleic acid sequence set forth as 5'-TTN-3', 5'-YYN-3', or 5'-HHN-3'. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 22, and the PAM sequence comprises a nucleic acid sequence set forth as 5'-TTN-3', 5'-YYN-3', or 5'-HHN-3'. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 24, and the PAM sequence comprises a nucleic acid sequence set forth as 5'-TTN-3' or 5'-YKN-3'. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 25, and the PAM sequence comprises a nucleic acid sequence set forth as 5'-TTN-3'. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 26, and the PAM sequence comprises a nucleic acid sequence set forth as 5'-TTN-3', 5'-YYN-3', or 5'-HBN-3'. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 28, and the PAM sequence comprises a nucleic acid sequence set forth as 5'-TTN-3' or 5'-YKN-3'. In some embodiments, the CRISPR-associated protein comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to the amino acid sequence of SEQ ID NO: 29, and the PAM sequence comprises a nucleic acid sequence set forth as 5'-TTN-3' or 5'-HHN-3'.

In some embodiments of any of the systems described herein, the spacer sequence of the RNA guide includes between about 14 nucleotides to about 50 nucleotides. In some embodiments of any of the systems described herein, the spacer sequence of the RNA guide includes between 20 and 35 nucleotides.

In some embodiments of any of the systems described herein, the CRISPR-associated protein comprises a catalytic residue (e.g., aspartic acid or glutamic acid). In some embodiments of any of the systems described herein, the CRISPR-associated protein cleaves the target nucleic acid. In some embodiments of any of the systems described herein, the CRISPR-associated protein further comprises a peptide tag, a fluorescent protein, a base-editing domain, a DNA methylation domain, a histone residue modification domain, a localization factor, a transcription modification factor, a light-gated control factor, a chemically inducible factor, or a chromatin visualization factor.

In some embodiments of any of the systems described herein, the nucleic acid encoding the CRISPR-associated protein is codon-optimized for expression in a cell, e.g., a eukaryotic cell, e.g., a mammalian cell, e.g., a human cell. In some embodiments of any of the systems described herein, the nucleic acid encoding the CRISPR-associated protein is operably linked to a promoter. In some embodiments of any of the systems described herein, the nucleic acid encoding the CRISPR-associated protein is in a vector. In some embodiments, the vector comprises a retroviral vector, a lentiviral vector, a phage vector, an adenoviral vector, an adeno-associated vector, or a herpes simplex vector.

In some embodiments of any of the systems described herein, the target nucleic acid is a DNA molecule. In some embodiments of any of the systems described herein, the target nucleic acid includes a PAM sequence.

In some embodiments of any of the systems described herein, the CRISPR-associated protein has non-specific nuclease activity.

In some embodiments of any of the systems described herein, recognition of the target nucleic acid by the CRISPR-associated protein and RNA guide results in a modification of the target nucleic acid. In some embodiments of any of the systems described herein, the modification of the target nucleic acid is a double-stranded cleavage event. In some embodiments of any of the systems described herein, the modification of the target nucleic acid is a single-stranded cleavage event. In some embodiments of any of the systems described herein, the modification of the target nucleic acid results in an insertion event. In some embodiments of any of the systems described herein, the modification of the target nucleic acid results in a deletion event. In some embodiments of any of the systems described herein, the modification of the target nucleic acid results in cell toxicity or cell death.

In some embodiments of any of the systems described herein, the system further includes a donor template nucleic acid. In some embodiments of any of the systems described herein, the donor template nucleic acid is a DNA molecule. In some embodiments of any of the systems described herein, wherein the donor template nucleic acid is an RNA molecule.

In some embodiments of any of the systems described herein, the system does not include a tracrRNA. In some embodiments of any of the systems described herein, the system optionally includes a tracrRNA. In some embodiments of any of the systems described herein, the CRISPR-associated protein is self-processing.

In some embodiments of any of the systems described herein, the system is present in a delivery composition comprising a nanoparticle, a liposome, an exosome, a microvesicle, or a gene-gun.

In some embodiments of any of the systems described herein, the systems are within a cell. In some embodiments, the cell is a eukaryotic cell. In some embodiments, the cell is a mammalian cell. In some embodiments, the cell is a human cell. In some embodiments, the cell is a prokaryotic cell.

In another aspect, the disclosure provides a genetically modified cell, wherein the cell includes: a CRISPR-associated protein, wherein the CRISPR-associated protein includes an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to an amino acid sequence set forth in any one of SEQ ID NOs: 1-29; and an RNA guide including a direct repeat sequence and a spacer sequence capable of hybridizing to a target nucleic acid. In another aspect, the disclosure provides a genetically modified cell, wherein the cell includes: a CRISPR-associated protein or a nucleic acid encoding the CRISPR-associated protein, wherein the CRISPR-associated protein includes an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to an amino acid sequence set forth in any one of SEQ ID NOs: 1-29; and an RNA guide including a direct repeat sequence and a spacer sequence capable of hybridizing to a target nucleic acid, or a nucleic acid encoding the RNA guide.

In some embodiments of any of the cells described herein, the CRISPR-associated protein includes at least one (e.g., one, two, or three) RuvC domain or at least one split RuvC domain.

In some embodiments of any of the cells described herein, the CRISPR-associated protein is a protein having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identity to an amino acid sequence set forth in SEQ ID NO: 1, SEQ ID NO: 25, SEQ ID NO: 26, SEQ ID NO: 28, or SEQ ID NO: 29.

In some embodiments of any of the cells described herein, the CRISPR-associated protein is capable of recognizing a PAM sequence including a nucleic acid sequence set forth as 5'-TTN-3', 5'-YYN-3', 5'-HHN-3', 5'-YKN-3', or 5'-HBN-3', wherein N is any nucleotide (e.g., A, G, T, or C), Y is C or T, K is G or T, B is G, T, or C, and H is A, C, or T.

In some embodiments of any of the cells described herein, the direct repeat sequence includes a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to a nucleotide sequence set forth in any one of SEQ ID NOs: 30-45, 77-94, or 122-138.

In some embodiments of any of the cells described herein, the spacer sequence includes between about 14 nucleotides to about 50 nucleotides. In some embodiments of any of the cells described herein, the spacer sequence includes between 20 and 35 nucleotides.

In some embodiments of any of the cells described herein, the CRISPR-associated protein comprises a catalytic residue (e.g., aspartic acid or glutamic acid). In some embodiments of any of the cells described herein, the CRISPR-associated protein cleaves the target nucleic acid. In some embodiments of any of the cells described herein, the CRISPR-associated protein further comprises a peptide tag, a fluorescent protein, a base-editing domain, a DNA methylation domain, a histone residue modification domain, a localization factor, a transcription modification factor, a light-gated control factor, a chemically inducible factor, or a chromatin visualization factor.

In some embodiments of any of the cells described herein, the nucleic acid encoding the CRISPR-associated protein is codon-optimized for expression in a cell, e.g., a eukaryotic cell, e.g., a mammalian cell, e.g., a human cell. In some embodiments of any of the cells described herein, the nucleic acid encoding the CRISPR-associated protein is operably linked to a promoter. In some embodiments of any of the cells described herein, the nucleic acid encoding the CRISPR-associated protein is in a vector. In some embodiments, the vector comprises a retroviral vector, a lentiviral vector, a phage vector, an adenoviral vector, an adeno-associated vector, or a herpes simplex vector.

In some embodiments of any of the cells described herein, the cell does not include a tracrRNA. In some embodiments of any of the cells described herein, the cell optionally includes a tracrRNA. In some embodiments of any of the cells described herein, the CRISPR-associated protein is self-processing.

In some embodiments of any of the cells described herein, the cell is a eukaryotic cell. In some embodiments of any of the cells described herein, the cell is a mammalian cell. In some embodiments of any of the cells described herein, the cell is a human cell. In some embodiments of any of the cells described herein, the cell is a prokaryotic cell.

In some embodiments of any of the cells described herein, the target nucleic acid is a DNA molecule. In some embodiments of any of the cells described herein, the target nucleic acid includes a PAM sequence.

In some embodiments of any of the cells described herein, the CRISPR-associated protein has non-specific nuclease activity.

In some embodiments of any of the cells described herein, recognition of the target nucleic acid by the CRISPR-associated protein and RNA guide results in a modification of the target nucleic acid. In some embodiments of any of the cells described herein, the modification of the target nucleic acid is a double-stranded cleavage event. In some embodiments of any of the cells described herein, the modification of the target nucleic acid is a single-stranded cleavage event. In some embodiments of any of the cells described herein, the modification of the target nucleic acid results in an insertion event. In some embodiments of any of the cells described herein, the modification of the target nucleic acid results in a deletion event. In some embodiments of any of the cells described herein, the modification of the target nucleic acid results in cell toxicity or cell death.

In another aspect, the disclosure provides a method of binding a system described herein to a target nucleic acid in a cell comprising: (a) providing the system; and (b) delivering the system to the cell, wherein the cell comprises the target nucleic acid, wherein the CRISPR-associated protein binds to the RNA guide, and wherein the spacer sequence binds to the target nucleic acid. In some embodiments, the cell is a eukaryotic cell, e.g., a mammalian cell, e.g., a human cell.

In another aspect, the disclosure provides methods of modifying a target nucleic acid, the method including delivering to the target nucleic acid an engineered, non-naturally occurring CRISPR-Cas system including: a CRISPR-associated protein, wherein the CRISPR-associated protein includes an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to an amino acid sequence set forth in any one of SEQ ID NOs: 1-29; and an RNA guide including a direct repeat sequence and a spacer sequence capable of hybridizing to the target nucleic acid; wherein the CRISPR-associated protein is capable of binding to the RNA guide; and wherein recognition of the target nucleic acid by the CRISPR-associated protein and RNA guide results in a modification of the target nucleic acid. In another aspect, the disclosure provides methods of modifying a target nucleic acid, the method including delivering to the target nucleic acid an engineered, non-naturally occurring CRISPR-Cas system including: a CRISPR-associated protein or a nucleic acid encoding the CRISPR-associated protein, wherein the CRISPR-associated protein includes an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to an amino acid sequence set forth in any one of SEQ ID NOs: 1-29; and an RNA guide including a direct repeat sequence and a spacer sequence capable of hybridizing to the target nucleic acid, or a nucleic acid encoding the RNA guide; wherein the CRISPR-associated protein is capable of binding to the RNA guide; and wherein recognition of the target nucleic acid by the CRISPR-associated protein and RNA guide results in a modification of the target nucleic acid.

In some embodiments of any of the methods described herein, the CRISPR-associated protein is a protein having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identity to an amino acid sequence set forth in SEQ ID NO: 1, SEQ ID NO: 25, SEQ ID NO: 26, SEQ ID NO: 28, or SEQ ID NO: 29.

In some embodiments of any of the methods described herein, the CRISPR-associated protein is capable of recognizing a PAM sequence including a nucleic acid sequence set forth as 5'-TTN-3', 5'-YYN-3', 5'-HHN-3', 5'-YKN-3', or 5'-HBN-3', wherein N is any nucleotide, Y is C or T, K is G or T, B is G, T, or C, and H is A, C, or T.

In some embodiments of any of the methods described herein, the direct repeat sequence includes a nucleotide sequence that is at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) identical to a nucleotide sequence set forth in any one of SEQ ID NOs: 30-45, 77-94, or 122-138.

In some embodiments of any of the methods described herein, the spacer sequence includes between about 14 nucleotides to about 50 nucleotides. In some embodiments of any of the methods described herein, the spacer sequence includes between 20 and 35 nucleotides.

In some embodiments of any of the methods described herein, the CRISPR-associated protein comprises a catalytic residue (e.g., aspartic acid or glutamic acid). In some embodiments of any of the methods described herein, the CRISPR-associated protein cleaves the target nucleic acid. In some embodiments of any of the methods described herein, the CRISPR-associated protein further comprises a peptide tag, a fluorescent protein, a base-editing domain, a DNA methylation domain, a histone residue modification domain, a localization factor, a transcription modification factor, a light-gated control factor, a chemically inducible factor, or a chromatin visualization factor.

In some embodiments of any of the methods described herein, the nucleic acid encoding the CRISPR-associated protein is codon-optimized for expression in a cell, e.g., a eukaryotic cell, e.g., a mammalian cell, e.g., a human cell. In some embodiments of any of the methods described herein, the nucleic acid encoding the CRISPR-associated protein is operably linked to a promoter. In some embodiments of any of the methods described herein, the nucleic acid encoding the CRISPR-associated protein is in a vector. In some embodiments, the vector comprises a retroviral vector, a lentiviral vector, a phage vector, an adenoviral vector, an adeno-associated vector, or a herpes simplex vector.

In some embodiments of any of the methods described herein, the cell does not include a tracrRNA. In some embodiments of any of the methods described herein, the cell optionally includes a tracrRNA.

In some embodiments of any of the methods described herein, the target nucleic acid is a DNA molecule. In some embodiments of any of the methods described herein, the target nucleic acid includes a PAM sequence.

In some embodiments of any of the methods described herein, the CRISPR-associated protein has non-specific nuclease activity.

In some embodiments of any of the methods described herein, the modification of the target nucleic acid is a double-stranded cleavage event. In some embodiments of any of the methods described herein, the modification of the target nucleic acid is a single-stranded cleavage event. In some embodiments of any of the methods described herein, the modification of the target nucleic acid results in an insertion event. In some embodiments of any of the methods described herein, the modification of the target nucleic acid results in a deletion event. In some embodiments of any of the methods described herein, the modification of the target nucleic acid results in cell toxicity or cell death.

In another aspect, the disclosure provides a method of editing a target nucleic acid, the method comprising contacting the target nucleic acid with a system described herein. In another aspect, the disclosure provides a method of modifying expression of a target nucleic acid, the method comprising contacting the target nucleic acid with a system described herein. In another aspect, the disclosure provides a method of targeting the insertion of a payload nucleic acid at a site of a target nucleic acid, the method comprising contacting the target nucleic acid with a system described herein. In another aspect, the disclosure provides a method of targeting the excision of a payload nucleic acid from a site at a target nucleic acid, the method comprising contacting the target nucleic acid with a system described herein. In another aspect, the disclosure provides a method of non-specifically degrading single-stranded DNA upon recognition of a DNA target nucleic acid, the method comprising contacting the target nucleic acid with a system described herein.

In another aspect, the disclosure provides a method of detecting a target nucleic acid in a sample, the method comprising: (a) contacting the sample with a system described herein and a labeled reporter nucleic acid, wherein hybridization of the spacer sequence to the target nucleic acid causes cleavage of the labeled reporter nucleic acid; and (b) measuring a detectable signal produced by cleavage of the labeled reporter nucleic acid, thereby detecting the presence of the target nucleic acid in the sample.

In some embodiments of any of the systems or methods provided herein, the contacting comprises directly contacting or indirectly contacting. In some embodiments of any of the systems or methods provided herein, contacting indirectly comprises administering one or more nucleic acids encoding an RNA guide or CRISPR-associated protein described herein under conditions that allow for production of the RNA guide and/or CRISPR-related protein. In some embodiments of any of the systems or methods provided herein, contacting includes contacting in vivo or contacting in vitro. In some embodiments of any of the systems or methods provided herein, contacting a target nucleic acid with the system comprises contacting a cell comprising the nucleic acid with the system under conditions that allow the CRISPR-related protein and guide RNA to reach the target nucleic acid. In some embodiments of any of the systems or methods provided herein, contacting a cell in vivo with the system comprises administering the system to the subject that comprises the cell, under conditions that allow the CRISPR-related protein and guide RNA to reach the cell or be produced in the cell.

In another aspect, the disclosure provides a system provided herein for use in an in vitro or ex vivo method of: (a) targeting and editing a target nucleic acid; (b) non-specifically degrading a single-stranded nucleic acid upon recognition of the nucleic acid; (c) targeting and nicking a non-spacer complementary strand of a double-stranded target upon recognition of a spacer complementary strand of the double-stranded target; (d) targeting and cleaving a double-stranded target nucleic acid; (e) detecting a target nucleic acid in a sample; (f) specifically editing a double-stranded nucleic acid; (g) base editing a double-stranded nucleic acid; (h) inducing genotype-specific or transcriptional-state-specific cell death or dormancy in a cell; (i) creating an indel in a double-stranded nucleic acid target; (j) inserting a sequence into a double-stranded nucleic acid target; or (k) deleting or inverting a sequence in a double-stranded nucleic acid target.

The effectors described herein provide additional features that include, but are not limited to, 1) novel nucleic acid editing properties and control mechanisms, 2) smaller size for greater versatility in delivery strategies, 3) genotype triggered cellular processes such as cell death, and 4) programmable RNA-guided DNA insertion, excision, and mobilization, and 5) differentiated profile of pre-existing immunity through a non-human commensal source. See, e.g., Examples 1-5 and FIGS. 1A-37. Addition of the novel DNA-targeting systems described herein to the toolbox of techniques for genome and epigenome manipulation enables broad applications for specific, programmed perturbations.

Other features and advantages of the invention will be apparent from the following detailed description and from the claims.

BRIEF FIGURE DESCRIPTION

The figures are a series of schematics that represent the results of analysis of a protein cluster referred to as CLUST.200916.

FIG. 1A is a schematic representation of the components of the in vivo negative selection screening assay described in Example 2. CRISPR array libraries were designed including non-representative spacers uniformly sampled from both strands of the pACYC184 or E. coli essential genes flanked by two DRs and expressed by J23119.

FIG. 1B is a schematic representation of the in vivo negative selection screening workflow described in Example 2. CRISPR array libraries were cloned into the effector plasmid. The effector plasmid and the non-coding plasmid were transformed into E. coli followed by outgrowth for negative selection of CRISPR arrays conferring interference against transcripts from pACYC184 or E. coli essential genes. Targeted sequencing of the effector plasmid was used to identify depleted CRISPR arrays. Small RNAseq can further be performed to identify mature crRNAs and potential tracrRNA requirements.

FIG. 2C discloses SEQ ID NOs: 162, 30, 41, 41, 31, 31, 31-32, 32-35, 35-36, 36, 40, 39, 39, 39, 39, 39, 39, 163, 163, 43, 43, 46, 44, 42, 45, 45, 164, 164, 164, 38, 38, 38 and 37, respectively, in order of appearance.

Figure 3:
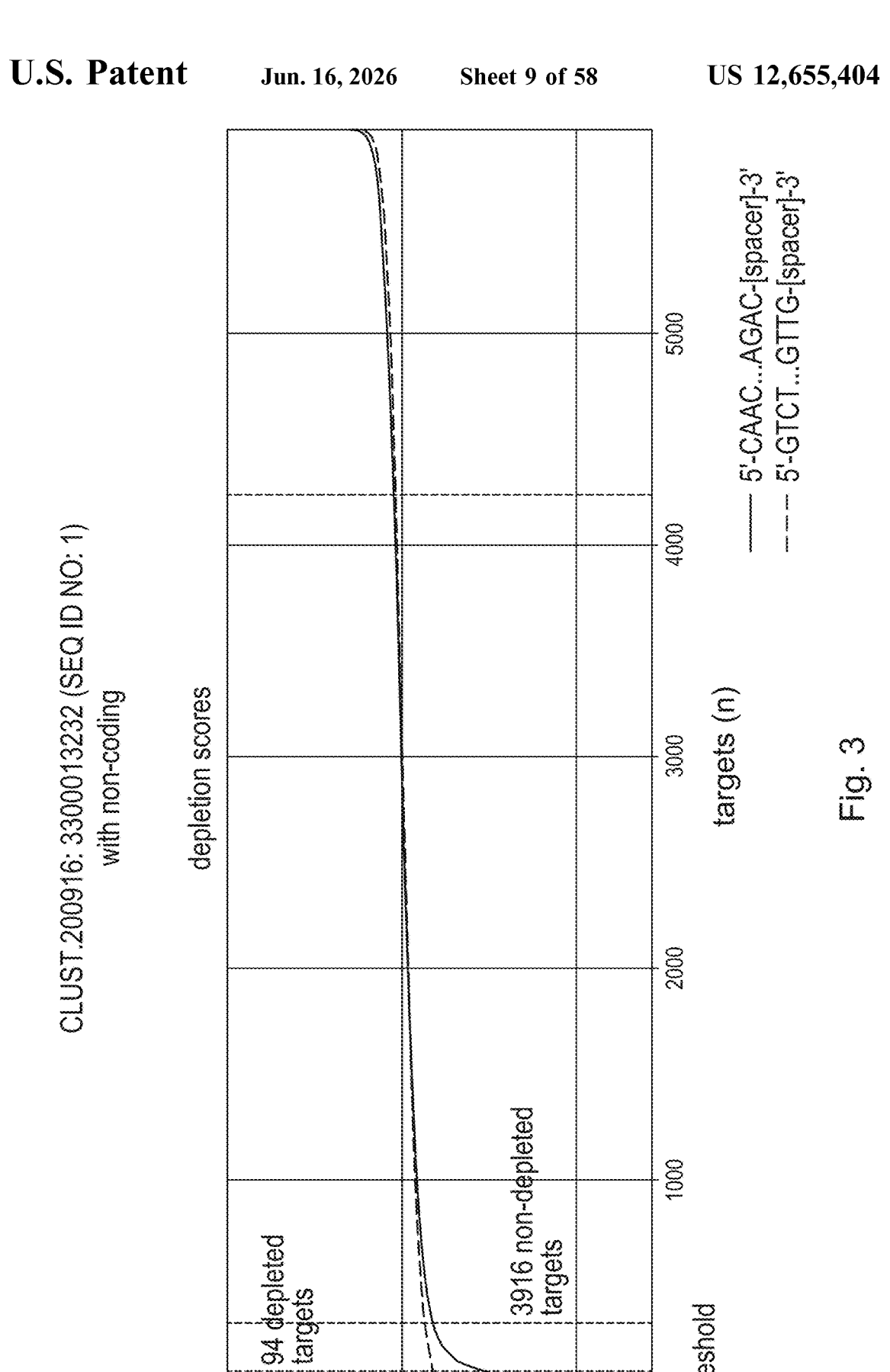

FIG. 3 is a graph for CLUST.200916 3300013232 (effector set forth in SEQ ID NO: 1) showing the degree of depletion activity of the engineered compositions for spacers targeting pACYC184 and direct repeat transcriptional orientations, with a non-coding sequence. The degree of depletion with the direct repeat in the "forward" orientation (5'-CAAC . . . AGAC-[spacer]-3') and with the direct repeat in the "reverse" orientation (5'-GTCT . . . GTTG-[spacer]-3') are depicted in a solid line and a dashed line, respectively.

Figure 4A:
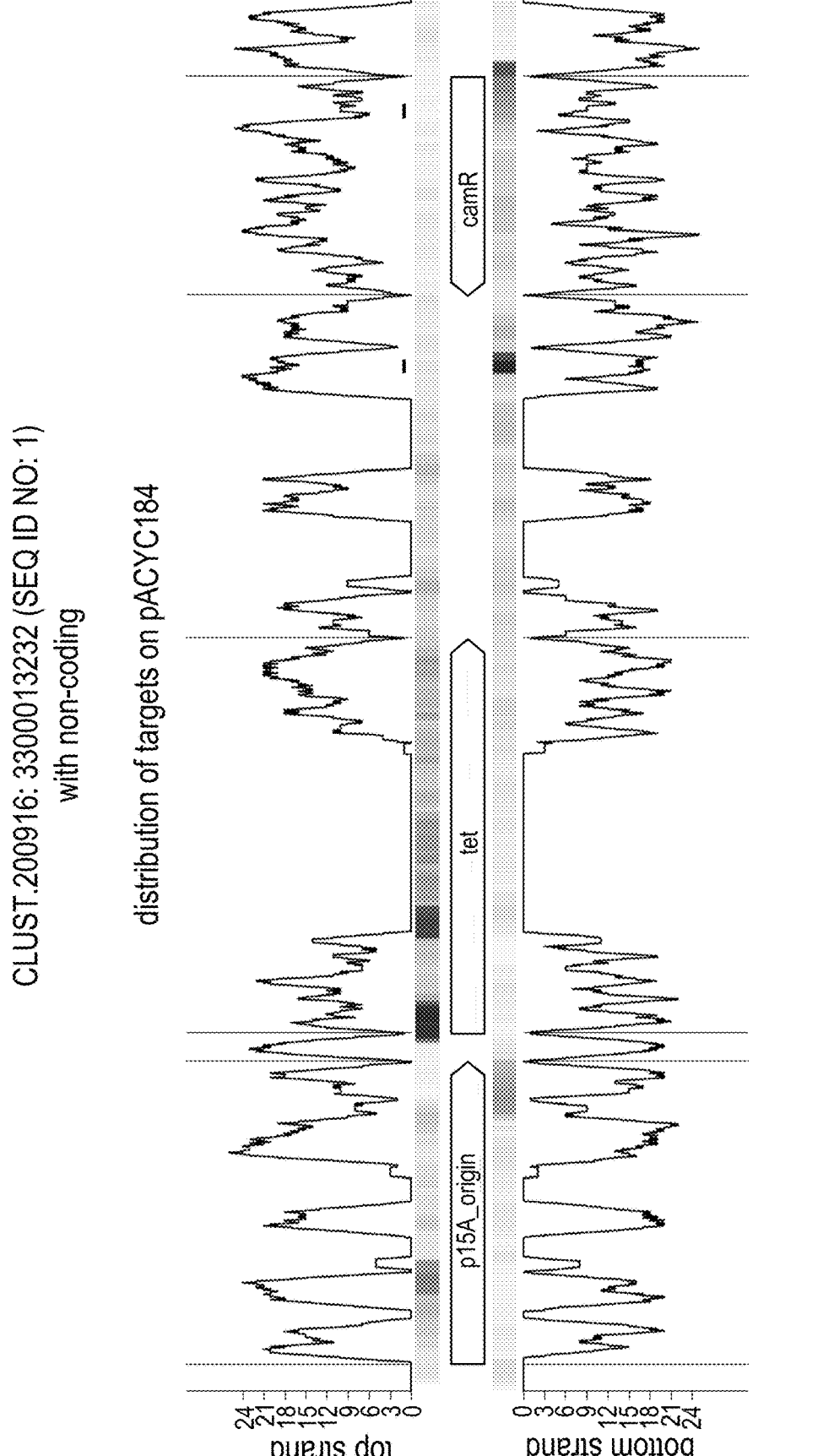
Figure 4B:
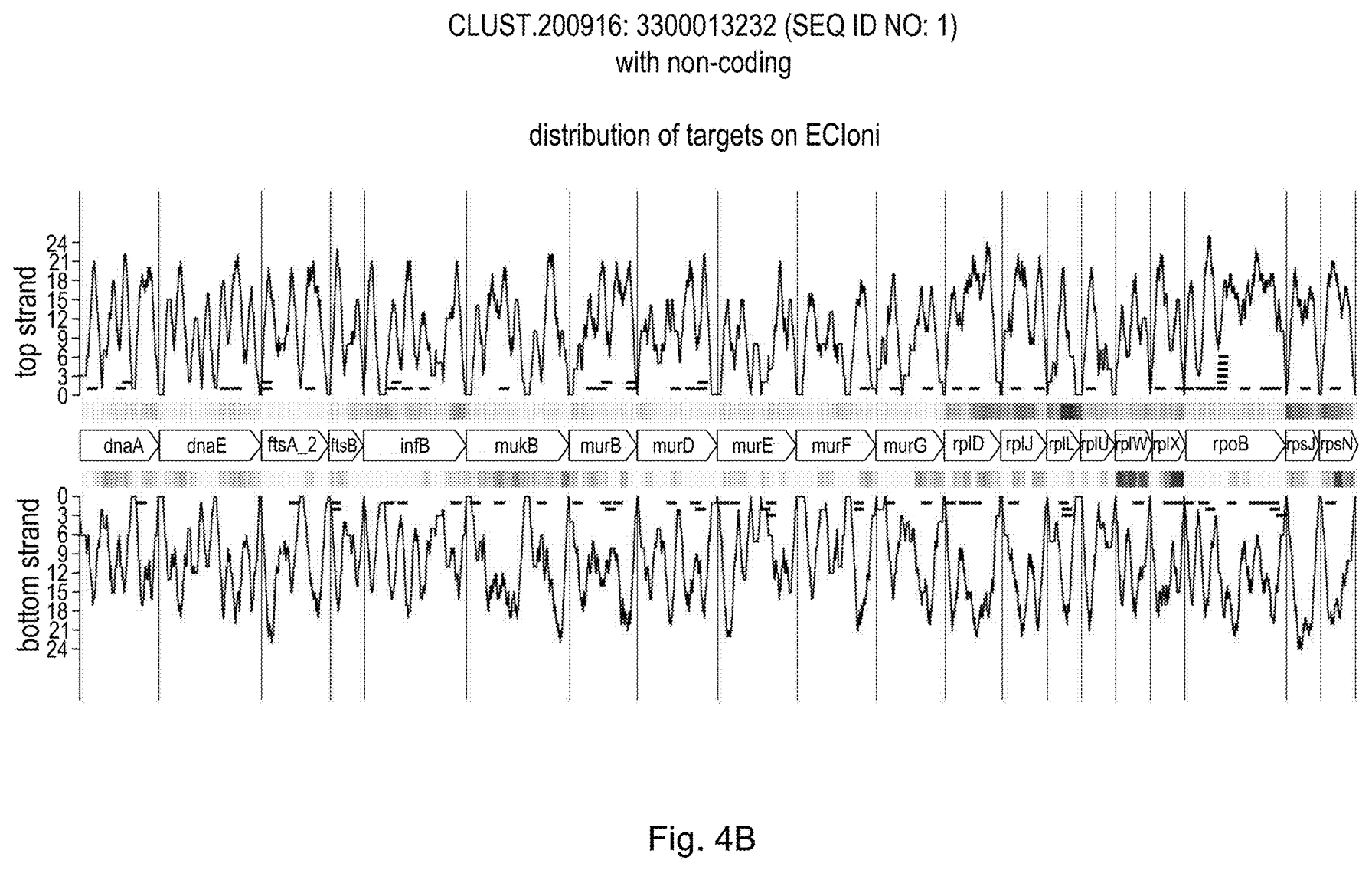

FIG. 4A is a graphical representation showing the density of depleted and non-depleted targets for CLUST.200916 3300013232, with a non-coding sequence, by location on the pACYC184 plasmid. FIG. 4B is a graphic representation showing the density of depleted and non-depleted targets for CLUST.200916 3300013232, with a non-coding sequence, by location on the E. coli strain, E. Cloni. Targets on the top strand and bottom strand are shown separately and in relation to the orientation of the annotated genes. The magnitude of the bands indicates the degree of depletion, wherein the lighter bands are close to the hit threshold of 3. The two gradients are heatmaps of RNA sequencing showing relative transcript abundance.

Figure 5:
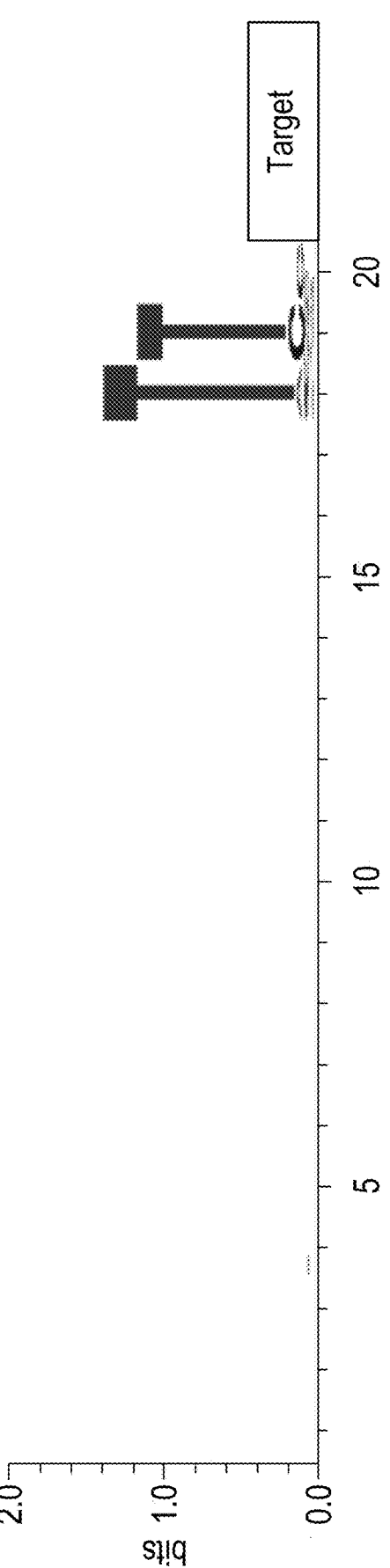

FIG. 5 is a WebLogo of the sequences flanking depleted targets in E. Cloni as a prediction of the PAM sequence for CLUST.200916 3300013232 (with a non-coding sequence).

Figure 6:
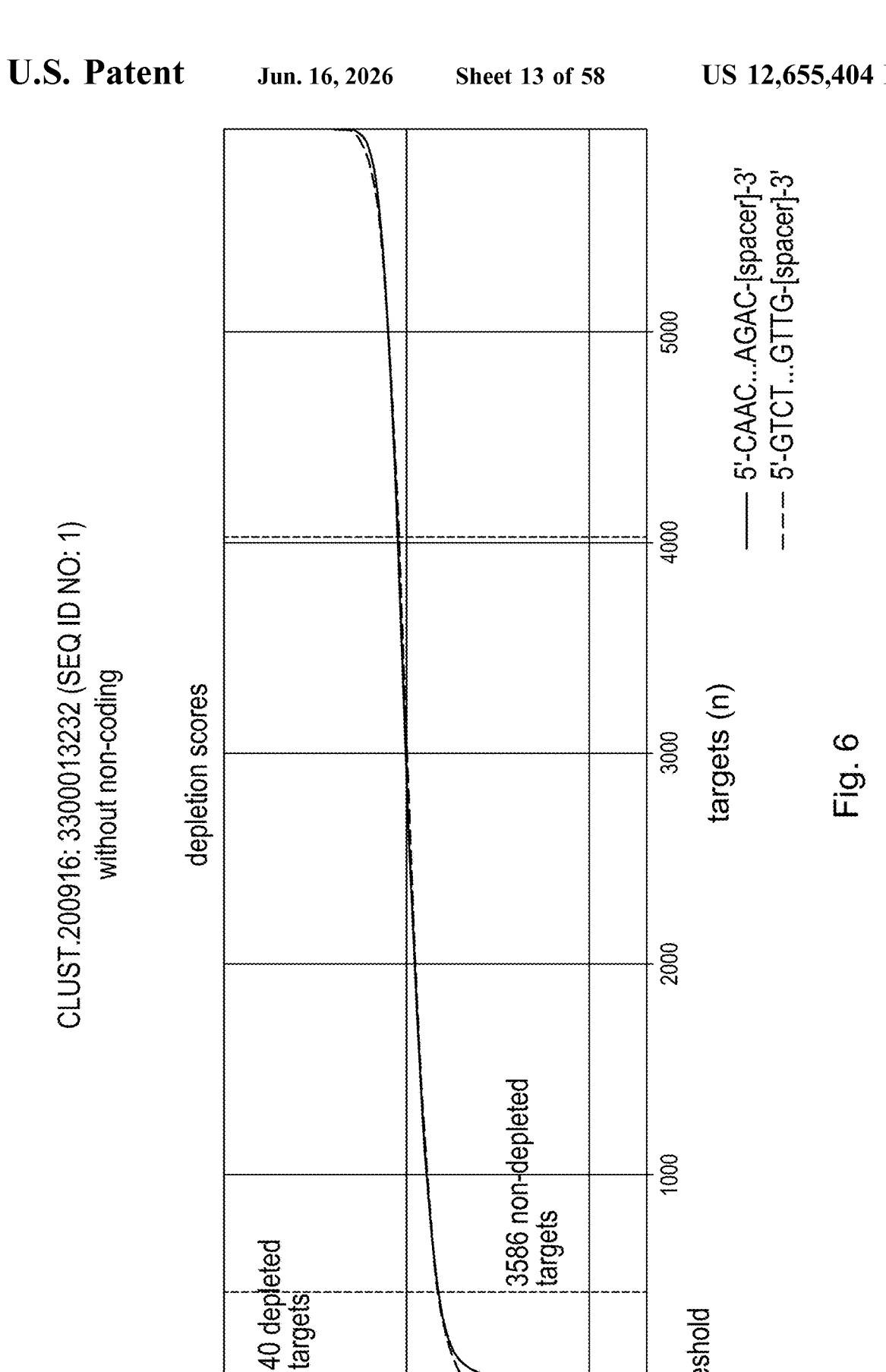

FIG. 6 is a graph for CLUST.200916 3300013232 (effector set forth in SEQ ID NO: 1) showing the degree of depletion activity of the engineered compositions for spacers targeting pACYC184 and direct repeat transcriptional orientations, without a non-coding sequence. The degree of depletion with the direct repeat in the "forward" orientation (5'-CAAC . . . AGAC-[spacer]-3') and with the direct repeat in the "reverse" orientation (5'-GTCT . . . GTTG-[spacer]-3') are depicted in a solid line and a dashed line, respectively.

Figure 7A:
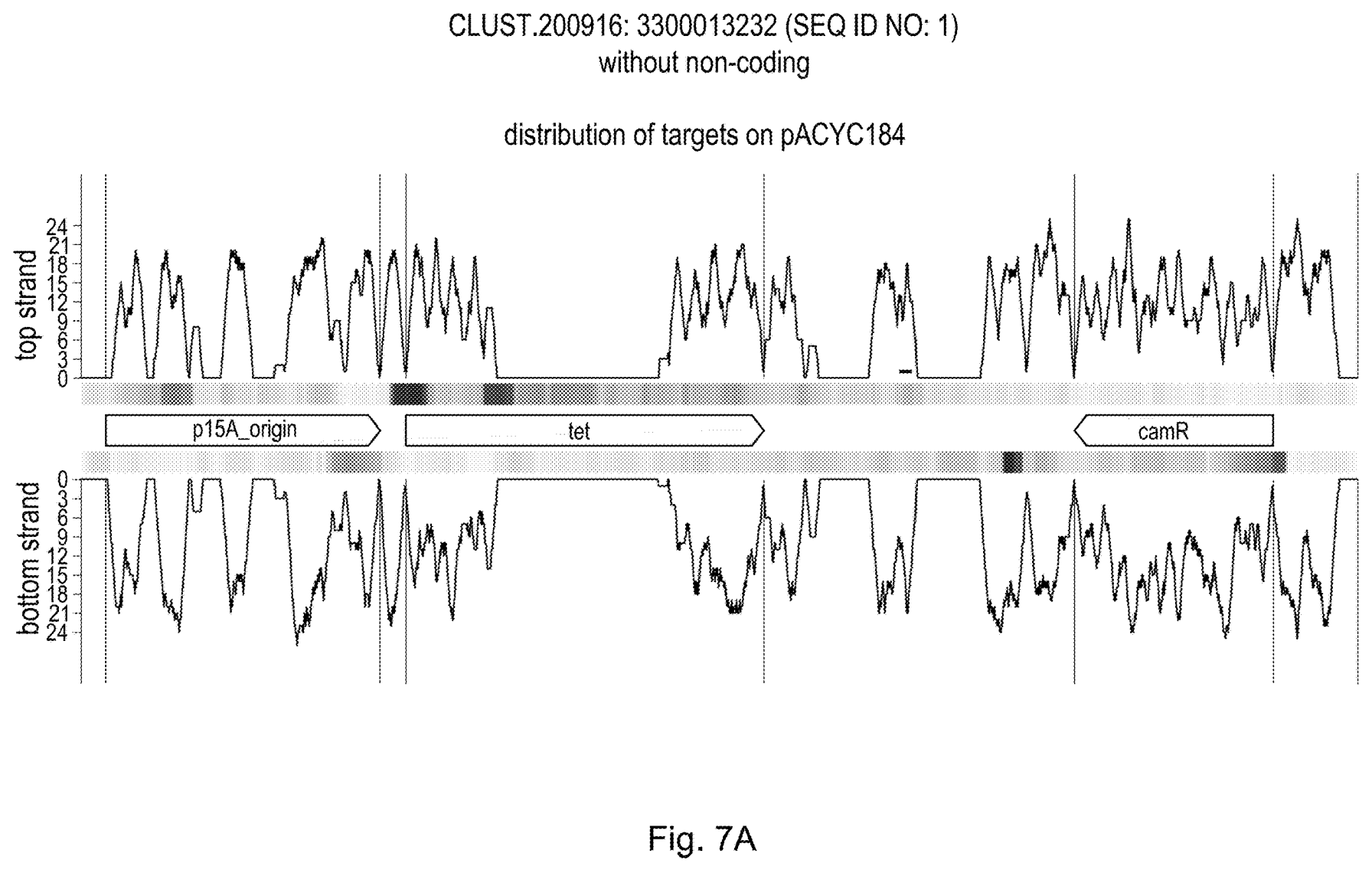
Figure 7B:
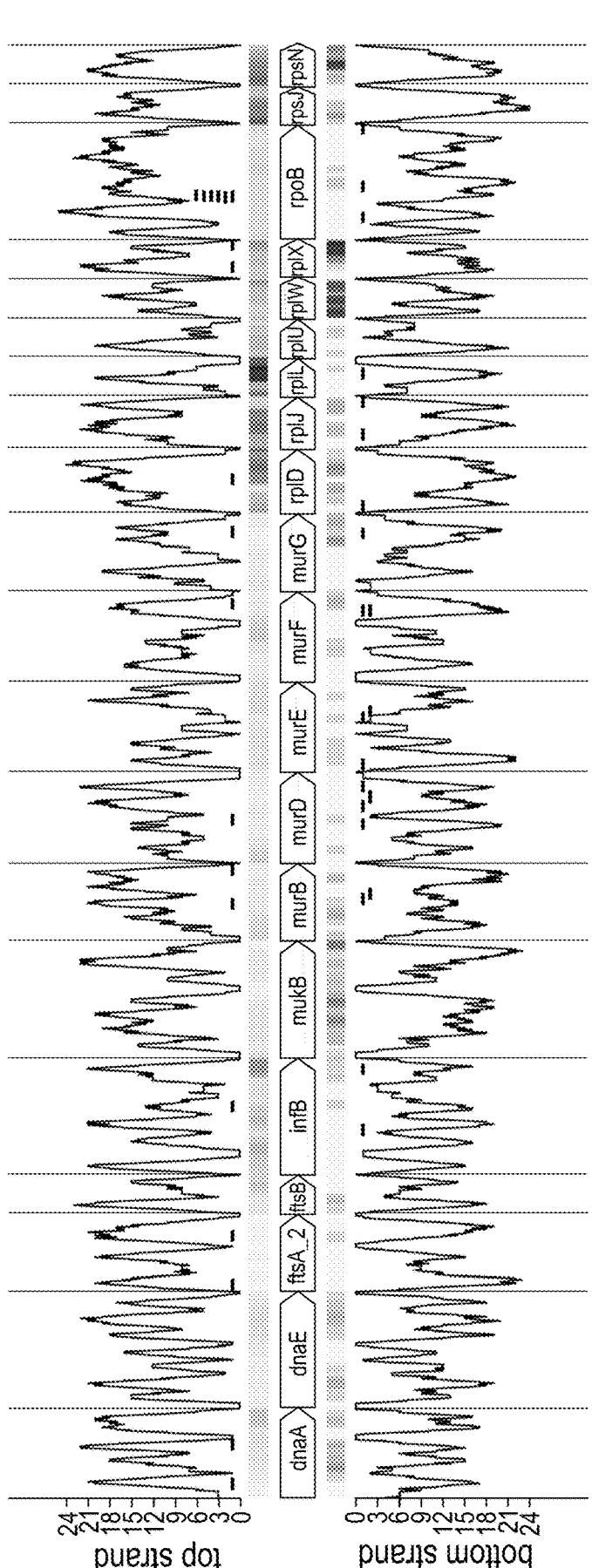

FIG. 7A is a graphical representation showing the density of depleted and non-depleted targets for CLUST.200916 3300013232, without a non-coding sequence, by location on the pACYC184 plasmid. FIG. 7B is a graphic representation showing the density of depleted and non-depleted targets for CLUST.200916 3300013232, without a non-coding sequence, by location on the *E. coli* strain, E. Cloni. Targets on the top strand and bottom strand are shown separately and in relation to the orientation of the annotated genes. The magnitude of the bands indicates the degree of depletion, wherein the lighter bands are close to the hit threshold of 3. The gradients are heatmaps of RNA sequencing showing relative transcript abundance.

Figure 8:
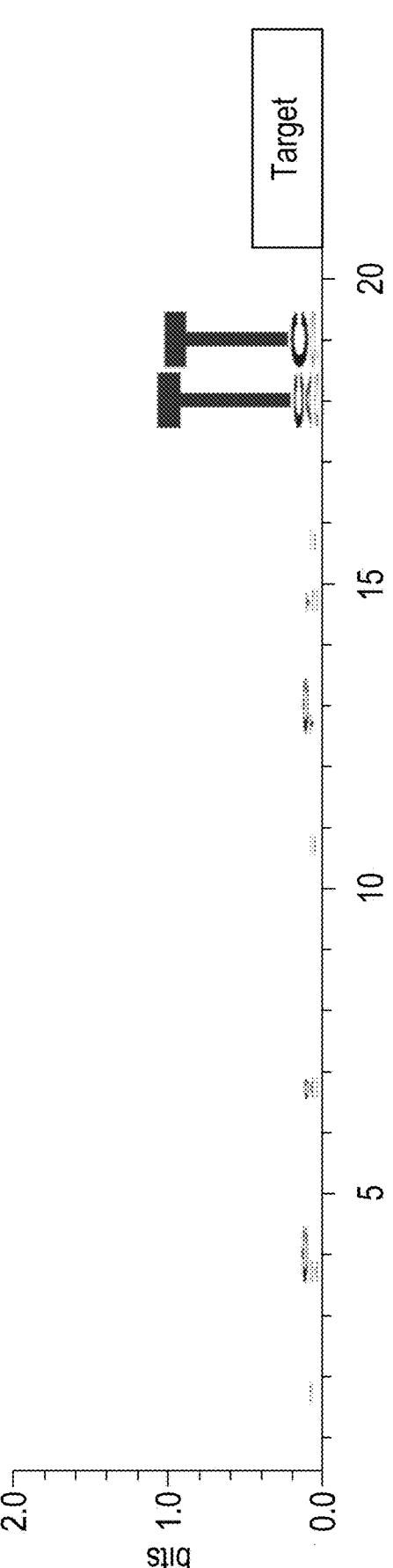

FIG. 8 is a Weblogo of the sequences flanking depleted targets in E. Cloni as a prediction of the PAM sequence for CLUST.200916 3300013232 (without a non-coding sequence).

Figure 9:
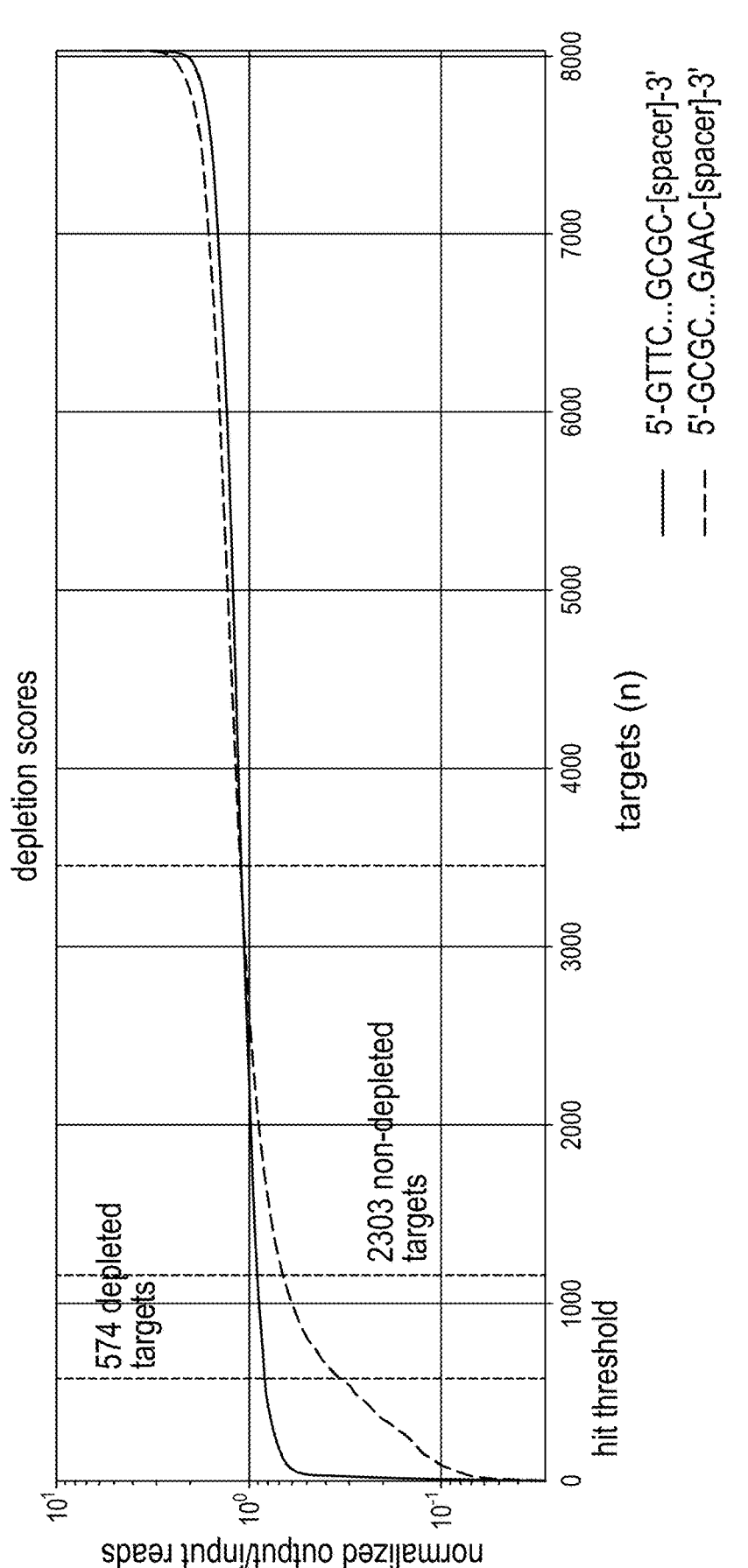

FIG. 9 is a graph for CLUST.200916 SRR6837570 (effector set forth in SEQ ID NO: 26) showing the degree of depletion activity of the engineered compositions for spacers targeting pACYC184 and direct repeat transcriptional orientations, with a non-coding sequence. The degree of depletion with the direct repeat in the "forward" orientation (5'-GTTC . . . GCGC-[spacer]-3') and with the direct repeat in the "reverse" orientation (5'-GCGC . . . GAAC-[spacer]-3') are depicted in a solid line and a dashed line, respectively.

Figure 10A:
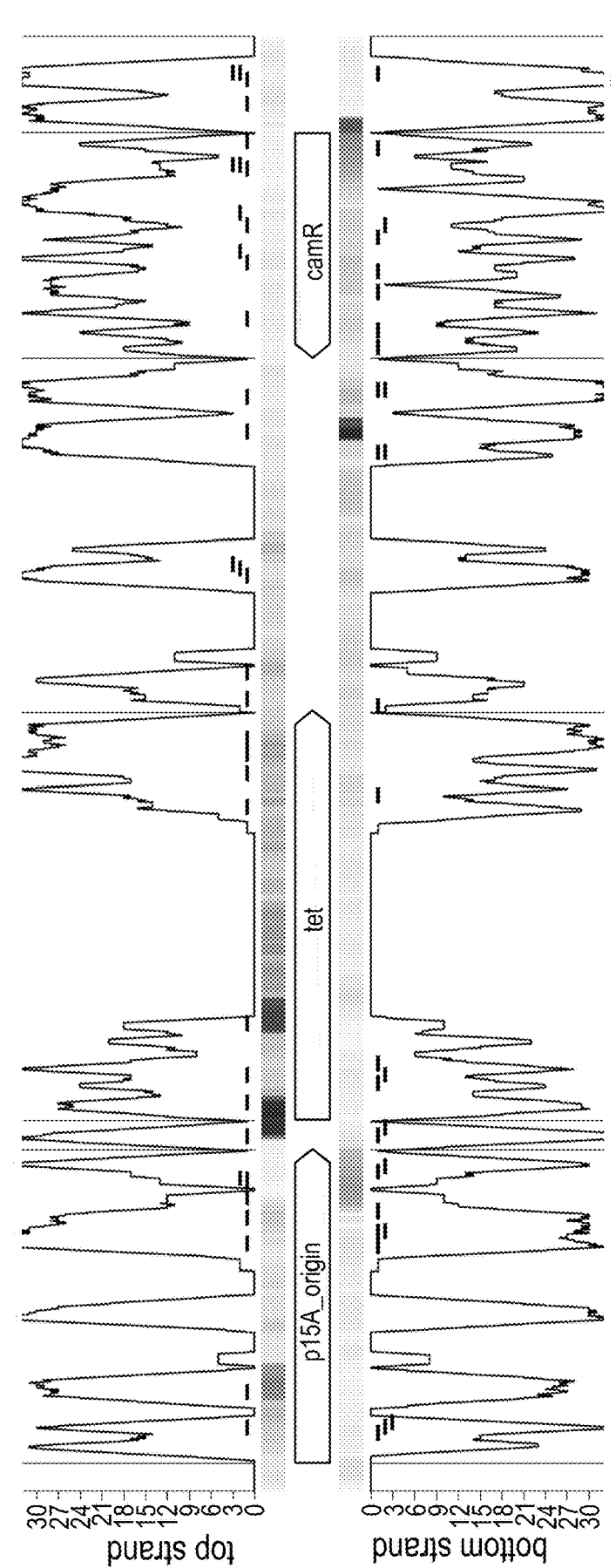
Figure 10B:
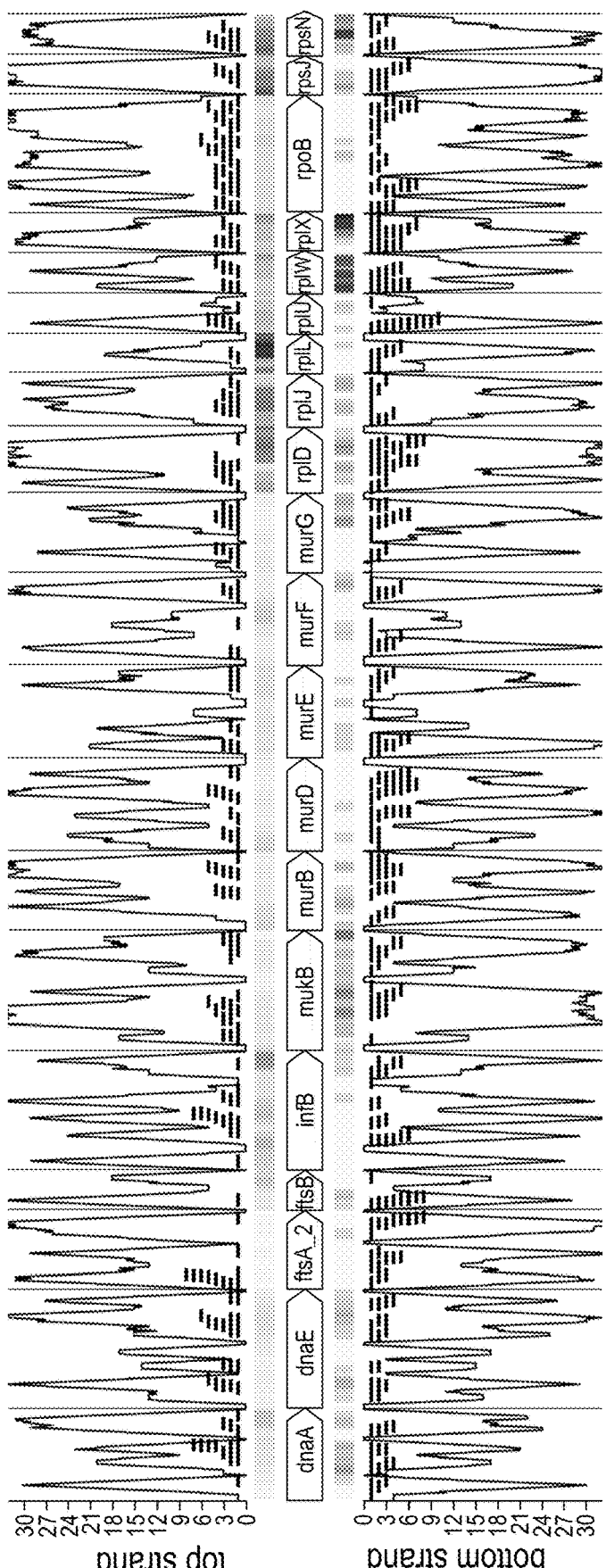

FIG. 10A is a graphical representation showing the density of depleted and non-depleted targets for CLUST.200916 SRR6837570, with a non-coding sequence, by location on the pACYC184 plasmid. FIG. 10B is a graphic representation showing the density of depleted and non-depleted targets for CLUST.200916 SRR6837570, with a non-coding sequence, by location on the *E. coli* strain, E. Cloni. Targets on the top strand and bottom strand are shown separately and in relation to the orientation of the annotated genes. The magnitude of the bands indicates the degree of depletion, wherein the lighter bands are close to the hit threshold of 3. The gradients are heatmaps of RNA sequencing showing relative transcript abundance.

Figure 11:
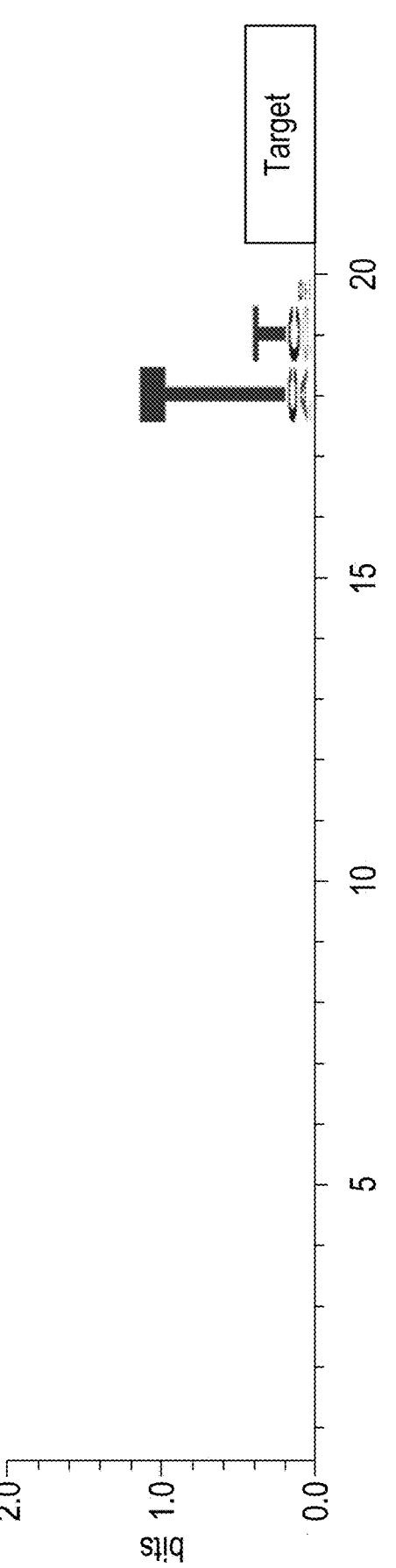

FIG. 11 is a WebLogo of the sequences flanking depleted targets in E. Cloni as a prediction of the PAM sequence for CLUST.200916 SRR6837570 (with a non-coding sequence).

Figure 12:
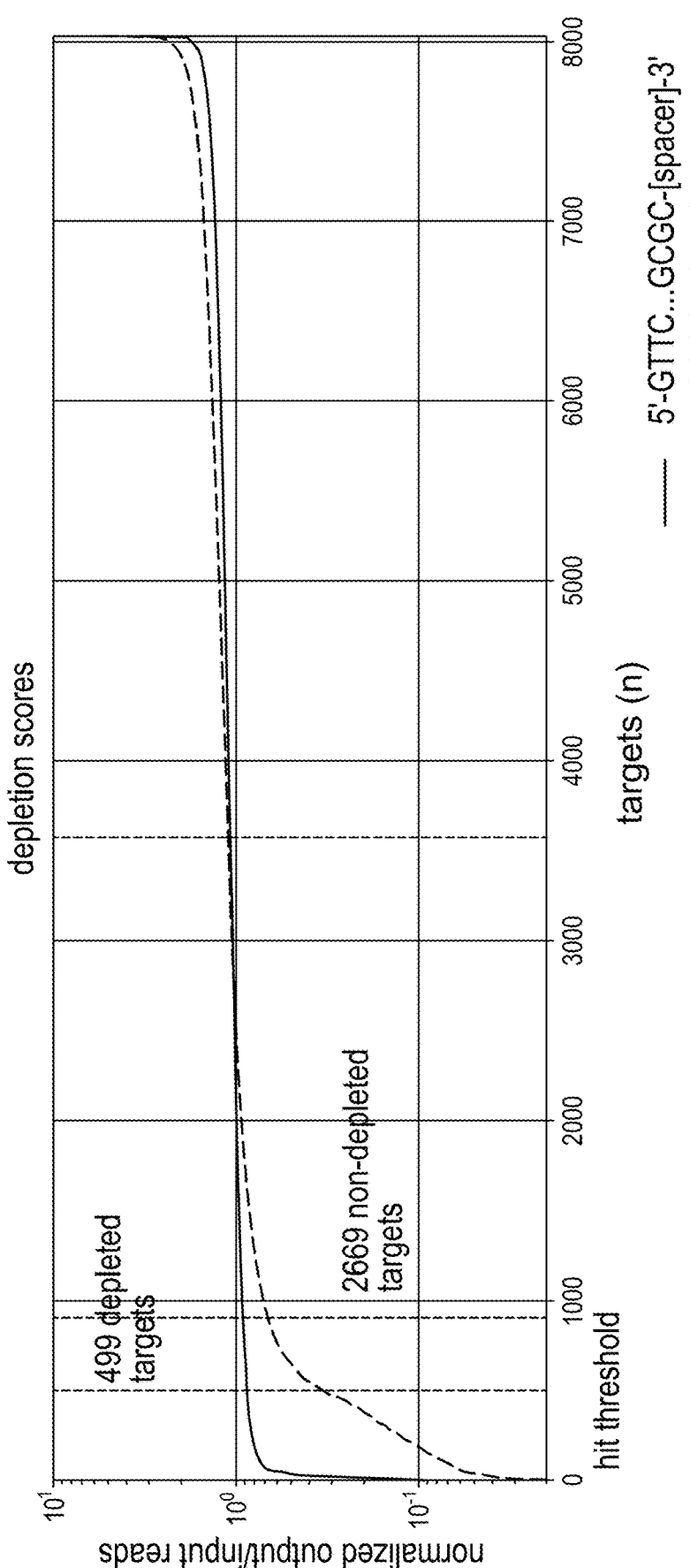

FIG. 12 is a graph for CLUST.200916 SRR6837570 (effector set forth in SEQ ID NO: 26) showing the degree of depletion activity of the engineered compositions for spacers targeting pACYC184 and direct repeat transcriptional orientations, without a non-coding sequence. The degree of depletion with the direct repeat in the "forward" orientation (5'-GTTC . . . GCGC-[spacer]-3') and with the direct repeat in the "reverse" orientation (5'-GCGC . . . GAAC-[spacer]-3') are depicted in a solid line and a dashed line, respectively.

Figure 13A:
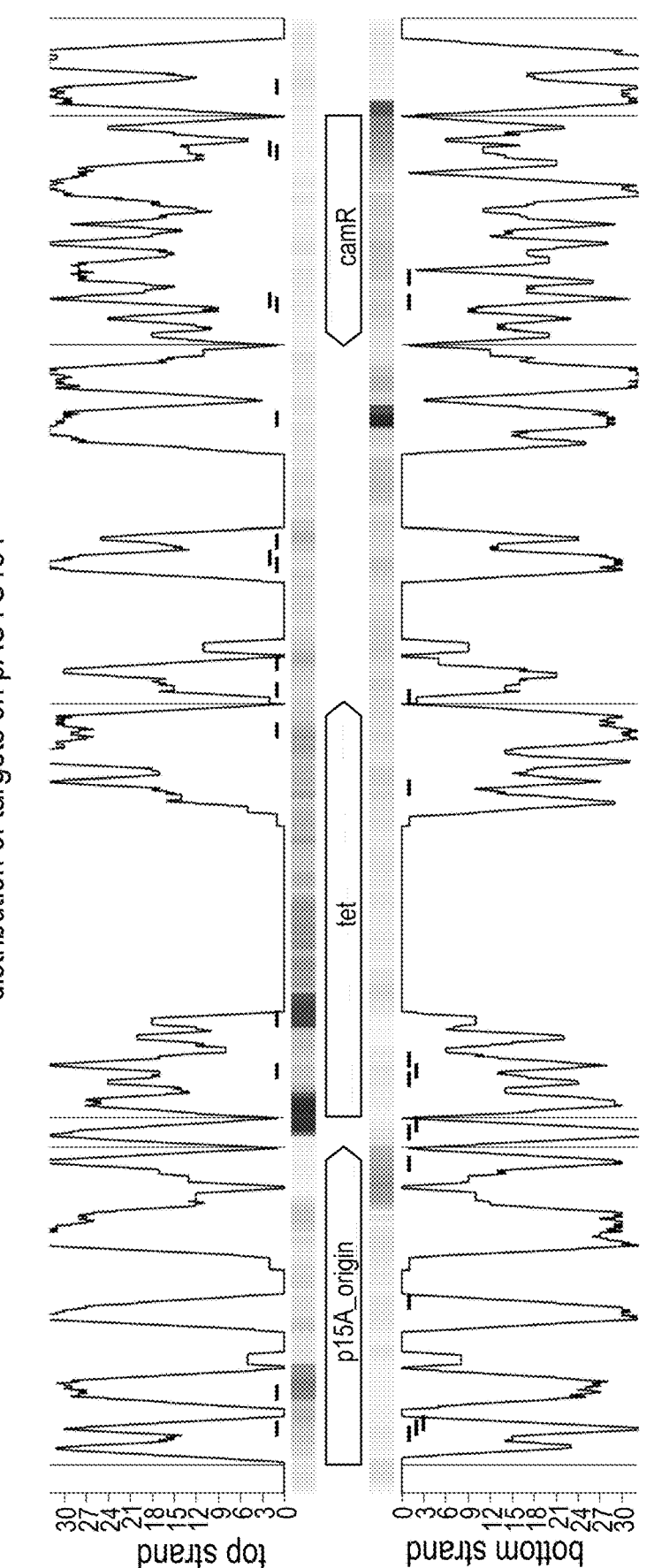
Figure 13B:
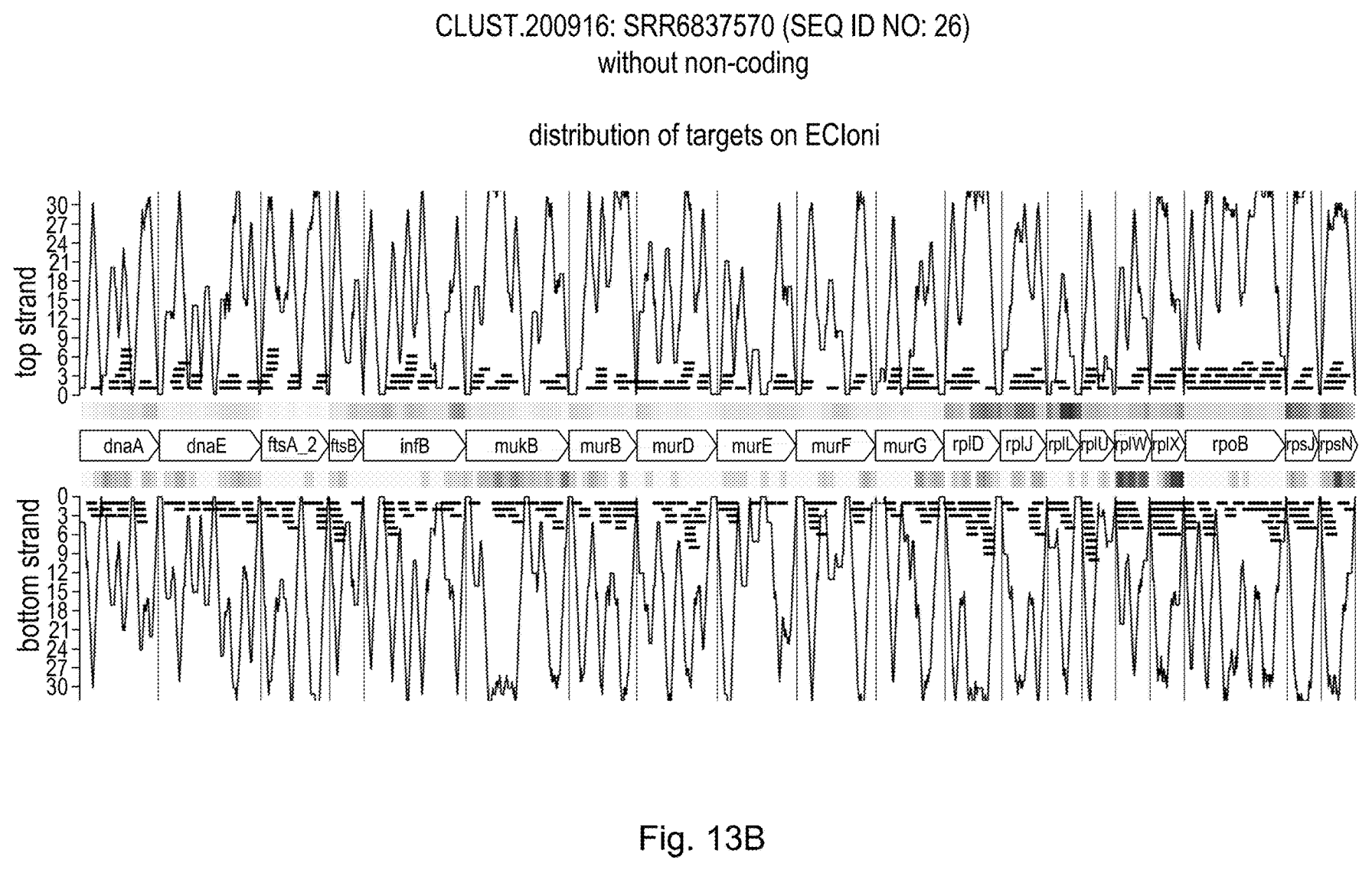

FIG. 13A is a graphical representation showing the density of depleted and non-depleted targets for CLUST.200916 SRR6837570, without a non-coding sequence, by location on the pACYC184 plasmid. FIG. 13B is a graphic representation showing the density of depleted and non-depleted targets for CLUST.200916 SRR6837570, without a noncoding sequence, by location on the *E. coli* strain, E. Cloni. Targets on the top strand and bottom strand are shown separately and in relation to the orientation of the annotated genes. The magnitude of the bands indicates the degree of depletion, wherein the lighter bands are close to the hit threshold of 3. The gradients are heatmaps of RNA sequencing showing relative transcript abundance.

Figure 14:
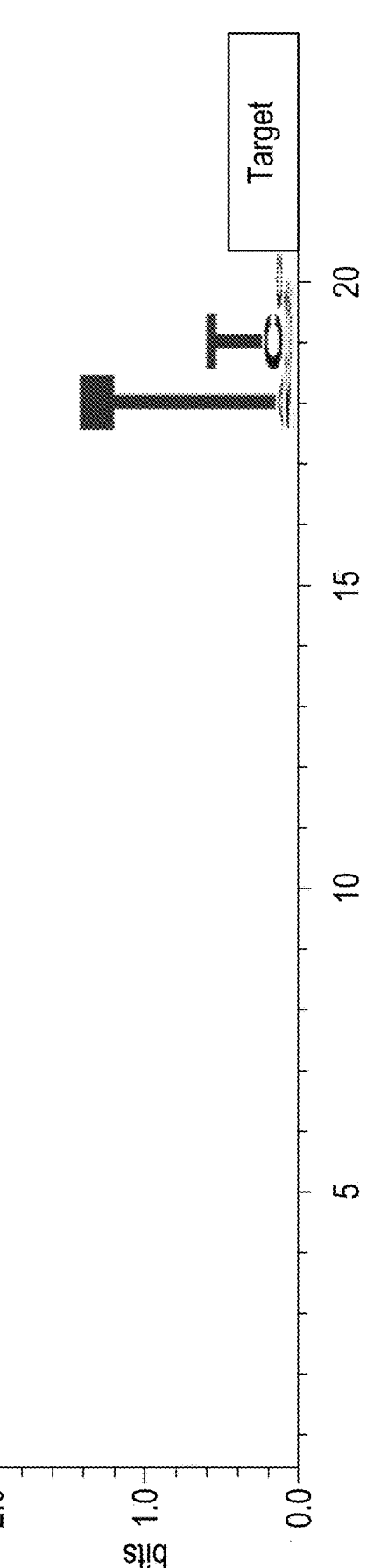

FIG. 14 is a WebLogo of the sequences flanking depleted targets in E. Cloni as a prediction of the PAM sequence for CLUST.200916 SRR6837570 (without a non-coding sequence).

Figure 15:
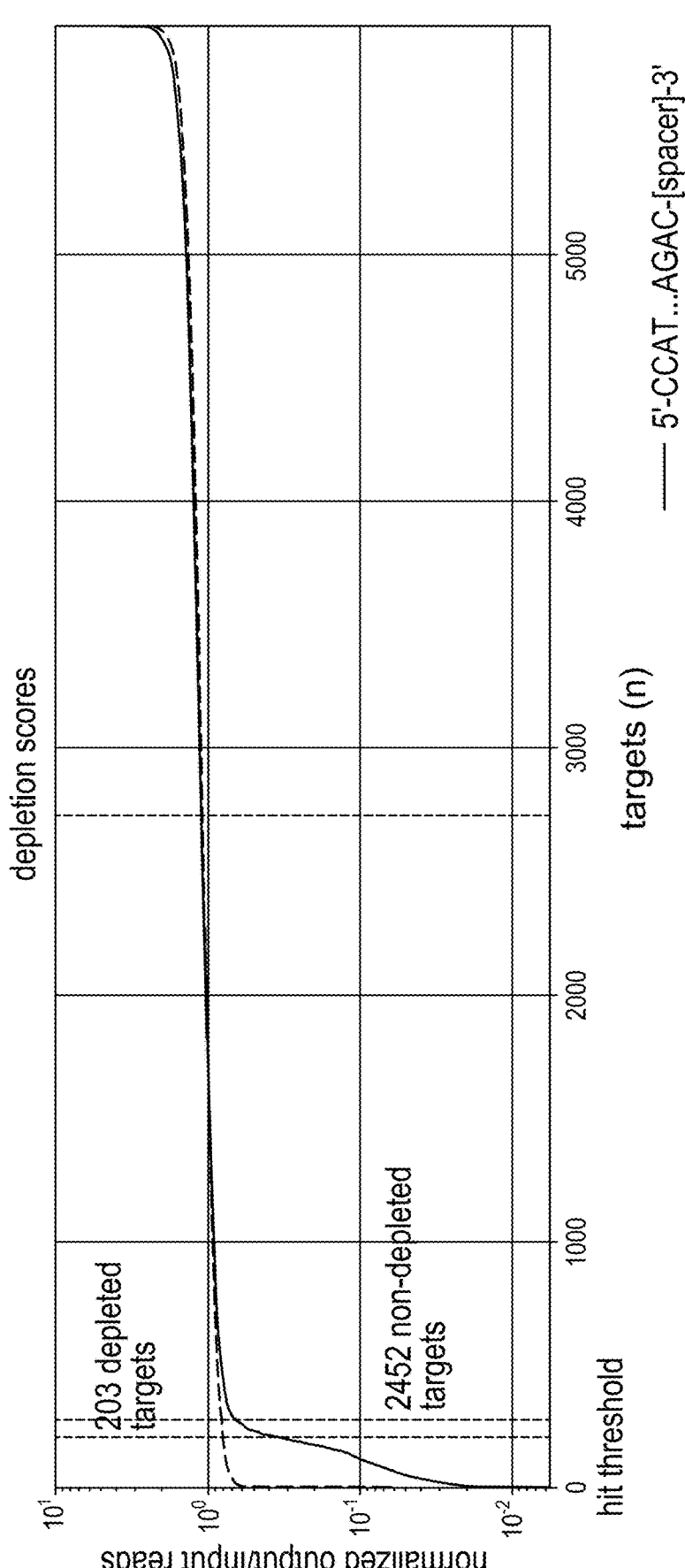

FIG. 15 is a graph for CLUST.200916 SRR6837575 (effector set forth in SEQ ID NO: 28) showing the degree of depletion activity of the engineered compositions for spacers targeting pACYC184 and direct repeat transcriptional orientations, with a non-coding sequence. The degree of depletion with the direct repeat in the "forward" orientation (5'-CCAT . . . AGAC-[spacer]-3') and with the direct repeat in the "reverse" orientation (5'-GTCT . . . ATGG-[spacer]-3') are depicted in a solid line and a dashed line, respectively.

Figure 16A:
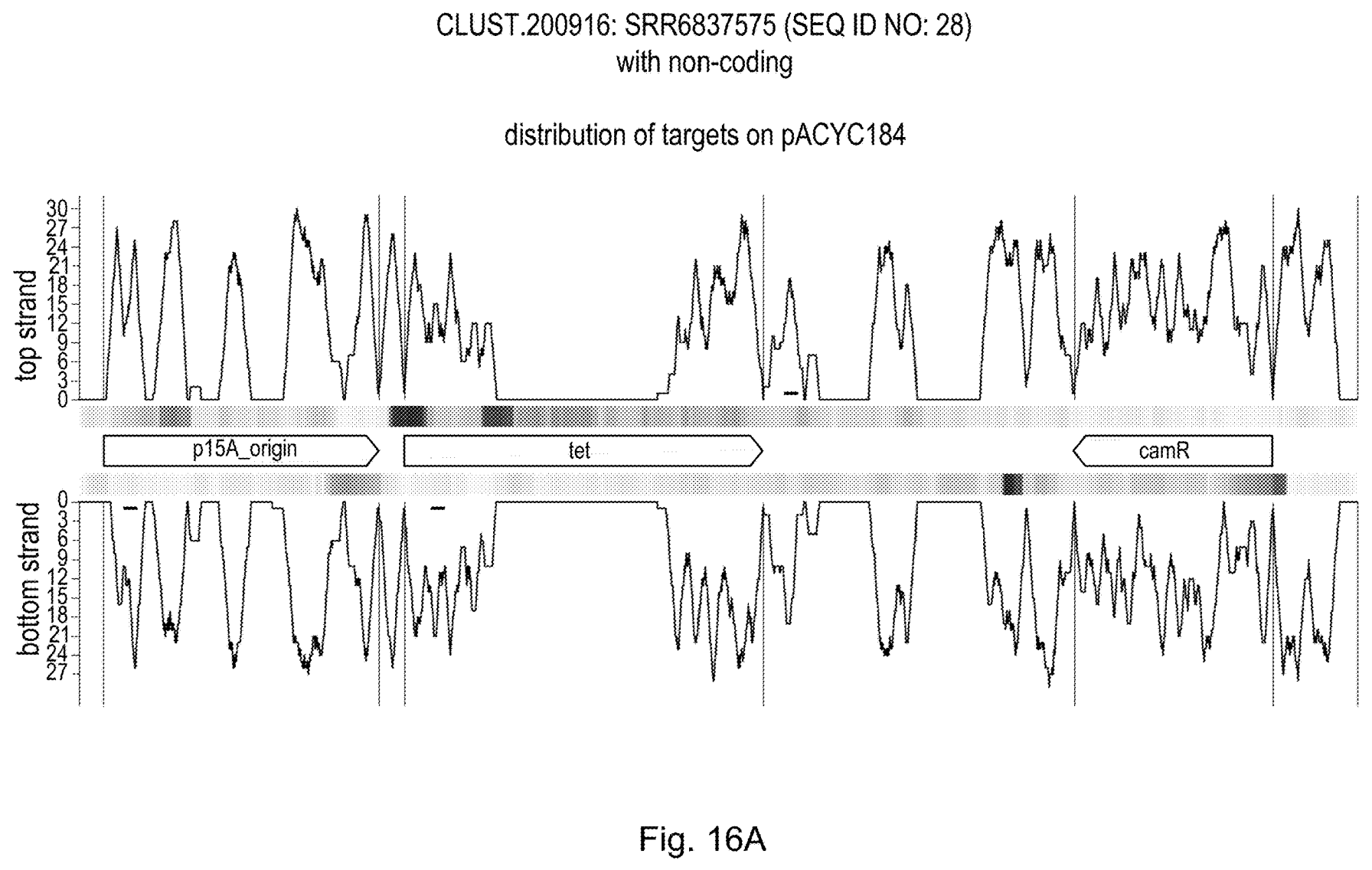

FIG. 16A is a graphical representation showing the density of depleted and non-depleted targets for CLUST.200916 SRR6837575, with a non-coding sequence, by location on the pACYC184 plasmid.

Figure 16B:
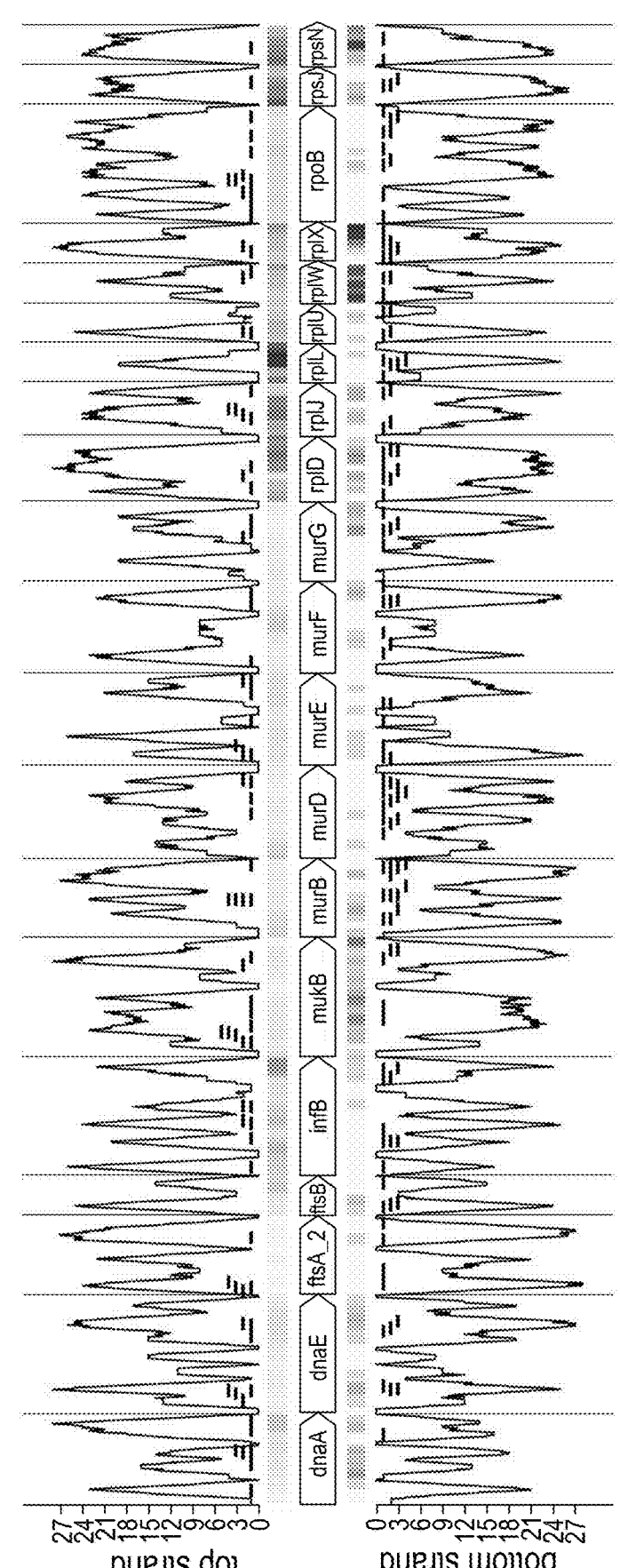

FIG. 16B is a graphic representation showing the density of depleted and non-depleted targets for CLUST.200916 SRR6837575, with a non-coding sequence, by location on the *E. coli* strain, E. Cloni. Targets on the top strand and bottom strand are shown separately and in relation to the orientation of the annotated genes. The magnitude of the bands indicates the degree of depletion, wherein the lighter bands are close to the hit threshold of 3. The gradients are heatmaps of RNA sequencing showing relative transcript abundance.

Figure 17:
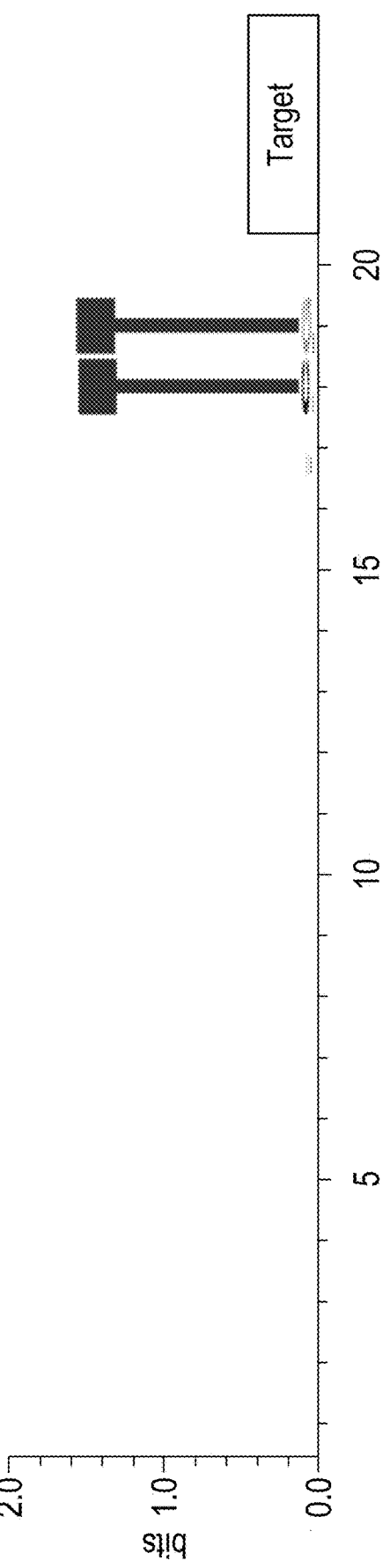

FIG. 17 is a WebLogo of the sequences flanking depleted targets in E. Cloni as a prediction of the PAM sequence for CLUST.200916 SRR6837575 (with a non-coding sequence).

Figure 18:
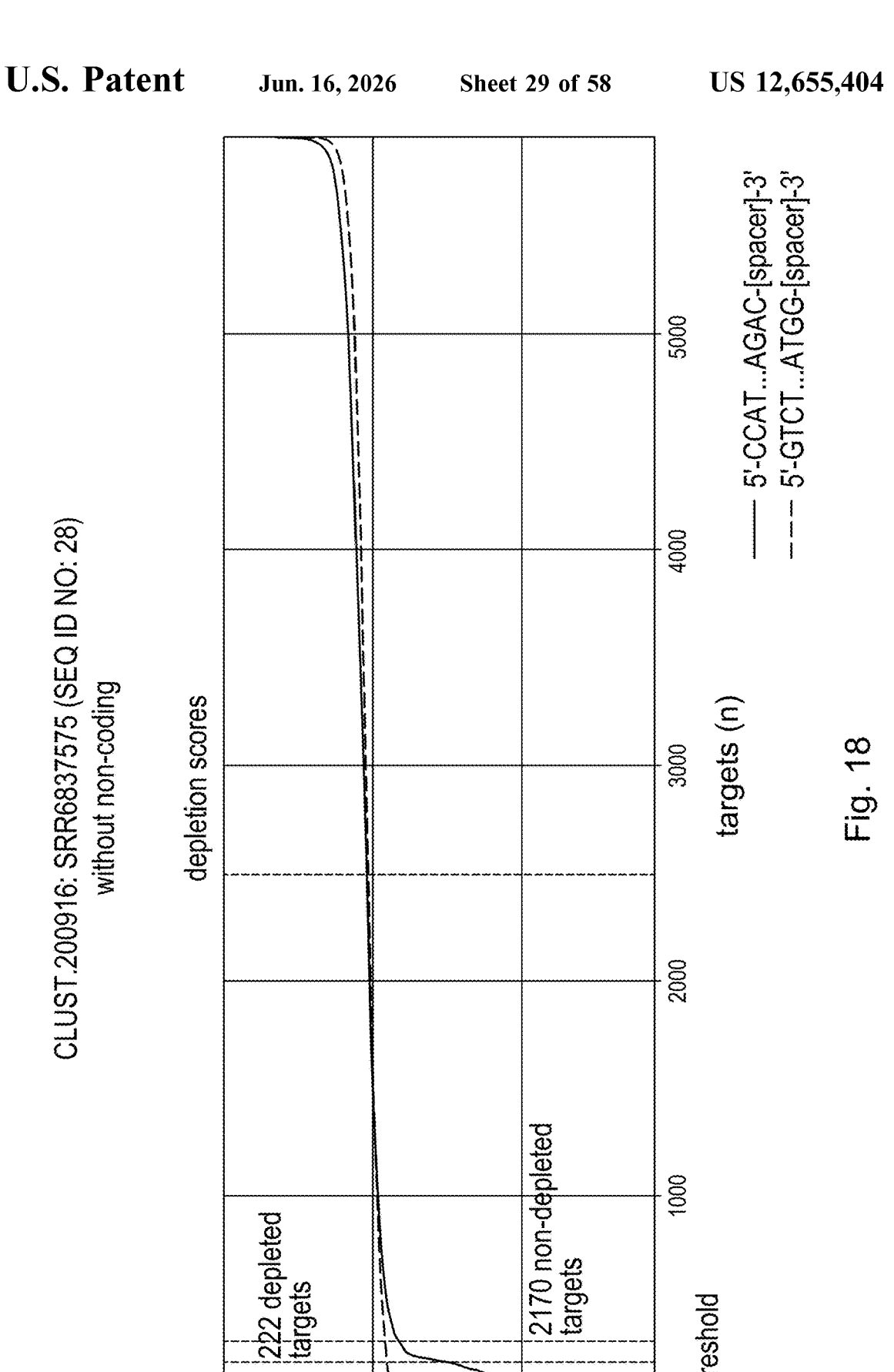

FIG. 18 is a graph for CLUST.200916 SRR6837575 (effector set forth in SEQ ID NO: 28) showing the degree of depletion activity of the engineered compositions for spacers targeting pACYC184 and direct repeat transcriptional orientations, without a non-coding sequence. The degree of depletion with the direct repeat in the "forward" orientation (5'CCAT . . . AGAC-[spacer]-3') and with the direct repeat in the "reverse" orientation (5'-GTCT . . . ATGG-[spacer]-3') are depicted in a solid line and a dashed line, respectively.

Figure 19A:
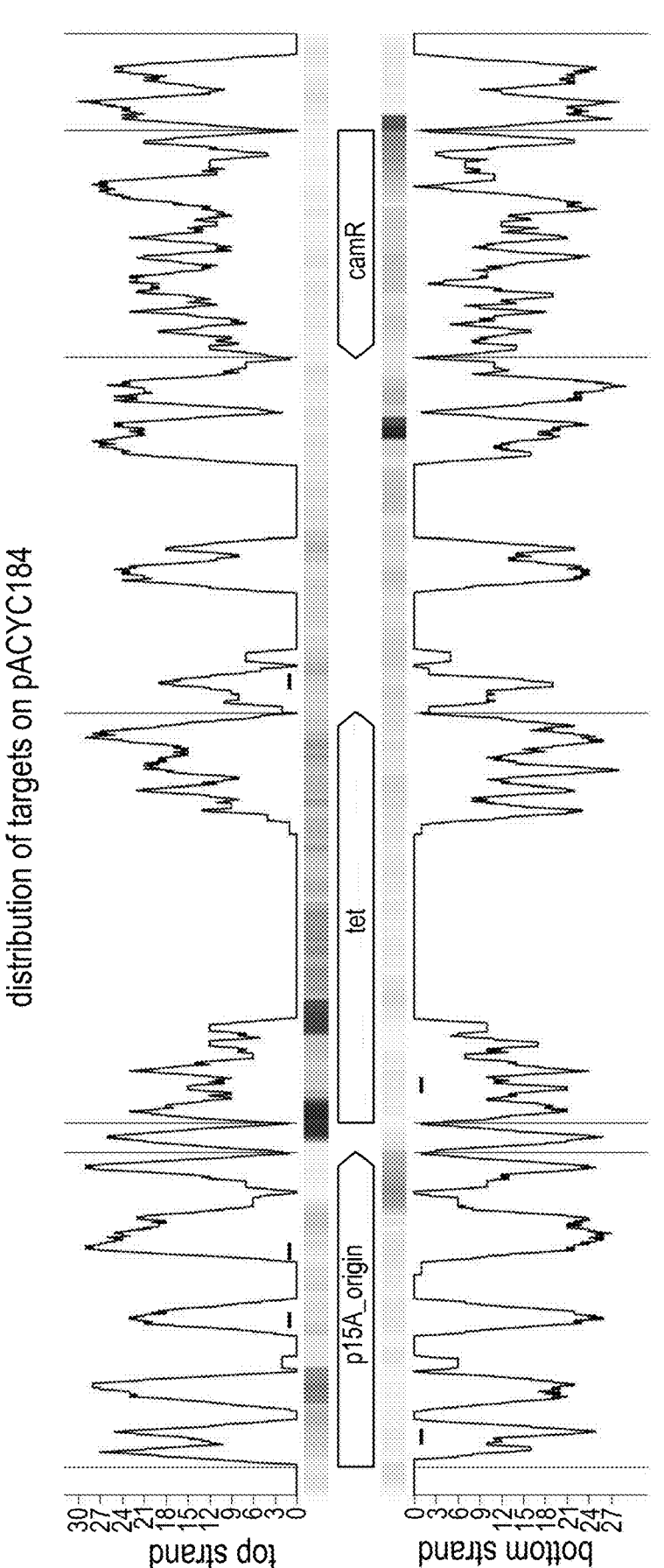
Figure 19B:
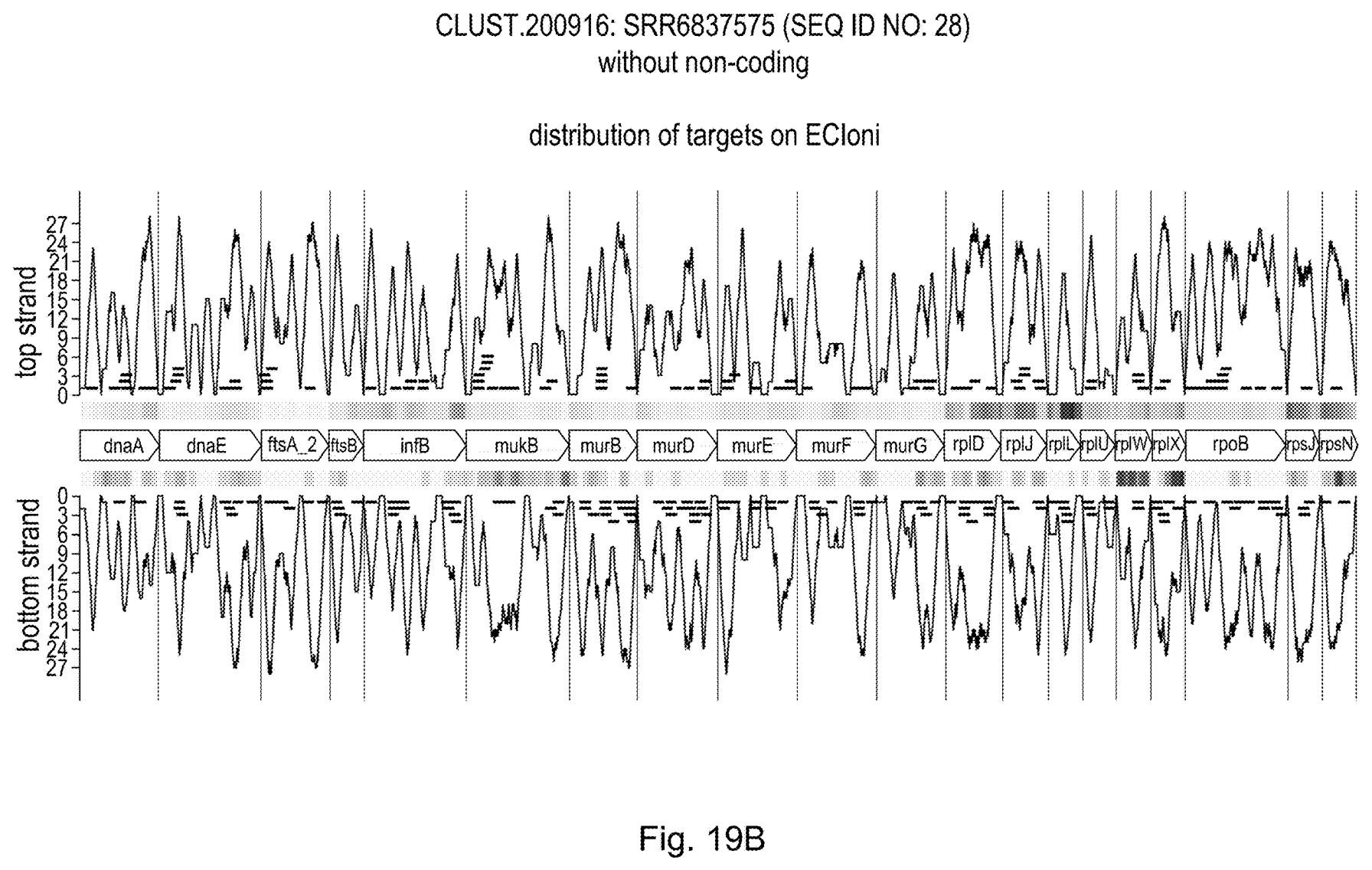

FIG. 19A is a graphical representation showing the density of depleted and non-depleted targets for CLUST.200916 SRR6837575, without a non-coding sequence, by location on the pACYC184 plasmid. FIG. 19B is a graphic representation showing the density of depleted and non-depleted targets for CLUST.200916 SRR6837575, without a non-coding sequence, by location on the *E. coli* strain, E. Cloni. Targets on the top strand and bottom strand are shown separately and in relation to the orientation of the annotated genes. The magnitude of the bands indicates the degree of depletion, wherein the lighter bands are close to the hit threshold of 3. The gradients are heatmaps of RNA sequencing showing relative transcript abundance.

Figure 20:
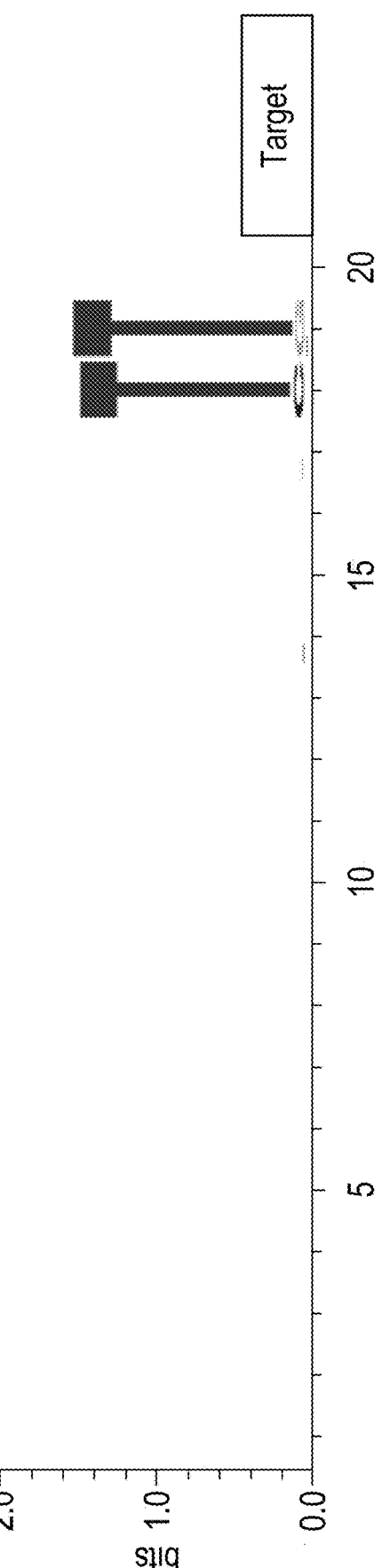

FIG. 20 is a WebLogo of the sequences flanking depleted targets in E. Cloni as a prediction of the PAM sequence for CLUST.200916 SRR6837575 (without a non-coding sequence).

Figure 21:

FIG. 21 is a graph for CLUST.200916 SRR6837577 (effector set forth in SEQ ID NO: 29) showing the degree of depletion activity of the engineered compositions for spacers targeting pACYC184 and direct repeat transcriptional orientations, with a non-coding sequence. The degree of depletion with the direct repeat in the "forward" orientation (5'-GTCG . . . CGAC-[spacer]-3') and with the direct repeat in the "reverse" orientation (5'-GTCG . . . CGAC-[spacer]-3') are depicted in a solid line and a dashed line, respectively.

Figure 22A:
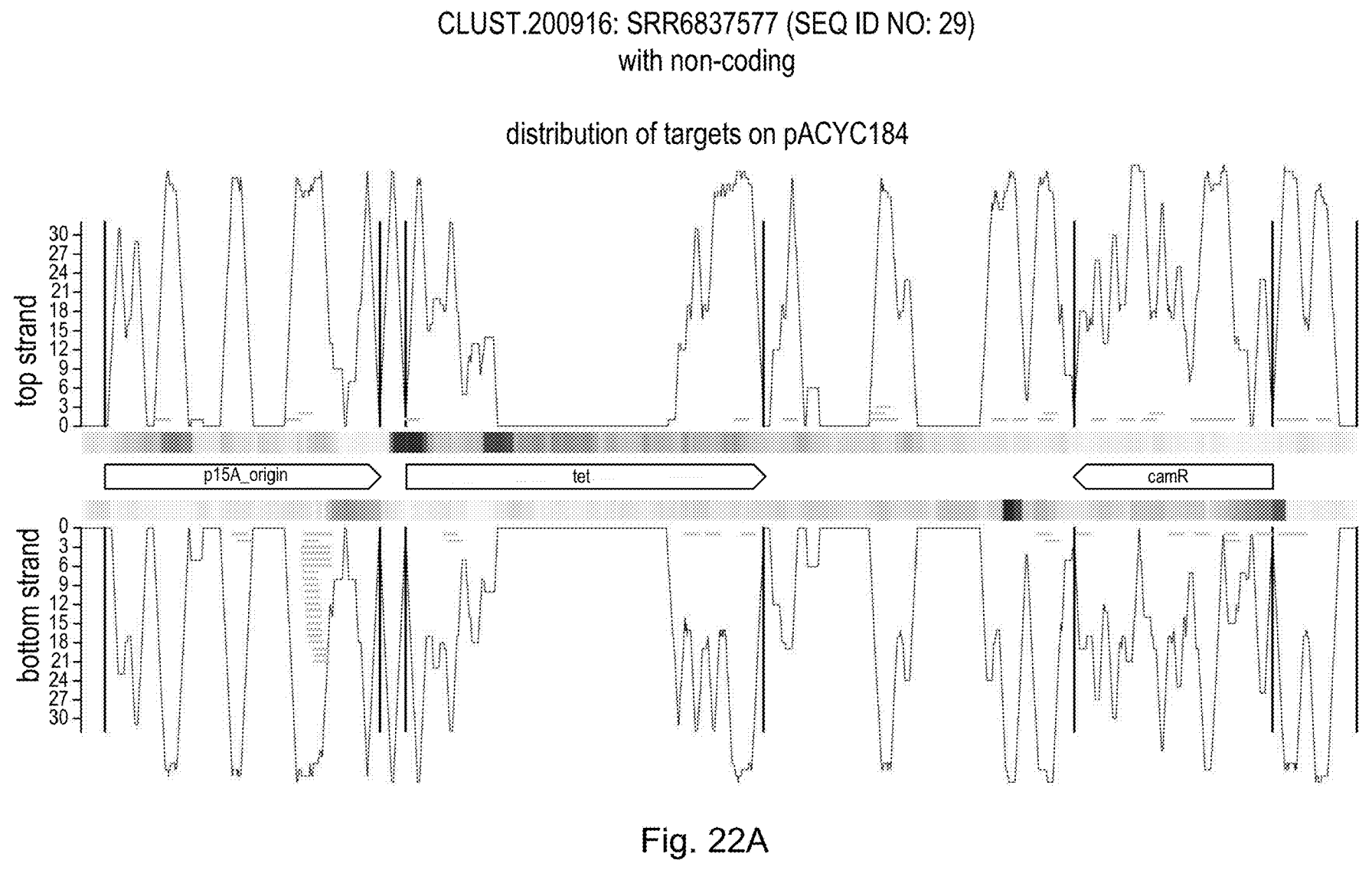
Figure 22B:
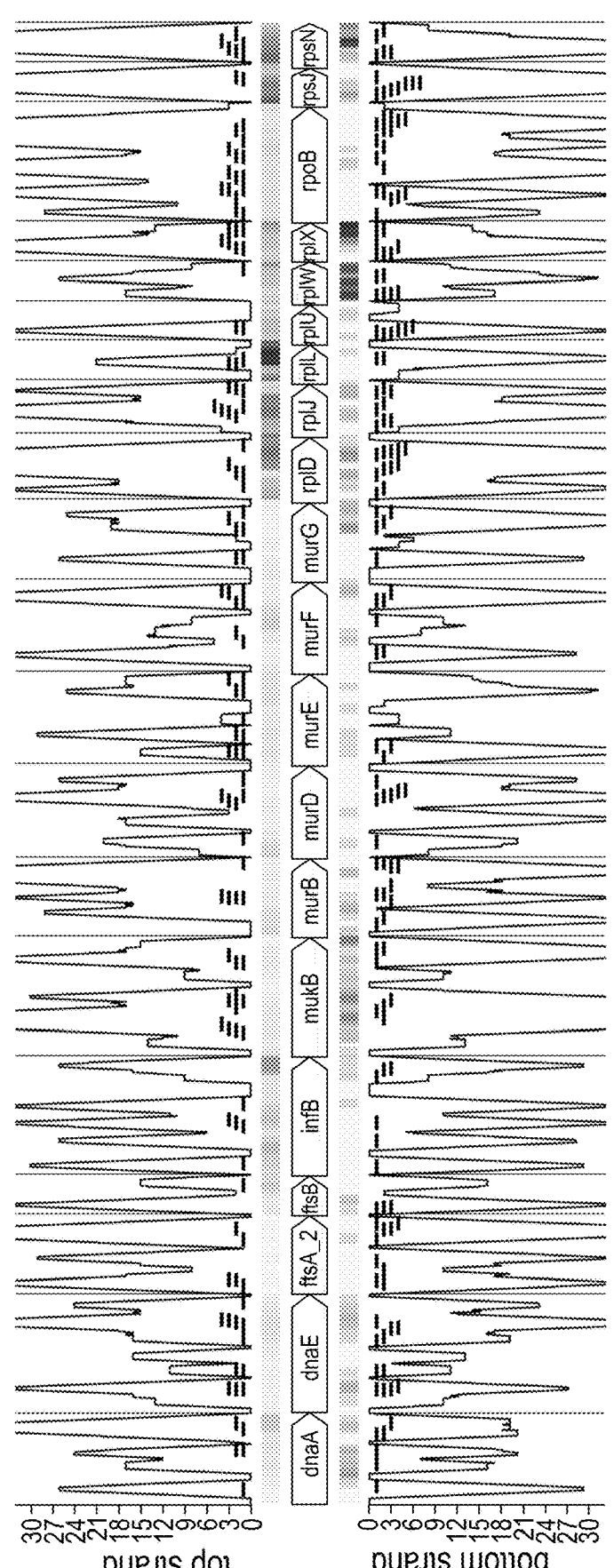

FIG. 22A is a graphical representation showing the density of depleted and non-depleted targets for CLUST.200916 SRR6837577, with a non-coding sequence, by location on the pACYC184 plasmid. FIG. 22B is a graphic representation showing the density of depleted and non-depleted targets for CLUST.200916 SRR6837577, with a non-coding sequence, by location on the *E. coli* strain, E. Cloni. Targets on the top strand and bottom strand are shown separately and in relation to the orientation of the annotated genes. The magnitude of the bands indicates the degree of depletion, wherein the lighter bands are close to the hit threshold of 3. The gradients are heatmaps of RNA sequencing showing relative transcript abundance.

Figure 23:
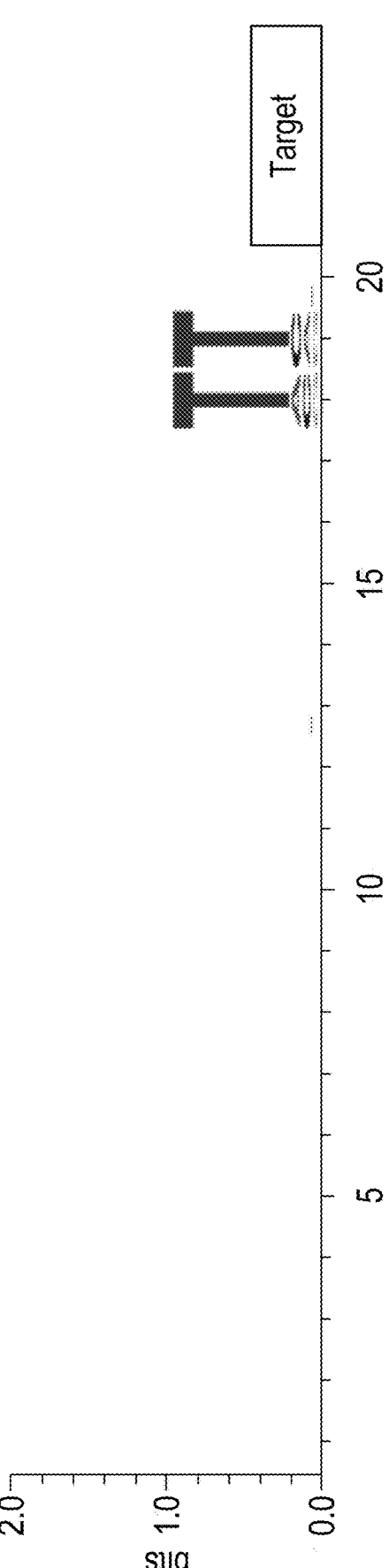

FIG. 23 is a WebLogo of the sequences flanking depleted targets in E. Cloni as a prediction of the PAM sequence for CLUST.200916 SRR6837577 (with a non-coding sequence).

Figure 24:
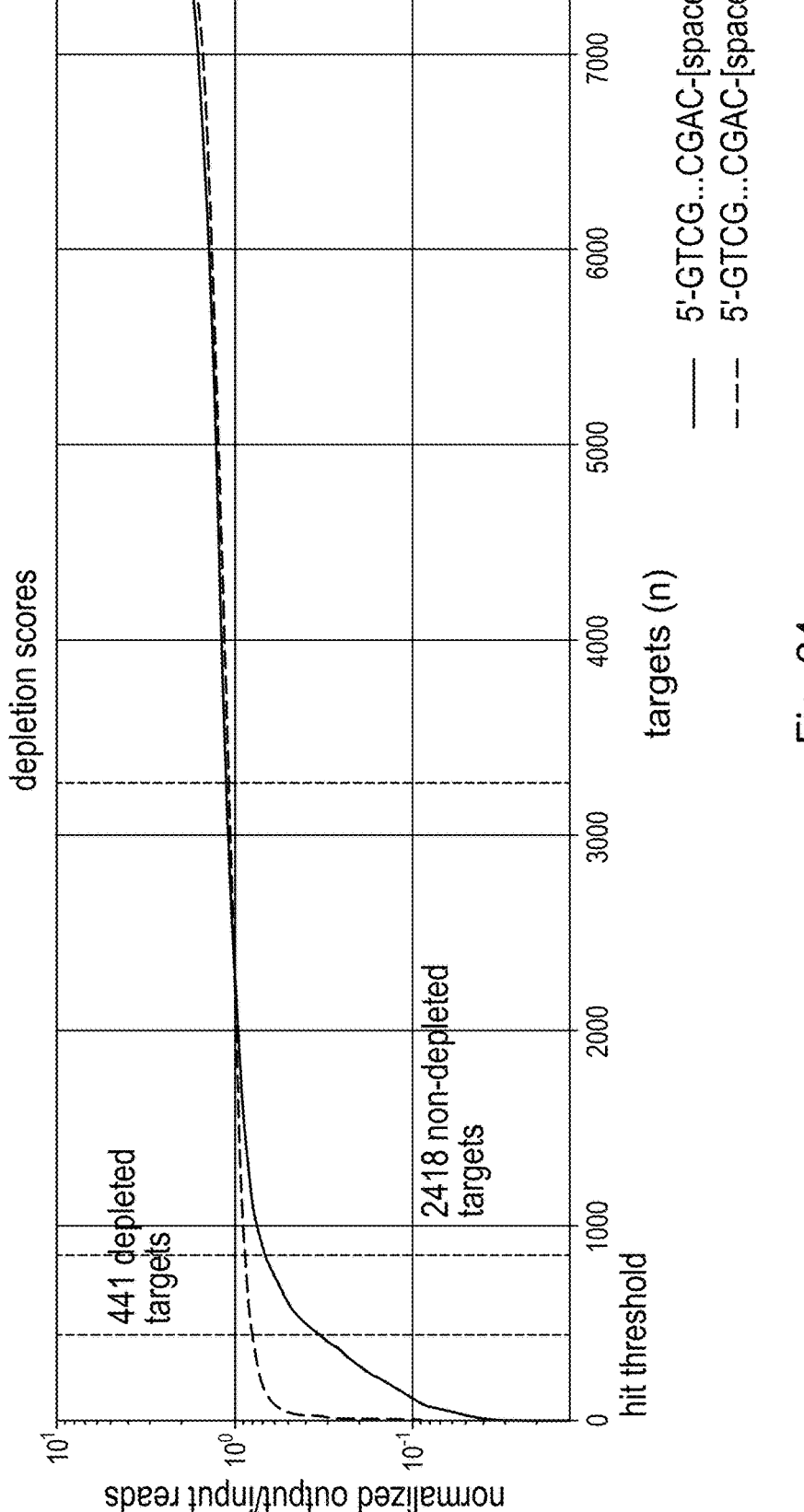

FIG. 24 is a graph for CLUST.20091_6 SRR6837577 (effector set forth in SEQ ID NO: 29) showing the degree of depletion activity of the engineered compositions for spacers targeting pACYC184 and direct repeat transcriptional orientations, without a non-coding sequence. The degree of depletion with the direct repeat in the "forward" orientation (5'-GTCG . . . CGAC-[spacer]-3') and with the direct repeat in the "reverse" orientation (5'-GTCG . . . CGAC-[spacer]-3') are depicted in a solid line and a dashed line, respectively.

Figure 25A:
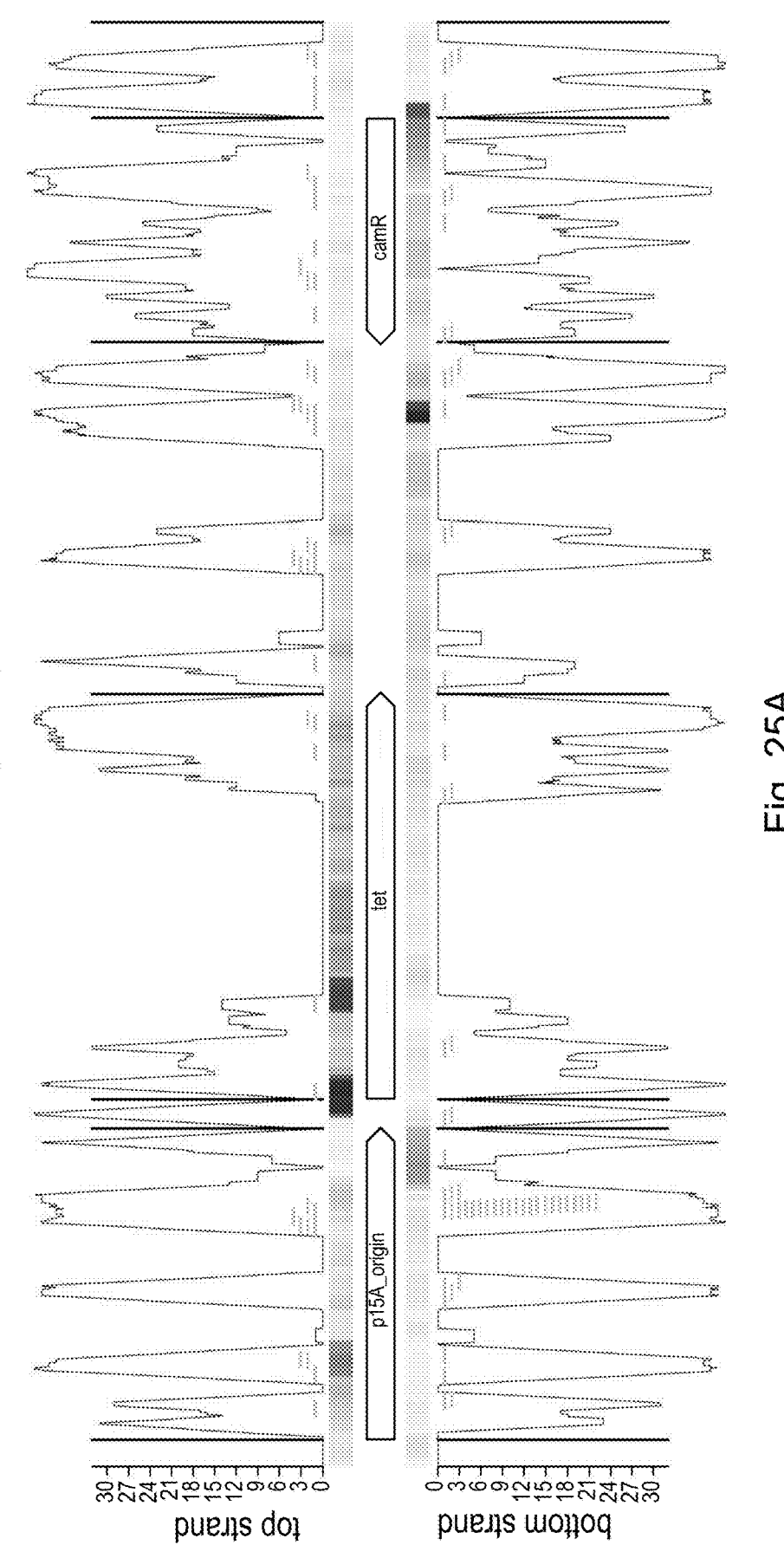
Figure 25B:
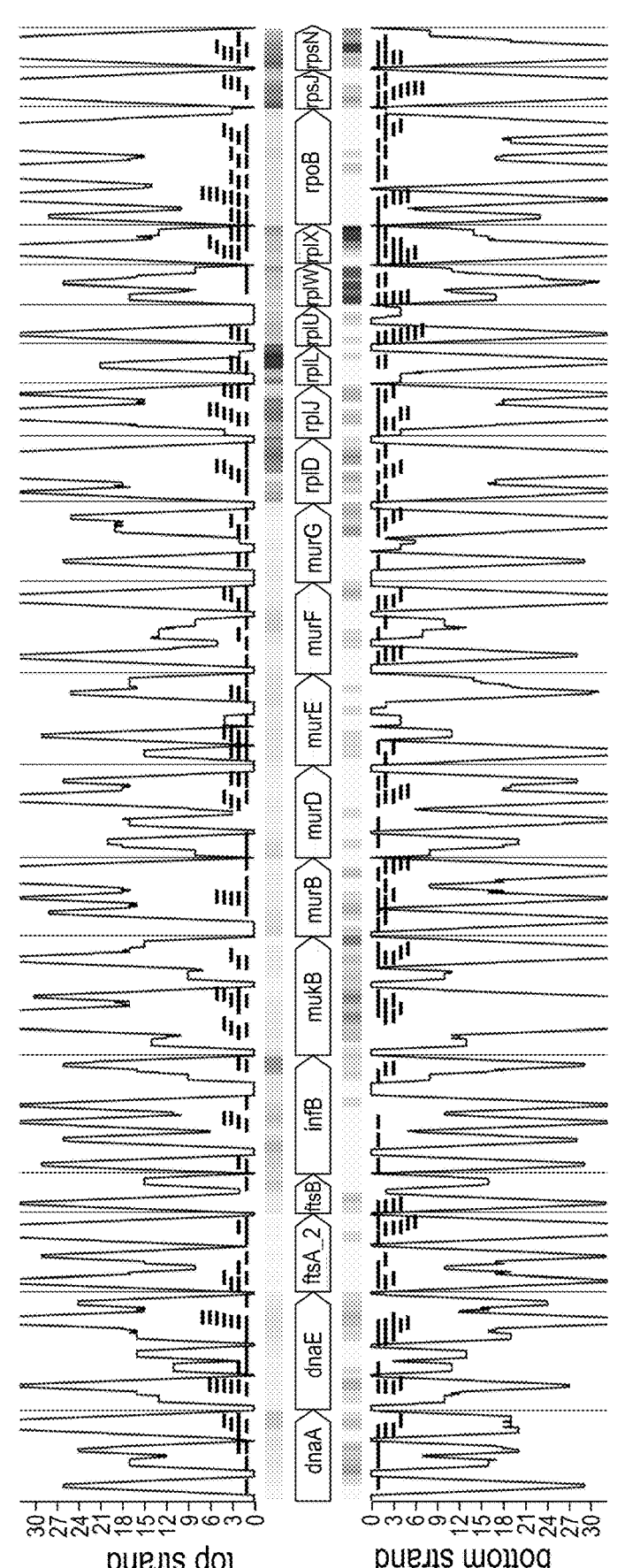

FIG. 25A is a graphical representation showing the density of depleted and non-depleted targets for CLUST.200916 SRR6837577, without a non-coding sequence, by location on the pACYC184 plasmid. FIG. 25B is a graphic representation showing the density of depleted and non-depleted targets for CLUST.200916 SRR6837577, without a non-coding sequence, by location on the *E. coli* strain, E. Cloni. Targets on the top strand and bottom strand are shown separately and in relation to the orientation of the annotated genes. The magnitude of the bands indicates the degree of depletion, wherein the lighter bands are close to the hit threshold of 3. The gradients are heatinaps of RNA sequencing showing relative transcript abundance.

Figure 26:
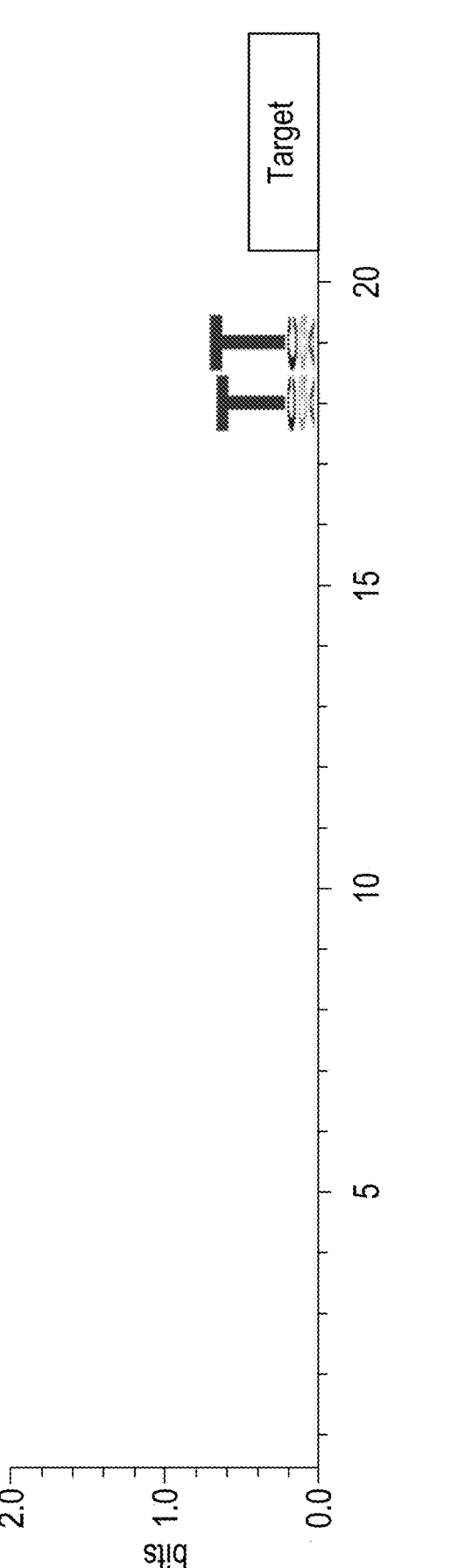

FIG. 26 is a WebLogo of the sequences flanking depleted targets in E. Cloni as a prediction of the PAM sequence for CLUST.200916 SRR6837577 (without a non-coding sequence).

Figure 27:

FIG. 27 is a graph for CLUST.200916 SRR6837569 (effector set forth in SEQ ID NO: 25) showing the degree of depletion activity of the engineered compositions for spacers targeting pACYC184 and direct repeat transcriptional orientations, with a non-coding sequence. The degree of depletion with the direct repeat in the "forward" orientation (5'-GTCT . . . CAGG-[spacer]-3') and with the direct repeat in the "reverse" orientation (5'-CCTG . . . AGAC-[spacer]-3') are depicted in a solid line and a dashed line, respectively.

Figure 28A:
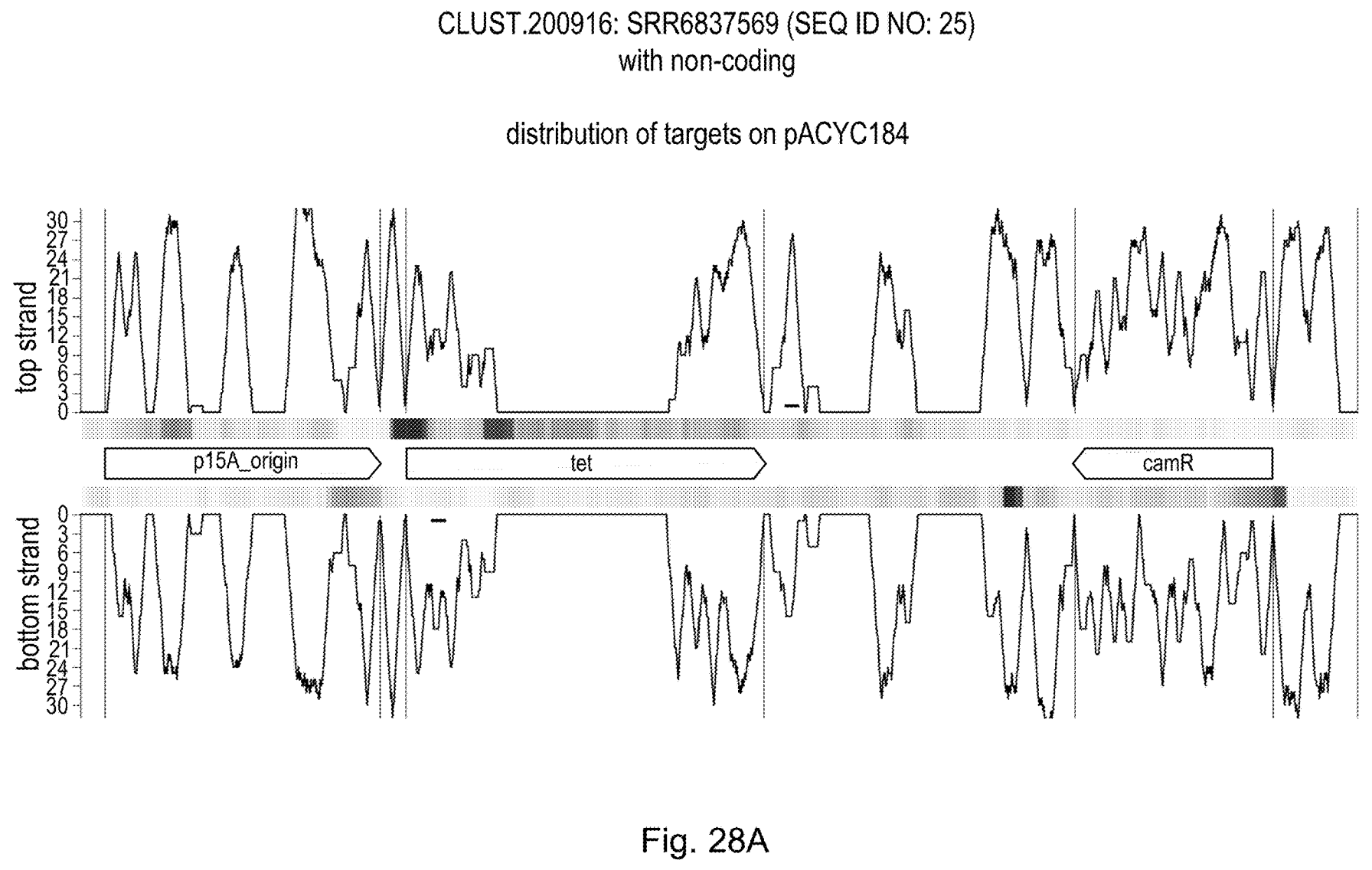

FIG. 28A is a graphical representation showing the density of depleted and non-depleted targets for CLUST.200916 SRR6837569, with a non-coding sequence, by location on the pACYC184 plasmid.

Figure 28B:
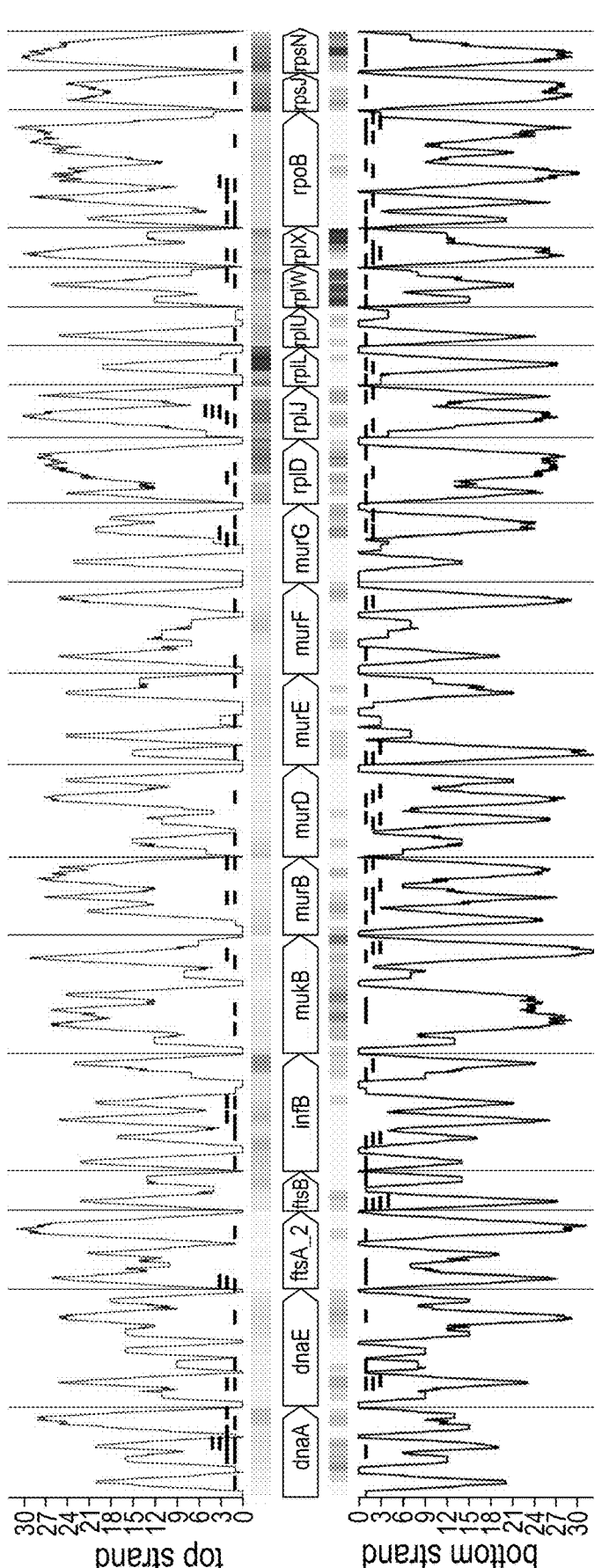

FIG. 28B is a graphic representation showing the density of depleted and non-depleted targets for CLUST.200916 SRR6837569, with a non-coding sequence, by location on the *E. coli* strain, E. Cloni. Targets on the top strand and bottom strand are shown separately and in relation to the orientation of the annotated genes. The magnitude of the bands indicates the degree of depletion, wherein the lighter bands are close to the hit threshold of 3. The gradients are heatmaps of RNA sequencing showing relative transcript abundance.

Figure 29:
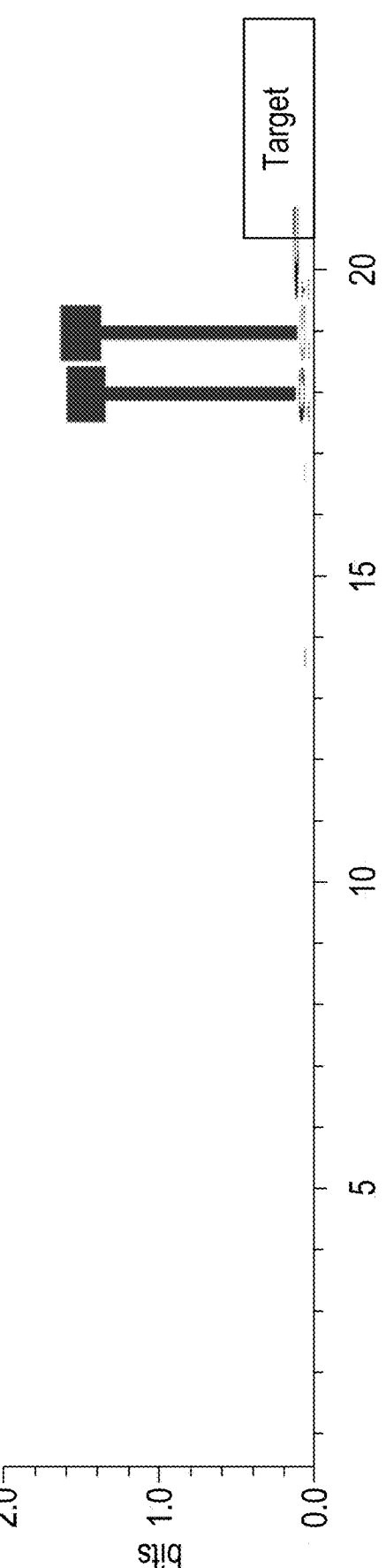

FIG. 29 is a WebLogo of the sequences flanking depleted targets in E. Cloni as a prediction of the PAM sequence for CLUST.200916 SRR6837569 (with a non-coding sequence).

Figure 30:
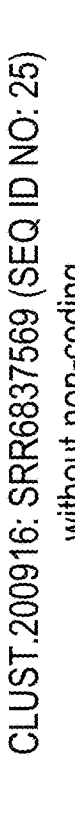

FIG. 30 is a graph for CLUST.200916 SRR6837569 (effector set forth in SEQ ID NO: 25) showing the degree of depletion activity of the engineered compositions for spacers targeting pACYC184 and direct repeat transcriptional orientations, without a non-coding sequence. The degree of depletion with the direct repeat in the "forward" orientation (5'-GTCT . . . CAGG-[spacer]-3') and with the direct repeat in the "reverse" orientation (5'-CCTG . . . AGAC-[spacer]-3') are depicted in a solid line and a dashed line, respectively.

Figure 31A:
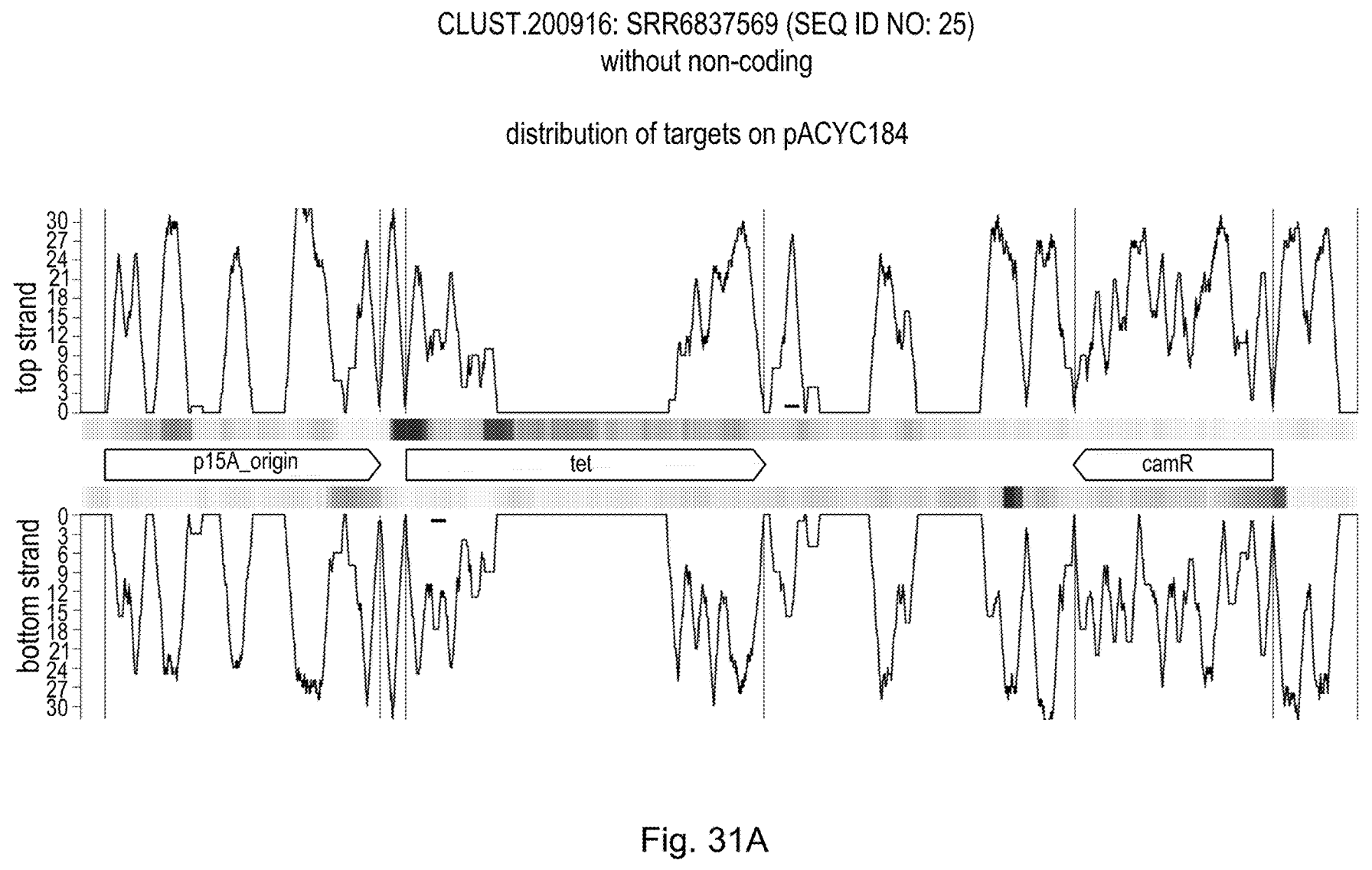
Figure 31B:
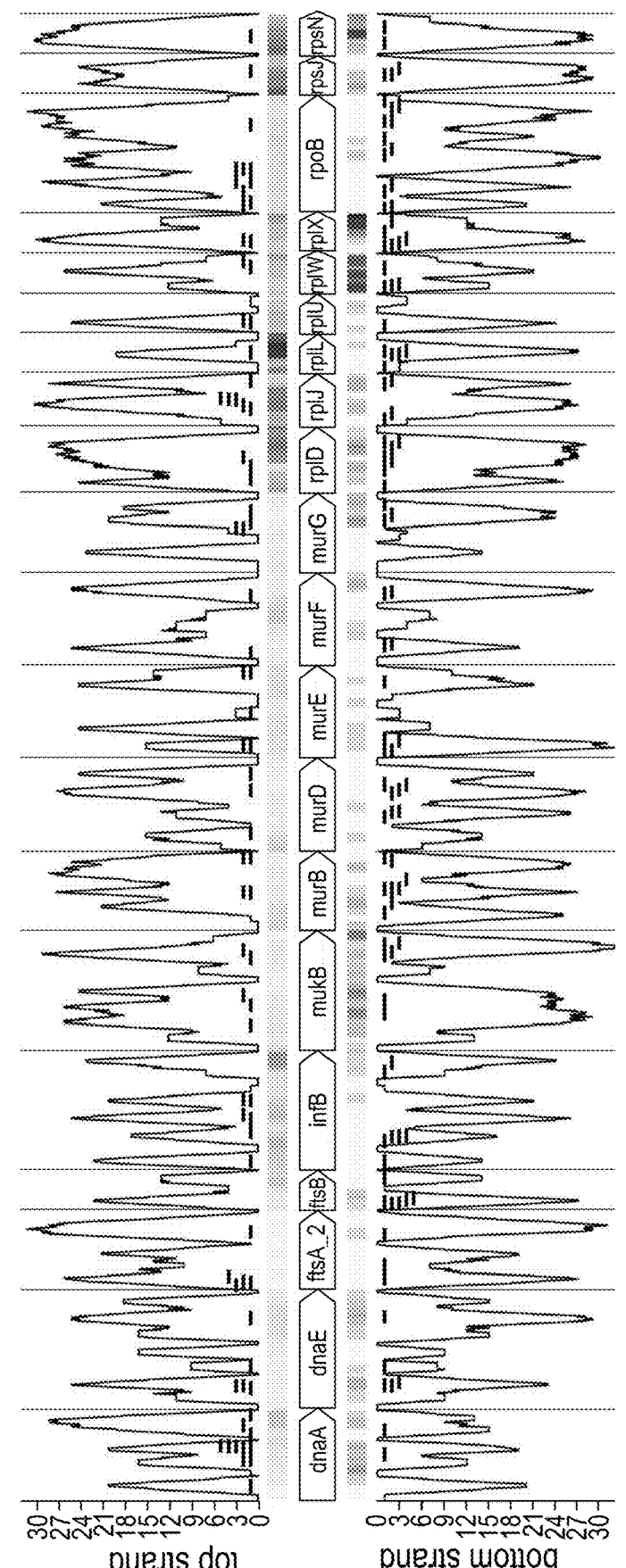

FIG. 31A is a graphical representation showing the density of depleted and non-depleted targets for CLUST.200916 SRR6837569, without a non-coding sequence, by location on the pACYC184 plasmid. FIG. 31B is a graphic representation showing the density of depleted and non-depleted targets for CLUST.200916 SRR6837569, without a non-coding sequence, by location on the E co/i strain, E. Cloni. Targets on the top strand and bottom strand are shown separately and in relation to the orientation of the annotated genes. The magnitude of the bands indicates the degree of depletion, wherein the lighter hands are close to the hit threshold of 3. The gradients are heatmaps of RNA sequencing showing relative transcript abundance.

Figure 32:
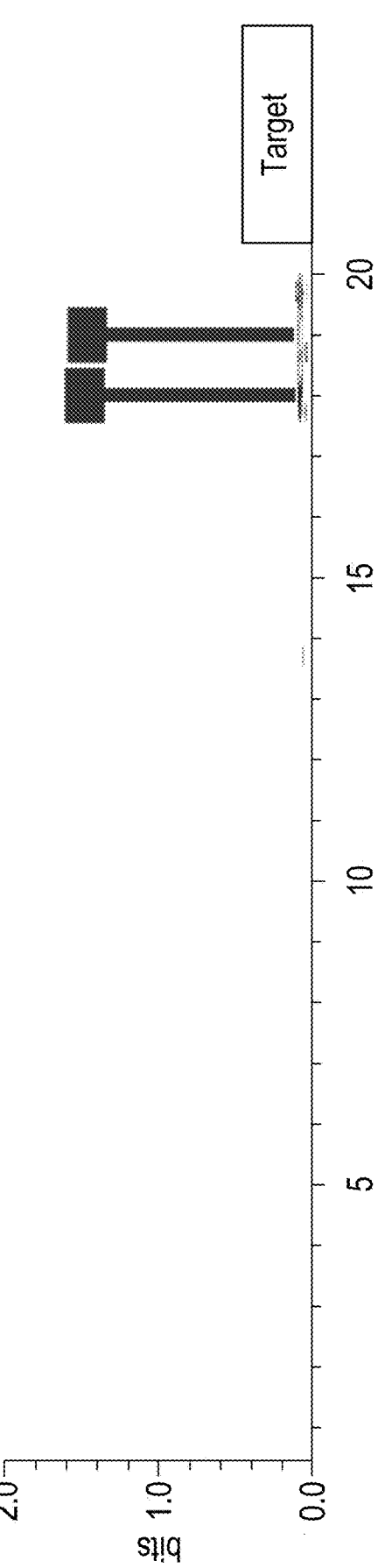

FIG. 32 is a WebLogo of the sequences flanking depleted targets in E. Cloni as a prediction of the PAM sequence for CLUST.200916 SRR6837569 (without a non-coding sequence).

Figure 33:
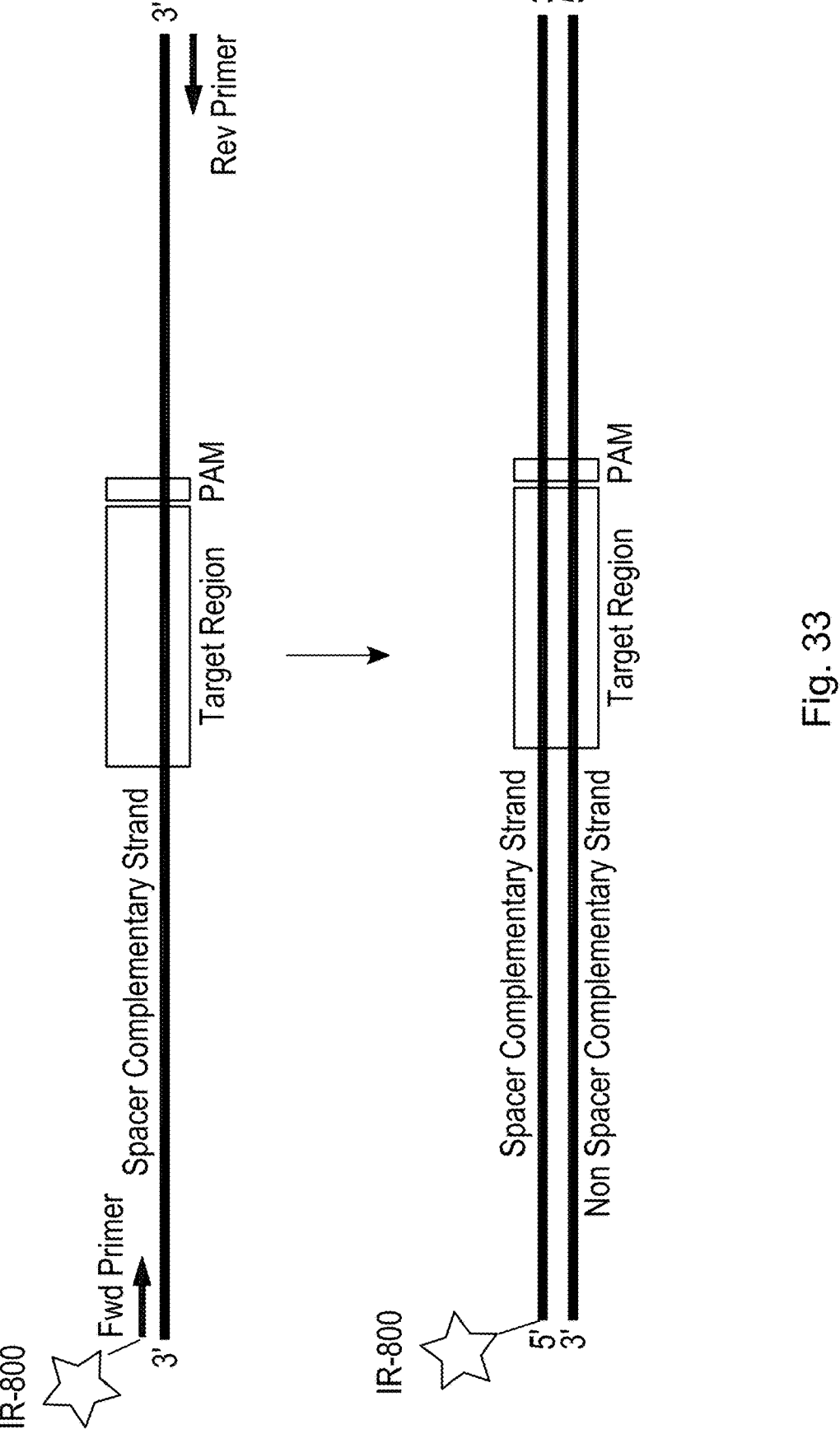

FIG. 33 is a schematic showing the preparation and labeling of a double-stranded DNA target substrate.

Figure 34A:
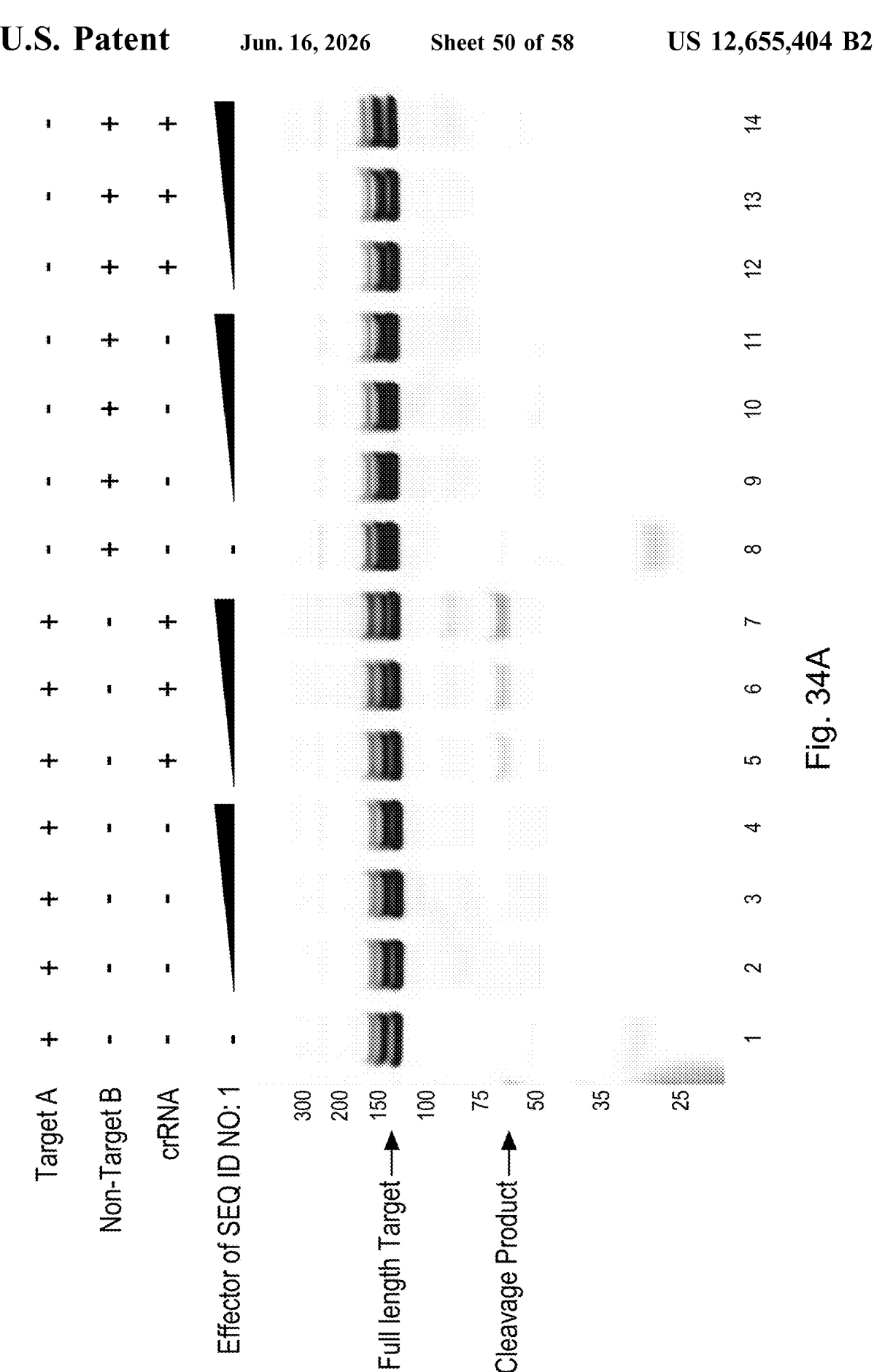
Figure 34B:
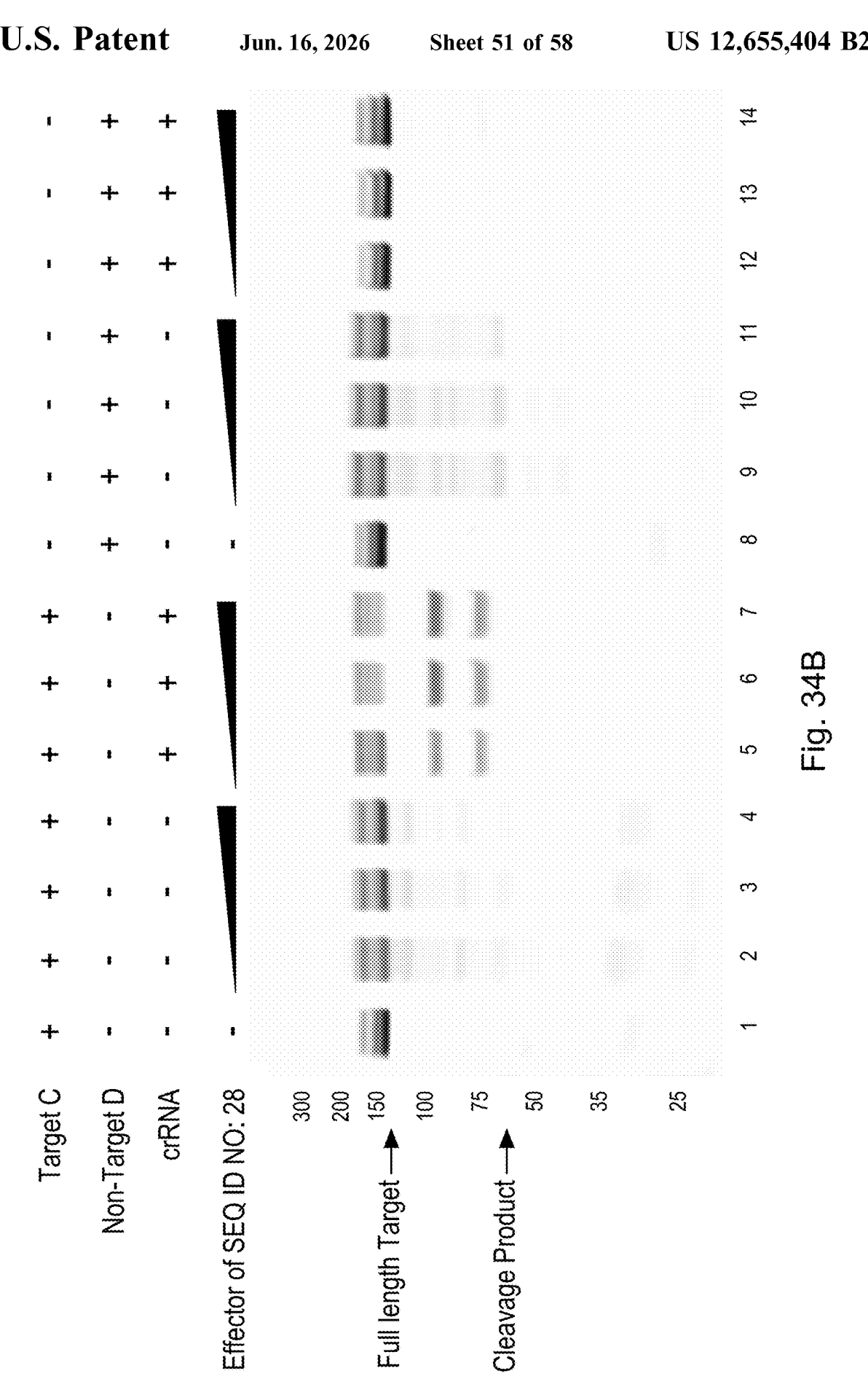
Figure 34C:
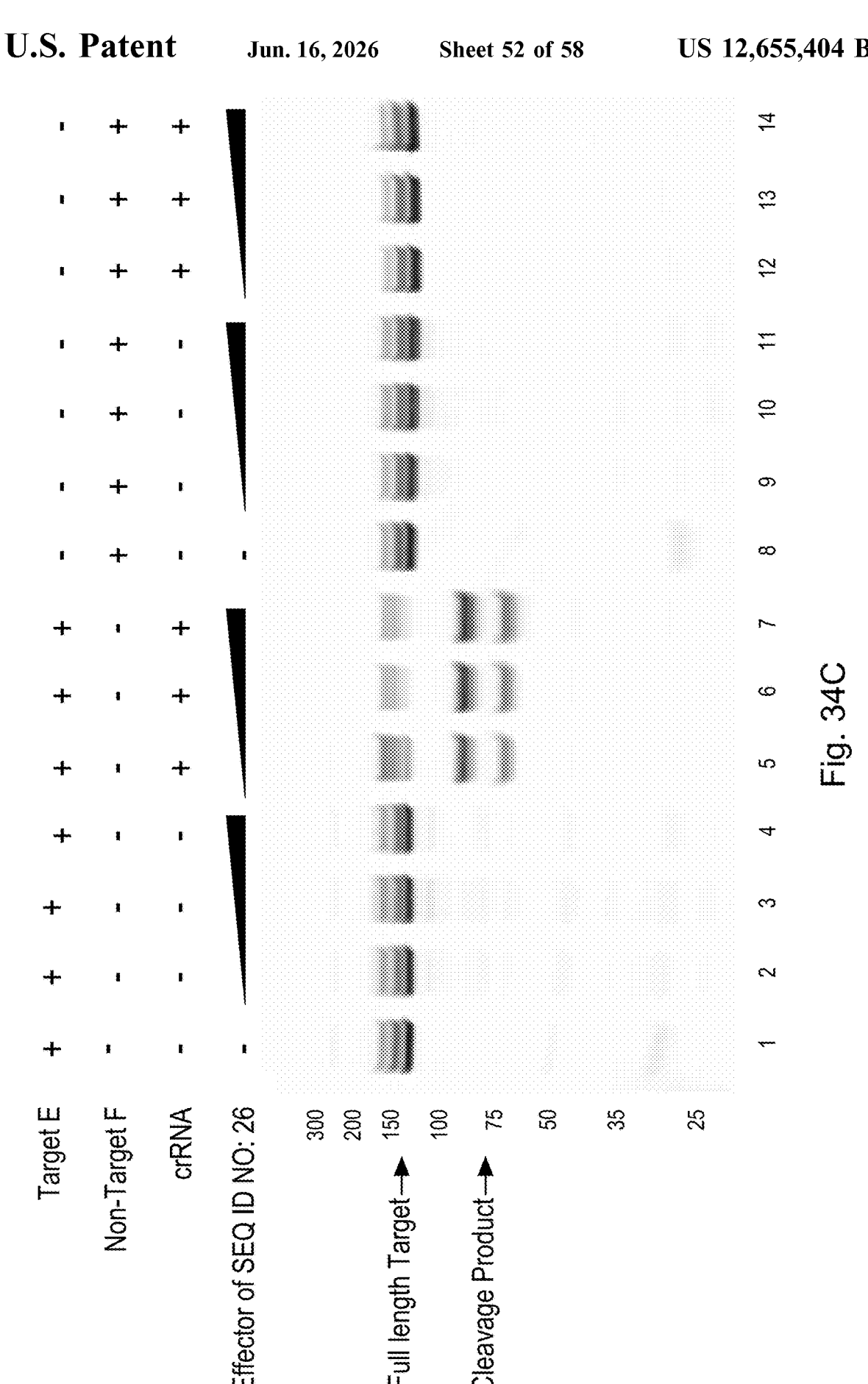
Figure 34D:
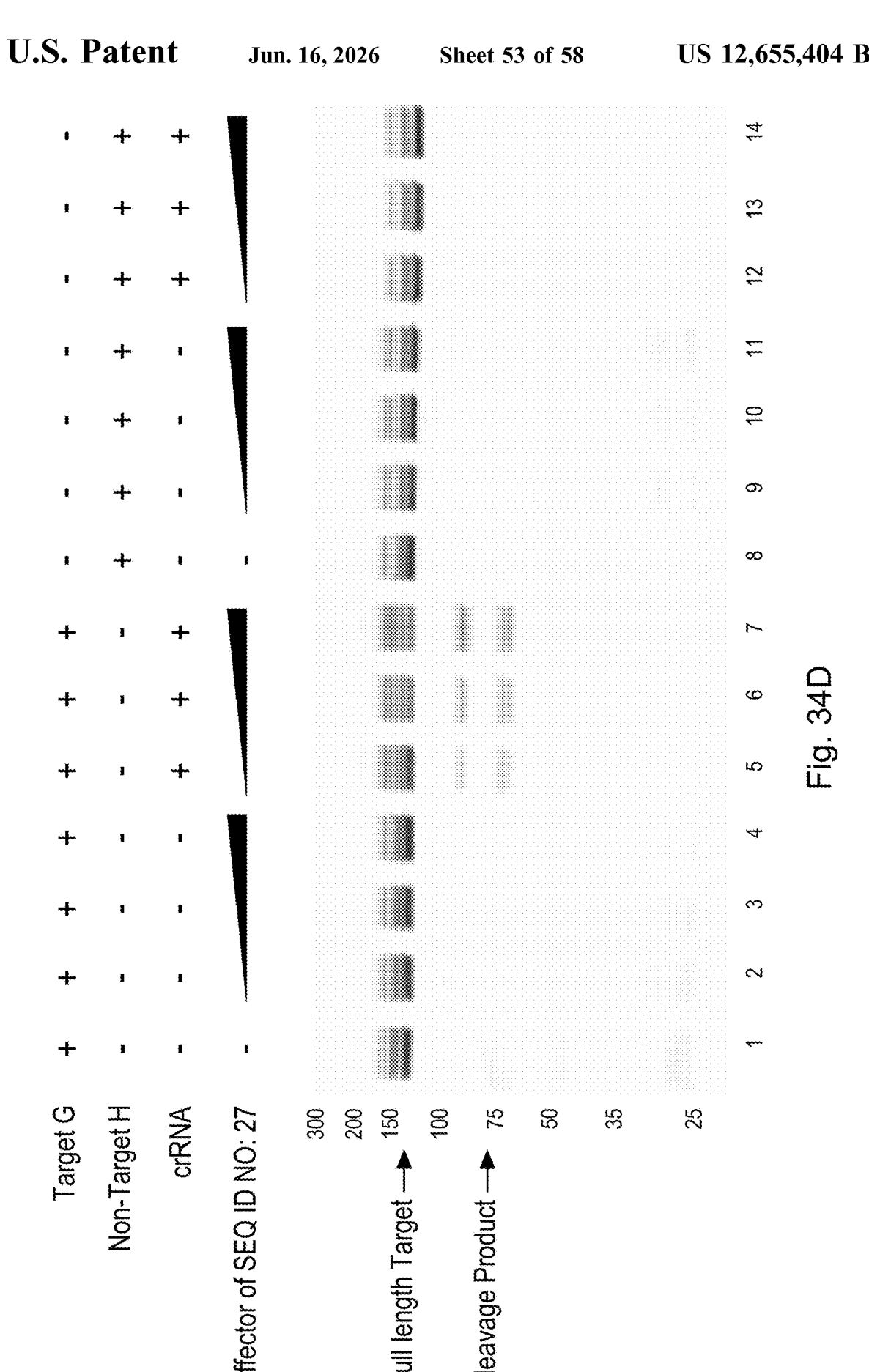
Figure 34E:
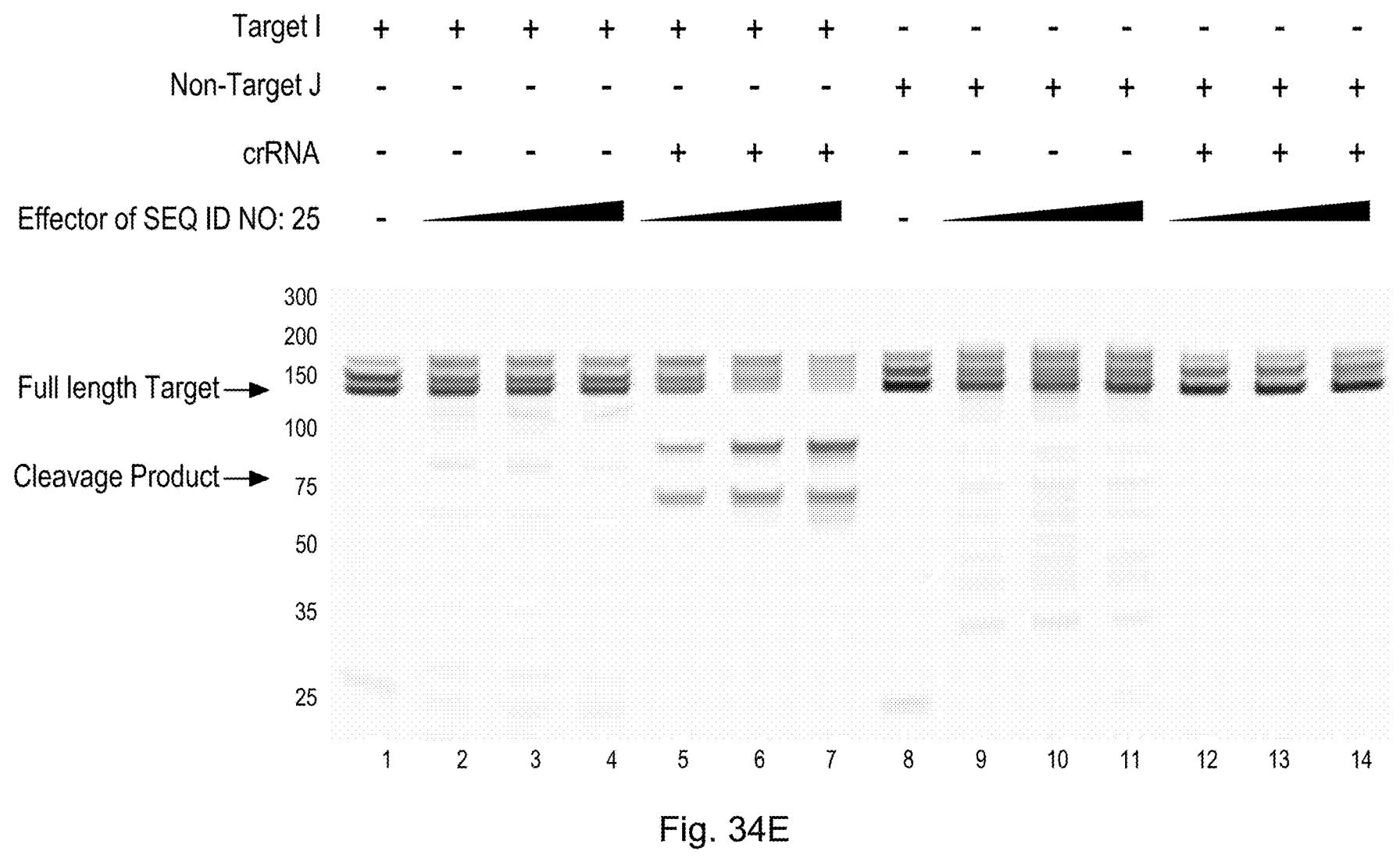

FIG. 34A shows cleavage of a double-stranded DNA target substrate (Target A; SEQ ID NO: 57) by the effector of SEQ ID NO: 1; the non-target substrate of SEQ ID NO: 58 (Non-Target B) is a negative control. FIG. 34B shows cleavage of a double-stranded DNA target substrate (Target C; SEQ ID NO: 59) by the effector of SEQ ID NO: 28; the non-target substrate of SEQ ID NO: 60 (Non-Target D) is a negative control. FIG. 34C shows cleavage of a double-stranded DNA target substrate (Target E; SEQ ID NO: 61) by the effector of SEQ ID NO: 26; the non-target substrate of SEQ ID NO: 62 (Non-Target F) is a negative control. FIG. 34D shows cleavage of a double-stranded DNA target substrate (Target G; SEQ ID NO: 63) by the effector of SEQ ID NO: 27; the non-target substrate of SEQ ID NO: 64 (Non-Target H) is a negative control. FIG. 34E shows cleavage of a double-stranded DNA target substrate (Target L; SEQ ID NO: 65) by the effector of SEQ ID NO: 25; the non-target substrate of SEQ ID NO: 66 (Non-Target J) is a negative control.

Figure 35:
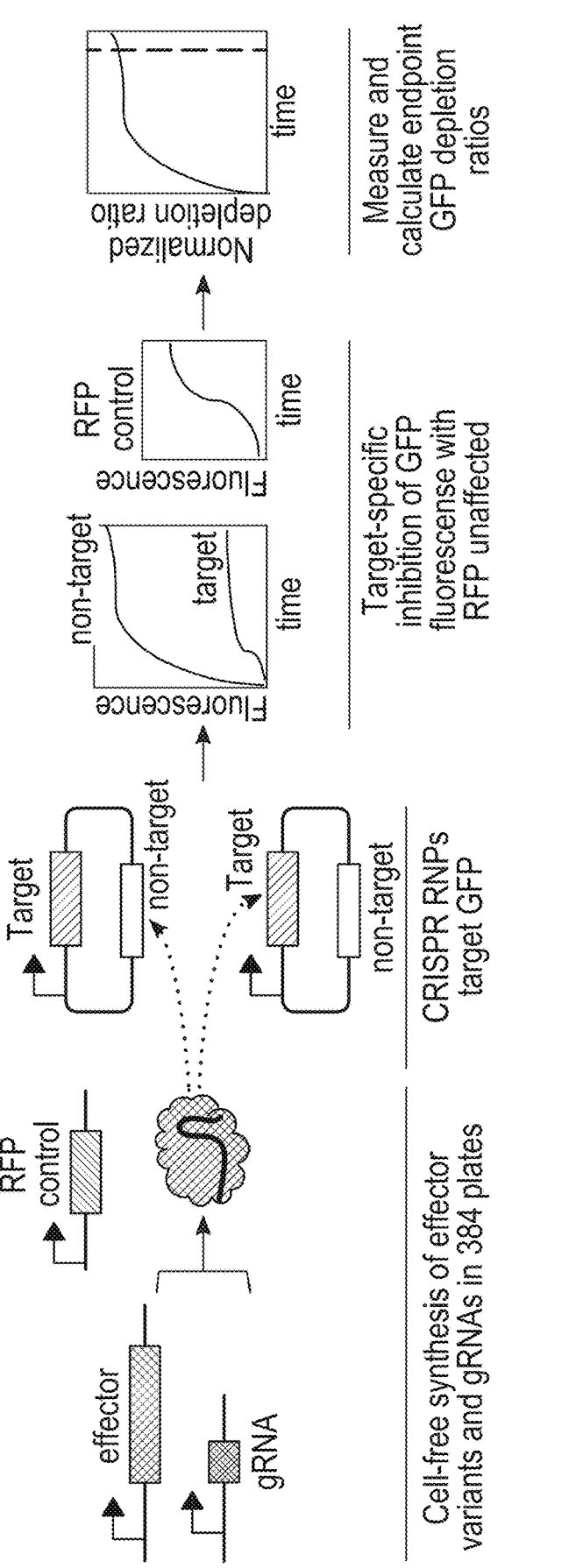

FIG. 35 is a schematic of the fluorescence depletion assay described in Example 4 to measure CLUST.200916 effector activity.

Figure 36A:
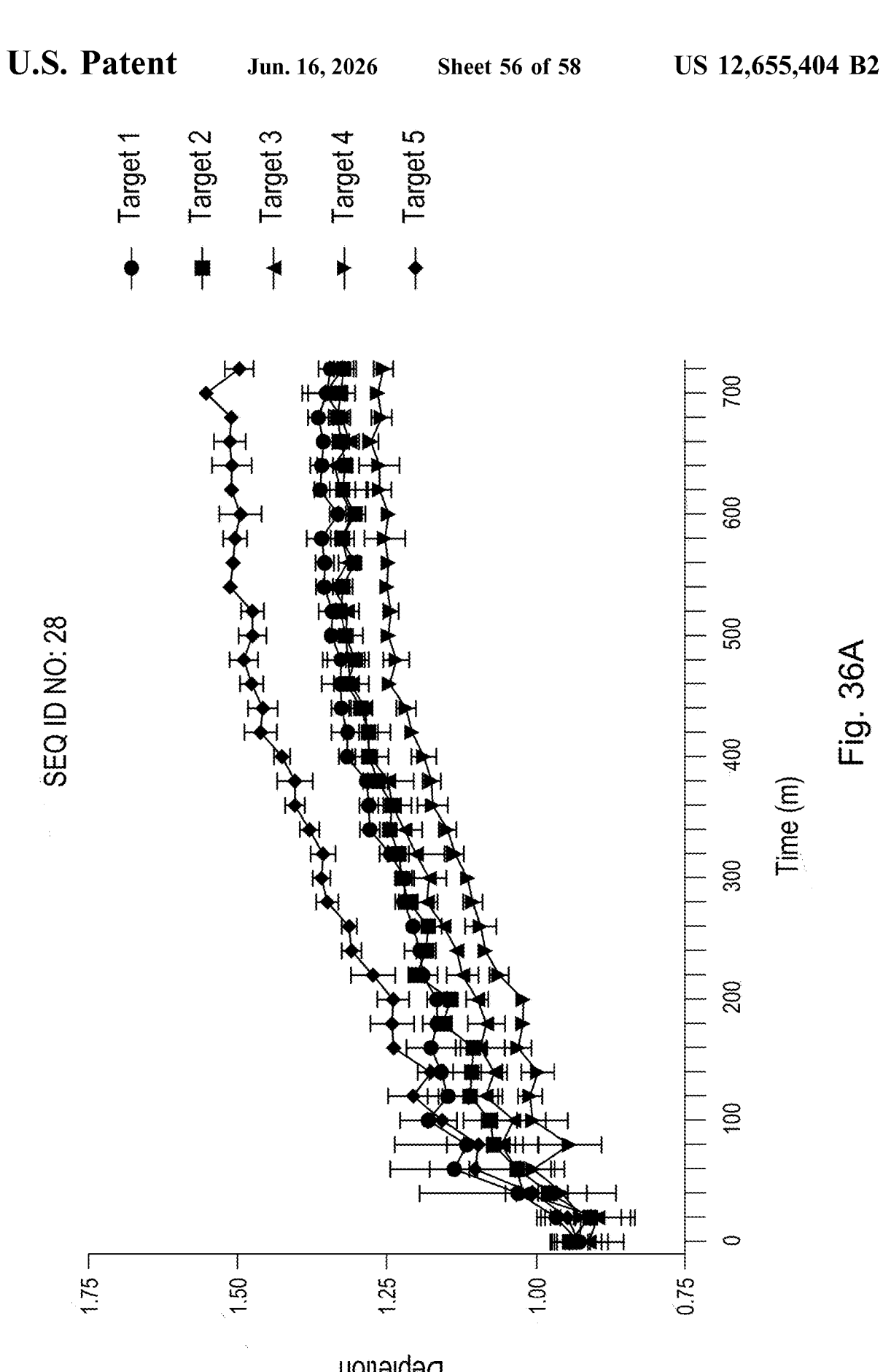
Figure 36B:
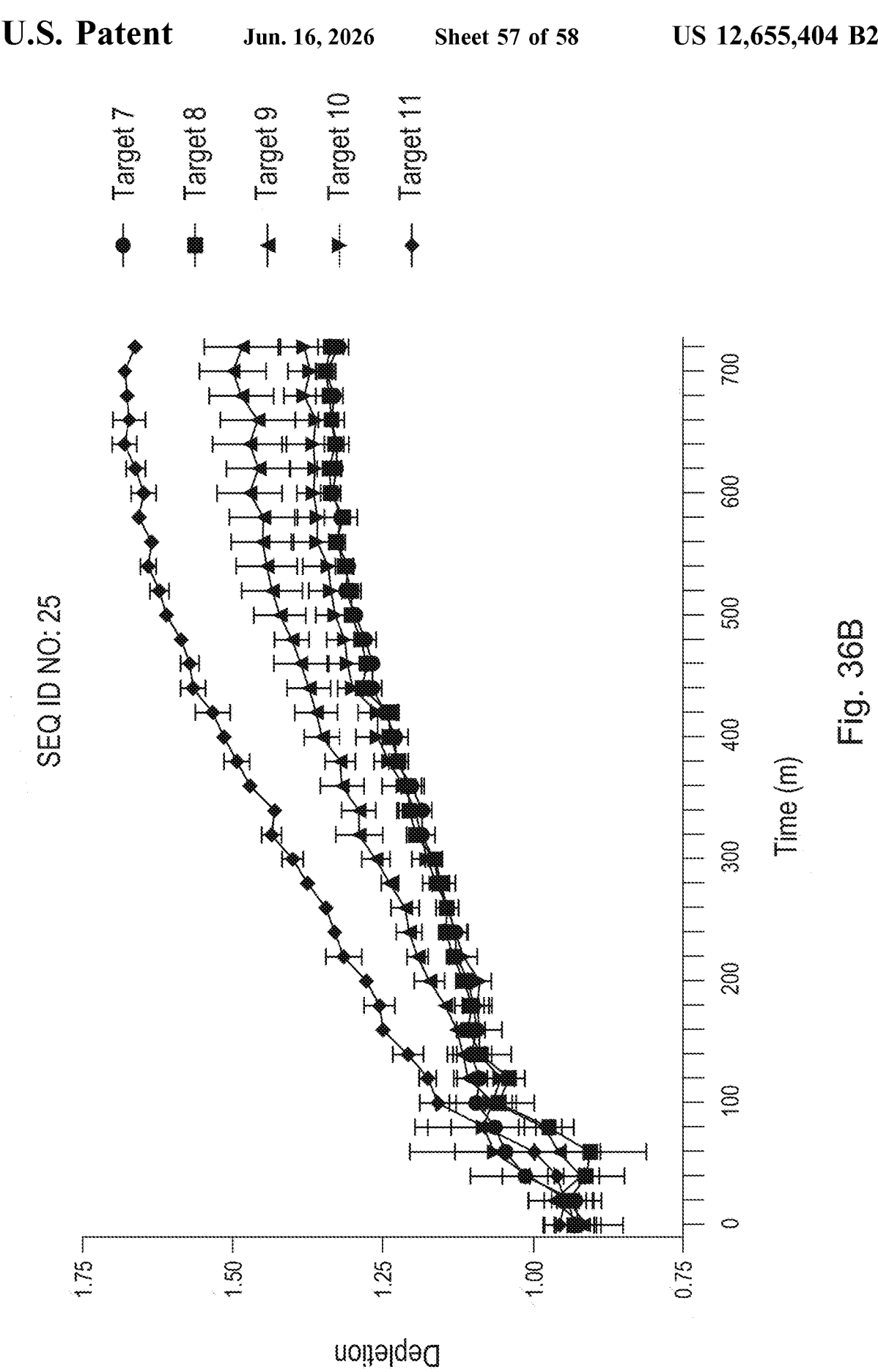

FIG. 36A shows plots of GFP Depletion Ratios (Non-target/target) for the effector of SEQ ID NO: 28 for Target 1 (SEQ ID NO: 67), Target 2 (SEQ ID NO: 68), Target 3 (SEQ ID NO: 69), Target 4 (SEQ ID NO: 70), and Target 5 (SEQ ID NO: 71). FIG. 36B shows plots of GFP Depletion Ratios (Non-target/target) for the effector of SEQ ID NO: 25 for Target 7 (SEQ ID NO: 72), Target 8 (SEQ ID NO: 73), Target 9 (SEQ ID NO: 74), Target 10 (SEQ ID NO: 75), and Target 11 (SEQ ID NO: 76). The Depletion Ratio values in FIG. 36A and FIG. 36B were calculated from measurements taken over a period of 12 hours.

Figure 37:
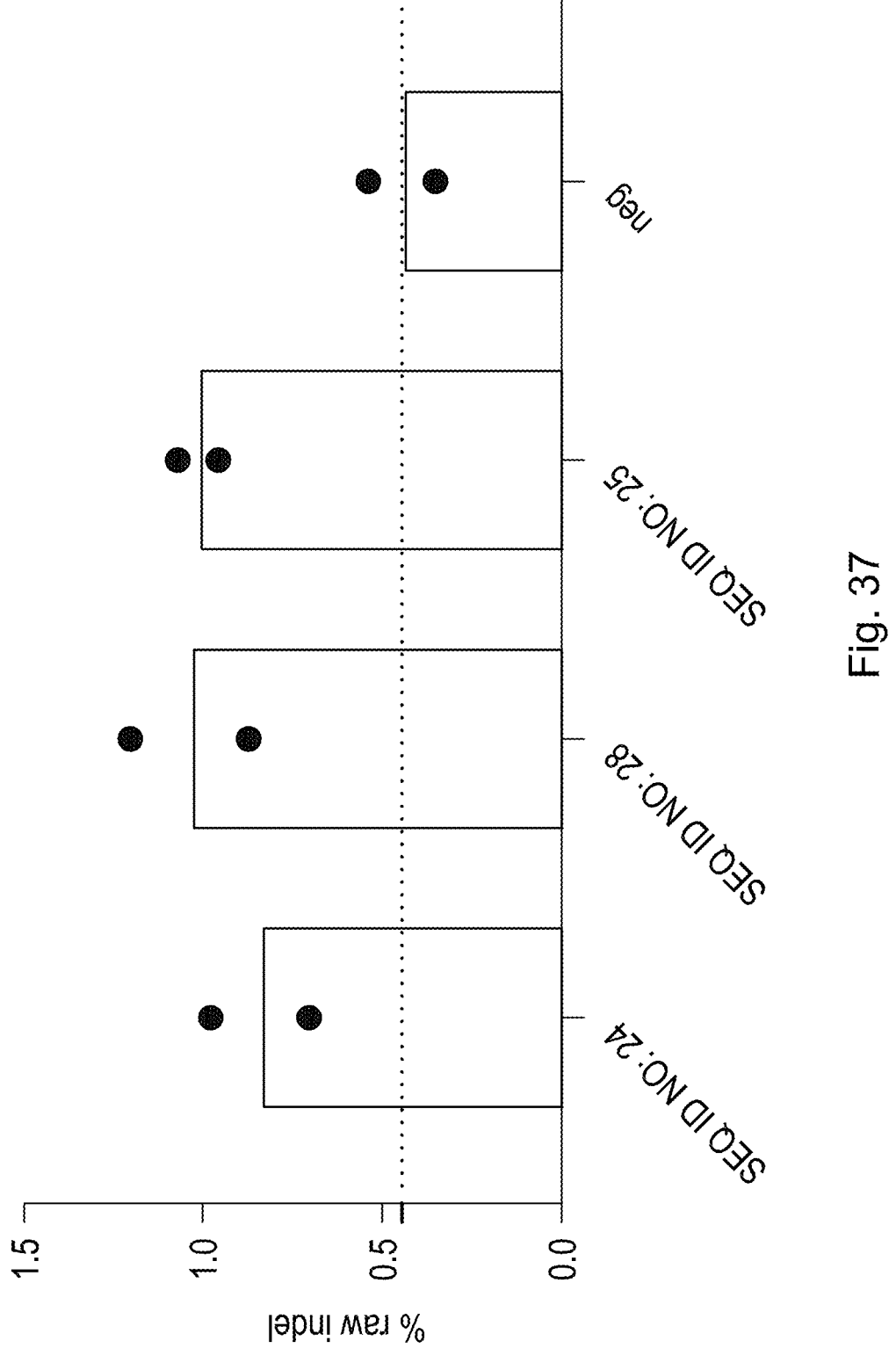

FIG. 37 shows indels induced by the effectors of SEQ ID NO: 24. SEQ ID NO: 28, and SEQ ID NO: 25 at an AAVS1 target locus in HEK293 cells.

DETAILED DESCRIPTION

CRISPR-Cas systems, which are naturally diverse, comprise a wide range of activity mechanisms and functional elements that can be harnessed for programmable biotechnologies. In nature, these systems enable efficient defense against foreign DNA and viruses while providing self versus non-self discrimination to avoid self-targeting. In an engineered setting, these systems provide a diverse toolbox of molecular technologies and define the boundaries of the targeting space. The methods described herein have been used to discover additional mechanisms and parameters within single subunit Class 2 effector systems, which expand the capabilities of RNA-programmable nucleic acid manipulation.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting. Applicant reserves the right to alternatively claim any disclosed invention using the transitional phrase "comprising," "consisting essentially of," or "consisting of," according to standard practice in patent law.

As used herein, the singular forms "a," "an," and "the" include plural referents unless the context clearly dictates otherwise. For example, reference to "a nucleic acid" means one or more nucleic acids.

It is noted that terms like "preferably," "suitably," "commonly," and "typically" are not utilized herein to limit the scope of the claimed invention or to imply that certain features are critical, essential, or even important to the structure or function of the claimed invention. Rather, these terms are merely intended to highlight alternative or additional features that can or cannot be utilized in a particular embodiment of the present invention.

For the purposes of describing and defining the present invention, it is noted that the term "substantially" is utilized herein to represent the inherent degree of uncertainty that can be attributed to any quantitative comparison, value, measurement, or other representation. The term "substantially" is also utilized herein to represent the degree by which a quantitative representation can vary from a stated reference without resulting in a change in the basic function of the subject matter at issue.

The term "CRISPR-Cas system," as used herein, refers to nucleic acids and/or proteins involved in the expression of, or directing the activity of, CRISPR effectors, including sequences encoding CRISPR effectors, RNA guides, and other sequences and transcripts from a CRISPR locus.

The terms "CRISPR-associated protein," "CRISPR-Cas effector," "CRISPR effector," "effector," "effector protein," "CRISPR enzyme," or the like, as used interchangeably herein, refer to a protein that carries out an enzymatic activity or that binds to a target site on a nucleic acid specified by an RNA guide. In some embodiments, a CRISPR effector has endonuclease activity, nickase activity, and/or exonuclease activity.

The terms "RNA guide," "guide RNA," "gRNA," and "guide sequence," as used herein, refer to any RNA molecule that facilitates the targeting of an effector described herein to a target nucleic acid, such as DNA and/or RNA. Exemplary "RNA guides" include, but are not limited to, crRNAs, as well as crRNAs hybridized to or fused to either tracrRNAs and/or modulator RNAs. In some embodiments, an RNA guide includes both a crRNA and a tracrRNA, either fused into a single RNA molecule or as separate RNA molecules. In some embodiments, an RNA guide includes a crRNA and a modulator RNA, either fused into a single RNA molecule or as separate RNA molecules. In some embodiments, an RNA guide includes a crRNA, a tracrRNA, and a modulator RNA, either fused into a single RNA molecule or as separate RNA molecules.

The term "CRISPR RNA" or "crRNA" as used herein refers to an RNA molecule comprising a guide sequence used by a CRISPR effector to specifically recognize a nucleic acid sequence. Typically, crRNAs contain a sequence that mediates target recognition and a sequence that forms a duplex with a tracrRNA. A crRNA may comprise a sequence that hybridizes to a tracrRNA. In turn, the crRNA: tracrRNA duplex may bind to a CRISPR effector. As used herein, the term "pre-crRNA" refers to an unprocessed RNA molecule comprising a DR-spacer-DR sequence. As used herein, the term "mature crRNA" refers to a processed form of a pre-crRNA; a mature crRNA may comprise a DR-spacer sequence, wherein the DR is a truncated form of the DR of a pre-crRNA and/or the spacer is a truncated form of the spacer of a pre-crRNA.

The terms "CRISPR effector complex," "effector complex," or "surveillance complex," as used herein, refer to a complex containing a CRISPR effector and an RNA guide. A CRISPR effector complex may further comprise one or more accessory proteins. The one or more accessory proteins may be non-catalytic and/or non-target binding.

The terms "trans-activating crRNA" or "tracrRNA," as used herein, refer to an RNA molecule comprising a sequence that forms a structure and/or sequence motif required for a CRISPR effector to bind to a specified target nucleic acid.

The term "CRISPR array," as used herein, refers to a nucleic acid (e.g., DNA) segment that comprises CRISPR repeats and spacers, starting with the first nucleotide of the first CRISPR repeat and ending with the last nucleotide of the final (terminal) CRISPR repeat. Typically, each spacer in a CRISPR array is located between two repeats. The terms "CRISPR repeat," "CRISPR direct repeat," and "direct repeat," as used herein, refer to multiple short direct repeating sequences, which show very little or no sequence variation within a CRISPR array.

The term "modulator RNA" as described herein refers to any RNA molecule that modulates (e.g., increases or decreases) an activity of a CRISPR effector or a nucleoprotein complex that includes a CRISPR effector. In some embodiments, a modulator RNA modulates a nuclease activity of a CRISPR effector or a nucleoprotein complex that includes a CRISPR effector.

As used herein, the term "target nucleic acid" refers to a nucleic acid that comprises a nucleotide sequence complementary to the entirety or a part of the spacer in an RNA guide. In some embodiments, the target nucleic acid comprises a gene. In some embodiments, the target nucleic acid comprises a non-coding region (e.g., a promoter). In some embodiments, the target nucleic acid is single-stranded. In some embodiments, the target nucleic acid is double-stranded. A "transcriptionally-active site," as used herein, refers to a site in a nucleic acid sequence being actively transcribed.

The terms "activated CRISPR effector complex," "activated CRISPR complex," and "activated complex," as used herein, refer to a CRISPR effector complex capable of modifying a target nucleic acid. In some embodiments, an activated CRISPR complex is capable of modifying a target nucleic acid following binding of the activated CRISPR complex to the target nucleic acid. In some embodiments, binding of an activated CRISPR complex to a target nucleic acid results in an additional cleavage event, such as collateral RNA cleavage.

The term "cleavage event," as used herein, refers to a break in a nucleic acid, such as DNA and/or RNA. In some embodiments, a cleavage event refers to a break in a target nucleic acid created by a nuclease of a CRISPR system described herein. In some embodiments, the cleavage event is a double-stranded DNA break. In some embodiments, the cleavage event is a single-stranded DNA break. In some embodiments, a cleavage event refers to a break in a collateral nucleic acid.

The term "collateral nucleic acid," as used herein, refers to a nucleic acid substrate that is cleaved non-specifically by an activated CRISPR complex. The term "collateral DNase activity," as used herein in reference to a CRISPR effector, refers to non-specific DNase activity of an activated CRISPR complex. The term "collateral RNase activity," as used herein in reference to a CRISPR effector, refers to non-specific RNase activity of an activated CRISPR complex.

The term "donor template nucleic acid," as used herein, refers to a nucleic acid molecule that can be used to make a templated change to a target sequence or target-proximal sequence after a CRISPR effector described herein has modified the target nucleic acid. In some embodiments, the donor template nucleic acid is a double-stranded nucleic acid. In some embodiments, the donor template nucleic acid is a single-stranded nucleic acid. In some embodiments, the donor template nucleic acid is linear. In some embodiments, the donor template nucleic acid is circular (e.g., a plasmid). In some embodiments, the donor template nucleic acid is an exogenous nucleic acid molecule. In some embodiments, the donor template nucleic acid is an endogenous nucleic acid molecule (e.g., a chromosome).

As used herein, the terms "polynucleotide," "nucleotide," "oligonucleotide," and "nucleic acid" can be used interchangeably to refer to nucleic acid comprising DNA, RNA, derivatives thereof, or combinations thereof. Methods well known to those skilled in the art can be used to construct genetic expression constructs and recombinant cells according to this invention. These methods include in vitro recombinant DNA techniques, synthetic techniques, in vivo recombination techniques, and polymerase chain reaction (PCR) techniques. See, for example, techniques as described in Maniatis et al., 1989, MOLECULAR CLONING: A LABORATORY MANUAL, Cold Spring Harbor Laboratory, New York; Ausubel et al., 1989, CURRENT PROTOCOLS IN MOLECULAR BIOLOGY, Greene Publishing Associates and Wiley Interscience, New York, and PCR Protocols: A Guide to Methods and Applications (Innis et al., 1990, Academic Press, San Diego, Calif.) The term "genetic modification" or "genetic engineering" broadly refers to manipulation of the genome or nucleic acids of a cell. Likewise, the terms "genetically engineered" and "engineered" refer to a cell comprising a manipulated genome or nucleic acids. Methods of genetic modification of include, for example, heterologous gene expression, gene or promoter insertion or deletion, nucleic acid mutation, altered gene expression or inactivation, enzyme engineering, directed evolution, knowledge-based design, random mutagenesis methods, gene shuffling, and codon optimization.

The term "recombinant" indicates that a nucleic acid, protein, or cell is the product of genetic modification, engineering, or recombination. Generally, the term "recombinant" refers to a nucleic acid, protein, or cell that contains or is encoded by genetic material derived from multiple sources. As used herein, the term "recombinant" may also be used to describe a cell that comprises a mutated nucleic acid or protein, including a mutated form of an endogenous nucleic acid or protein. The terms "recombinant cell" and "recombinant host" can be used interchangeably. In some embodiments, a recombinant cell comprises a CRISPR effector disclosed herein. The CRISPR effector can be codon-optimized for expression in the recombinant cell. In some embodiments, a recombinant cell disclosed herein further comprises an RNA guide. In some embodiments, an RNA guide of a recombinant cell disclosed herein comprises a tracrRNA. In some embodiments, a recombinant cell disclosed herein comprises a modulator RNA. In some embodiments, the recombinant cell is a prokaryotic cell, such as an *E. coli* cell. In some embodiments, the recombinant cell is a eukaryotic cell, such as a mammalian cell, including a human cell.

Identification of CLUST.200916

Figure 2A:
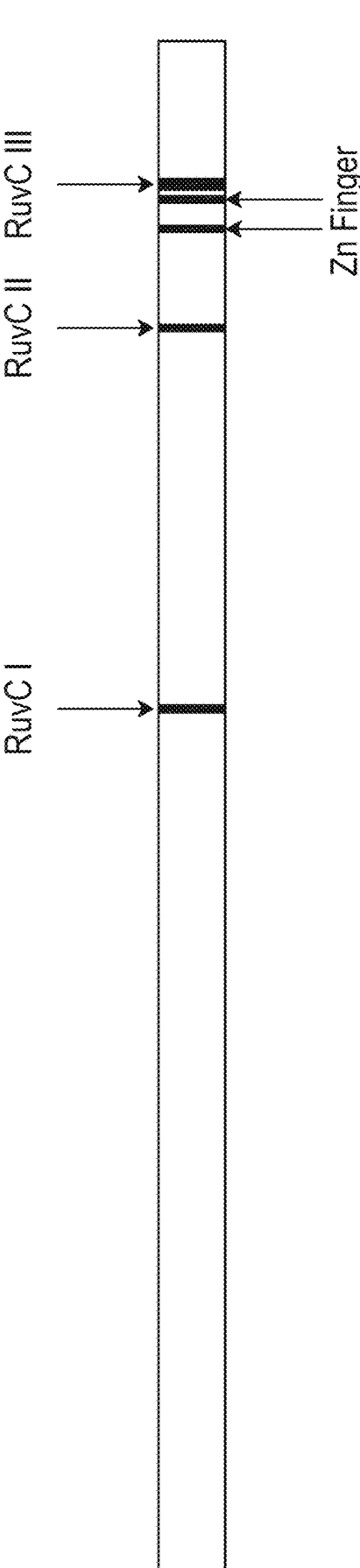
FIG. 2A is a schematic showing the RuvC and Zn finger domains of CLUST.200916 effectors, which is based upon the consensus sequence of the sequences shown in Table 7.
Figure 2B:
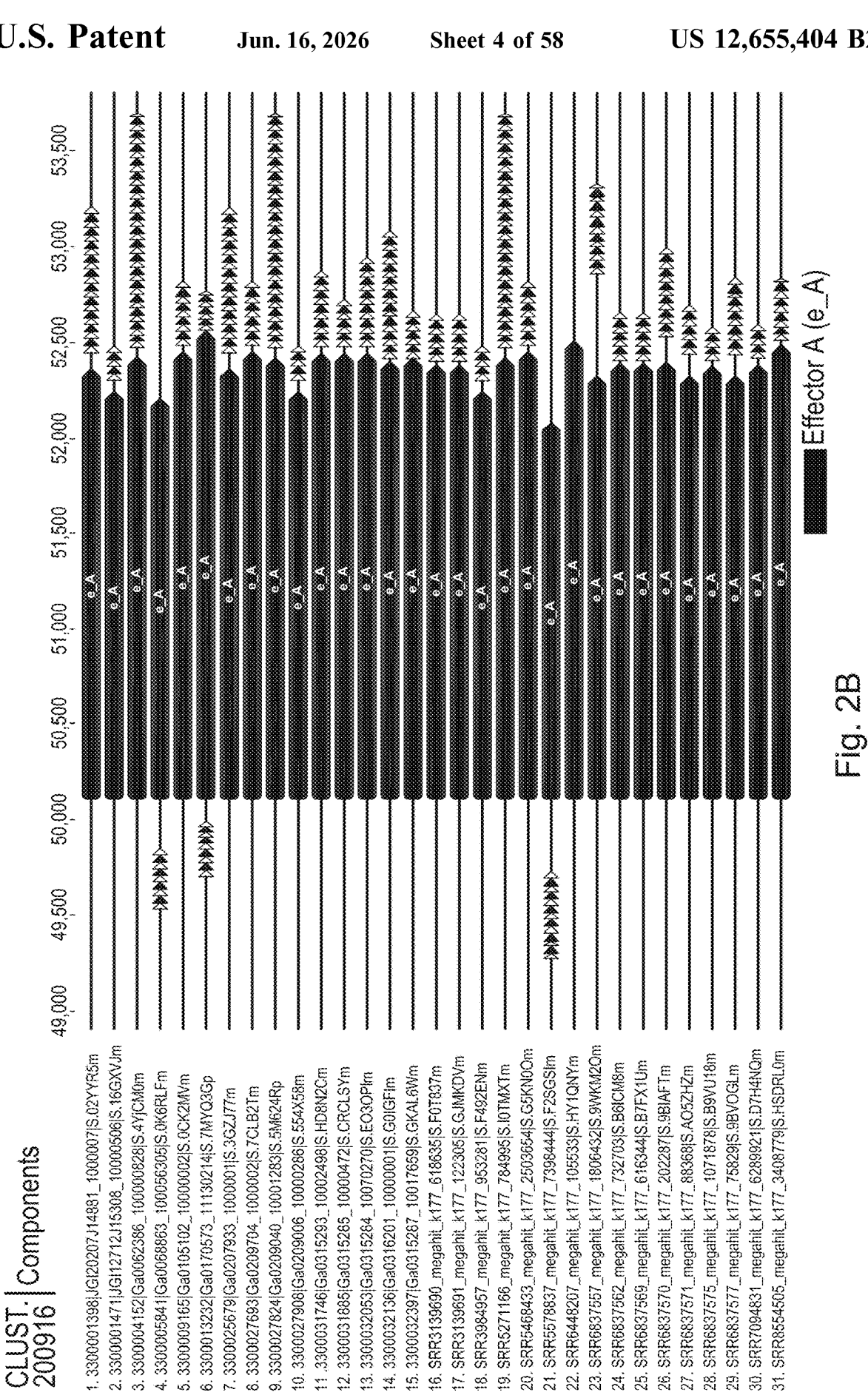
FIG. 2B is a schematic sequence representation that shows conserved effector (e_A) and CRISPR array elements for representative CLUST.200916 loci.
Figure 2C:
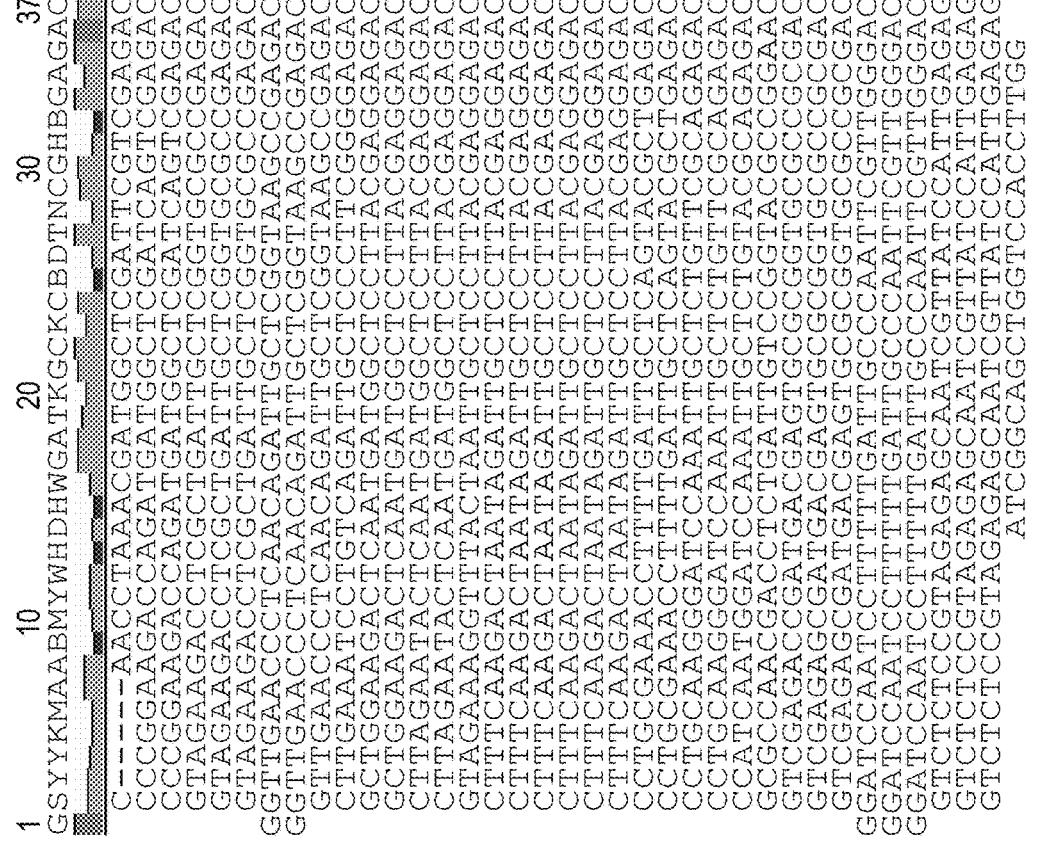
FIG. 2C is a series of sequences that show multiple sequence alignment of examples of CRISPR direct repeat elements for CLUST.200916.
Figure 2D:
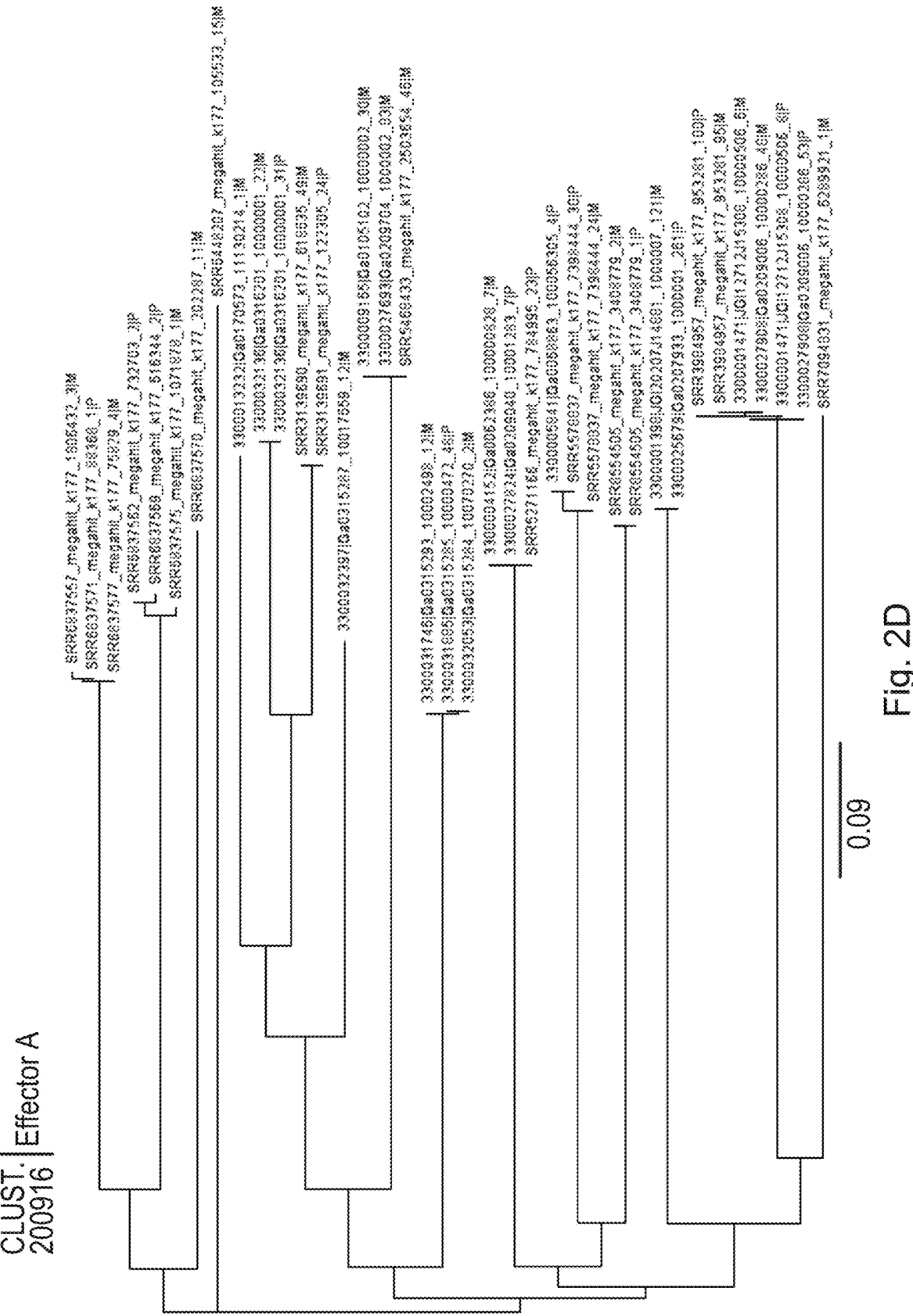
FIG. 2D is a schematic representation of a phylogenetic tree of CL UST.200916 effector proteins.
Figures 1, 2E:
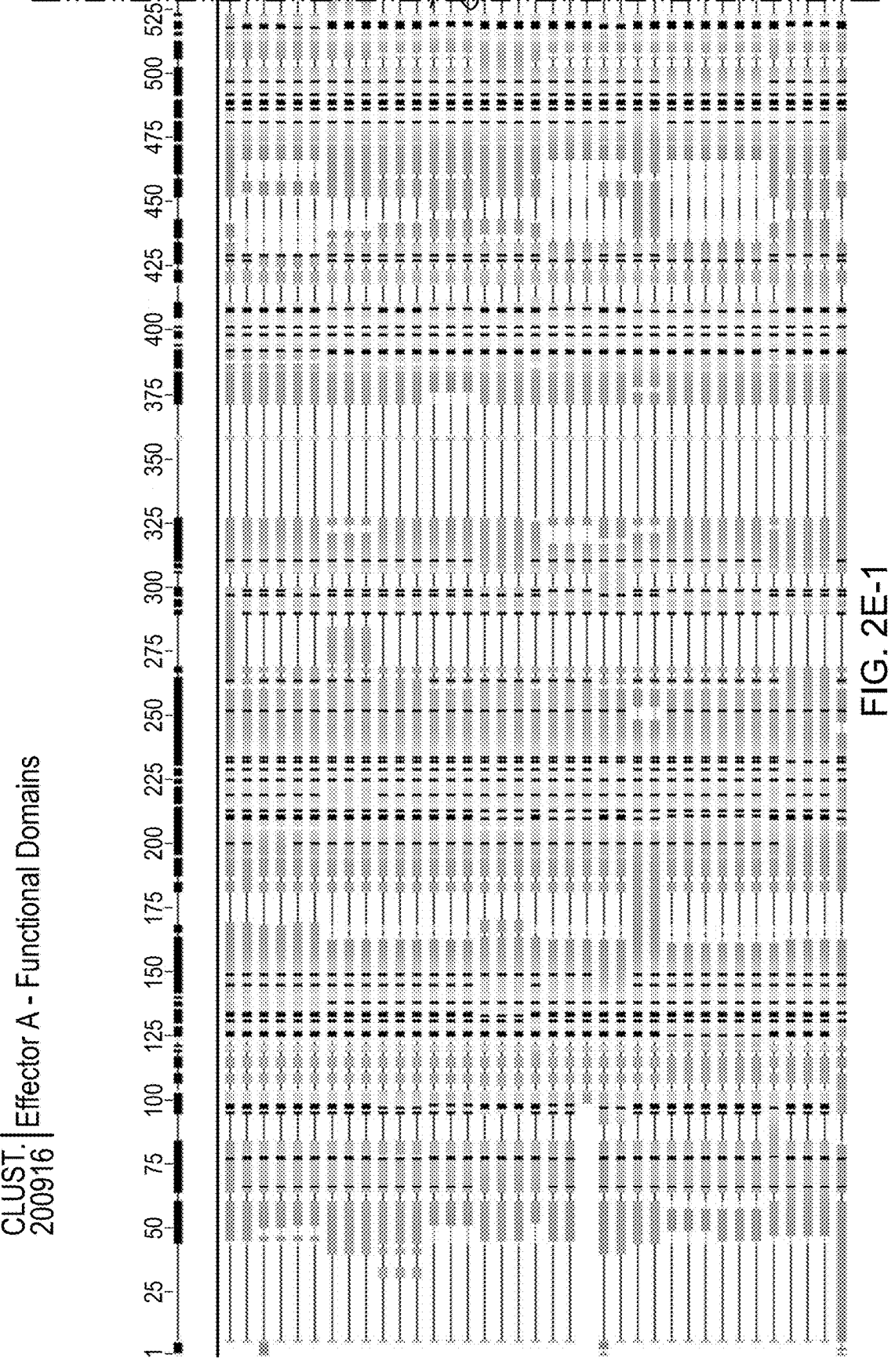
FIG. 2E is a schematic representation of a multiple sequence alignment of CLUST.200916 effector proteins, with the locations of the conserved catalytic residues of the RuvC domain and the locations of the conserved catalytic residues of Zinc finger domain indicated.
Figures 2, 2E:
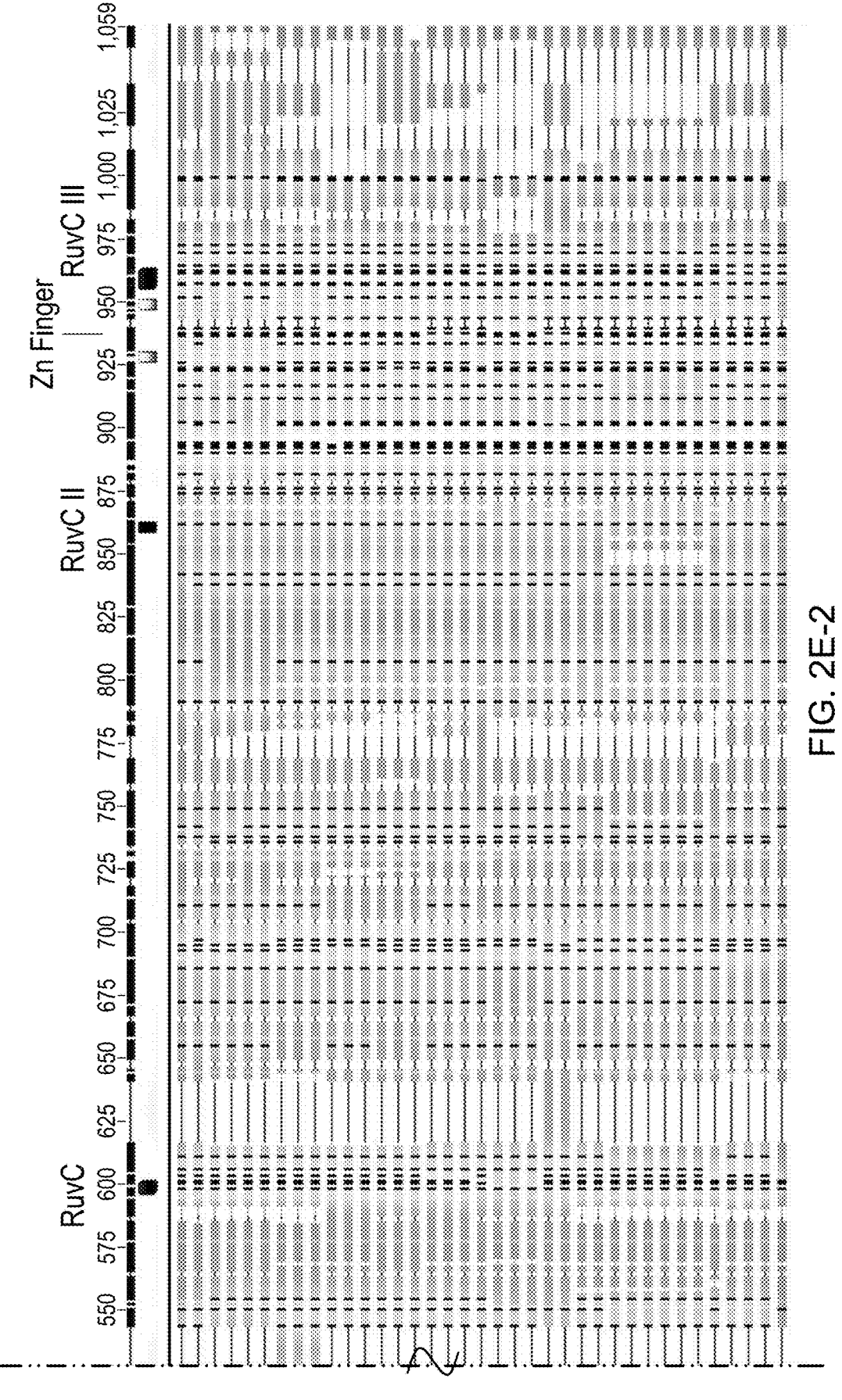

This application relates to the identification, engineering, and use of a novel protein family referred to herein as "CLUST.200916." As shown in FIG. 2A, the proteins of CLUST.200916 comprise a RuvC domain (denoted RuvC I, RuvC II, and RuvC III) and a Zn finger domain. As shown in TABLE 6, effectors of CLUST.200916 range in size from about 650 amino acids to about 850 amino acids. Therefore, the effectors of CLUST.200916 are smaller than effectors known in the art, as shown below. See, e.g., TABLE 1.

TABLE 1

| Sizes of known CRISPR-Cas system effectors. | |
| --- | --- |
| Effector | Size (aa) |
| StCas9 | 1128 |
| SpCas9 | 1368 |
| SaCas9 | 1053 |
| FnCpf1 | 1300 |
| AsCpf1 | 1307 |
| LbCpf1 | 1246 |
| C2c1 | 1127 (average) |
| CasX | 982 (average) |
| CasY | 1189 (average) |
| C2c2 | 1232 (average) |

The effectors of CLUST.200916 were identified using computational methods and algorithms to search for and identify proteins exhibiting a strong co-occurrence pattern with certain other features. In certain embodiments, these computational methods were directed to identifying proteins that co-occurred in close proximity to CRISPR arrays. The methods disclosed herein are also useful in identifying proteins that naturally occur within close proximity to other features, both non-coding and protein-coding (e.g., fragments of phage sequences in non-coding areas of bacterial loci or CRISPR Cas1 proteins). It is understood that the methods and calculations described herein may be performed on one or more computing devices.

Sets of genomic sequences were obtained from genomic or metagenomic databases. The databases comprised short reads, or contig level data, or assembled scaffolds, or complete genomic sequences of organisms. Likewise, the databases may comprise genomic sequence data from prokaryotic organisms, or eukaryotic organisms, or may include data from metagenomic environmental samples. Examples of database repositories include the National Center for Biotechnology Information (NCBI) RefSeq, NCBI GenBank, NCBI Whole Genome Shotgun (WGS), and the Joint Genome Institute (JGI) Integrated Microbial Genomes (IMG).

In some embodiments, a minimum size requirement is imposed to select genome sequence data of a specified minimum length. In certain exemplary embodiments, the minimum contig length may be 100 nucleotides, 500 nt, 1 kb, 1.5 kb, 2 kb, 3 kb, 4 kb, 5 kb, 10 kb, 20 kb, 40 kb, or 50 kb.

In some embodiments, known or predicted proteins are extracted from the complete or a selected set of genome sequence data. In some embodiments, known or predicted proteins are taken from extracting coding sequence (CDS) annotations provided by the source database. In some embodiments, predicted proteins are determined by applying a computational method to identify proteins from nucleotide sequences. In some embodiments, the GeneMark Suite is used to predict proteins from genome sequences. In some embodiments, Prodigal is used to predict proteins from genome sequences. In some embodiments, multiple protein prediction algorithms may be used over the same set of sequence data with the resulting set of proteins de-duplicated.

In some embodiments, CRISPR arrays are identified from the genome sequence data. In some embodiments, PILER-CR is used to identify CRISPR arrays. In some embodiments, CRISPR Recognition Tool (CRT) is used to identify CRISPR arrays. In some embodiments, CRISPR arrays are identified by a heuristic that identifies nucleotide motifs repeated a minimum number of times (e.g., 2, 3, or 4 times), where the spacing between consecutive occurrences of a repeated motif does not exceed a specified length (e.g., 50, 100, or 150 nucleotides). In some embodiments, multiple CRISPR array identification tools may be used over the same set of sequence data with the resulting set of CRISPR arrays de-duplicated.

In some embodiments, proteins in close proximity to CRISPR arrays (referred to herein as "CRISPR-proximal protein clusters") are identified. In some embodiments, proximity is defined as a nucleotide distance, and may be within 20 kb, 15 kb, or 5 kb. In some embodiments, proximity is defined as the number of open reading frames (ORFs) between a protein and a CRISPR array, and certain exemplary distances may be 10, 5, 4, 3, 2, 1, or 0 ORFs. The proteins identified as being within close proximity to a CRISPR array are then grouped into clusters of homologous proteins. In some embodiments, blastclust is used to form CRISPR-proximal protein clusters. In certain other embodiments, mmseqs2 is used to form CRISPR-proximal protein clusters.

To establish a pattern of strong co-occurrence between the members of a CRISPR-proximal protein cluster, a BLAST search of each member of the protein cluster may be performed over the complete set of known and predicted proteins previously compiled. In some embodiments, UBLAST or mmseqs2 may be used to search for similar proteins. In some embodiments, a search may be performed only for a representative subset of proteins in the family.

In some embodiments, the CRISPR-proximal protein clusters are ranked or filtered by a metric to determine co-occurrence. One exemplary metric is the ratio of the number of elements in a protein cluster against the number of BLAST matches up to a certain E value threshold. In some embodiments, a constant E value threshold may be used. In other embodiments, the E value threshold may be determined by the most distant members of the protein cluster. In some embodiments, the global set of proteins is clustered and the co-occurrence metric is the ratio of the number of elements of the CRISPR-proximal protein cluster against the number of elements of the containing global cluster(s).

In some embodiments, a manual review process is used to evaluate the potential functionality and the minimal set of components of an engineered system based on the naturally occurring locus structure of the proteins in the cluster. In some embodiments, a graphical representation of the protein cluster may assist in the manual review and may contain information including pairwise sequence similarity, phylogenetic tree, source organisms/environments, predicted functional domains, and a graphical depiction of locus structures. In some embodiments, the graphical depiction of locus structures may filter for nearby protein families that have a high representation. In some embodiments, representation may be calculated by the ratio of the number of related nearby proteins against the size(s) of the containing global cluster(s). In certain exemplary embodiments, the graphical representation of the protein cluster may contain a depiction of the CRISPR array structures of the naturally occurring loci. In some embodiments, the graphical representation of the protein cluster may contain a depiction of the number of conserved direct repeats versus the length of the putative CRISPR array or the number of unique spacer sequences versus the length of the putative CRISPR array. In some embodiments, the graphical representation of the protein cluster may contain a depiction of various metrics of co-occurrence of the putative effector with CRISPR arrays predict new CRISPR-Cas systems and identify their components.

Pooled-Screening of CLUST.200916

To efficiently validate the activity, mechanisms, and functional parameters of the engineered CLUST.200916 CRISPR-Cas systems identified herein, a pooled-screening approach in *E. coli* was used, as described in Example 2. First, from the computational identification of the conserved protein and noncoding elements of the CLUST.200916 CRISPR-Cas system, DNA synthesis and molecular cloning were used to assemble the separate components into a single artificial expression vector, which in one embodiment is based on a pET-28a+ backbone. In a second embodiment, the effectors and noncoding elements are transcribed on an mRNA transcript, and different ribosomal binding sites are used to translate individual effectors.

Second, the natural crRNA and targeting spacers were replaced with a library of unprocessed crRNAs containing non-natural spacers targeting a second plasmid, pACYC184. This crRNA library was cloned into the vector backbone comprising the effectors and noncoding elements (e.g., pET-28a+), and the library was subsequently transformed into *E. coli* along with the pACYC184 plasmid target. Consequently, each resulting *E. coli* cell contains no more than one targeting array. In an alternate embodiment, the library of unprocessed crRNAs containing non-natural spacers additionally target *E. coli* essential genes, drawn from resources such as those described in Baba et al. (2006) *Mol. Syst. Biol.* 2: 2006.0008; and Gerdes et al. (2003) *J. Bacteriol.* 185(19): 5673-84, the entire contents of each of which are incorporated herein by reference. In this embodiment, positive, targeted activity of the novel CRISPR-Cas systems that disrupts essential gene function results in cell death or growth arrest. In some embodiments, the essential gene targeting spacers can be combined with the pACYC184 targets.

Third, the *E. coli* were grown under antibiotic selection. In one embodiment, triple antibiotic selection is used: kanamycin for ensuring successful transformation of the pET-28a+ vector containing the engineered CRISPR effector system and chloramphenicol and tetracycline for ensuring successful co-transformation of the pACYC184 target vector. Since pACYC184 normally confers resistance to chloramphenicol and tetracycline, under antibiotic selection, positive activity of the novel CRISPR-Cas system targeting the plasmid will eliminate cells that actively express the effectors, noncoding elements, and specific active elements of the crRNA library. Typically, populations of surviving cells are analyzed 12-14 h post-transformation. In some embodiments, analysis of surviving cells is conducted 6-8 h post-transformation, 8-12 h post-transformation, up to 24 h post-transformation, or more than 24 h post-transformation. Examining the population of surviving cells at a later time point compared to an earlier time point results in a depleted signal compared to the inactive crRNAs.

In some embodiments, double antibiotic selection is used. Withdrawal of either chloramphenicol or tetracycline to remove selective pressure can provide novel information about the targeting substrate, sequence specificity, and potency. For example, cleavage of dsDNA in a selected or unselected gene can result in negative selection in *E. coli*, wherein depletion of both selected and unselected genes is observed. If the CRISPR-Cas system interferes with transcription or translation (e.g., by binding or by transcript cleavage), then selection will only be observed for targets in the selected resistance gene, rather than in the unselected resistance gene.

In some embodiments, only kanamycin is used to ensure successful transformation of the pET-28a+ vector comprising the engineered CRISPR-Cas system. This embodiment is suitable for libraries containing spacers targeting *E. coli* essential genes, as no additional selection beyond kanamycin is needed to observe growth alterations. In this embodiment, chloramphenicol and tetracycline dependence is removed, and their targets (if any) in the library provide an additional source of negative or positive information about the targeting substrate, sequence specificity, and potency.

Since the pACYC184 plasmid contains a diverse set of features and sequences that may affect the activity of a CRISPR-Cas system, mapping the active crRNAs from the pooled screen onto pACYC184 provides patterns of activity that can be suggestive of different activity mechanisms and functional parameters. In this way, the features required for reconstituting the novel CRISPR-Cas system in a heterologous prokaryotic species can be more comprehensively tested and studied.

The key advantages of the in vivo pooled-screen described herein include:

(1) Versatility—Plasmid design allows multiple effectors and/or noncoding elements to be expressed; library cloning strategy enables both transcriptional directions of the computationally predicted crRNA to be expressed;

(2) Comprehensive tests of activity mechanisms & functional parameters—Evaluates diverse interference mechanisms, including nucleic acid cleavage; examines co-occurrence of features such as transcription, plasmid DNA replication; and flanking sequences for crRNA library can be used to reliably determine PAMs with complexity equivalence of 4N's;

(3) Sensitivity—pACYC184 is a low copy plasmid, enabling high sensitivity for CRISPR-Cas activity since even modest interference rates can eliminate the antibiotic resistance encoded by the plasmid; and (4) Efficiency—Optimized molecular biology steps to enable greater speed and throughput RNA-sequencing and protein expression samples can be directly harvested from the surviving cells in the screen.

The novel CLUST.200916 CRISPR-Cas family described herein was evaluated using this in vivo pooled-screen to evaluate is operational elements, mechanisms, and parameters, as well as its ability to be active and reprogrammed in an engineered system outside of its endogenous cellular environment.

CRISPR Effector Activity and Modifications

In some embodiments, a CRISPR effector of CLUST.200916 and an RNA guide form a "binary" complex that may include other components. The binary complex is activated upon binding to a nucleic acid substrate that is complementary to a spacer sequence in the RNA guide (i.e., a sequence-specific substrate or target nucleic acid). In some embodiments, the sequence-specific substrate is a double-stranded DNA. In some embodiments, the sequence-specific substrate is a single-stranded DNA. In some embodiments, the sequence-specific substrate is a single-stranded RNA. In some embodiments, the sequence-specific substrate is a double-stranded RNA. In some embodiments, the sequence-specificity requires a complete match of the spacer sequence in the RNA guide (e.g., crRNA) to the target substrate. In other embodiments, the sequence specificity requires a partial (contiguous or non-contiguous) match of the spacer sequence in the RNA guide (e.g., crRNA) to the target substrate.

In some embodiments, the binary complex becomes activated upon binding to the target substrate. In some embodiments, the activated complex exhibits "multiple turnover" activity, whereby upon acting on (e.g., cleaving) the target substrate the activated complex remains in an activated state. In some embodiments, the activated binary complex exhibits "single turnover" activity, whereby upon acting on the target substrate the binary complex reverts to an inactive state. In some embodiments, the activated binary complex exhibits non-specific (i.e., "collateral") cleavage activity whereby the complex cleaves non-target nucleic acids. In some embodiments, the non-target nucleic acid is a DNA molecule (e.g., a single-stranded or a double-stranded DNA). In some embodiments, the non-target nucleic acid is an RNA molecule (e.g., a single-stranded or a double-stranded RNA).

In some embodiments, a CRISPR effector described herein can be fused to one or more peptide tags, including a His-tag, GST-tag, FLAG-tag, or myc-tag. In some embodiments, a CRISPR effector described herein can be fused to a detectable moiety such as a fluorescent protein (e.g., green fluorescent protein or yellow fluorescent protein). In some embodiments, a CRISPR effector and/or accessory protein of this disclosure is fused to a peptide or non-peptide moiety that allows the protein to enter or localize to a tissue, a cell, or a region of a cell. For instance, a CRISPR effector of this disclosure may comprise a nuclear localization sequence (NLS) such as an SV40 (simian virus 40) NLS, c-Myc NLS, or other suitable monopartite NLS. The NLS may be fused to the N-terminus and/or C-terminus of the CRISPR effector, and may be fused singly (i.e., a single NLS) or concatenated (e.g., a chain of 2, 3, 4, etc. NLS).

In some embodiments, at least one Nuclear Export Signal (NES) is attached to a nucleic acid sequences encoding the CRISPR effector. In some embodiments, a C-terminal and/or N-terminal NLS or NES is attached for optimal expression and nuclear targeting in eukaryotic cells, e.g., human cells.

In those embodiments where a tag is fused to a CRISPR effector, such tag may facilitate affinity-based or charge-based purification of the CRISPR effector, e.g., by liquid chromatography or bead separation utilizing an immobilized affinity or ion-exchange reagent. As a non-limiting example, a recombinant CRISPR effector of this disclosure comprises a polyhistidine (His) tag, and for purification is loaded onto a chromatography column comprising an immobilized metal ion (e.g., a $Zn^{2+}$, $Ni^{2+}$, $Cu^{2+}$ ion chelated by a chelating ligand immobilized on the resin, which resin may be an individually prepared resin or a commercially available resin or ready to use column such as the HisTrap FF column commercialized by GE Healthcare Life Sciences, Marlborough, Mass. Following the loading step, the column is optionally rinsed, e.g., using one or more suitable buffer solutions, and the His-tagged protein is then eluted using a suitable elution buffer. Alternatively, or additionally, if the recombinant CRISPR effector of this disclosure utilizes a FLAG-tag, such protein may be purified using immunoprecipitation methods known in the industry. Other suitable purification methods for tagged CRISPR effectors or accessory proteins of this disclosure will be evident to those of skill in the art.

The proteins described herein (e.g., CRISPR effectors or accessory proteins) can be delivered or used as either nucleic acid molecules or polypeptides. When nucleic acid molecules are used, the nucleic acid molecule encoding the CRISPR effector can be codon-optimized. The nucleic acid can be codon optimized for use in any organism of interest, in particular human cells or bacteria. For example, the nucleic acid can be codon-optimized for any non-human eukaryote including mice, rats, rabbits, dogs, livestock, or non-human primates. Codon usage tables are readily available, for example, at the "Codon Usage Database" available at www.kazusa.orjp/codon/ and these tables can be adapted in a number of ways. See Nakamura et al. *Nucl. Acids Res.* 28:292 (2000), which is incorporated herein by reference in its entirety. Computer algorithms for codon optimizing a particular sequence for expression in a particular host cell are also available, such as Gene Forge (Aptagen; Jacobus, Pa.).

In some instances, nucleic acids of this disclosure which encode CRISPR effectors for expression in eukaryotic (e.g., human, or other mammalian cells) cells include one or more introns, i.e., one or more non-coding sequences comprising, at a first end (e.g., a 5' end), a splice-donor sequence and, at second end (e.g., the 3' end) a splice acceptor sequence. Any suitable splice donor/splice acceptor can be used in the various embodiments of this disclosure, including without limitation simian virus 40 (SV40) intron, beta-globin intron, and synthetic introns. Alternatively, or additionally, nucleic acids of this disclosure encoding CRISPR effectors or accessory proteins may include, at a 3' end of a DNA coding sequence, a transcription stop signal such as a polyadenylation (polyA) signal. In some instances, the polyA signal is located in close proximity to, or adjacent to, an intron such as the SV40 intron.

Deactivated/Inactivated CRISPR Effectors

The CRISPR effectors described herein can be modified to have diminished nuclease activity, e.g., nuclease inactivation of at least 50%, at least 60%, at least 70%, at least 80%, at least 90%, at least 95%, at least 97%, or 100% as compared with the wild type CRISPR effectors. The nuclease activity can be diminished by several methods known in the art, e.g., introducing mutations into the nuclease domains of the proteins. In some embodiments, catalytic residues for the nuclease activities are identified, and these amino acid residues can be substituted by different amino acid residues (e.g., glycine or alanine) to diminish the nuclease activity.

The inactivated CRISPR effectors can comprise or be associated with one or more functional domains (e.g., via fusion protein, linker peptides, "GS" linkers, etc.). These functional domains can have various activities, e.g., methylase activity, demethylase activity, transcription activation activity, transcription repression activity, transcription release factor activity, histone modification activity, RNA cleavage activity, DNA cleavage activity, nucleic acid binding activity, and switch activity (e.g., light inducible). In some embodiments, the functional domains are Krüppel associated box (KRAB), VP64, VP16, Fok1, P65, HSF1, MyoD1, and biotin-APEX.

The positioning of the one or more functional domains on the inactivated CRISPR effectors is one that allows for correct spatial orientation for the functional domain to affect the target with the attributed functional effect. For example, if the functional domain is a transcription activator (e.g., VP16, VP64, or p65), the transcription activator is placed in a spatial orientation that allows it to affect the transcription of the target. Likewise, a transcription repressor is positioned to affect the transcription of the target, and a nuclease (e.g., Fok1) is positioned to cleave or partially cleave the target. In some embodiments, the functional domain is positioned at the N-terminus of the CRISPR effector. In some embodiments, the functional domain is positioned at the C-terminus of the CRISPR effector. In some embodiments, the inactivated CRISPR effector is modified to comprise a first functional domain at the N-terminus and a second functional domain at the C-terminus.

Split Enzymes

The present disclosure also provides a split version of the CRISPR effectors described herein. The split version of the CRISPR effectors may be advantageous for delivery. In some embodiments, the CRISPR effectors are split to two parts of the enzymes, which together substantially comprises a functioning CRISPR effector.

The split can be done in a way that the catalytic domain(s) are unaffected. The CRISPR effectors may function as a nuclease or may be inactivated enzymes, which are essentially RNA-binding proteins with very little or no catalytic activity (e.g., due to mutation(s) in its catalytic domains).

In some embodiments, the nuclease lobe and α-helical lobe are expressed as separate polypeptides. Although the lobes do not interact on their own, the RNA guide recruits them into a ternary complex that recapitulates the activity of full-length CRISPR effectors and catalyzes site-specific DNA cleavage. The use of a modified RNA guide abrogates split-enzyme activity by preventing dimerization, allowing for the development of an inducible dimerization system. The split enzyme is described, e.g., in Wright et al. "Rational design of a split-Cas9 enzyme complex," Proc. Natl. Acad. Sci., 112.10 (2015): 2984-2989, which is incorporated herein by reference in its entirety.

In some embodiments, the split enzyme can be fused to a dimerization partner, e.g., by employing rapamycin sensitive dimerization domains. This allows the generation of a chemically inducible CRISPR effector for temporal control of CRISPR effector activity. The CRISPR effector can thus be rendered chemically inducible by being split into two fragments, and rapamycin-sensitive dimerization domains can be used for controlled reassembly of the CRISPR effector.

The split point is typically designed in silico and cloned into the constructs. During this process, mutations can be introduced to the split enzyme and non-functional domains can be removed. In some embodiments, the two parts or fragments of the split CRISPR effector (i.e., the N-terminal and C-terminal fragments) can form a full CRISPR effector, comprising, e.g., at least 70%, at least 80%, at least 90%, at least 95%, or at least 99% of the sequence of the wild-type CRISPR effector.

Self-Activating or Inactivating Enzymes

The CRISPR effectors described herein can be designed to be self-activating or self-inactivating. In some embodiments, the CRISPR effectors are self-inactivating. For example, the target sequence can be introduced into the CRISPR effector coding constructs. Thus, the CRISPR effectors can cleave the target sequence, as well as the construct encoding the enzyme thereby self-inactivating their expression. Methods of constructing a self-inactivating CRISPR system is described, e.g., in Epstein et al., "Engineering a Self-Inactivating CRISPR System for AAV Vectors," Mol. Ther., 24 (2016): S50, which is incorporated herein by reference in its entirety.

In some other embodiments, an additional RNA guide, expressed under the control of a weak promoter (e.g., 7SK promoter), can target the nucleic acid sequence encoding the CRISPR effector to prevent and/or block its expression (e.g., by preventing the transcription and/or translation of the nucleic acid). The transfection of cells with vectors expressing the CRISPR effector, RNA guides, and RNA guides that target the nucleic acid encoding the CRISPR effector can lead to efficient disruption of the nucleic acid encoding the CRISPR effector and decrease the levels of CRISPR effector, thereby limiting the genome editing activity.

In some embodiments, the genome editing activity of a CRISPR effector can be modulated through endogenous RNA signatures (e.g., miRNA) in mammalian cells. The CRISPR effector switch can be made by using a miRNA-complementary sequence in the 5'-UTR of mRNA encoding the CRISPR effector. The switches selectively and efficiently respond to miRNA in the target cells. Thus, the switches can differentially control the genome editing by sensing endogenous miRNA activities within a heterogeneous cell population. Therefore, the switch systems can provide a framework for cell-type selective genome editing and cell engineering based on intracellular miRNA information (Hirosawa et al. "Cell-type-specific genome editing with a microRNA-responsive CRISPR-Cas9 switch," Nucl. Acids Res., 2017 Jul. 27; 45(13): e118).

Inducible CRISPR Effectors

The CRISPR effectors can be inducible, e.g., light inducible or chemically inducible. This mechanism allows for activation of the functional domain in a CRISPR effector. Light inducibility can be achieved by various methods known in the art, e.g., by designing a fusion complex wherein CRY2 PHR/CIBN pairing is used in split CRISPR effectors (see, e.g., Konermann et al., "Optical control of mammalian endogenous transcription and epigenetic states," Nature, 500.7463 (2013): 472). Chemical inducibility can be achieved, e.g., by designing a fusion complex wherein FKBP/FRB (FK506 binding protein/FKBP rapamycin binding domain) pairing is used in split CRISPR effectors. Rapamycin is required for forming the fusion complex, thereby activating the CRISPR effectors (see, e.g., Zetsche et al., "A split-Cas9 architecture for inducible genome editing and transcription modulation," Nature Biotech., 33.2 (2015): 139-142).

Furthermore, expression of a CRISPR effector can be modulated by inducible promoters, e.g., tetracycline or doxycycline controlled transcriptional activation (Tet-On and Tet-Off expression system), hormone inducible gene expression system (e.g., an ecdysone inducible gene expression system), and an arabinose-inducible gene expression system. When delivered as RNA, expression of the RNA targeting effector protein can be modulated via a riboswitch, which can sense a small molecule like tetracycline (see, e.g., Goldfless et al., "Direct and specific chemical control of eukaryotic translation with a synthetic RNA-protein interaction," Nucl. Acids Res., 40.9 (2012): e64-e64).

Various embodiments of inducible CRISPR effectors and inducible CRISPR systems are described, e.g., in U.S. Pat. No. 8,871,445, US 20160208243, and WO 2016205764, each of which is incorporated herein by reference in its entirety.

Functional Mutations

Various mutations or modifications can be introduced into a CRISPR effector as described herein to improve specificity and/or robustness. In some embodiments, the amino acid residues that recognize the Protospacer Adjacent Motif (PAM) are identified. The CRISPR effectors described herein can be modified further to recognize different PAMs, e.g., by substituting the amino acid residues that recognize PAM with other amino acid residues. In some embodiments, the CRISPR effectors can recognize, e.g., 5'-TTN-3', wherein "N" is any nucleobase.

In some embodiments, the CRISPR effectors described herein can be mutated at one or more amino acid residue to modify one or more functional activities. For example, in some embodiments, the CRISPR effector is mutated at one or more amino acid residues to modify its helicase activity. In some embodiments, the CRISPR effector is mutated at one or more amino acid residues to modify its nuclease activity (e.g., endonuclease activity or exonuclease activity). In some embodiments, the CRISPR effector is mutated at one or more amino acid residues to modify its ability to functionally associate with an RNA guide. In some embodiments, the CRISPR effector is mutated at one or more amino acid residues to modify its ability to functionally associate with a target nucleic acid.

In some embodiments, the CRISPR effectors described herein are capable of cleaving a target nucleic acid molecule. In some embodiments, the CRISPR effector cleaves both strands of the target nucleic acid molecule. However, in some embodiments, the CRISPR effector is mutated at one or more amino acid residues to modify its cleaving activity. For example, in some embodiments, the CRISPR effector may comprise one or more mutations that increase the ability of the CRISPR effector to cleave a target nucleic acid. In another example, in some embodiments, the CRISPR effector may comprise one or more mutations that render the enzyme incapable of cleaving a target nucleic acid. In other embodiments, the CRISPR effector may comprise one or more mutations such that the enzyme is capable of cleaving a strand of the target nucleic acid (i.e., nickase activity). In some embodiments, the CRISPR effector is capable of cleaving the strand of the target nucleic acid that is complementary to the strand that the RNA guide hybridizes to. In some embodiments, the CRISPR effector is capable of cleaving the strand of the target nucleic acid that the RNA guide hybridizes to.

In some embodiments, one or more residues of a CRISPR effector disclosed herein are mutated to an arginine moiety. In some embodiments, one or more residues of a CRISPR effector disclosed herein are mutated to a glycine moiety. In some embodiments, one or more residues of a CRISPR effector disclosed herein are mutated based upon consensus residues of a phylogenetic alignment of CRISPR effectors disclosed herein.

In some embodiments, a CRISPR effector described herein may be engineered to comprise a deletion in one or more amino acid residues to reduce the size of the enzyme while retaining one or more desired functional activities (e.g., nuclease activity and the ability to interact functionally with an RNA guide). The truncated CRISPR effector may be used advantageously in combination with delivery systems having load limitations.

In one aspect, the present disclosure provides nucleic acid sequences that are at least 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, or 99% identical to the nucleic sequences described herein, while maintaining the domain architecture shown in FIG. 2A. In another aspect, the present disclosure also provides amino acid sequences that are at least 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, or 99% identical to the amino acid sequences described herein, while maintaining the domain architecture shown in FIG. 2A.

In some embodiments, the nucleic acid sequences have at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides) that are the same as the sequences described herein. In some embodiments, the nucleic acid sequences have at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides) that is different from the sequences described herein.

In some embodiments, the amino acid sequences have at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is the same as the sequences described herein. In some embodiments, the amino acid sequences have at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is different from the sequences described herein.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In general, the length of a reference sequence aligned for comparison purposes should be at least 80% of the length of the reference sequence, and in some embodiments at least 90%, 95%, or 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences. For purposes of the present disclosure, the comparison of sequences and determination of percent identity between two sequences can be accomplished using a Blossum 62 scoring matrix with a gap penalty of 12, a gap extend penalty of 4, and a frameshift gap penalty of 5.

RNA Guide and RNA Guide Modifications

In some embodiments, an RNA guide described herein comprises a uracil (U). In some embodiments, an RNA guide described herein comprises a thymine (T). In some embodiments, a direct repeat sequence of an RNA guide described herein comprises a uracil (U). In some embodiments, a direct repeat sequence of an RNA guide described herein comprises a thymine (T). In some embodiments, a direct repeat sequence according to Table 3 or 8 comprises a sequence comprising a uracil, in one or more places indicated as thymine in the corresponding sequences in Table 3 or 8.

In some embodiments, the direct repeat comprises only one copy of a sequence that is repeated in an endogenous CRISPR array. In some embodiments, the direct repeat is a full-length sequence adjacent to (e.g., flanking) one or more spacer sequences found in an endogenous CRISPR array. In some embodiments, the direct repeat is a portion (e.g., processed portion) of a full-length sequence adjacent to (e.g., flanking) one or more spacer sequences found in an endogenous CRISPR array.

Spacer Lengths

The spacer length of RNA guides can range from about 14 to 50 nucleotides. The spacer length of RNA guides can range from about 20 to 35 nucleotides. In some embodiments, the spacer length of an RNA guide is at least 15 nucleotides, at least 16 nucleotides, at least 17 nucleotides, at least 18 nucleotides, at least 19 nucleotides, at least 20 nucleotides, at least 21 nucleotides, or at least 22 nucleotides. In some embodiments, the spacer length is from 15 to 17 nucleotides, from 15 to 23 nucleotides, from 16 to 22 nucleotides, from 17 to 20 nucleotides, from 20 to 24 nucleotides (e.g., 20, 21, 22, 23, or 24 nucleotides), from 23 to 25 nucleotides (e.g., 23, 24, or 25 nucleotides), from 24 to 27 nucleotides, from 27 to 30 nucleotides, from 30 to 45 nucleotides (e.g., 30, 31, 32, 33, 34, 35, 40, or 45 nucleotides), from 30 or 35 to 40 nucleotides, from 41 to 45 nucleotides, from 45 to 50 nucleotides, or longer. Approximate spacer lengths corresponding to mature crRNAs of the present application are shown in Table 2. In some embodiments, the spacer lengths identified in Table 2 are the preferred spacer lengths for mature crRNAs of the present application. In some embodiments, the preferred spacer length for RNA guides (pre-crRNAs or mature crRNAs) of the present application is about 24 nucleotides.

TABLE 2

Exemplary spacer lengths for mature crRNAs.

| Effector | Spacer Length |
|---|---|
| 3300013232 (SEQ ID NO: 1) | 16 or 17 nucleotides |
| 3300027824 (SEQ ID NO: 3) | 30 to 35 nucleotides |
| SRR6837557 (SEQ ID NO: 23) | 12 nucleotides |
| SRR6837562 (SEQ ID NO: 24) | 11 to 14 nucleotides |
| SRR6837569 (SEQ ID NO: 25) | 11 to 13 nucleotides |

TABLE 2-continued

Exemplary spacer lengths for mature crRNAs.

| Effector | Spacer Length |
|---|---|
| SRR6837570 (SEQ ID NO: 26) | 17 nucleotides |
| SRR6837575 (SEQ ID NO: 28) | 11 nucleotides |
| SRR6837577 (SEQ ID NO: 29) | 14 nucleotides |

In some embodiments, the direct repeat length of the RNA guide is at least 16 nucleotides, or is from 16 to 20 nucleotides (e.g., 16, 17, 18, 19, or 20 nucleotides). In some embodiments, the direct repeat length of the RNA guide is about 22 to 36 nucleotides. Exemplary full-length direct repeat sequences (e.g., direct repeat sequences of pre-crRNAs or unprocessed crRNAs) and direct repeat sequences of mature crRNAs (e.g., direct repeat sequences of processed crRNAs) are shown in Table 3. See also TABLE 8.

TABLE 3

Exemplary direct repeat sequences of pre-crRNA and mature crRNA sequences.

| Effector | pre-crRNA Direct Repeat Sequence | Mature crRNA Direct Repeat Sequence |
|---|---|---|
| 3300013232 (SEQ ID NO: 1) | CAACCTAAACGA TGGCTCGATTC GTCGAGAC (SEQ ID NO: 77) | CTAAACGATGG CTCGATTCGTC GAGAC (SEQ ID NO: 78) |
| 3300027824 (SEQ ID NO: 3) | GTAGAAGACCT CGCTGATTGCTC GGTGCGCCGAGAC (SEQ ID NO: 79) | TGATTGCTCGG TGCGCCGAGA (SEQ ID NO: 80) |
| 3300027908 (SEQ ID NO: 22) | CTTTCAAGACT AATAGATTGCTC CTTACGAGGAGAC (SEQ ID NO: 81) | CTAATAGATTG CTCCTTACGAG GAGAC (SEQ ID NO: 82) |
| SRR6837557 (SEQ ID NO: 23) | GTCGAGACCGA TGACGAGTGCG CGGTGCGCCGC GAC (SEQ ID NO: 83) | TGACGAGTGC GCGGTGCGCC GCGAC (SEQ ID NO: 84) |
| SRR6837562 (SEQ ID NO: 24) | CCTGCAAGGGA TCCAAATTGCT CTGTTCGCAGA GAC (SEQ ID NO: 85) | TCCAAATTGC TCTGTTCGCA GAGAC (SEQ ID NO: 86) |
| SRR6837569 (SEQ ID NO: 25) | CCTGCAAGGGA TCCAAATTGCT CTGTTCGCAGA GAC (SEQ ID NO: 87) | ATCCAAATTG CTCTGTTCGC AGAGAC (SEQ ID NO: 88) |
| SRR6837570 (SEQ ID NO: 26) | GCGCCAACGAC CTCTGATTGTC CGGTACGCCGG AAC (SEQ ID NO: 89) | TCTGATTGTC CGGTACGCCG CGAA (SEQ ID NO: 90) |
| SRR6837575 (SEQ ID NO: 28) | CCATCAATGGA TCCAAATTGCT CTGTACGCAGA GAC (SEQ ID NO: 91) | ATCCAAATTG CTCTGTACGC GAGAAC (SEQ ID NO: 92) |

TABLE 3-continued

Exemplary direct repeat sequences of pre-crRNA and mature crRNA sequences.

| Effector | pre-crRNA Direct Repeat Sequence | Mature crRNA Direct Repeat Sequence |
|---|---|---|
| SRR6837577 (SEQ ID NO: 29) | GTCGAGAGCGA TGACGAGTGCG CGGTGCGCCGC GAC (SEQ ID NO: 93) | TGACGAGTGCG CGGTGCGCCGC GAC (SEQ ID NO: 94) |

As used herein, the term "protospacer adjacent motif" or "PAM" refers to a DNA sequence adjacent to a target sequence to which a complex comprising an effector and an RNA guide binds. In some embodiments, a PAM is required for enzyme activity. As used herein, the term "adjacent" includes instances in which an RNA guide of the complex specifically binds, interacts, or associates with a target sequence that is immediately adjacent to a PAM. In such instances, there are no nucleotides between the target sequence and the PAM. The term "adjacent" also includes instances in which there are a small number (e.g., 1, 2, 3, 4, or 5) of nucleotides between the target sequence, to which the targeting moiety binds, and the PAM. In some embodiments, PAMs corresponding to effectors of the present application are shown in Table 4. As used herein, N's can each be any nucleotide (e.g., A, G, T, or C) or a subset thereof (e.g., Y (C or T), K (G or T), B (G, T, or C), H (A, C, or T). For example, in some embodiments, a PAM sequence of 5'-TTN-3' refers to a PAM sequence of 5'-TTT-3' or 5'-TTG-3'.

TABLE 4

PAM sequences corresponding to effectors of the present invention.

| Effector | PAM Sequence |
|---|---|
| 3300013232 (SEQ ID NO: 1) | 5'-TTN-3' 5'-YYN-3' 5'-HHN-3' |
| 3300027908 (SEQ ID NO: 22) | 5'-TTN-3' 5'-YYN-3' 5'-HHN-3' |
| SRR6837562 (SEQ ID NO: 24) | 5'-TTN-3' 5'-YKN-3' |
| SRR6837569 (SEQ ID NO: 25) | 5'-TTN-3' |
| SRR6837570 (SEQ ID NO: 26) | 5'-TTN-3' 5'-YYN-3' 5'-HBN-3' |
| SRR6837575 (SEQ ID NO: 28) | 5'-TTN-3' 5'-YKN-3' |
| SRR6837577 (SEQ ID NO: 29) | 5'-TTN-3' 5'-HHN-3' |

In some embodiments, an RNA guide further comprises a tracrRNA. In some embodiments, the tracrRNA is not required (e.g., the tracrRNA is optional). In some embodiments, the tracrRNA is a portion of the non-coding sequences shown in TABLE 9. For example, in some embodiments, the optional tracrRNA is a sequence of Table 5.

TABLE 5

Exemplary tracrRNA sequences.

| Effector | TracrRNA |
|---|---|
| 3300013232 (SEQ ID NO: 1) | GCTGGATTGATTCCTGCGGTGTAGAATAGCATAACCAGGGTCCGCTGGACTATCCAGC AACGACGGCTCGATACGTCGAGCCGATGGAGAAGTCATGCCAAAGATCAAGAA (SEQ ID NO: 95) TCGATGCTGGATTGATTCCTGCGGTGTAGAATAGCATAACCAGGGTCCGCTGGACTAT CCAGCAACGACGGCTCGATACGTCGAGCCGATGGAGAAGTCATGCCAAAGATCA (SEQ ID NO: 96) ATTGATTCCTGCGGTGTAGAATAGCATAACCAGGGTCCGCTGGACTATCCAGCAACGA CGGCTCGATACGTCGAGCCGATGGAGAAGTCATGCCAAAG (SEQ ID NO: 97) ATAGCATAACCAGGGTCCGCTGGACTATCCAGCAACGACGGCTCGATACGTCGAGCCG ATGGAGAAGTCATGCCAAAGAT (SEQ ID NO: 98) TAGCATAACCAGGGTCCGCTGGACTATCCAGCAACGACGGCTCGATACGTCGAGCCGA TGGAGAAGTCATGCCAAAGA (SEQ ID NO: 99) GCCAAAGATCAAGAAACCGACTGAGATTTCCCTGCTACGCAAGGAGGTGTTCCCTGA (SEQ ID NO: 100) ATTCTACACCGCAGGAATCAATCCAGCATCGAGTAGACCGTTGC (SEQ ID NO: 101) ATTCTACACCGCAGGAATCAATCCAGCATCGAGTAGACCGTTGCA (SEQ ID NO: 102) |
| 3300027908 (SEQ ID NO: 22) | CTTGTAAGAAATTCGTTCGAGAAAATGAAATTCCTGTCGCTATAACGGCCCAGTCGAT GCCGAAACCAACTTGCGAGCGCTCGGGCGACGCTAAAAAGCCTGTCCGTGCTCGCAAG GCTAAAGCACCGGAATTTCAC (SEQ ID NO: 103) GGCTTGTAAGAAATTCGTTCGAGAAAATGAAATTCCTGTCGCTATAACGGCCCAGTCG ATGCCGAAACCAACTTGCGAGCGCTCGGGCGACGCTAAAAAGCCTGTCCGTGCTCGCA AGGCTAAAGCACCGGAATTT (SEQ ID NO: 104) |
| SRR6837557 (SEQ ID NO: 23) | TGTCGAGAGCGATGACGAGTGCGCGGTGCGCCGCGACCAGCTCTGTGTGTAGTTGACC CGTAGTCAGGACAAGGAGAGGTCGAGAGCGATGACGAGTGCGCGGTGCGCCGCGACGT GCTGTTGATCTGATAGACGGGG (SEQ ID NO: 105) TCGAGAGCGATGACGAGTGCGCGGTGCGCCGCGACGTGCTGTTGATCTGATAGACG (SEQ ID NO: 106) GGTTCCGAATTTCTCGGTGGCTGTCGAGAGCGATGACGAGTGCGCGGTGCGCCGCGAC CAGCTCTGTGTGTAGTTGACCCG (SEQ ID NO: 107) GGTTCCGAATTTCTCGGTGGCTGTCGAGAGCGATGACGAGTGCGCGGTGCGCCGCGAC CAGCTCTGTGTGTAGTTGACC (SEQ ID NO: 108) |
| SRR6837570 (SEQ ID NO: 26) | TGCTACAGGCAATCACAAACAGCGGGAGACGAACAATGACTCTGGCCGAGCTGCGCGA CAAATACTTCTACAAGATCAA (SEQ ID NO: 109) CTACAGGCAATCACAAACAGCGGGAGACGAACAATGACTCTGGCCGAGCTGCGCGACA AATACTTCTACAAGATC (SEQ ID NO: 110) GAGACGAACAATGACTCTGGCCGAGCTGCGCGACAAATACTTCTACAAGATCAAGTTC CGCAAGATCGATCTCAGGCAAGCCGGCAAGATCCT (SEQ ID NO: 111) GGGAGACGAACAATGACTCTGGCCGAGCTGCGCGACAAATACTTCTACAAGATCAAGT TCCGCAAGATCGATCTCAGGCAAGCCGGCAAGATCCTCAAG (SEQ ID NO: 112) GCGGCCGGTGCTCGCAGACGAGCTGCTAGGTCTTTGAAAATTGAATAGATTGTAATGG TGAGTTGC (SEQ ID NO: 113) CGGCCGGTGCTCGCAGACGAGCTGCTAGGTCTTTGAAAATTGAATAGATTGTAATGGT GAGTTGC (SEQ ID NO: 114) |
| SRR683757 5 (SEQ ID NO: 28) | CGTCTACACCGAACGTAAAATCTTAGAAAACGTCATGAAGGAGGCGCAATACCTATCG TGCG (SEQ ID NO: 115) |
| SRR683757 7 (SEQ ID NO: 29) | GGTTGGCGTCAGTGAAAACTGAATAGACGAAGATACGAGCCGCTCGCAGGGTGGAGCG GAAGATCTCGATCTG (SEQ ID NO: 116) GCTGGTTGGCGTCAGTGAAAACTGAATAGACGAAGATACGAGCCGCTCGCAGGGTGGA GCGGAAGATCTCGATCTGG (SEQ ID NO: 117) CCCGCATGTCGCCAGAACAGACGCACAAGAAGTTCGTGAAGATCGTCGAGTCCGAGGG CACGACCAAGGTCGCCGCCCGTCTCGGCTGCTCCG (SEQ ID NO: 118) CCCCGCATGTCGCCAGAACAGACGCACAAGAAGTTCGTGAAGATCGTCGAGTCCGAGG GCACGACCAAGGTCGCCGCCCGTCTCGGCTGCTCCGTGGCGC (SEQ ID NO: 119) AGGTGCGAGCATGCCCGACAAGCAGACGCCCAAGGACACCAAGGACAAGCCCGAGAGC CCCG (SEQ ID NO: 120) AGGTGCGAGCATGCCCGACAAGCAGACGCCCAAGGACACCAAGGACAAGCCCGAGAGC CCC (SEQ ID NO: 121) |

The RNA guide sequences can be modified in a manner that allows for formation of the CRISPR complex and successful binding to the target, while at the same time not allowing for successful nuclease activity (i.e., without nuclease activity/without causing indels). These modified guide sequences are referred to as "dead guides" or "dead guide sequences." These dead guides or dead guide sequences may be catalytically inactive or conformationally inactive with regard to nuclease activity. Dead guide sequences are typically shorter than respective guide sequences that result in active cleavage. In some embodiments, dead guides are 5%, 10%, 20%, 30%, 40%, or 50% shorter than respective RNA guides that have nuclease activity. Dead guide sequences of RNA guides can be from 13 to 15 nucleotides in length (e.g., 13, 14, or 15 nucleotides in length), from 15 to 19 nucleotides in length, or from 17 to 18 nucleotides in length (e.g., 17 nucleotides in length).

Thus, in one aspect, the disclosure provides non-naturally occurring or engineered CRISPR systems including a functional CLUST.200916 CRISPR effector as described herein, and an RNA guide wherein the RNA guide comprises a dead guide sequence, whereby the RNA guide is capable of hybridizing to a target sequence such that the CRISPR system is directed to a genomic locus of interest in a cell without detectable cleavage activity. A detailed description of dead guides is described, e.g., in WO 2016094872, which is incorporated herein by reference in its entirety.

Inducible RNA Guides

RNA guides can be generated as components of inducible systems. The inducible nature of the systems allows for spatiotemporal control of gene editing or gene expression. In some embodiments, the stimuli for the inducible systems include, e.g., electromagnetic radiation, sound energy, chemical energy, and/or thermal energy.

In some embodiments, the transcription of RNA guide can be modulated by inducible promoters, e.g., tetracycline or doxycycline controlled transcriptional activation (Tet-On and Tet-Off expression systems), hormone inducible gene expression systems (e.g., ecdysone inducible gene expression systems), and arabinose-inducible gene expression systems. Other examples of inducible systems include, e.g., small molecule two-hybrid transcription activations systems (FKBP, ABA, etc.), light inducible systems (Phytochrome, LOV domains, or cryptochrome), or Light Inducible Transcriptional Effector (LITE). These inducible systems are described, e.g., in WO 2016205764 and U.S. Pat. No. 8,795,965, each of which is incorporated herein by reference in its entirety.

Chemical Modifications

Chemical modifications can be applied to the phosphate backbone, sugar, and/or base of the RNA guide. Backbone modifications such as phosphorothioates modify the charge on the phosphate backbone and aid in the delivery and nuclease resistance of the oligonucleotide (see, e.g., Eckstein, "Phosphorothioates, essential components of therapeutic oligonucleotides," *Nucl. Acid Ther.,* 24 (2014), pp. 374-387); modifications of sugars, such as 2'-O-methyl (2'-OMe), 2'-F, and locked nucleic acid (LNA), enhance both base pairing and nuclease resistance (see, e.g., Allerson et al. "Fully 2'-modified oligonucleotide duplexes with improved in vitro potency and stability compared to unmodified small interfering RNA," *J. Med. Chem.,* 48.4 (2005): 901-904). Chemically modified bases such as 2-thiouridine or N6-methyladenosine, among others, can allow for either stronger or weaker base pairing (see, e.g., Bramsen et al., "Development of therapeutic-grade small interfering RNAs by chemical engineering," *Front. Genet.,* 2012 Aug. 20; 3:154). Additionally, RNA is amenable to both 5' and 3' end conjugations with a variety of functional moieties including fluorescent dyes, polyethylene glycol, or proteins.

A wide variety of modifications can be applied to chemically synthesized RNA guide molecules. For example, modifying an oligonucleotide with a 2'-OMe to improve nuclease resistance can change the binding energy of Watson-Crick base pairing. Furthermore, a 2'-OMe modification can affect how the oligonucleotide interacts with transfection reagents, proteins or any other molecules in the cell. The effects of these modifications can be determined by empirical testing.

In some embodiments, the RNA guide includes one or more phosphorothioate modifications. In some embodiments, the RNA guide includes one or more locked nucleic acids for the purpose of enhancing base pairing and/or increasing nuclease resistance.

A summary of these chemical modifications can be found, e.g., in Kelley et al., "Versatility of chemically synthesized guide RNAs for CRISPR-Cas9 genome editing," *J. Biotechnol.* 2016 Sep. 10; 233:74-83; WO 2016205764; and U.S. Pat. No. 8,795,965, each which is incorporated by reference in its entirety.

Sequence Modifications

The sequences and the lengths of the RNA guides, tracrRNAs, and crRNAs described herein can be optimized. In some embodiments, the optimized length of RNA guide can be determined by identifying the processed form of tracrRNA and/or crRNA, or by empirical length studies for RNA guides, tracrRNAs, crRNAs, and the tracrRNA tetraloops.

The RNA guides can also include one or more aptamer sequences. Aptamers are oligonucleotide or peptide molecules that can bind to a specific target molecule. The aptamers can be specific to gene effectors, gene activators, or gene repressors. In some embodiments, the aptamers can be specific to a protein, which in turn is specific to and recruits/binds to specific gene effectors, gene activators, or gene repressors. The effectors, activators, or repressors can be present in the form of fusion proteins. In some embodiments, the RNA guide has two or more aptamer sequences that are specific to the same adaptor proteins. In some embodiments, the two or more aptamer sequences are specific to different adaptor proteins. The adaptor proteins can include, e.g., MS2, PP7, Qβ, F2, GA, fr, JP501, M12, R17, BZ13, JP34, JP500, KU1, M11, MX1, TW18, VK, SP, FI, ID2, NL95, TW19, AP205, φCb5, φCb8r, φCb12r, φCb23r, 7s, and PRR1. Accordingly, in some embodiments, the aptamer is selected from binding proteins specifically binding any one of the adaptor proteins as described herein. In some embodiments, the aptamer sequence is a MS2 loop. A detailed description of aptamers can be found, e.g., in Nowak et al., "Guide RNA engineering for versatile Cas9 functionality," *Nucl. Acid. Res.,* 2016 Nov. 16; 44(20):9555-9564; and WO 2016205764, each of which is incorporated herein by reference in its entirety.

Guide: Target Sequence Matching Requirements

In CRISPR systems, the degree of complementarity between a guide sequence and its corresponding target sequence can be about 50%, 60%, 75%, 80%, 85%, 90%, 95%, 97.5%, 99%, or 100%. To reduce off-target interactions, e.g., to reduce the guide interacting with a target sequence having low complementarity, mutations can be introduced to the CRISPR systems so that the CRISPR systems can distinguish between target and off-target sequences that have greater than 80%, 85%, 90%, or 95% complementarity. In some embodiments, the degree of complementarity is from 80% to 95%, e.g., about 83%, 84%, 85%, 86%, 87%, 88%, 89%, 90%, 91%, 92%, 93%, 94%, or 95% (for example, distinguishing between a target having 18 nucleotides from an off-target of 18 nucleotides having 1, 2, or 3 mismatches). Accordingly, in some embodiments, the degree of complementarity between a guide sequence and its corresponding target sequence is greater than 94.5%, 95%, 95.5%, 96%, 96.5%, 97%, 97.5%, 98%, 98.5%, 99%, 99.5%, or 99.9%. In some embodiments, the degree of complementarity is 100%.

It is known in the field that complete complementarity is not required provided that there is sufficient complementarity to be functional. Modulations of cleavage efficiency can be exploited by introduction of mismatches, e.g., one or more mismatches, such as 1 or 2 mismatches between spacer sequence and target sequence, including the position of the mismatch along the spacer/target. Typically, the more central (i.e., not at the 3' or 5' ends) a mismatch, e.g., a double mismatch, is located; the more cleavage efficiency is affected. Accordingly, by choosing mismatch positions along the spacer sequence, cleavage efficiency can be modulated. For example, if less than 100% cleavage of targets is desired (e.g., in a cell population), 1 or 2 mismatches between spacer and target sequence can be introduced in the spacer sequences.

Methods of Using CRISPR Systems

The CRISPR systems described herein have a wide variety of utilities including modifying (e.g., deleting, inserting, translocating, inactivating, or activating) a target polynucleotide in a multiplicity of cell types. The CRISPR systems have a broad spectrum of applications in, e.g., DNA/RNA detection (e.g., specific high sensitivity enzymatic reporter unlocking (SHERLOCK)), tracking and labeling of nucleic acids, enrichment assays (extracting desired sequence from background), detecting circulating tumor DNA, preparing next generation library, drug screening, disease diagnosis and prognosis, and treating various genetic disorders.

DNA/RNA Detection

In one aspect, the CRISPR systems described herein can be used in DNA/RNA detection. Single effector RNA-guided DNases can be reprogrammed with CRISPR RNAs (crRNAs) to provide a platform for specific single-stranded DNA (ssDNA) sensing. Upon recognition of its DNA target, activated Type V single effector DNA-guided DNases engage in "collateral" cleavage of nearby non-targeted ssD-NAs. This crRNA-programmed collateral cleavage activity allows the CRISPR systems to detect the presence of a specific DNA by nonspecific degradation of labeled ssDNA.

The collateral ssDNA activity can be combined with a reporter in DNA detection applications such as a method called the DNA Endonuclease-Targeted CRISPR trans reporter (DETECTR) method, which achieves attomolar sensitivity for DNA detection (see, e.g., Chen et al., Science, 360(6387):436-439, 2018), which is incorporated herein by reference in its entirety. One application of using the enzymes described herein is to degrade non-specific ssDNA in an in vitro environment. A "reporter" ssDNA molecule linking a fluorophore and a quencher can also be added to the in vitro system, along with an unknown sample of DNA (either single-stranded or double-stranded). Upon recognizing the target sequence in the unknown piece of DNA, the effector complex cleaves the reporter ssDNA resulting in a fluorescent readout.

In other embodiments, the SHERLOCK method (Specific High Sensitivity Enzymatic Reporter UnLOCKing) also provides an in vitro nucleic acid detection platform with attomolar (or single-molecule) sensitivity based on nucleic acid amplification and collateral cleavage of a reporter ssDNA, allowing for real-time detection of the target. Methods of using CRISPR in SHERLOCK are described in detail, e.g., in Gootenberg, et al. "Nucleic acid detection with CRISPR-Cas13a/C2c2," Science, 356(6336):438-442 (2017), which is incorporated herein by reference in its entirety.

In some embodiments, the CRISPR systems described herein can be used in multiplexed error-robust fluorescence in situ hybridization (MERFISH). These methods are described in, e.g., Chen et al., "Spatially resolved, highly multiplexed RNA profiling in single cells," Science, 2015 Apr. 24; 348(6233):aaa6090, which is incorporated herein by reference in its entirety.

Tracking and Labeling of Nucleic Acids

Cellular processes depend on a network of molecular interactions among proteins, RNAs, and DNAs. Accurate detection of protein-DNA and protein-RNA interactions is key to understanding such processes. In vitro proximity labeling techniques employ an affinity tag combined with, a reporter group, e.g., a photoactivatable group, to label polypeptides and RNAs in the vicinity of a protein or RNA of interest in vitro. After UV irradiation, the photoactivatable groups react with proteins and other molecules that are in close proximity to the tagged molecules, thereby labelling them. Labelled interacting molecules can subsequently be recovered and identified. The RNA targeting effector proteins can for instance be used to target probes to selected RNA sequences. These applications can also be applied in animal models for in vivo imaging of diseases or difficult-to culture cell types. The methods of tracking and labeling of nucleic acids are described, e.g., in U.S. Pat. No. 8,795,965; WO 2016205764; and WO 2017070605, each of which is incorporated herein by reference in its entirety.

High-Throughput Screening

The CRISPR systems described herein can be used for preparing next generation sequencing (NGS) libraries. For example, to create a cost-effective NGS library, the CRISPR systems can be used to disrupt the coding sequence of a target gene, and the CRISPR effector transfected clones can be screened simultaneously by next-generation sequencing (e.g., on the Ion Torrent PGM system). A detailed description regarding how to prepare NGS libraries can be found, e.g., in Bell et al., "A high-throughput screening strategy for detecting CRISPR-Cas9 induced mutations using next-generation sequencing," BMC Genomics, 15.1 (2014): 1002, which is incorporated herein by reference in its entirety.

Engineered Cells

Microorganisms (e.g., E. coli, yeast, and microalgae) are widely used for synthetic biology. The development of synthetic biology has a wide utility, including various clinical applications. For example, the programmable CRISPR systems can be used to split proteins of toxic domains for targeted cell death, e.g., using cancer-linked RNA as target transcript. Further, pathways involving protein-protein interactions can be influenced in synthetic biological systems with, e.g., fusion complexes with the appropriate effectors such as kinases or enzymes.

In some embodiments, RNA guide sequences that target phage sequences can be introduced into the microorganism. Thus, the disclosure also provides methods of "vaccinating" a microorganism (e.g., a production strain) against phage infection.

In some embodiments, the CRISPR systems provided herein can be used to engineer microorganisms, e.g., to improve yield or improve fermentation efficiency. For example, the CRISPR systems described herein can be used to engineer microorganisms, such as yeast, to generate biofuel or biopolymers from fermentable sugars, or to degrade plant-derived lignocellulose derived from agricultural waste as a source of fermentable sugars. More particularly, the methods described herein can be used to modify the expression of endogenous genes required for biofuel production and/or to modify endogenous genes, which may interfere with the biofuel synthesis. These methods of engineering microorganisms are described e.g., in Verwaal et al., "CRISPR/Cpfl enables fast and simple genome editing of Saccharomyces cerevisiae," Yeast, 2017 Sep. 8. doi: 10.1002/yea.3278; and Hlavova et al., "Improving microalgae for biotechnology—from genetics to synthetic biology,"

*Biotechnol. Adv.,* 2015 Nov. 1; 33:1194-203, each of which is incorporated herein by reference in its entirety.

In some embodiments, the CRISPR systems provided herein can be used to engineer eukaryotic cells or eukaryotic organisms. For example, the CRISPR systems described herein can be used to engineer eukaryotic cells not limited to a plant cell, a fungal cell, a mammalian cell, a reptile cell, an insect cell, an avian cell, a fish cell, a parasite cell, an arthropod cell, an invertebrate cell, a vertebrate cell, a rodent cell, a mouse cell, a rat cell, a primate cell, a non-human primate cell, or a human cell. In some embodiments, eukaryotic cell is in an in vitro culture. In some embodiments, the eukaryotic cell is in vivo. In some embodiments, the eukaryotic cell is ex vivo.

Gene Drives

Gene drive is the phenomenon in which the inheritance of a particular gene or set of genes is favorably biased. The CRISPR systems described herein can be used to build gene drives. For example, the CRISPR systems can be designed to target and disrupt a particular allele of a gene, causing the cell to copy the second allele to fix the sequence. Because of the copying, the first allele will be converted to the second allele, increasing the chance of the second allele being transmitted to the offspring. A detailed method regarding how to use the CRISPR systems described herein to build gene drives is described, e.g., in Hammond et al., "A CRISPR-Cas9 gene drive system targeting female reproduction in the malaria mosquito vector *Anopheles gambiae,*" *Nat. Biotechnol.,* 2016 January; 34(1):78-83, which is incorporated herein by reference in its entirety.

Pooled-Screening

As described herein, pooled CRISPR screening is a powerful tool for identifying genes involved in biological mechanisms such as cell proliferation, drug resistance, and viral infection. Cells are transduced in bulk with a library of RNA guide-encoding vectors described herein, and the distribution of gRNAs is measured before and after applying a selective challenge. Pooled CRISPR screens work well for mechanisms that affect cell survival and proliferation, and they can be extended to measure the activity of individual genes (e.g., by using engineered reporter cell lines). Arrayed CRISPR screens, in which only one gene is targeted at a time, make it possible to use RNA-seq as the readout. In some embodiments, the CRISPR systems as described herein can be used in single-cell CRISPR screens. A detailed description regarding pooled CRISPR screenings can be found, e.g., in Datlinger et al., "Pooled CRISPR screening with single-cell transcriptome read-out," *Nat. Methods.,* 2017 March; 14(3):297-301, which is incorporated herein by reference in its entirety.

Saturation Mutagenesis ("Bashing")

The CRISPR systems described herein can be used for in situ saturating mutagenesis. In some embodiments, a pooled RNA guide library can be used to perform in situ saturating mutagenesis for particular genes or regulatory elements. Such methods can reveal critical minimal features and discrete vulnerabilities of these genes or regulatory elements (e.g., enhancers). These methods are described, e.g., in Canver et al., "BCL11A enhancer dissection by Cas9-mediated in situ saturating mutagenesis," *Nature,* 2015 Nov. 12; 527(7577):192-7, which is incorporated herein by reference in its entirety.

Therapeutic Applications

In some embodiments, the CRISPR systems described herein can be used to edit a target nucleic acid to modify the target nucleic acid (e.g., by inserting, deleting, or mutating one or more amino acid residues). For example, in some embodiments the CRISPR systems described herein comprise an exogenous donor template nucleic acid (e.g., a DNA molecule or an RNA molecule), which comprises a desirable nucleic acid sequence. Upon resolution of a cleavage event induced with the CRISPR system described herein, the molecular machinery of the cell can utilize the exogenous donor template nucleic acid in repairing and/or resolving the cleavage event. Alternatively, the molecular machinery of the cell can utilize an endogenous template in repairing and/or resolving the cleavage event. In some embodiments, the CRISPR systems described herein may be used to modify a target nucleic acid resulting in an insertion, a deletion, and/or a point mutation). In some embodiments, the insertion is a scarless insertion (i.e., the insertion of an intended nucleic acid sequence into a target nucleic acid resulting in no additional unintended nucleic acid sequence upon resolution of the cleavage event). Donor template nucleic acids may be double-stranded or single-stranded nucleic acid molecules (e.g., DNA or RNA). Methods of designing exogenous donor template nucleic acids are described, for example, in WO 2016094874, the entire contents of which is expressly incorporated herein by reference.

In another aspect, the disclosure provides the use of a system described herein in a method selected from the group consisting of RNA sequence specific interference; RNA sequence-specific gene regulation; screening of RNA, RNA products, lncRNA, non-coding RNA, nuclear RNA, or mRNA; mutagenesis; inhibition of RNA splicing; fluorescence in situ hybridization; breeding; induction of cell dormancy; induction of cell cycle arrest; reduction of cell growth and/or cell proliferation; induction of cell anergy; induction of cell apoptosis; induction of cell necrosis; induction of cell death; or induction of programmed cell death.

The CRISPR systems described herein can have various therapeutic applications. In some embodiments, the new CRISPR systems can be used to treat various diseases and disorders, e.g., genetic disorders (e.g., monogenetic diseases) or diseases that can be treated by nuclease activity (e.g., Pcsk9 targeting or BCL11a targeting). In some embodiments, the methods described here are used to treat a subject, e.g., a mammal, such as a human patient. The mammalian subject can also be a domesticated mammal, such as a dog, cat, horse, monkey, rabbit, rat, mouse, cow, goat, or sheep.

The methods can include the condition or disease being infectious, and wherein the infectious agent is selected from the group consisting of human immunodeficiency virus (HIV), herpes simplex virus-1 (HSV1), and herpes simplex virus-2 (HSV2).

In one aspect, the CRISPR systems described herein can be used for treating a disease caused by overexpression of RNAs, toxic RNAs and/or mutated RNAs (e.g., splicing defects or truncations). For example, expression of the toxic RNAs may be associated with the formation of nuclear inclusions and late-onset degenerative changes in brain, heart, or skeletal muscle. In some embodiments, the disorder is myotonic dystrophy. In myotonic dystrophy, the main pathogenic effect of the toxic RNAs is to sequester binding proteins and compromise the regulation of alternative splicing (see, e.g., Osborne et al., "RNA-dominant diseases," *Hum. Mol. Genet.,* 2009 Apr. 15; 18(8):1471-81). Myotonic dystrophy (dystrophia myotonica (DM)) is of particular interest to geneticists because it produces an extremely wide range of clinical features. The classical form of DM, which is now called DM type 1 (DM1), is caused by an expansion of CTG repeats in the 3'-untranslated region (UTR) of DMPK, a gene encoding a cytosolic protein kinase. The CRISPR systems as described herein can target overexpressed RNA or toxic RNA, e.g., the DMPK gene or any of the mis-regulated alternative splicing in DM1 skeletal muscle, heart, or brain.

The CRISPR systems described herein can also target trans-acting mutations affecting RNA-dependent functions that cause various diseases such as, e.g., Prader Willi syndrome, Spinal muscular atrophy (SMA), and Dyskeratosis congenita. A list of diseases that can be treated using the CRISPR systems described herein is summarized in Cooper et al., "RNA and disease," *Cell,* 136.4 (2009): 777-793, and WO 2016205764, each of which is incorporated herein by reference in its entirety.

The CRISPR systems described herein can also be used in the treatment of various tauopathies, including, e.g., primary and secondary tauopathies, such as primary age-related tauopathy (PART)/Neurofibrillary tangle (NFT)-predominant senile dementia (with NFTs similar to those seen in Alzheimer Disease (AD), but without plaques), dementia pugilistica (chronic traumatic encephalopathy), and progressive supranuclear palsy. A useful list of tauopathies and methods of treating these diseases are described, e.g., in WO 2016205764, which is incorporated herein by reference in its entirety.

The CRISPR systems described herein can also be used to target mutations disrupting the cis-acting splicing codes that can cause splicing defects and diseases. These diseases include, e.g., motor neuron degenerative disease that results from deletion of the SMN1 gene (e.g., spinal muscular atrophy), Duchenne Muscular Dystrophy (DMD), frontotemporal dementia, and Parkinsonism linked to chromosome 17 (FTDP-17), and cystic fibrosis.

The CRISPR systems described herein can further be used for antiviral activity, in particular, against RNA viruses. The effector proteins can target the viral RNAs using suitable RNA guides selected to target viral RNA sequences.

Furthermore, in vitro RNA sensing assays can be used to detect specific RNA substrates. The RNA targeting effector proteins can be used for RNA-based sensing in living cells. Examples of applications are diagnostics by sensing of, for examples, disease-specific RNAs.

A detailed description of therapeutic applications of the CRISPR systems described herein can be found, e.g., in U.S. Pat. No. 8,795,965, EP 3009511, WO 2016205764, and WO 2017070605, each of which is incorporated herein by reference in its entirety.

Applications in Plants

The CRISPR systems described herein have a wide variety of utility in plants. In some embodiments, the CRISPR systems can be used to engineer genomes of plants (e.g., improving production, making products with desired post-translational modifications, or introducing genes for producing industrial products). In some embodiments, the CRISPR systems can be used to introduce a desired trait to a plant (e.g., with or without heritable modifications to the genome) or regulate expression of endogenous genes in plant cells or whole plants.

In some embodiments, the CRISPR systems can be used to identify, edit, and/or silence genes encoding specific proteins, e.g., allergenic proteins (e.g., allergenic proteins in peanuts, soybeans, lentils, peas, green beans, and mung beans). A detailed description regarding how to identify, edit, and/or silence genes encoding proteins is described, e.g., in Nicolaou et al., "Molecular diagnosis of peanut and legume allergy," *Curr. Opin. Allergy Clin. Immunol.,* 11(3):

222-8 (2011) and WO 2016205764, each of which is incorporated herein by reference in its entirety.

Delivery of CRISPR Systems

Through this disclosure and knowledge in the art, the CRISPR systems described herein, components thereof, nucleic acid molecules thereof, or nucleic acid molecules encoding or providing components thereof can be delivered by various delivery systems such as vectors, e.g., plasmids or viral delivery vectors. The CRISPR effectors and/or any of the RNAs (e.g., RNA guides) disclosed herein can be delivered using suitable vectors, e.g., plasmids or viral vectors, such as adeno-associated viruses (AAV), lentiviruses, adenoviruses, and other viral vectors, or combinations thereof. An effector and one or more RNA guides can be packaged into one or more vectors, e.g., plasmids or viral vectors.

In some embodiments, vectors, e.g., plasmids or viral vectors, are delivered to the tissue of interest by, e.g., intramuscular injection, intravenous administration, transdermal administration, intranasal administration, oral administration, or mucosal administration. Such delivery may be either via one dose or multiple doses. One skilled in the art understands that the actual dosage to be delivered herein may vary greatly depending upon a variety of factors, including, but not limited to, the vector choices, the target cells, organisms, tissues, the general conditions of the subject to be treated, the degrees of transformation/modification sought, the administration routes, the administration modes, and the types of transformation/modification sought.

In certain embodiments, delivery is via adenoviruses, which can be one dose containing at least $1 \times 10^5$ particles (also referred to as particle units, pu) of adenoviruses. In some embodiments, the dose preferably is at least about $1 \times 10^6$ particles, at least about $1 \times 10^7$ particles, at least about $1 \times 10^8$ particles, and at least about $1 \times 10^9$ particles of the adenoviruses. The delivery methods and the doses are described, e.g., in WO 2016205764 and U.S. Pat. No. 8,454,972, each of which is incorporated herein by reference in its entirety.

In some embodiments, delivery is via plasmids. The dosage can be a sufficient number of plasmids to elicit a response. In some cases, suitable quantities of plasmid DNA in plasmid compositions can be from about 0.1 to about 2 mg. Plasmids will generally include (i) a promoter; (ii) a sequence encoding a nucleic acid-targeting CRISPR effector, operably linked to the promoter; (iii) a selectable marker; (iv) an origin of replication; and (v) a transcription terminator downstream of and operably linked to (ii). The plasmids can also encode the RNA components of a CRISPR complex, but one or more of these may instead be encoded on different vectors. The frequency of administration is within the ambit of the medical or veterinary practitioner (e.g., physician, veterinarian), or a person skilled in the art.

In another embodiment, delivery is via liposomes or lipofectin formulations or the like and can be prepared by methods known to those skilled in the art. Such methods are described, for example, in WO 2016205764, U.S. Pat. Nos. 5,593,972, 5,589,466, and 5,580,859, each of which is incorporated herein by reference in its entirety.

In some embodiments, delivery is via nanoparticles or exosomes. For example, exosomes have been shown to be particularly useful in delivery RNA.

Further means of introducing one or more components of the CRISPR systems described herein to a cell is by using cell-penetrating peptides (CPP). In some embodiments, a cell penetrating peptide is linked to a CRISPR effector. In some embodiments, a CRISPR effector and/or RNA guide is coupled to one or more CPPs for transportation into a cell (e.g., plant protoplasts). In some embodiments, the CRISPR effector and/or RNA guide(s) are encoded by one or more circular or non-circular DNA molecules that are coupled to one or more CPPs for cell delivery.

CPPs are short peptides of fewer than 35 amino acids derived either from proteins or from chimeric sequences capable of transporting biomolecules across cell membrane in a receptor independent manner.

CPPs can be cationic peptides, peptides having hydrophobic sequences, amphipathic peptides, peptides having proline-rich and anti-microbial sequences, and chimeric or bipartite peptides. Examples of CPPs include, e.g., Tat (which is a nuclear transcriptional activator protein required for viral replication by HIV type 1), penetratin, Kaposi fibroblast growth factor (FGF) signal peptide sequence, integrin f3 signal peptide sequence, polyarginine peptide Args sequence, Guanine rich-molecular transporters, and sweet arrow peptide. CPPs and methods of using them are

EXAMPLES

The invention is further described in the following examples, which do not limit the scope of the invention described in the claims.

Example 1—Identification of Components of CLUST.200916 CRISPR-Cas System

This protein family was identified using the computational methods described above. The CLUST.200916 system comprises single effectors associated with CRISPR systems found in uncultured metagenomic sequences collected from environments not limited to wastewater, freshwater bog forest soil, freshwater sediment, crustacean, microbial mat, rhizosphere, and soil environments (TABLE 6). Exemplary CLUST.200916 effectors include those shown in TABLES 6 and 7, below. Examples of direct repeat sequences and spacer lengths for these systems are shown in TABLE 8. Optionally, the system includes a tracrRNA that is contained in a non-coding sequence listed in TABLE 9.

TABLE 6

Representative CLUST.200916 Effector Proteins

| Source | Effector Accession | # Spacers | Effector Size | SEQ ID NO |
|---|---|---|---|---|
| wastewater-industrial wastewater-sediment | 3300013232\|Ga0170573__11130214__1\|M | 7 | 830 | 1 |
| aquatic-freshwater-bog forest soil | 3300004152\|Ga0062386__100000828__7\|M | 17 | 781 | 2 |
| aquatic-freshwater-bog forest soil | 3300027824\|Ga0209040__10001283__7\|P | 17 | 781 | 3 |
| aquatic-freshwater-sediment | 3300031746\|Ga0315293__10002498__12\|M | 5 | 790 | 4 |
| aquatic-freshwater-sediment | 3300031885\|Ga0315285__10000472__48\|P | 3 | 790 | 5 |
| aquatic-freshwater-sediment | 3300032053\|Ga0315284__10070270__2\|M | 6 | 790 | 6 |
| aquatic-freshwater-sediment | 3300032397\|Ga0315287__10017659__12\|M | 3 | 782 | 7 |
| aquatic-marine-worm burrow | 3300032136\|Ga0316201__10000001__22\|M | 9 | 774 | 8 |
| aquatic-marine-worm burrow | 3300032136\|Ga0316201__10000001__31\|P | 9 | 769 | 9 |
| crustacean metagenome | SRR3139690__618635__49\|M | 3 | 769 | 10 |
| crustacean metagenome | SRR3139691__122305__24\|P | 3 | 769 | 11 |
| microbial mat metagenome | SRR6448207__105533__15\|M | 2 | 812 | 12 |
| plants-rhizoplane-switchgrass rhizosphere | 3300005841\|Ga0068863__100056305__4\|P | 4 | 708 | 13 |
| rhizosphere metagenome | SRR5578837__7398444__24\|M | 6 | 666 | 14 |
| rhizosphere metagenome | SRR5578837__7398444__30\|P | 6 | 708 | 15 |
| soil metagenome | SRR3984957__953281__100\|P | 2 | 717 | 16 |
| soil metagenome | SRR5271166__784995__23\|P | 17 | 781 | 17 |
| soil metagenome | SRR7094831__6289921__1\|M | 2 | 769 | 18 |
| soil metagenome | SRR8554505__3408779__2\|M | 4 | 805 | 19 |
| soil metagenome | SRR8554505__3408779__1\|P | 4 | 801 | 20 |
| terrestrial-soil-forest soil | 3300001471\|JGI12712J15308__10000506__8\|P | 2 | 717 | 21 |
| terrestrial-soil-forest soil | 3300027908\|Ga0209006__10000286__53\|P | 2 | 717 | 22 |
| wastewater metagenome | SRR6837557__1806432__3\|M | 6 | 749 | 23 |
| wastewater metagenome | SRR6837562__732703__2\|P | 3 | 773 | 24 |
| wastewater metagenome | SRR6837569__616344__2\|P | 3 | 773 | 25 |
| wastewater metagenome | SRR6837570__202287__11\|M | 6 | 774 | 26 |
| wastewater metagenome | SRR6837571__88368__1\|P | 3 | 749 | 27 |
| wastewater metagenome | SRR6837575__1071878__1\|M | 2 | 767 | 28 |
| wastewater metagenome | SRR6837577__75829__4\|M | 5 | 749 | 29 | described, e.g., in Hallbrink et al., "Prediction of cell-penetrating peptides," *Methods Mol. Biol.*, 2015; 1324:39-58; Ramakrishna et al., "Gene disruption by cell-penetrating peptide-mediated delivery of Cas9 protein and guide RNA," *Genome Res.*, 2014 June; 24(6):1020-7; and WO 2016205764, each of which is incorporated herein by reference in its entirety.

Various delivery methods for the CRISPR systems described herein are also described, e.g., in U.S. Pat. No. 8,795,965, EP 3009511, WO 2016205764, and WO 2017070605, each of which is incorporated herein by reference in its entirety.

TABLE 7

Amino acid sequences of Representative
CLUST.200916 Effector Proteins

```
>3300013232|Ga0170573_11130214_1|M
[wastewater-industrial wastewater-sediment]
MPKIKKPTEISLLRKEVFPDLHFAKDRMRAASLVLKNEGREA
AIEYLRVNHEDKPPNFMPPAKTPYVALSRPLEQWPIAQASIA
IQKYIFGLTKDEFSATKKLLYGDKSTPNTESRKRWFEVTGVP
NFGYMSAQGLNAIFSGALARYEGVVQKVENRNKKRFEKLSEK
NQLLIEEGQPVKDYVPDTAYHTPETLQKLAENNHVRVEDLGD
MIDRLVHPPGIHRSIYGYQQVPPFAYDPDNPKGIILPKAYAG
YTRKPHDIIEAMPNRLNIPEGQAGYIPEHQRDKLKKGGRVKR
LRTTRVRVDATETVRAKAEALNAEKARLRGKEAILAVFQIEE
```

TABLE 7-continued

Amino acid sequences of Representative
CLUST.200916 Effector Proteins

DWALIDMRGLLRNVYMRKLIAAGELTPTTLLGYFTETLTLDP
RRTEATFCYHLRSEGALHAEYVRHGKNTRELLLDLTKDNEKI
ALVTIDLGQRNPLAAAIFRVGRDASGDLTENSLEPVSRMLLP
QAYLDQIKAYRDAYDSFRQNIWDTALASLTPEQQRQILAYEA
YTPDDSKENVLRLLLGGNVMPDDLPWEDMTKNTHYISDRYLA
DGGDPSKVWFVPGPRKRKKNAPPLKKPPKPRELVKRSDHNIS
HLSEFRPQLLKETRDAFEKAKIDTERGHVGYQKLSTRKDQLC
KEILNWLEAEAVRLTRCKTMVLGLEDLNGPFFNQGKGKVRGW
VSFFRQKQENRWIVNGFRKNALARAHDKGKYILELWPSWTSQ
TCPKCKHVHADNRHGDDFVCLQCGARLHADAEVATWNLAVVA
IQGHSLPGPVREKSNDRKKSGSARKSKKANESGKVVGAWAAQ
ATPKRATSKKETGTARNPVYNPLETQASCPAP (SEQ ID
NO: 1)

>3300004152|Ga0062386_100000828_7|M
[aquatic-freshwater-bog forest soil]
MRQPAEKTAFQVFRQEVIGTQKLSGGDAKTAGRLYKQGKMEA
AREWLLKGARDDVPNFQPPAKCLVVAVSHPFEEWDISKTNH
DVQAYIYAQPLQAEGHLNGLSEKWEDTSADQHKLWFEKTGVP
DRGLPVQAINKIAKAAVNRAFGVVRKVENRNEKRRSRDNRIA
EHNRENGLTEVVREAPEVATNADGFLLHPPGIDPSILSYASV
SPVPYNSSKHSFVRLPEEYQAYNVEPDAPIPQFVVEDRFAIP
PGQPGYVPEWQRLKCSTNKHRRMRQWSNQDYKPKAGRRAKPL
EFQAHLTRERAKGALLVVMRIKEDWVVFDVRGLLRNVEWRKV
LSEEAREKLTLKGLLDLFTGDPVIDTKRGIVTFLYKAEITKI
LSKRTVKTKNARDLLLRLTEPGEDGLRREVGLVAVDLGQTHP
IAAAIYRIGRTSAGALESTVLHRQGLREDQKEKLKEYRKRHT
ALDSRLRKEAFETLSVEQQKEIVTVSGSGAQITKDKVCNYLG
VDPSTLPWEKMGSYTHFISDDFLRRGGDPNIVHFDRQPKKGK
VSKKSQRIKRSDSQWVGRMRPRLSQETAKARMEADWAAQNEN
EEYKRLARSKQELARWCVNTLLQNTRCITQCDEIVWIEDLNV
KSLHGKGAREPGWDNFFTPKTENRWFIQILHKTFSELPKHR
GEHVIEGCPLRTSITCPACSYCDKNSRNGEKFVCVACGATFH
ADFEVATYNLVRLATTGMPMPKSLERQGGGEKAGGARKARKK
AKQVEKIVVQANANVTMNGASLHSP (SEQ ID NO: 2)

>3300027824|Ga0209040_10001283_7|P
[aquatic-freshwater-bog forest soil]
MRQPAEKTAFQVFRQEVIGTQKLSGGDAKTAGRLYKQGKMEA
AREWLLKGARDDVPPNFQPPAKCLVVAVSHPFEEWDISKTNH
DVQAYIYAQPLQAEGHLNGLSEKWEDTSADQHKLWFEKTGVP
DRGLPVQAINKIAKAAVNRAFGVVRKVENRNEKRRSRDNRIA
EHNRENGLTEVVREAPEVATNADGFLLHPPGIDPSILSYASV
SPVPYNSSKHSFVRLPEEYQAYNVEPDAPIPQFVVEDRFAIP
PGQPGYVPEWQRLKCSTNKHRRMRQWSNQDYKPKAGRRAKPL
EFQAHLTRERAKGALLVVMRIKEDWVVFDVRGLLRNVEWRKV
LSEEAREKLTLKGLLDLFTGDPVIDTKRGIVTFLYKAEITKI
LSKRTVKTKNARDLLLRLTEPGEDGLRREVGLVAVDLGQTHP
IAAAIYRIGRTSAGALESTVLHRQGLREDQKEKLKEYRKRHT
ALDSRLRKEAFETLSVEQQKEIVTVSGSGAQITKDKVCNYLG
VDPSTLPWEKMGSYTHFISDDFLRRGGDPNIVHFDRQPKKGK
VSKKSQRIKRSDSQWVGRMRPRLSQETAKARMEADWAAQNEN
EEYKRLARSKQELARWCVNTLLQNTRCITQCDEIVVVIEDLN
VKSLHGKGAREPGWDNFFTPKTENRWFIQILHKTFSELPKHR
GEHVIEGCPLRTSITCPACSYCDKNSRNGEKFVCVACGATFH
ADFEVATYNLVRLATTGMPMPKSLERQGGGEKAGGARKARKK
AKQVEKIVVQANANVTMNGASLHSP (SEQ ID NO: 3)

>3300031746|Ga0315293_10002498_12|M
[aquatic-freshwater-sediment]
MTPSPQIARLVETPLAAALKAHHPGKKFRSDYLKKAGKILKD
QGVEAAMAHLDGKDQAEPPNFKPPAKCRIVARSREFSEWPIV
KASVEIQKYIYGLTLEERKACDPGKSSASHKAWFAKTGVNTF
GYSSVQGFNLIFGHTLGRYDGVLVKTENLNKKRAEKNERFRA
KALAEGRAEPVCPPLVTATNDTGQDVTLEDGRVVRPGQLLQP
PGINPNIYAYQQVSPKAYVPGIIELPEEFQGYSRDPNAVILP
LVPRDRLSIPKGQPGYVPEPHREGLTGRKDRRMRRYYETERG
TKLKRPPLTAKGRADKANEALLVVVRIDSDWVVMDVRGLLRN
ARWRRLVSKEGITLNGLLDLFTGDPVLNPKDCSVSRDTGDPV
NDPRHGVVTFCYKLGVVDVCSKDRPIKGFRTKEVLERLTSSG
TVGMVSIDLGQTNPVAAAVSRVTKGLQAETLETFTLPDDLLG
KVRAYRAKTDRMEEGFRRNALRKLTAEQQAEITRYNDATEQQ
AKALVCSTYGIGPEEVPWERMTSNTTYISDHILDHGGDPDTV
FFMATKRGQNKPTLHKRKDKAWGQKFRPAISVETRLARQAAE
WELRRASLEFQKLSVWKTELCRQAVNYVMERTKKRTQCDVII
PVIEDLPVPLFHGSGKRDPGWANFFVHKRENRWFIDGLHKAF
SELGKHRGIYVFEVCPQRTSITCPKCGHCDPDNRDGEKFVCL TABLE 7-continued Amino acid sequences of Representative
CLUST.200916 Effector Proteins SCQATLHADLDVATTNLVRVALTGKVMPRSERSGDAQTPGPA
RKARTGKIKGSKPTSAPQGATQTDAKAHLSQTGV
(SEQ ID NO: 4)

>3300031885|Ga0315285_10000472_48|P
[aquatic-freshwater-sediment]
MTPSPQIARLVETPLAAALKAHHPGKKFRSDYLKKAGKILKD
QGVEAAMAHLDGKDQAEPPNFKPPAKCRIVARSREFSEWPIV
KASVEIQKYIYGLTLEERKACDPGKSSASHKAWFAKTGVNTF
GYSSVQGFNLIFGHTLGRYDGVLVKTENLNKKRAEKNERFRA
KALAEGRAEPVCPPLVTATNDTGQDVTLEDGRVVRPGQLLQP
PGINPNIYAYQQVSPKAYVPGIIELPEEFQGYSRDPNAVILP
LVPRDRLSIPKGQPGYVPEPHREGLTGRKDRRMRRYYETERG
TKLKRPPLTAKGRADKANEALLVVVRIDSDWVVMDVRGLLRN
ARWRRLVSKEGITLNGLLDLFTGDPVLNPKDCSVSRDTGDPV
NDPRHGVVTFCYKLGVVDVCSKDRPIKGFRTKEVLERLTSSG
TVGMVSIDLGQTNPVAAAVSRVTKGLQAETLETFTLPDDLLG
KVRAYRAKTDRMEEGFRRNALRKLTAEQQAEITRYNDATEQQ
AKALVCSTYGIGPEEVPWERMTSNTTYISDHILDHGGDPDTV
FFMATKRGQNKPTLHKRKDKAWGQKFRPAISVETRLARQAAE
WELRRASLEFQKLSVWKTELCRQAVNYVMERTKKRTQCDVII
PVIEDLPVPLFHGSGKRDPGWANFFVHKRENRWFIDGLHKAF
SELGKHRGIYVFEVCPQRTSITCPKCGHCDPDNRDGEKFVCL
SCQATLNADLDVATTNLVRVALTGKVMPRSERSGDAQTPGPA
RKARTGKIKGSKPTSAPQGATQTDAKAHLSQTGV
(SEQ ID NO: 5)

>3300032053|Ga0315284_1_0070270_2|M
[aquatic-freshwater-sediment]
MTPSPQIARLVETPLAAALKAHHPGKKFRSDYLKKAGKILKD
QGVEAAMAHLDGKDQAEPPNFKPPAKCRIVARSREFSEWPIV
KASVEIQKYIYGLTLEERKACDPGKSSASHKAWFAKTGVNTF
GYSSVQGFNLIFGHTLGRYDGVLVKTENLNKKRAEKNERFRA
KALAEGRAEPVCPPLVTATNDTGQDVTLEDGRVVRPGQLLQP
PGINPNIYAYQQVSPKAYVPGIIELPEEFQGYSRDPNAVILP
LVPRDRLSIPKGQPGYVPEPHREGLTGRKDRRMRRYYETERG
TKLKRPPLTAKGRADKANEALLVVVRIDSDWVVMDVRGLLRN
ARWRRLVSKEGITLNGLLDLFTGDPVLNPKDCSVSRDTGDPV
NDPRHGVVTFCYKLGVVDVCSKDRPIKGFRTKEVLERLTSSG
TVGMVSIDLGQTNPVAAAVSRVTKGLQAETLETFTLPDDLLG
KVRAYRAKTDRMEEGFRRNALRKLTAEQQAEITRYNDATEQQ
AKALVCSTYGIGPEEVPWERMTSNTTYISDHILDHGGDPDTV
FFMATKRGQNKPTLHKRKDKAWGQKFRPAISVETRLARQAAE
WELRRASLEFQKLSVWKTELCRQAVNYVMERTKKRTQCDVII
PVIEDLPVPLFHGSGKRDPGWANFFVHKRENRWFIDGLHKAF
SELGKHRGIYVFEVCPQRTSITCPKCGHCDPDNRDGEKFVCL
SCQATLNADLDVATTNLVRVALTGKVMPRSERSGDAQTPGPA
RKARTGKIKGSKPTSAPQGATQTDAKAHLSQTGV
(SEQ ID NO: 6)

>3300032397|Ga0315287_10017659_12|M
[aquatic-freshwater-sediment]
MKTEKPKTALTLLREEVFPGKKYRLDVLKEAGKKLSTKGREA
TIEFLTGKDEERPQNFQPPAKTSIVAQSRPFDQWPIVQVSLA
VQKYIYGLTQSFEEANKKALYGETGKAISTESRRAWFEATGV
DNFGFTAAQGINPIFSQAVARYEGVIKKVENRNEKKLKKLTK
KNLLRLESGEEIEDFEPEATFNEEGRLLQPPGANPNIYCYQQ
ISPRIYDPSDPKGVILPQIYAGYDRKPEDIISAGVPNRLAIP
EGQPGYIPEHQRAGLKTQGRIRCRASVEAKARAAILAVVHLG
EDWVVLDLRGLLRNVYWRKLASPGTLTLKGLLDFFTGGPVLD
ARRGIATFSYTLKSAAAVHAENTYKGKGTREVLLKLTENNSV
ALVTVDLGQRNPLAAMIARVSRTSQGDLTYPESVEPLTRLFL
PDPFLEEVRKYRSSYDALRLSIREAAIASLTPEQQAEIRYIE
KFSAGDAKKNVAEVFGIDPTQLPWDAMTPRTTYISDLFLRMG
GDRSRVFFEVPPKKAKKAPKKPPKKPAGPRIVKRTDGMIARL
REIRPRLSAETNKAFQEARWEGERSNVAFQKLSVRRKQFART
VVNHLVQTAQKMSRCDTVVLGIEDLNVPFFHGRGKYQPGWEG
FFRQKKENRWLINDMHKALSERGPHRGGYVLELTPFWTSLRC
PKCGHTDSANRDGDDFVCVKCGAKLHSDLEVATANLALVAIT
GQSIPRPPREQSSGKKSTGTARMKKTSGETQGKGSKACVSEA
LNKIEQGTARDPVYNPLNSQVSCPAP (SEQ ID NO: 7)

>3300032136|Ga0316201_10000001_22|M
[aquatic-marine-worm burrow]
MYNPDMKKPNNIRRIREEHFEGLCFGKDVLTKAGKIYEKDGE
EAAIDFLMGKDEEDPPNFKPPAKTTIVAQSRPFDQWPIYQVS
QAVQERVFAYTEEEFNASKEALFSGDISSKSRDFWFKTNNIS TABLE 7-continued Amino acid sequences of Representative
CLUST.200916 Effector Proteins

```
DQGIGAQGLNTILSHAFSRYSGVIKKVENRNKKRLKKLSKKN
QLKIEEGLEILEFKPDSAFNENGLLAQPPGINPNIYGYQAVT
PFVFDPDNPGDVILPKQYEGYSRKPDDIIEKGPSRLDIPKGQ
PGYVPEHQRKNLKKKGRVRLYRRTPPKTKALASILAVLQIGK
DWVLFDMRGLLRSVYMREAATPGQISAKDLLDTFTGCPVLNT
RTGEFTFCYKLRSEGALHARKIYTKGETRTLLTSLTSENNTI
ALVTVDLGQRNPAAIMISRLSRKEELSEKDIQPVSRRLLPDR
YLNELKRYRDAYDAFRQEVRDEAFTSLCPEHQEQVQQYEALT
PEKAKNLVLKHFFGTHDPDLPWDDMTSNTHYIANLYLERGGD
PSKVFFTRPLKKDSKSKKPRKPTKRTDASISRLPEIRPKMPE
DARKAFEKAKWEIYTGHEKFPKLAKRVNQLCREIANWIEKEA
KRLTLCDTVVVGIEDLSLPPKRGKGKFQETWQGFFRQKFENR
WVIDTLKKAIQNRAHDKGKYVLGLAPYWTSQRCPACGFIHKS
NRNGDHFKCLKCEALFHADSEVATWNLALVAVLGKGITNPDS
KKPSGQKKTGTTRKKQIKGKNKGKETVNVPPTTQEVEDIIAF
FEKDDETVRNPVYKPTGT (SEQ ID NO: 8)

>3300032136|Ga0316201_10000001_31|P
[aquatic-marine-worm burrow]
MKKPNNIRRIREEHFEGLCFGKDVLTKAGKIYEKDGEEAAID
FLMGKDEEDPPNFKPPAKTTIVAQSRPFDQWPIYQVSQAVQE
RVFAYTEEEFNASKEALFSGDISSKSRDFWFKTNNISDQGIG
AQGLNTILSHAFSRYSGVIKKVENRNKKRLKKLSKKNQLKIE
EGLEILEFKPDSAFNENGLLAQPPGINPNIYGYQAVTPFVFD
PDNPGDVILPKQYEGYSRKPDDIIEKGPSRLDIPKGQPGYVP
EHQRKNLKKKGRVRLYRRTPPKTKALASILAVLQIGKDWVLF
DMRGLLRSVYMREAATPGQISAKDLLDTFTGCPVLNTRTGEF
TFCYKLRSEGALHARKIYTKGETRTLLTSLTSENNTIALVTV
DLGQRNPAAIMISRLSRKEELSEKDIQPVSRRLLPDRYLNEL
KRYRDAYDAFRQEVRDEAFTSLCPEHQEQVQQYEALTPEKAK
NLVLKHFFGTHDPDLPWDDMTSNTHYIANLYLERGGDPSKVF
FTRPLKKDSKSKKPRKPTKRTDASISRLPEIRPKMPEDARKA
FEKAKWEIYTGHEKFPKLAKRVNQLCREIANWIEKEAKRLTL
CDTWVGIEDLSLPPKRGKGKFQETWQGFFRQKFENRWVIDTL
KKAIQNRAHDKGKYVLGLAPYWTSQRCPACGFIHKSNRNGD
HFKCLKCEALFHADSEVATWNLALVAVLGKGITNPDSKKPSG
QKKTGTTRKKQIKGKNKGKETVNVPPTTQEVEDIIAFFEKDD
ETVRNPVYKPTGT (SEQ ID NO: 9)

>SRR3139690_618635_49|M
[crustacean metagenome]
MEKSNTRKVIDEHFKGLLFRKDILQKAGKIYKKEGEEATISF
LMGKDEEAPPNFQPPAKTSIVAQSRPFNQWPIYQVSEAIQKR
VFGYTEDEFYAQKKALFGEGGASSKSRDAWFKANGISDRGIV
AQGLNMILGHAFARYEGVIQKVENRNKKRLDKLSKKNQLRVK
EGLEVYEFTPESAFIDGSGLLAQPPGISPNIYGYQAIAPFVF
DPDDPRDIVLPKEYEGYSRKPDDIIEKGPNRLDIPKGQPGYV
PEHQRSGLKKGGRVWLYRRATTAKAKALASILGVLQIGEDWVL
FDMRGLLRNAYMRKALTPGKASARDLLGTFTEYPVLNARTGE
FTFCYKLRSGGSLYARQVYKKGKTREILTELTSEGKTIALVT
VDLGQRNPVAAMVARVSRDGELSESCIDPVSRFLLPEYYARQ
IQKYRDDFDAFRQEVWDEAFASMPPEYQEQIRQYEAYTPDQA
KSLVLKHFFGDEVSLDDLPWEKMTSNTCYISNLYIKRGGDPS
RVTFTPSPGKNSKKPRKPVKRTDSGISRLPEVRPGLPKDTRD
AFEEAKWDVYRGHEKFPKLAKRVNQLCREIANWLEKEAGRIT
LCDTVVFGIEDMGAKFCGKGKGKFQETWEGFFRQKSENRWVM
NLLKSSIHMRAHDKGRYVLELAPFYTSQRCPKCGYIHKNNRK
GDRFECLSCGALLHADSEVATWNLAVVAILGKALKKPSLKCE
KSSGQKKARTSRKIQIKVGNKAETSSSPQENGEVLAPPEENS
GTSRDPVYNPSGT (SEQ ID NO: 10)

>SRR3139691_122305_24|P
[crustacean metagenome]
MEKSNTRKVIDEHFKGLLFRKDILQKAGKIYKKEGEEATISF
LMGKDEEAPPNFQPPAKTSIVAQSRPFNQWPIYQVSEAIQKR
VFGYTEDEFYAQKKALFGEGGASSKSRDAWFKANGISDRGIV
AQGLNMILGHAFARYEGVIQKVENRNKKRLDKLSKKNQLRVK
EGLEVYEFTPESAFIDGSGLLAQPPGISPNIYGYQAIAPFVF
DPDDPRDIVLPKEYEGYSRKPDDIIEKGPNRLDIPKGQPGYV
PEHQRSGLKKGGRVWLYRRATTAKAKALASILGVLQIGEDWVL
FDMRGLLRNAYMRKALTPGKASARDLLGTFTEYPVLNARTGE
FTFCYKLRSGGSLYARQVYKKGKTREILTELTSEGKTIALVT
VDLGQRNPVAAMVARVSRDGELSESCIDPVSRFLLPEYYARQ
IQKYRDDFDAFRQEVWDEAFASMPPEYQEQIRQYEAYTPDQA
KSLVLKHFFGDEVSLDDLPWEKMTSNTCYISNLYIKRGGDPS
RVTFTPSPGKNSKKPRKPVKRTDSGISRLPEVRPGLPKDTRD
AFEEAKWDVYRGHEKFPKLAKRVNQLCREIANWLEKEAGRIT
```

TABLE 7-continued

Amino acid sequences of Representative
CLUST.200916 Effector Proteins

```
LCDTVVFGIEDMGAKFCGKGKGKFQETWEGFFRQKSENRWVM
NLLKSSIHMRAHDKGRYVLELAPFYTSQRCPKCGYIHKNNRK
GDRFECLSCGALLHADSEVATWNLAVVAILGKALKKPSLKCE
KSSGQKKARTSRKIQIKVGNKAETSSSPQENGEVLAPPEENS
GTSRDPVYNPSGT (SEQ ID NO: 11)

>SRR6448207_105533_15|M
[microbial mat metagenome]
MDMLDTETNYATETPSQQQDYSPKPPKKDRRAPKGFSKKARP
EKKPPKPITLFTQKHFSGVRFLKRVIRDASKILKLSESRTIT
FLEQAIERDGSAPPDVTPPVHNTIMAVTRPFEEWPEVILSKA
LQKHCYALTKKIKIKTWPKKGPGKKCLAAWSARTKIPLIPGQ
VQATNGLFDRIGSIYDGVEKKVTNRNANKKLEYDEAIKEGRN
PAVPEYETAYNIDGTLINKPGYNPNLYITQSRTPRLITEADR
PLVEKILWQMVEKKTQSRNQARRARLEKAAHLQGLPVPKFVP
EKVDRSQKIEIRIIDPLDKIEPYMPQDRMAIKASQDGHVPYW
QRPFLSKRRNRRVRAGWGKQVSSIQAWLTGALLVIVRLGNEA
FLADIRGALRNAQWRKLLKPDATYQSLFNLFTGDPVVNTRTN
HLTMAYREGVVDIVKSRSFKGRQTREHLLTLLGQGKTVAGVS
FDLGQKHAAGLLAAHFGLGEDGNPVFTPIQACFLPQRYLDSL
TNYRNRYDALTLDMRRQSLLALTPAQQQEFADAQRDPGGQAK
RACCLKLNLNPDEIRWDLVSGISTMISDLYIERGGDPRDVHQ
QVETKPKGKRKSEIRILKIRDGKWAYDFRPKIADETRKAQRE
QLWKLQKASSEFERLSRYKINIARAIANWALQWGRELSGCDI
VIPVLEDLNVGSKFFDGKGKWLLGWDNRFTPKKENRWFIKVL
HKAVAELAPHRGVPVYEVMPHRTSMTCPACHYCHPTNREGDR
FECQSCHVVKNTDRDVAPYNILRVAVEGKTLDRWQAEKKPQA
EPDRPMILIDNQES (SEQ ID NO: 12)

>330000584|Ga0068863_100056305_4|P
[plants-rhizoplane-switchgrass rhizosphere]
MSKTKELNDYQEALARRLPGVRHQKSVRRAARLVYDRQGEDA
MVAFLDGKEVDEPYTLQPPAKCHILAVSRPIEEWPIARVTMA
VQEHVYALPVHEVEKSRPETTEGSRSAWFKNSGVSNHGVTHA
QTLNAILKNAYNVYNGVIKKVENRNAKKRDSLAAKNKSRERK
GLPHFKADPPELATDEQGYLLQPPSPNSSVYLVQQHLRTPQI
DLPSGYTGPVVDPRSPIPSLIPIDRLAIPPGQPGYVPLHDRE
KLTSNKHRRMKLPKSLRAQGALPVCFRVFDDWAVVDGRGLLR
HAQYRRLAPKNVSIAELLELYTGDPVIDIKRNLMTFRFAEAV
VEVTARKIVEKYHNKYLLKLTEPKGKPVREIGLVSIDLNVQR
LIALAIYRVHQTGESQLALSPCLHREILPAKGLGDFDKYKSK
FNQLTEEILTAAVQTLTSAQQEEYQRYVEESSHEAKADLCLK
YSITPHELAWDKMTSSTQYISRWLRDHGWNASDFTQITKGRK
KVERLWSDSRWAQELKPKLSNETRRKLEDAKHDLQRANPEWQ
RLAKRKQEYSRHLANTVLSMAREYTACETVVIAIENLPMKGG
FVDGNGSRESGWDNFFTHKKENRWMIKDIHKALSDLAPNRGV
HVLEVNPQYTSQTCPECGHRDKANRDPIQRERFCCTHCGAQR
HADLEVATHNIAMVATTGKSLTGKSLAPQRLQEAAE
(SEQ ID NO: 13)

>SRR5578837_7398444_24|M
[rhizosphere metagenome]
MVAFLDGKEVDEPYTLQPPAKCHILAVSRPIEEWPIARVTMA
VQEHVYALPVHEVEKSRPETTEGSRSAWFKNSGVSNHGVTHA
QTLNAILKNAYNVYNGVIKKVENRNAKKRDSLAAKNKSRERK
GLPHFKADPPELATDEQGYLLQPPSPNSSVYLVQQHLRTPQI
DLPSGYTGPVVDPRSPIPSLIPIDRLAIPPGQPGYVPLHDRE
KLTSNKHRRMKLPKSLRAQGALPVCFRVFDDWAVVDGRGLLR
HAQYRRLAPKNVSIAELLELYTGDPVIDIKRNLMTFRFAEAV
VEVTARKIVEKYHNKYLLKLTEPKGKPVREIGLVSIDLNVQR
LIALAIYRVHQTGESQLALSPCLHREILPAKGLGDFDKYKSK
FNQLTEEILTAAVQTLTSAQQEEYQRYVEESSHEAKADLCLK
YSITPHELAWDKMTSSTQYISRWLRDHGWNASDFTQITKGRK
KVERLWSDSRWAQELKPKLSNETRRKLEDAKHDLQRANPEWQ
RLAKRKQEYSRHLANTVLSMAREYTACETVVIAIENLPMKGG
FVDGNGSRESGWDNFFTHKKENRWMIKDIHKALSDLAPNRGV
HVLEVNPQYTSQTCPECGHRDKANRDPIQRERFCCTHCGAQR
HADLEVATHNIAMVATTGKSLTGKSLAPQRLQEAAE (SEQ
ID NO: 14)

>SRR5578837_7398444_30|P
[rhizosphere metagenome]
MSKTKELNDYQEALARRLPGVRHQKSVRRAARLVYDRQGEDA
MVAFLDGKEVDEPYTLQPPAKCHILAVSRPIEEWPIARVTMA
VQEHVYALPVHEVEKSRPETTEGSRSAWFKNSGVSNHGVTHA
QTLNAILKNAYNVYNGVIKKVENRNAKKRDSLAAKNKSRERK
GLPHFKADPPELATDEQGYLLQPPSPNSSVYLVQQHLRTPQI
```

TABLE 7-continued

Amino acid sequences of Representative
CLUST.200916 Effector Proteins

DLPSGYTGPVVDPRSPIPSLIPIDRLAIPPGQPGYVPLHDRE
KLTSNKHRRMKLPKSLRAQGALPVCFRVFDDWAVVDGRGLLR
HAQYRRLAPKNVSIAELLELYTGDPVIDIKRNLMTFRFAEAV
VEVTARKIVEKYHNKYLLKLTEPKGKPVREIGLVSIDLNVQR
LIALAIYRVHQTGESQLALSPCLHREILPAKGLGDFDKYKSK
FNQLTEEILTAAVQTLTSAQQEEYQRYVEESSHEAKADLCLK
YSITPHELAWDKMTSSTQYISRWLRDHGWNASDFTQITKGRK
KVERLWSDSRWAQELKPKLSNETRRKLEDAKHDLQRANPEWQ
RLAKRKQEYSRHLANTVLSMAREYTACETVVIAIENLPMKGG
FVDGNGSRESGWDNFFTHKKENRWMIKDIHKALSDLAPNRGV
HVLEVNPQYTSQTCPECGHRDCKANRDPIQRERFCCTHCGAQR
HADLEVATHNIAMVATTGKSLTGKSLAPQRLQEAAE
(SEQ ID NO: 15)

>SRR3984957_953281_100|P
[soil metagenome]
MIKPTVSQFLTPGFKLIRNHSRTAGLKLKNEGEEACKKFVRE
NEIPKDECPNFQGGPAIANIIAKSREFTEWEIYQSSLAIQEV
IFTLPKDKLPEPILKEEWRAQWLSEHGLDTVPYKEAAGLNLI
IKNAVNTYKGVQVKVDNKNKNNLAKINRKNEIAKLNGEQEIS
FEEIKAFDDKGYLLQKPSPNKSIYCYQSVSPKPFITSKYHNV
NLPEEYIGYYRKSNEPIVSPYQFDRLRIPIGEPGYVPKWQYT
FLSKKENKRRKLSKRIKNVSPILGIICIKKDWCVFDMRGLLR
TNHWKKYHKPTDSINDLFDYFTGDPVIDTKANVVRFRYKMEN
GIVNYKPVREKKGKELLENICDQNGSCKLATVDVGQNNPVAI
GLFELKKVNGELTKTLISRHPTPIDFCNKITAYRERYDKLES
SIKLDAIKQLTSEQKIEVDNYNNNFTPQNTKQIVCSKLNINP
NDLPWDKMISGTHFISEKAQVSNKSEIYFTSTDKGKTKDVMK
SDYKWFQDYKPKLSKEVRDALSDIEWRLRRESLEFNKLSKSR
EQDARQLANWISSMCDVIGIENLVKKNNFFGGSGKREPGWDN
FYKPKKENRWWINAIHKALTELSQNKGKRVILLPAMRTSITC
PKCKYCDSKNRNGEKFNCLKCGIELNADIDVATENLATVAIT
AQSMPKPTCERSGDAKKPVRARKAKAPEFHDKLAPSYTVVLR
EAV (SEQ ID NO: 16)

>SRR5271166_784995_23|P
[soil metagenome]
MRQPAEKTAFQVFRQEVIGTQKLSGGDAKTAGRLYKQGKMEA
AREWLLKGARDDVPPNFQPPAKCLVVAVSHPFEEWDISKTNH
DVQAYIYAQPLQAEGHLNGLSEKWEDTSADQHKLWFEKTGVP
DRGLPVQAINKIAKAAVNRAFGVVRKVENRNEKRRSRDNRIA
EHNRENGLTEVVREAPEVATNADGFLLHPPGIDPSILSYASV
SPVPYNSSKHSFVRLPEEYQAYNVEDPAPIPQFVVEDRFAIP
PGQPGYVPEWQRLKCSTNKHRRMRQWSNQDYKPKAGRRAKPL
EFQAHLTRERAKGALLVVMRIKEDWVVFDVRGLLRNVEWRKV
LSEEAREKLTLKGLLDLFTGDPVIDTKRGIVTFLYKAEITKI
LSKRTVKTKNARDLLLRLTEPGEDGLRREVGLVAVDLGQTHP
IAAAIYRIGRTSAGALESTVLHRQGLREDQKEKLKEYRKRHT
ALDSRLRKEAFETLSVEQQKEIVTVSGSGAQITKDKVCNYLG
VDPSTLPWEKMGSYTHFISDDFLRRGGDPNIVHFDRQPKKGK
VSKKSQRIKRSDSQWVGRMRPRLSQETAKARMEADWAAQNEN
EEYKRLARSKQELARWCVNTLLQNTRCITQCDEIVVVIEDLN
VKSLHGKGAREPGWDNFFTPKTENRWFIQILHKTFSELPKHR
GEHVIEGCPLRTSITCPACSYCDKNSRNGEKFVCVACGATFH
ADFEVATYNLVRLATTGMPMPKSLERQGGGEKAGGARKARKK
AKQVEKIVVQANANVTMNGASLHSP (SEQ ID NO: 17)

>SRR7094831_6289921_1|M
[soil metagenome]
MEKHKTKLSIIMKEFFPGERFPKNVLMQIGKKITNNKDGKET
IDVKEKEDVVSFLTGKGSKKLLDFQPPAKALIVAKSRPFEEW
PIYQASKIFQEYIYGLPHNQLSIPGTSKSEHKLWLEKIGLNI
GTYKDVQGLNLIFRHTKNIYEGVIKKVENKNKKNKEKIEIKN
KFEKEHGFLLTPFEEETAFDDNGKLKNPPGINNSIYCYSQVS
PEATKSTTKLDNVPSIYLGYYRDIDTNIKIEYINRLSIPKGD
PGYIPLWQHELLSKKENNTRRQRKWYSNNRMKRVKRKGVSKY
SDEQINQARLQDAILGKISIGEDWVLFDMRGLLRNLHWRKLV
PSQGFSPKEILEQFTGDPVIDPVRNVITFIYKDGLAHKEEIV
LTKKAPDLLCKLTLNNPIGIVSIDVGQTHPQSAKFSLLKLED
DKLVAECKDRQFLPDYLLNKLFAYRERSDQLRGEINQLAMQS
LSEEHQKEFNDLKIENDPTAVRIRIEKQLGIDFNNLPINDMI
YDRTTYIADAYLSIPGVDKLLVMLGTSSKKKYDSRIVKDFFK
KVSKEAREALKVAFGEIQKLHPGYKKLSKSLQQWARECVNFT
HKYANKITGCTNIVFVIENLKNIRKRNGSGKRAKGYDNFFVY
KKENRWVMNALQKAYIDLATHKGINIIEIQAARTSITCPKCN TABLE 7-continued Amino acid sequences of Representative
CLUST.200916 Effector Proteins CQDKNNRKGDQFNCVKCNHQANTDLEIATDNIELVALNGKGM
PKIDCERSSGEENAVGARKGKKTRKIKEIQETDKNIKMDNAG
GDLLKNNRSQTAA (SEQ ID NO: 18)

>SRR8554505_3408779_2|M
[soil metagenome]
MDPGMTITEGKPQEEPTELAKLLREHYPGKKLSKKDLLMAGK
ILAGKVAKTRPEGLVEWLADKVVDEPPNFSPPAKANIVAMSR
PFEEWPIAKATLAIESYVFGMTVDERNRLCPKETEEDRDEWF
RVTGVSNYGFTSAQGLNHIFKNAFNTFDGVVTRGSNANEKKR
KEIEAQNEKRAERGEAPVPFEPRPVLTEDGHLVHPPGSKSGL
RLNKIQLYQQVTDKGRGFRGQVELPLEYEDYVRDPEAPIPFG
VPRDRLCIPEGEPGYVPEWQRPLLSTKKKRRRRGWGPAGPEQ
VRAKAKAALLWYLPLGDDWVVLDVRGLLRNVRWRGLAPEGLS
LNGLMELFTGYPIIHNKTGDVTFKFCPEVAGVRSHEPLKKAE
GRKLLLHLTKPRGEFHPRVGMVAIDLGQTNPAAFSVSRLHQV
EVEREVEVKRKLPDGETEKVTELRMVGEVRQTILSTHFLPDE
LVAEIKRYRNLYSAMNERHHAEAVLRLPKEAQDVYHAWQNFS
ADEAKRQLCAKYGLDPAKMPWDQMTSSTMHISKAVLAAGHDR
SEVHRMVKKKGKKEREVKKRDRAWVSDFKPTLPEEVWRPKRE
HLLDIQRESEEYRRLTIFKQQLVRRCVNHVVKVGERESQCEK
LVFAIEDLNVKGFFFGKGKNLPGWEGFFQHKRENRFIIREFH
RAFSELGPHRGYYVLEANPGYTSCTCPDCRHPDPVSRNGERF
KCTRCGATHHADSEVATYNIAQVAIMGKALPRPKKQKKPKRE
RSGAVKKAETARKRNGRKSNGKGGQRQEAPLLRPPVRGTARE
PVANASC (SEQ ID NO: 19)

>SRR8554505_3408779_1|P
[soil metagenome]
MTITEGKPQEEPTELAKLLREHYPGKKLSKKDLLMAGKILAG
KVAKTRPEGLVEWLADKVVDEPPNFSPPAKANIVAMSRPFEE
WPIAKATLAIESYVFGMTVDERNRLCPKETEEDRDEWFRVTG
VSNYGFTSAQGLNHIFKNAFNTFDGVVTRGSNANEKKRKEIE
AQNEKRAERGEAPVPFEPRPVLTEDGHLVHPPGSKSGLRLNK
IQLYQQVTDKGRGFRGQVELPLEYEDYVRDPEAPIPFGVPRD
RLCIPEGEPGYVPEWQRPLLSTKKKRRRRGWGPAGPEQVRAK
AKAALLWYLPLGDDWVVLDVRGLLRNVRWRGLAPEGLSLNGL
MELFTGYPIIHNKTGDVTFKFCPEVAGVRSHEPLKKAEGRKL
LLHLTKPRGEFHPRVGMVAIDLGQTNPAAFSVSRLHQVEVER
EVEVKRKLPDGETEKVTELRMVGEVRQTILSTHFLPDELVAE
IKRYRNLYSAMNERHHAEAVLRLPKEAQDVYHAWQNFSADEA
KRQLCAKYGLDPAKMPWDQMTSSTMHISKAVLAAGHDRSEVH
RMVKKKGKKEREVKKRDRAWVSDFKPTLPEEVWRPKREHLLD
IQRESEEYRRLTIFKQQLVRRCVNHVVKVGERESQCEKLVFA
IEDLNVKGFFFGKGKNLPGWEGFFQHKRENRFIIREFHRAFS
ELGPHRGYYVLEANPGYTSCTCPDCRHPDPVSRNGERFKCTR
CGATHHADSEVATYNIAQVAIMGKALPRPKKQKKPKRERSGA
VKKAETARKRNGRKSNGKGGQRQEAPLLRPPVRGTAREPVAN
ASC (SEQ ID NO: 20)

>3300001471|JGI12712J15308_10000506_8|P
[terrestrial-soil-forest soil]
MIKPTVSQFLTPGFKLIRNHSRTAGLKLKNEGEEACKKFVRE
NEIPKDECPNFQGGPAIANIIAKSREFTEWEIYQSSLAIQEV
IFTLPKDKLPEPILKEEWRAQWLSEHGLDTVPYKEAAGLNLI
IKNAVNTYKGVQVKVDNKNKNNLAKINRKNEIAKLNGEQEIS
FEEIKAFDDKGYLLQKPSPNKSIYCYQSVSPKPFITSKYHNV
NLPEEYIGYYRKSNEPIVSPYQFDRLRIPIGEPGYVPKWQYT
FLSKKENKRRKLSKRIKNVSPILGIICIKKDWCVFDMRGLLR
TNHWKKYHKPTDSINDLFDYFTGDPVIDTKANVVRFRYKMEN
GIVNYKPVREKKGKELLENICDQNGSCKLATVDVGQNNPVAI
GLFELKKVNGELTKTLISRHPTPIDFCNKITAYRERYDKLES
SIKLDAIKQLTSEQKIEVDNYNNNFTPQNTKQIVCSKLNINP
NDLPWDKMISGTHFISEKAQVSNKSEIYFTSTDKGKTKDVMK
SDYKWFQDYKPKLSKEVRDALSDIEWRLRRESLEFNKLSKSR
EQDARQLANWISSMCDVIGIENLVKKNNFFGGSGKREPGWDN
FYKPKKENRWWINAIHKALTELSQNKGKRVILLPAMRTSITC
PKCKYCDSKNRNGEKFNCLKCGIELNADIDVATENLATVAIT
AQSMPKPTCERSGDAKKPVRARKAKAPEFHDKLAPSYTVVLR
EAV (SEQ ID NO: 21)

>3300027908|Ga0209006_10000286_53|P
[terrestrial-soil-forest soil]
MIKPTVSQFLTPGFKLIRNHSRTAGLKLKNEGEEACKKFVRE
NEIPKDECPNFQGGPAIANIIAKSREFTEWEIYQSSLAIQEV
IFTLPKDKLPEPILKEEWRAQWLSEHGLDTVPYKEAAGLNLI
IKNAVNTYKGVQVKVDNKNKNNLAKINRKNEIAKLNGEQEIS TABLE 7-continued Amino acid sequences of Representative
CLUST.200916 Effector Proteins FEEIKAFDDKGYLLQKPSPNKSIYCYQSVSPKPFITSKYHNV
NLPEEYIGYYRKSNEPIVSPYQFDRLRIPIGEPGYVPKWQYT
FLSKKENKRRKLSKRIKNVSPILGIICIKKDWCVFDMRGLLR
TNHWKKYHKPTDSINDLFDYFTGDPVIDTKANVVRFRYKMEN
GIVNYKPVREKKGKELLENICDQNGSCKLATVDVGQNNPVAI
GLFELKKVNGELTKTLISRHPTPIDFCNKITAYRERYDKLES
SIKLDAIKQLTSEQKIEVDNYNNNFTPQNTKQIVCSKLNINP
NDLPWDKMISGTHFISEKAQVSNKSEIYFTSTDKGKTKDVMK
SDYKWFQDYKPKLSKEVRDALSDIEWRLRRESLEFNKLSKSR
EQDARQLANWISSMCDVIGIENLVKKNNFFGGSGKREPGWDN
FYKPKKENRWWINAIHKALTELSQNKGKRVILLPAMRTSITC
PKCKYCDSKNRNGEKFNCLKCGIELNADIDVATENLATVAIT
AQSMPKPTCERSGDAKKPVRARKAKAPEFHDKLAPSYTVVLR
EAV (SEQ ID NO: 22)

>SRR6837557_1806432_3|M
[wastewater metagenome]
MPDKQTPKDTKDKPESPVSAFLKKHFPGKHFFGHAGTLARLL
KTKGEEVARDYAAKKVRDEKLDFRPPAKCQIVAWSRDFSEWP
IARASATIQQHVSGLTKEDFERFDPGKSKAAHDAWFQESGVD
CHGYRHVQGLNLIFANARDYYEGVVKKVENKNAQRRRRVEAL
NARRAEEGEEPIPLDVEESPFGEDGRLAHPPGVNPSIYVYQA
VSPRPLKKSDLETVVLPPAYAGYDRDPSAPIPVMGDRLSIPE
GQRGHVPAWQRDQLSPDKHRRMRAWYSAANTKPKPGRTSVPD
AAAIERARAEGALLVVIRIGEDWVVLDARGLLRNARWRRIAD
KEISLDGLLDLFTGDPVIDSKRNVVTFIYKAEHATATSRKVV
HRKASRKALLDMTSPGEDGLPREVALASVDLGQTNAAAVRYA
RVHREGDDITSECLVRELLPDEISRDIARYRAASDRMEAEIR
EAAIAGLPEPMQAEVRAADASSPEAARAAVVALVGDGLPWEK
MSSATYHISDALVALGRGREAYLLSKSKDGEEKSVQRSDYGW
SRHLRPRLSEETRKAMNEAVWSIKDAHEGYQKLSRRKTEIGR
RAANHVVRRLRKLAKTDKVAIAVEDLNVRMFHGGGSRSTGWD
NFFVAKRENLWFVQVLHKSFCDLALHRGEVVIEVDTARTSQT
CPACGHCDPKNRSSVDREVFRCVVCGRTFHADLEVATFNIER
VALTGESMPKGEEGARERGGGGKSRGGARGRNKLK (SEQ
ID NO: 23)

>SRR6837562_732703_2|P
[wastewater metagenome]
MSEITDLLKANFKGKTFKSADMRRMAGRILKKSGAQAVIKYLS
DKGAVDPPDFRPPAKCNIIAQSRPFDEWPICKASMAIQQHIY
GLTKNEFDESSPGTSSASHEQWFAKTGVDTHGFTHVQGLNLI
FQHAKKRYEGVIKKVENYNEKERKKFEGINERRSKEGMPLLE
PRLRTAFGDDGKFAEKPGVNPSIYLYQQTSPRPYDKTKHPYV
HAPFELKEITTIPTQDDRLKIPFGAPGHVPEKHRSQLSMAKH
KRRRAWYALSQNKPRPPKDGSKGRRSVRDLADLKAASLADAI
PLVSRVGFDWVVIDGRGLLRNLRWRKLAHEGMTVEEMLGFFS
GDPVIDPRRNVATFIYKAEHATVKSRKPIGGAKRAREELLKA
TASSDGVIRQVGLISVDLGQTNPVAYEISRMHQANGELVAEH
LEYGLLNDEQVNSIQRYRAAWDSMNESFRQKAIESLSMEAQD
EIMQASTGAAKRTREAVLTMFGPNATLPWSRMSSNTTCISDA
LIEVGKEEETNFVTSNGPRKRTDAQWAAYLRPRVNPETRALL
NQAVWDLMKRSDEYERLSKRKLEMARQCVNFVVARAEKLTQC
NNIGIVLENLVVRNFHGSGRRESGWEGFFEPKRENRWFMQVL
HKAFSDLAQHRGVMVFEVHPAYSSQTCPACRYVDPKNRSSED
RERFKCLKCGRSFNADREVATFNIREIARTGVGLPKPDCERS
RDVQTPGTARKSGRSLKSNKNPSEPKHVLRSKTRSNITSTLS
QNEPLATDQKTAPKTGP (SEQ ID NO: 24)

>SRR6837569_616344_2|P
[wastewater metagenome]
MSEITDLLKANFKGKTFKSADMRRMAGRILKKSGAQAVIKYLS
DKGAVDPPDFRPPAKCNIIAQSRPFDEWPICKASMAIQQHIY
GLTKNEFDESSPGTSSASHEQWFAKTGVDTHGFTHVQGLNLI
FQHAKKRYEGVIKKVENYNEKERKKFEGINERRSKEGMPLLE
PRLRTAFGDDGKFAEKPGVNPSIYLYQQTSPRPYDKTKHPYV
HAPFELKEITTIPTQDDRLKIPFGAPGHVPEKHRSQLSMAKH
KRRRAWYALSQNKPRPPKDGSKGRRSVRDLADLKAASLADAI
PLVSRVGFDWVVIDGRGLLRNLRWRKLAHEGMTVEEMLGFFS
GDPVIDPRRNVATFIYKAEHATVKSRKPIGGAKRAREELLKA
TASSDGVIRQVGLISVDLGQTNPVAYEISRMHQANGELVAEH
LEYGLLNDEQVNSIQRYRAAWDSMNESFRQKAIESLSMEAQD
EIMQASTGAAKRTREAVLTMFGPNATLPWSRMSSNTTCISDA
LIEVGKEEETNFVTSNGPRKRTDAQWAAYLRPRVNPETRALL
NQAVWDLMKRSDEYERLSKRKLEMARQCVNFVVARAEKLTQC
NNIGIVLENLVVRNFHGSGRRESGWEGFFEPKRENRWFMQVL
HKAFSDLAQHRGVMVFEVHPAYSSQTCPACRYVDPKNRSSED TABLE 7-continued Amino acid sequences of Representative
CLUST.200916 Effector Proteins RERFKCLKCGRSFNADREVATFNIREIARTGVGLPKPDCERS
RGVQTTGTARNPGRSLKSNKNPSEPKHVLRSKTRSNITSTLS
QNEPLATDQKTAPKTGP (SEQ ID NO: 25)

>SRR6837570_202287_1|M
[wastewater metagenome]
MTLAELRDKYFYKIKFRKIDLRQAGKILKREGEEAARRYLDE
QRESPPEGNFCPPAKCQIVGWSRPVGEWPISIASANMQQYVY
DLPKVERDKMTKFDLTSEEYAVWFAQTGIDNAGYTHVQGLNK
AFKNAFRTYDGVIKKVANRNEKRKLKAEKAAERALLRGREPE
VFVPEEALDERGFLKEKPGINRSIWTYQQVSPRPYDPTRDLK
IKEKLAQRRGRSEPVAYADRLAIPEGQPGHVPQWQRDAGLLS
ANKHRRMRAHYSWHNNKPRPNRKTSRTAEECRDLGAPEAILA
VIEIGEDWLAVDLRGLLRSAYYRRILSPKEVPTAAELLKLFT
GDPTIDPVREVVTFIYKEDVVPVLSTKPLRERQGLKKILDLT
APVNGVRDFIAIASIDLGVTNPAAMAYSRVRQTAAGGFDIEE
LAREFLPAAVLDQLAHHRQQWDEMEDRFRQQAVRALPEADQA
ECEAVFGHTGDQYAADIARALQLDGAALPWAQMSSRTTYITD
ALLARGGSPATYHTFVHSERKKGKKKKGKKKKGQEGAKPELK
IKEKPSDFDWAYDFARKQLSKEVRERFNKALWEIKRTSPDYA
RMSKQKRDLGRQVANHVVKQARKLAGTQTLVVVVENINVFF
HGTGKRYGVWHQCFLPKKENRWFVQTIHKALTEIAMHKGIYV
IEVSPYYTSLHCPKCEHIDSGNRCGEQFRCLKCGYTAHADLE
VAPYNIRLVALRGAGLRKVETEAEVEAVDEAPAAASVEKPRK
RRKSASGEAATFEAAPLA (SEQ ID NO: 26)

>SRR6837571_88368_1|P
[wastewater metagenome]
MPDKQTPKDTKDKPESPVSAFLKKHFPGKHFFGHAGTLARLL
KTKGEEVARDYAAKKVRDEKLDFRPPAKCQIVAWSRDFSEWP
IARASATIQQHVSGLTKEDFERFDPGKSKAAHDAWFQESGVD
CHGYRHVQGLNLIFANARDYYEGVVKKVENKNAQRRRRVEAL
NARRAEEGEEPIPLDVEESPFGEDGRLAHPPGVNPSIYVYQA
VSPRPLKKSDLETVVLPPAYAGYDRDPSAPIPVMGDRLSIPE
GQRGHVPAWQRDQLSPDKHRRMRAWYSAANTKPKPGRTSVPD
AAAIERARAEGALLVVIRIGEDWVVLDARGLLRNARWRRIAD
KEISLDGLLDLFTGDPVIDSKRNVVTFIYKAEHATATSRKVV
HRKASRKALLDMTSPGEDGLPREVALASVDLGQTNAAAVRYA
RVHREGDDITSECLVRELLPDEISRDIARYRAASDRMEAEIR
EAAIAGLPEPMQAEVRAADASSPEAARAAVVALVGDGLPWEK
MSSATYHISDALVALGRGREAYLLSKSKDGEEKSVQRSDYGW
SRHLRPRLSEETRKAMNEAVWSIKDAHEGYQKLSRRKTEIGR
RAANHVVRRLRKLAKTDKVAIAVEDLNVRMFHGGGSRSTGWD
NFFVAKRENRWFVQVLHKSFCDLALHRGEVVIEVDPARTSQT
CPACGHCDPKNRSSVDREVFRCVVCGRTFHADLEVATFNIER
VALTGESMPKGEEGARERGGGGKSRGGARGRNKLK (SEQ
ID NO: 27)

>SRR6837575_1071878_1|M
[wastewater metagenome]
MSEITDLLKANFKGKTFKSADMRRMAGRILKKSGAQAVIKYLS
DKGAVDPPDFRPPAKCNIIAQSRPFDEWPICKASMAIQQHIY
GLTKNEFDESSPGTSSASHEQWFAKTGVDTHGFTHVQGLNLI
FQHAKKRYEGVIKKVENYNEKERKKFEGINERRSKEGMPLLE
PRLRTAFGDDGKFAEKPGVNPSIYLYQQTSPRPYDKTKHPYV
HAPFELKEITTIPTQDDRLKIPFGAPGHVPEKHRSQLSMAKH
KRRRAWYALSQNKPRPPKDGSKGRRSVRDLADLKAASLADAI
PLVSRVGFDWVVIDGRGLLRNLRWRKLAHEGMTVEEMLGFFS
GDPVIDPRRNVATFIYKAEHATVKSRKPIGGAKRAREELLKA
TASSDGVIRQVGLISVDLGQTNPVAYEISRMHQANGELVAEH
LEYGLLNDEQVNSIQRYRAAWDSMNESFRQKAIESLSMEAQD
EIMQASTGAAKRTREAVLTMFGPNATLPWSRMSSNTTCISDA
LIEVGKEEETNFVTSNGPRKRTDAQWAAYLRPRVNPETRALL
NQAVWDLMKRSDEYERLSKRKLEMARQCVNFVVARAEKLTQC
NNIGIVLENLVVRNFHGSGRRESGWEGFFEPKRENRWFMQVL
HKAFSDLAQHRGVMVFEVHPAYSSQTCPACRYVDPKNRSSED
RERFKCLKCGRSFNADREVATFNIREIARTGVGLPKPDRERS
RDVQTPGTARKSGRSLKSQDNPSEPKRVLQSKTRKKITSTET
QNEPLATDLKT (SEQ ID NO: 28)

>SRR6837577_75829_4:M
[wastewater metagenome]
MPDKQTPKDTKDKPESPVSAFLKKHFPGKHFFGHAGTLARLL
KTKGEEVARDYAAKKVRDEKLDFRPPAKCQIVAWSRDFSEWP
IARASATIQQHVSGLTKEDFERFDPGKSKAAHDAWFQESGVD
CHGYRHVQGLNLIFANARDYYEGVVKKVENKNAQRRRRVEAL
NARRAEEGEEPIPLDVEESPFGEDGRLAHPPGVNPSIYVYQA TABLE 7-continued Amino acid sequences of Representative
CLUST.200916 Effector Proteins VSPRPLKKSDLETVVLPPAYAGYDRDPSAPIPVMGDRLSIPE
GQRGHVPAWQRDQLSPDKHRRMRAWYSAANTKPKPGRTSVPD
AAAIERARAEGALLVVIRIGEDWVVLDARGLLRNARWRRIAD
KEISLDGLLDLFTGDPVIDSKRNVVTFIYKAEHATATSRKVV
HRKASRKALLDMTSPGEDGLPREVALASVDLGQTNAAAVRYA
RVHREGDDITSECLVRELLPDEISRDIARYRAASDRMEAEIR
EAAIAGLPEPMQAEVRAADASSPEAARAAVVALVGDGLPWEK
MSSATYHISDALVALGRGREAYLLSKSKDGEEKSVQRSDYGW
SRHLRPRLSEETRKAMNEAVWSIKDAHEGYQKLSRRKTEIGR
RAANHVVRRLRKLAKTDKVAIAVEDLNVRMFHGGGSRSTGWD
NFFVAKRENRWFVQVLHKSFCDLALHRGEVVIEVDPARTSQT
CPACGHCDPKNRSSVDREVFRCVVCGRTFHADLEVATFNIER
VALTGESMPKGEEGARERGGGGKSRGGARGRNKLK (SEQ
ID NO: 29)

TABLE 8

Nucleotide sequences of Representative
CLUST.200916 Direct Repeats and
Spacer Lengths

| CLUST.164091 Effector Protein Accession | Direct Repeat Nucleotide Sequence | Spacer Length(s) |
|---|---|---|
| 3300013232\|Ga0170573_111 30214_1\|M (SEQ ID NO: 1) | CAACCTAAAC GATGGCTCGA TTCGTCGAGA C (SEQ ID NO: 30) GTCTCGACGA ATCGAGCCAT CGTTTAGGTT G (SEQ ID NO: 122) | 25-38 |
| 3300004152\|Ga0062386_100 000828_7\|M (SEQ ID NO: 2) | GTAGAAGACC TCGCTGATTG CTCGGTGCGC CGAGAC (SEQ ID NO: 31) GTCTCGGCGC ACCGAGCAAT CAGCGAGGTC TTCTAC (SEQ ID NO: 123) | 34-39 |
| 3300027824\|Ga0209040_100 01283_7\|P (SEQ ID NO: 3) | GTAGAAGACC TCGCTGATTG CTCGGTGCGC CGAGAC (SEQ ID NO: 31) GTCTCGGCGC ACCGAGCAAT CAGCGAGGTC TTCTAC (SEQ ID NO: 123) | 34-39 |
| 3300031746\|Ga0315293_100 02498_12\|M (SEQ ID NO: 4) | GGTTGAACCC TCAACAGATT GCTCGGTAAG CCGAGAC (SEQ ID NO: 32) | 35-43 |

TABLE 8-continued

Nucleotide sequences of Representative
CLUST.200916 Direct Repeats and
Spacer Lengths

| CLUST.164091 Effector Protein Accession | Direct Repeat Nucleotide Sequence | Spacer Length(s) |
|---|---|---|
| | GTCTCGGCTT ACCGAGCAAT CTGTTGAGGG TTCAACC (SEQ ID NO: 124) | |
| 3300031885\|Ga0315285_100 00472_48\|P (SEQ ID NO: 5) | GGTTGAACCC TCAACAGATT GCTCGGTAAG CCGAGAC (SEQ ID NO: 32) GTCTCGGCTT ACCGAGCAAT CTGTTGAGGG TTCAACC (SEQ ID NO: 124) | 35-36 |
| 3300032053\|Ga0315284_100 70270_2\|M (SEQ ID NO: 6) | GTTGAACCCT CAACAGATTG CTCGGTAAGC CGAGAC (SEQ ID NO: 33) GTCTCGGCTT ACCGAGCAAT CTGTTGAGGG TTCAAC (SEQ ID NO: 125) | 36-44 |
| 3300032397\|Ga0315287_100 17659_12\|M (SEQ ID NO: 7) | CTTGAAATCC TGTCAGATTG CTCCCTTCGG GGAGAC (SEQ ID NO: 34) GTCTCCCCGA AGGGAGCAAT CTGACAGGAT TTCAAG (SEQ ID NO: 126) | 36-37 |
| 3300032136\|Ga0316201_100 00001_22\|M (SEQ ID NO: 8) | GCTGGAAGAC TCAATGATGG CTCCTTACGA GGAGAC (SEQ ID NO: 35) GTCTCCTCGT AAGGAGCCAT CATTGAGTCT TCCAGC (SEQ ID NO: 127) | 30-46 |
| 3300032136\|Ga0316201_100 00001_31\|P (SEQ ID NO: 9) | GCTGGAAGAC TCAATGATGG CTCCTTACGA GGAGAC (SEQ ID NO: 35) GTCTCCTCGT AAGGAGCCAT CATTGAGTCT TCCAGC (SEQ ID NO: 127) | 30-46 |

TABLE 8-continued

Nucleotide sequences of Representative
CLUST.200916 Direct Repeats and
Spacer Lengths

| CLUST.164091 Effector Protein Accession | Direct Repeat Nucleotide Sequence | Spacer Length(s) |
|---|---|---|
| SRR3139690_ 618635_49\|M (SEQ ID NO: 10) | CTTAGAATAC TCAATGATGG CTCCTTACGA GGAGAC (SEQ ID NO: 36) GTCTCCTCGT AAGGAGCCAT CATTGAGTAT TCTAAG (SEQ ID NO: 128) | 36-37 |
| SRR3139691_ 122305_24\|P (SEQ ID NO: 11) | CTTAGAATAC TCAATGATGG CTCCTTACGA GGAGAC (SEQ ID NO: 36) GTCTCCTCGT AAGGAGCCAT CATTGAGTAT TCTAAG (SEQ ID NO: 128) | 36-37 |
| SRR6448207_ 105533_15\|M (SEQ ID NO: 12) | ATCGGCAGCT GGTCCACCTT GG (SEQ ID NO: 37) CCAAGGTGGA CCAGCTGCCG AT (SEQ ID NO: 129) | 20-22 |
| 3300005841\| Ga0068863_100 056305_4\|P (SEQ ID NO: 13) | GTCTCTCCGT AGAGAGCAAT CGTTATCCAT TGAGAG (SEQ ID NO: 38) CTCTCAATGG ATAACGATTG CTCTCTACGG AGAGAC (SEQ ID NO: 130) | 36-38 |
| SRR5578837_ 7398444_24\|M (SEQ ID NO: 14) | GTCTCTCCGT AGAGAGCAAT CGTTATCCAT TGAGAG (SEQ ID NO: 38) CTCTCAATGG ATAACGATTG CTCTCTACGG AGAGAC (SEQ ID NO: 130) | 36-46 |
| SRR5578837_ 7398444_30\|P (SEQ ID NO: 15) | GTCTCTCCGT AGAGAGCAAT CGTTATCCAT TGAGAG (SEQ ID NO: 38) CTCTCAATGG | 36-46 |

TABLE 8-continued

Nucleotide sequences of Representative
CLUST.200916 Direct Repeats and
Spacer Lengths

| CLUST.164091 Effector Protein Accession | Direct Repeat Nucleotide Sequence | Spacer Length(s) |
|---|---|---|
| | ATAACGATTG CTCTCTACGG AGAGAC (SEQ ID NO: 130) | |
| SRR3984957_ 953281_100\|P (SEQ ID NO: 16) | CTTTCAAGAC TAATAGATTG CTCCTTACGA GGAGAC (SEQ ID NO: 39) GTCTCCTCGT AAGGAGCAAT CTATTAGTCT TGAAAG (SEQ ID NO: 131) | 36-38 |
| SRR5271166_ 784995_23\|P (SEQ ID NO: 17) | GTAGAAGACC TCGCTGATTG CTCGGTGCGC CGAGAC (SEQ ID NO: 31) GTCTCGGCGC ACCGAGCAAT CAGCGAGGTC TTCTAC (SEQ ID NO: 123) | 34-39 |
| SRR7094831_ 6289921_1\|M (SEQ ID NO: 18) | GTAGAAAGGT TTACTAATTG CTCCTTACGA GGAGAC (SEQ ID NO: 40) GTCTCCTCGT AAGGAGCAAT TAGTAAACCT TTCTAC (SEQ ID NO: 132) | 39 |
| SRR8554505_ 3408779_2\|M (SEQ ID NO: 19) | CCCGGAAGAC CAGATGATGG CTCGATCAGT CGAGAC (SEQ ID NO: 41) GTCTCGACTG ATCGAGCCAT CATCTGGTCT TCCGGG (SEQ ID NO: 133) | 35-50 |
| SRR8554505_ 3408779_1\|P (SEQ ID NO: 20) | CCCGGAAGAC CAGATGATGG CTCGATCAGT CGAGAC (SEQ ID NO: 41) GTCTCGACTG ATCGAGCCAT CATCTGGTCT TCCGGG (SEQ ID NO: 133) | 35-50 |

TABLE 8-continued

| Nucleotide sequences of Representative CLUST.200916 Direct Repeats and Spacer Lengths | | |
|---|---|---|
| CLUST.164091 Effector Protein Accession | Direct Repeat Nucleotide Sequence | Spacer Length(s) |
| 3300001471\| JGI12712J15308_ 10000506_8\|P (SEQ ID NO: 21) | CTTTCAAGAC TAATAGATTG CTCCTTACGA GGAGAC (SEQ ID NO: 39) GTCTCCTCGT AAGGAGCAAT CTATTAGTCT TGAAAG (SEQ ID NO: 131) | 36-38 |
| 3300027908\| Ga0209006_100 00286_53\|P (SEQ ID NO: 22) | CTTTCAAGAC TAATAGATTG CTCCTTACGA GGAGAC (SEQ ID NO: 39) GTCTCCTCGT AAGGAGCAAT CTATTAGTCT TGAAAG (SEQ ID NO: 131) | 36-38 |
| SRR6837557_ 1806432_3\|M (SEQ ID NO: 23) | GTCGAGACCG ATGACGAGTG CGCGGTGCGC CGCGAC (SEQ ID NO: 42) GTCGCGGCGC ACCGCGCACT CGTCATCGGT CTCGAC (SEQ ID NO: 134) | 36-48 |
| SRR6837562_ 732703_2\|P (SEQ ID NO: 24) | CCTGCAAGGG ATCCAAATTG CTCTGTTCGC AGAGAC (SEQ ID NO: 43) GTCTCTGCGA ACAGAGCAAT TTGGATCCCT TGCAGG (SEQ ID NO: 135) | 36-42 |
| SRR6837569_ 616344_2\|P (SEQ ID NO: 25) | CCTGCAAGGG ATCCAAATTG CTCTGTTCGC AGAGAC (SEQ ID NO: 43) GTCTCTGCGA ACAGAGCAAT TTGGATCCCT TGCAGG (SEQ ID NO: 135) | 38-39 |
| SRR6837570_ 202287_11\|M (SEQ ID NO: 26) | GCGCCAACGA CCTCTGATTG TCCGGTACGC CGGAAC (SEQ ID NO: 44) | 36-38 |

TABLE 8-continued

| Nucleotide sequences of Representative CLUST.200916 Direct Repeats and Spacer Lengths | | |
|---|---|---|
| CLUST.164091 Effector Protein Accession | Direct Repeat Nucleotide Sequence | Spacer Length(s) |
| | GTTCCGGCGT ACCGGACAAT CAGAGGTCGT TGGCGC (SEQ ID NO: 136) | |
| SRR6837571_ 88368_1\|P (SEQ ID NO: 27) | GTCGAGAGCG ATGACGAGTG CGCGGTGCGC CGCGAC (SEQ ID NO: 45) GTCGCGGCGC ACCGCGCACT CGTCATCGCT CTCGAC (SEQ ID NO: 137) | 38-41 |
| SRR6837575_ 1071878_1\|M (SEQ ID NO: 28) | CCATCAATGG ATCCAAATTG CTCTGTACGC AGAGAC (SEQ ID NO: 46) GTCTCTGCGT ACAGAGCAAT TTGGATCCAT TGATGG (SEQ ID NO: 138) | 36-37 |
| SRR6837577_ 75829_4\|M (SEQ ID NO: 29) | GTCGAGAGCG ATGACGAGTG CGCGGTGCGC CGCGAC (SEQ ID NO: 45) GTCGCGGCGC ACCGCGCACT CGTCATCGCT CTCGAC (SEQ ID NO: 137) | 36-50 |

TABLE 9

| Non-coding Sequences of Representative CLUST.200916 Systems |
|---|
| >3300005841\|Ga0068863_100056305_4\|P (Effector of SEQ ID NO: 13) GAGGATAAGCTCGCGTTCGGCCGCCAGCTCTTCTGGGCTCAT GTCGGCGAGCTTGTGGGCTACCACAGCGAACGGCTTGCTCAT GGTCTGCAAGTGTTCTGGCAGGTGGGCGTACGTGAAAAATTG GAGCGTGTGGTTTGTGTCAATCATGACGTTGACTACACCGAC GTGACATCTCTGTGCCTTTGGTTTTGGACGGGCACCGGTGGT GTAGGGTTGGACAGCAGCCGTGTCGCAGCGGGGGAGGTCTTG GGGAGAATGGTTCTCTTTGGGGCCTTTTCTATTGGTGGTCTT GGTTCGCCATCCTCGTCCATACCAACCCTCCAAGTATTTCCC GCGGAGGATAACACGAAATGCTGCGATGGCGTCTCTCCGTAG AGAGCAATCGTTACTCGTTGAGATATGTACAGCAACTTAGAC ACTGGGTGCTGGGCCAGCTGTCTCCCCGTAGGGAGCAATCGT GCGCGAACACGATCACTTGTCTCGTACGGCTACCACGGCTCC AGCAGAAGCTCAATCATACTCACCACATACACCGCAGATTGC GAGAGGGACGGAAGAAAAACCATGAACTGTGAAAAATAGTAC AAAGATTCTGTGCAGATTAAACTACTGAGCTTTTGATATTAT |

TABLE 9-continued

Non-coding Sequences of Representative
CLUST.200916 Systems

```
TGGTTTTCGAGCGGGTAACAGCCTTTGTGCACAACCAAACCA
CTCGCATTTCAAACCTTCGTATGGCCCAGGAGCGGTGTAATG
CAGCTTCGGTTGCCCACCGAGGTGGGACTTCAGGAGCAAGGA
CATGTCGAAAACCAAAGAACTCAATGACTATCAAGAAGCGCT
AGCGCGTCGCCTTCCTGGTGTCCGACACCAAAAGTCGGTACG
CCGAGCTGCGCGACTCGTCTACGACAGACAAGGGGAAGATGC
CATGGTCGCCTTCCTCGACGGCAAACGTGAGCGTTTTTGCTG
CACCCACTGCGGAGCACAGCGACACGCTGACCTCGAAGTGGC
GACACACAACATCGCCATGGTAGCCACCACAGGCAAATCTCT
AACAGGCAAATCGTTGGCGCCCACAACGACTCCAGGAAGCTGC
AGAGTAACGATTGCTCCCTATG
(SEQ ID NO: 47)
```

```
>3300027824|Ga0209040_10001283_7|P
(Effector of SEQ ID NO: 3)
CTTGATGCCGTCGACGACGAAGCTCGCCGGCAGCGCCCGGCG
CTCGCCCTCGGGGTACTACTGGCTCGGCCAGCCGCCCCAGAA
GAGAACGAAATTCCCACGGACAGTGACTTCGTAGAGATCGGC
GTGCGTAGGGCCTTCGGCGGGCATGGAGAACTCCCTGGTGAA
GACGCCTTTAGGAGCTAGGCGGCAGGATTGCCGCTGTTTTCA
CGCTTGTGCGTGACCTCGACCTCGAACGCGGAGGACACGCTA
ACACGTAAGAATCTAACTTGGCAAGTACAGGCTTTCTTTTCT
TGATCCCGAATTAGATGCGTAGTAGCCGTGAAATAGGAGACA
AGATCCTCATGCGTCAGCCCGCGGAGAAGACCGCGTTCCAAG
TCTTTCGTCAGGAAGTGATCGGGACACAGAAACTATCGGGAG
GCGATGCCAAGACTGCCGGACGGCTCTACAAGCAGGGAAAGA
TGGAAGCAGCACGTGAGTGGTTGCTCAAAGGT
(SEQ ID
NO: 48)
```

```
>3300013232|Ga0170573_11130214_1|M
(Effector of SEQ ID NO: 1)
CGCATCTGCAACGGTCTACTCGATGCTGGATTGATTCCTGCG
GTGTAGAATAGCATAACCAGGGTCCGCTGGACTATCCAGCAA
CGACGGCTCGATACGTCGAGCCGATGGAGAAGTCATGCCAAA
GATCAAGAAACCGACTGAGATTTCCCTGCTACGCAAGGAGGT
GTTCCCTGACCTCCACTTTGCCAAGGACCGGATGCGTGCTGC
ATCCTTGGTCCTTAAGAATGAGGGCCGGGAAGCCGCCATCGA
GTACCTCCGGGTGAAT
(SEQ ID NO: 49)
```

```
>3300027908|Ga0209006_10000286_48|M
(Effector of SEQ ID NO: 22)
GGAATGAGTGGAGAAGGAGTGGTTTGTAAAGGTACTTGGAAT
AAGAAAAAGAATAGACCAAACATGTTCAAGATTAAGTCTAAT
GCTTGGATTGGAAGACTTAAAGAATACTGCAACGGTAATATG
GACCTAATGGCCAGACTACTATAATGTTTGATCTTAAAGCAG
AAATTGTATAAATAATGATATCAAAAATGATTAAGCCTACGG
TAAGTCAGTTTCTTACGCCTGGATTTAAGTTAATTCGGAATC
ACTCAAGAACTGCTGGTCTAAAACTAAAAAATGAAGGCGAAG
AGGCTTGTAAGAAATTCGTTCGAGAAAATGAAATTCCTGTCG
CTATAACGGCCCAGTCGATGCCGAAACCAACTTGCGAGCGCT
CGGGCGACGCTAAAAAGCCTGTCCGTGCTCGCAAGGCTAAAG
CACCGGAATTTCACGATAAATTGGCACCAAGCTATACGGTTG
TGCTAAGGGAGGCTGTTTGAAGACATAACCGCTCGCAAACCG
AACGATAAATATGCGAAATCATTGAAGAATGGCGAGGCAT
(SEQ ID NO: 50)
```

```
>SRR6837562_732703_2|P
(Effector of SEQ ID NO: 24)
GTCGCGCCGAGGCCCATTGGCTTTTATGACTATGGCTCTTTC
GACATGGCTCGATGGGAGGACTTCATCGAAAATGGATACCG
GAGCAGTTGCCAACGTCGTGGGATCACCTCATGGATGACTTG
GAGATCGCGGATGCCGCACGATAGGTATTGCGCCTCCTTCAT
GACGTTTTCTAAGATTTTACGTTCGGTGTAGACGTGAGTATG
TCCGAAATCACTGATCTGCTCAAAGCCAATTTCAAAGGGAAG
ACATTCAAAAGTGCAGACATGAGGATGGCTGGGAGGATCTTC
AAGAAAAGCGGCGCGCAGGCCGTTATCAAATACTTGTCGGAC
AAGGGGGCAGTTGATCCGCCTAAGTCCGGCAGGTCCTTGAAA
TCAAACAAGAATCCGAGCGAGCCCAAACACGTTTTGCGGTCA
AAAACACGTAGCAACATAACATCTACGTTGTCGCAAAATGAA
CCGCTCGCAACGGACCAAAAAACCGCTCCAAAAACAGGACCT
TAGACCCCACGCCCCGCGGTTCCCGCTTTT
(SEQ ID NO: 51)
```

TABLE 9-continued

Non-coding Sequences of Representative
CLUST.200916 Systems

```
>SRR6837557_1806432_3|M
(Effector of SEQ ID NO: 23)
CGCCCTCGCGACGCGCATCCCGGGGTTTCGTTTTCCGGAGAC
GATGCAGCTCACCTGCGCCACGGAGCAGCCGAGACGGGCGGC
GACCTTGGTCGTGCCCTCGGACTCGACGATCTTCACGAACTT
CTTGTGCGTCGTTCTGGCGACATGCGGGGTAGCTTGCGACG
GTTTAGGTCGCCTGTCAAGCGAGCTGGCGAAAAGCTGTTGAC
AGGAGCATGGGCTTTGGCTAAGGTGCGAGCATGCCCGACAAG
CAGACGCCCAAGGACACCAAGGACAAGCCCGAGAGCCCCGTC
TCCGCCTTCCTCAAGAAGCACTTCCCCGGGAAGCATTTCTTC
GGGCATGCCGGGACGCTCGCCCGCCTCCTCAAGACCAAGGGT
GAGGAGGTTGCGTTCCACGCCGACCTCGAAGTGGCGACTTTC
AACATCGAGCGGGTGGCGCTGACGGGCGAGTCGATGCCGAAA
GGCGAGGAGGGCGCACGCGAGCGGGGAGGTGGTGGGAAGAGC
AGGGGAGGCGCTCGCGGGCGAAATAAATTGAAATAGTTCGCG
AAATCGGGTAAGCTGGTTGGCGTCAGTGAAAACTGAATAGAC
GAAGATACGAGCCGCTCGCAGGGTGGAGCGGAAGATCTCGAT
CTGGTTCCGAATTTCTCGGTGGCTGTCGAGAGCGATGACGAG
TGCGCGGTGCGCCGCGACCAGCTCTGTGTGTAGTTGACCCGT
AGTCAGGACAAGGAGAGGTCGAGAGCGATGACGAGTGCGCGG
TGCGCCGCGACGTGCTGTTGATCTGATAGACGGGGGTGGGCA
CCTGCGCGGTGTCGAGAGCGATGACGAGTGCGCGGTGCGCCG
CGACTTTCGTACAGAGCCTCCGGACGGCGTCCGGATGCCGGA
GTCGAGAGCGATGACGAGTGCGCGGTGCGCCGCGACGCCGTC
GCCTCGAAGGCGGGCGCGGGTGAACTACTTCGTCAAGACCGA
TGACGATTGCGGTGCCGACGGCTTGCGCGAGGACTTTT
TGGTCGGCTTCTTGCCGTCGTCAAGACCGATGACGAGTGCGC
GGTGCGCCGCGACGACTTGGCCTTCGCCTCGGTCAGGGCGCG
TCGGTCGACAATTTCAGTGCAATGGCTCGGTACACCGGGACT
ATGATTGTTCGGTACGCCGAGACACGGTCGGCCAGCTGGTTA
TCTCACGTCCCTCACCACCCCCACGTACGCCATCATCTCCCT
CATCCTCACCTCCCACCCGTGGTTCTCCGCCGCGAGCCTCGC
CCCCCGCTCGGCGAT
(SEQ ID NO: 52)
```

```
>SRR6837575_1071878_1|M
(Effector of SEQ ID NO: 28)
GTCGCGCCGAGGCCCATTGGCTTTTATGACTATGGCTCTTTC
GACATGGCTCGATGGGAGGACTTCATCGAAAATGGGTACTG
GAGCAGTTGCCAACGTCGTGGGATCACCTCATGGATGACTTG
GAGATCGCGGATGCCGCACGATAGGTATTGCGCCTCCTTCAT
GACGTTTTCTAAGATTTTACGTTCGGTGTAGACGTGAGTATG
TCCGAAATCACTGATCTGCTCAAAGCCAATTTCAAAGGGAAG
ACATTCAAAAGTGCAGACATGAGGATGGCTGGGAGGATCTTC
AAGAAAAGCGGCGCGCAGGCCGTTATCAAATACTTGTCGGAC
AAGGGGCAGTTGATCCGCCTACCCCGGGGACCGCTCGCAAG
TCCGGCAGGTCCTTGAAATCACAAGATAATCCGAGCGAGCCC
AAACGCGTTTTGCAGTCAAAAACACGTAAGAAAATCACATCT
ACGGAGACACAAAACGAACCGCTCGCAACGGACCTAAAAACC
TAAGTGAAAACAGGGGCCTAGACACACATCCAAGGATGTCGC
AAAGGGCCTCGTCGAGATCCCAAG
(SEQ ID NO: 53)
```

```
>SRR6837570_202287_11|M
(Effector of SEQ ID NO: 26)
CTGCTGCGCGCGTACCCGCTCTGGGAGAGTCGCGACTGCGGT
CAGCACGACTCGCGGCGCGAGGGCGTGGAGGGCTGCTATTGC
GCGCGACAAGATCTGAAGCACCTGATCGGCTGGCCGGAGCCG
AAGCAAAAAGCTCCTGCAAATGATCTATCTCTGTTGACTTC
GCATCAGACGATCACTAGATTGCTACAGGCAATCACAAACAG
CGGGAGACGAACAATGACTCTGGCCGAGCTGCGCGACAAATA
CTTCTACAAGATCAAGTTCCGCAAGATCGATCTCAGGCAAGC
CGGCAAGATCCTCAAGACAGAGGCGAGGAAGCGGCTCGCCG
CTATCTTGACGAGCAGCGGGAGTCGCCGCCCGAGGGCCGCGG
CGCGGGGCTGCGGAAGGTCGAGACTGAGGCCGAGGTCGAGGC
GGTCGACGAGGCCCCCGCGGCCGCGAGCGTGGAGAAGCCGCG
CAAGCGGCGCAAGAGCGCGACCGGCGCGAGGCGGCGACTTTCGA
GGCCGCACCGCTCGCGTAGTCTAAGATCGCGTTCTCGCAAGA
GAATGCGAGCACCGGCCGCGAACACCGCTCTAGTTGTGCGAA
CGTTCGCGGCCGGTGCTCGCAGACGAGCTGCTAGGTCTTTGA
AAATTGAATAGATTGTAATGGTGAGTTGCCCGAGCCCGCACT
CGCGGCGCGCTACCTCTTCGCGCCAACGACC
(SEQ ID NO: 54)
```

TABLE 9-continued

Non-coding Sequences of Representative
CLUST.200916 Systems

```
>SRR6837577_75829_4|M
(Effector of SEQ ID NO: 29)
CGCCCTCGCGACGCGCATCCCGGGGTTTCGTTTTCCGGAGAC
GATGCAGCTCACCTGCGCCACGGAGCAGCCGAGACGGGCGGC
GACCTTGGTCGTGCCCTCGGACTCGACGATCTTCACGAACTT
CTTGTGCGTCTGTTCTGGCGACATGCGGGGTAGCTTGCGACG
GTTTAGGTCGCCTGTCAAGCGAGCTGGCGAAAAGCTGTTGAC
AGGAGCATGGGCTTTGGCTAAGGTGCGAGCATGCCCGACAAG
CAGACGCCCAAGGACACCAAGGACAAGCCCGAGAGCCCCGTC
TCCGCCTTCCTCAAGAAGCACTTCCCCGGGAAGCATTTCTTC
GGGCATGCCGGGACGCTCGCCCGCCTCCTCAAGACCAAGGGT
GAGGAGGTTGCGTTCCACGCCGACCTCGGGGTGGCGACTTTC
AACATCGAGCGGGTGGCGCTGACGGGCGAGTCGATGCCGAAA
GGCGAGGAGGGCGCACGCGAGCGGGGAGGTGGTGGGAAGAGC
AGGGGAGGCGCTCGCGGGCGAAATAAATTGAAATAGTTCGCG
AAATCGGGTAAGCTGGTTGGCGTCAGTGAAAACTGAATAGAC
GAAGATACGAGCCGCTCGCAGGGTGGAGCGGAAGATCTCGAT
CTGGTTCCGAATTTCTCGGTGGCT
(SEQ ID NO: 55)

>SRR6837569_616344_2|P
(Effector of SEQ ID NO: 25)
GTCGCGCCGAGGCCCATTGGCTTTTATGACTATGGCTCTTTC
GACATGGCTCGATGGGAGGACTTCATCGAAAAATGGGTGCCG
GAGCAGTTGCCAACGTCGTGGGATCACCTCATGGATGACTTG
GAGATCGCGGATGCCGCACGATAGGTATTGCGCCTCCTTCAT
GACGTTTTCTAAGATTTTACGTTCGGTGTAGACGTGAGTATG
TCCGAAATCACTGATCTGCTCAAAGCCAATTTCAAAGGGAAG
ACATTCAAAAGTGCAGCATGAGGATGGCTGGGAGGGACCCTC
AAGAAAAGCGGCGCGCAGGCCGTTATCAAATACTTGTCGGAC
AAGGGGGCGGTTGATCCGCCTAATCCCGGCAGGTCCTTGAAA
TCAAACAAGAATCCGAGCGAGCCCAAACACGTTTTGCGGTCA
AAAACACGTAGCAACATAACATCTACGTTGTCGCAAAATGAA
CCGCTCGCAACGGACCAAAAAACCGCTCCAAAAACAGGACCT
TAGACCCCACGCCGGAAGTCGCT
(SEQ ID NO: 56)
```

Example 2—Functional Validation of Engineered
CLUST.200916 CRISPR-Cas Systems

Figure 1A:
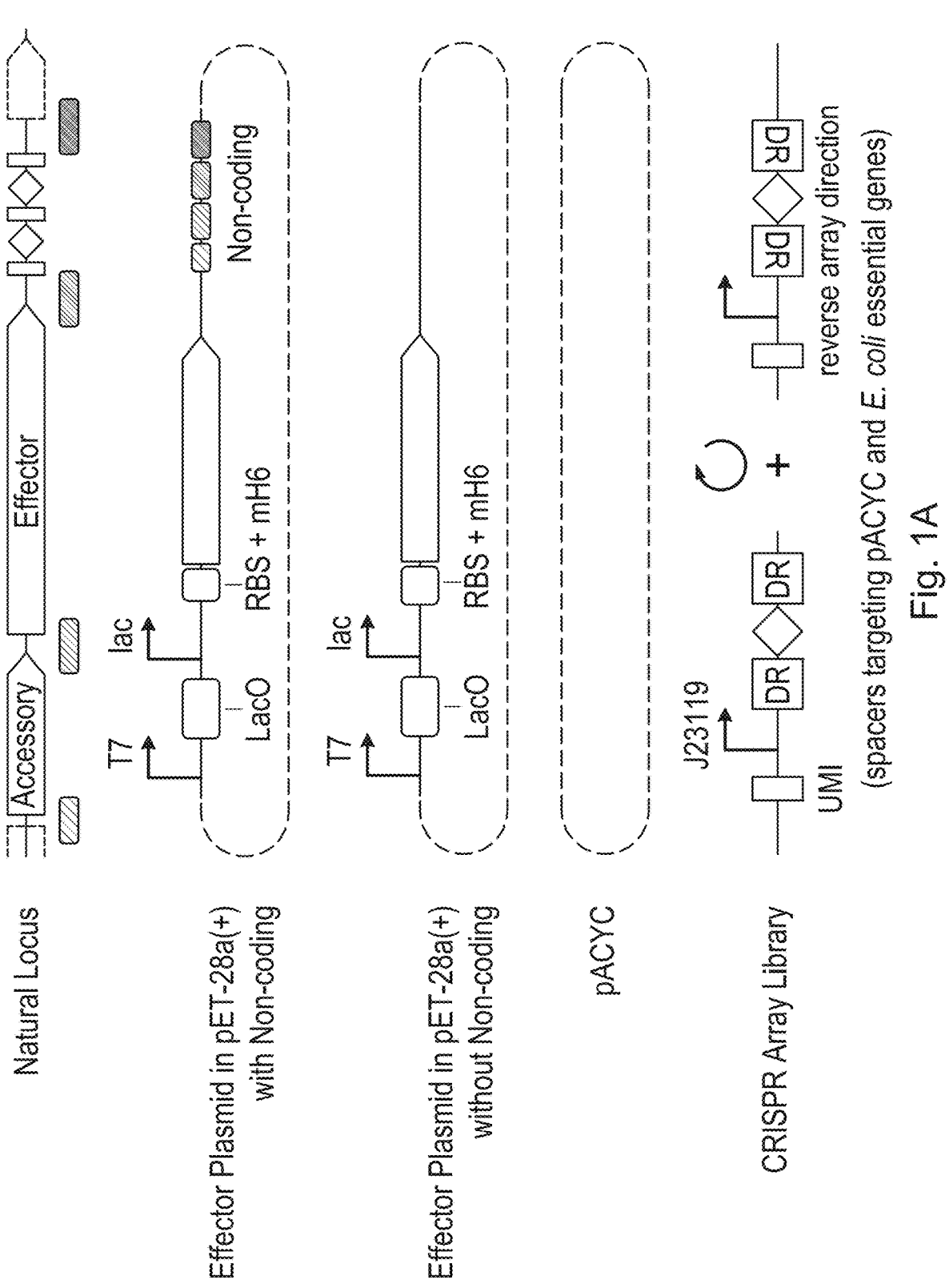

Having identified components of CLUST.200916
CRISPR-Cas systems, the following loci were selected for
functional validation: 1) a locus from the metagenomic
source designated 3300013232 (SEQ ID NO: 1), 2) a locus
from the metagenomic source designated SRR6837570
(SEQ ID NO: 26), 3) a locus from the metagenomic source
designated SRR6837575 (SEQ ID NO: 28), 4) a locus from
the metagenomic source designated SRR6837577 (SEQ ID
NO: 29), and 5) a locus from the metagenomic source
designated SRR6837569 (SEQ ID NO: 25).
DNA Synthesis and Effector Library Cloning To test the activity of the exemplary CLUST.200916
CRISPR-Cas systems, systems were designed and synthe-
sized using a pET28a(+) vector. Briefly, E. coli codon-
optimized nucleic acid sequences encoding the
CLUST.200916 3300013232 effector (SEQ ID NO: 1), the
CLUST.200916 SRR6837570 effector (SEQ ID NO: 26), the
CLUST.200916 SRR6837575 effector (SEQ ID NO: 28), the
CLUST.200916 SRR6837577 effector (SEQ ID NO: 29),
and the CLUST.200916 SRR6837569 effector (SEQ ID NO:
25), as shown in TABLE 7, were synthesized (Genscript)
and individually cloned into a custom expression system
derived from pET-28a(+) (EMD-Millipore). The vectors
included the nucleic acid encoding the CLUST.200916
effector under the control of a lac promoter and an E. coli
ribosome binding sequence. The vectors also included an
acceptor site for a CRISPR array library driven by a J23119 promoter following the open reading frame for the
CLUST.200916 effector. The non-coding sequence used for
the CLUST.200916 3300013232 effector (SEQ ID NO: 1) is
set forth in SEQ ID NO: 49, the non-coding sequence used
for the CLUST.200916 SRR6837570 effector (SEQ ID NO:
26) is set forth in SEQ ID NO: 54, the non-coding sequence
used for the CLUST.200916 SRR6837575 effector (SEQ ID
NO: 28) is set forth in SEQ ID NO: 53, the non-coding
sequence used for the CLUST.200916 SRR6837577 effector
(SEQ ID NO: 29) is set forth in SEQ ID NO: 55, and the
non-coding sequence used for the CLUST.200916
SRR6837569 effector (SEQ ID NO: 25) is set forth in SEQ
ID NO: 56, as shown in TABLE 9. An additional condition
was tested, wherein the CLUST.200916 effectors were indi-
vidually cloned into pET28a(+) without the non-coding
sequences. See FIG. 1A.

An oligonucleotide library synthesis (OLS) pool contain-
ing "repeat-spacer-repeat" sequences was computationally
designed, where "repeat" represents the consensus direct
repeat sequence found in the CRISPR array associated with
the effector, and "spacer" represents sequences tiling the
pACYC184 plasmid or E. coli essential genes. In particular,
the repeat sequence used for the CLUST.200916
3300013232 effector (SEQ ID NO: 1) is set forth in SEQ ID
NO: 30, the repeat sequence used for the CLUST.200916
SRR6837570 effector (SEQ ID NO: 26) is set forth in SEQ
ID NO: 44, the repeat sequence used for the CLUST.200916
SRR6837575 effector (SEQ ID NO: 28) is set forth in SEQ
ID NO: 46, the repeat sequence used for the CLUST.200916
SRR6837577 effector (SEQ ID NO: 29) is set forth in SEQ
ID NO: 45, and the repeat sequence used for the
CLUST.200916 SRR6837569 effector (SEQ ID NO: 25) is
set forth in SEQ ID NO: 43, as shown in TABLE 8. The
spacer length was determined by the mode of the spacer
lengths found in the endogenous CRISPR array. The repeat-
spacer-repeat sequence was appended with restriction sites
enabling the bi-directional cloning of the fragment into the
aforementioned CRISPR array library acceptor site, as well
as unique PCR priming sites to enable specific amplification
of a specific repeat-spacer-repeat library from a larger pool.

Next, the repeat-spacer-repeat library was cloned into the
plasmid using the Golden Gate assembly method. Briefly,
each repeat-spacer-repeat was first amplified from the OLS
pool (Agilent Genomics) using unique PCR primers and
pre-linearized the plasmid backbone using BsaI to reduce
potential background. Both DNA fragments were purified
with Ampure XP (Beckman Coulter) prior to addition to
Golden Gate Assembly Master Mix (New England Biolabs)
and incubated per the manufacturer's instructions. The
Golden Gate reaction was further purified and concentrated
to enable maximum transformation efficiency in the subse-
quent steps of the bacterial screen.

Figure 1B:
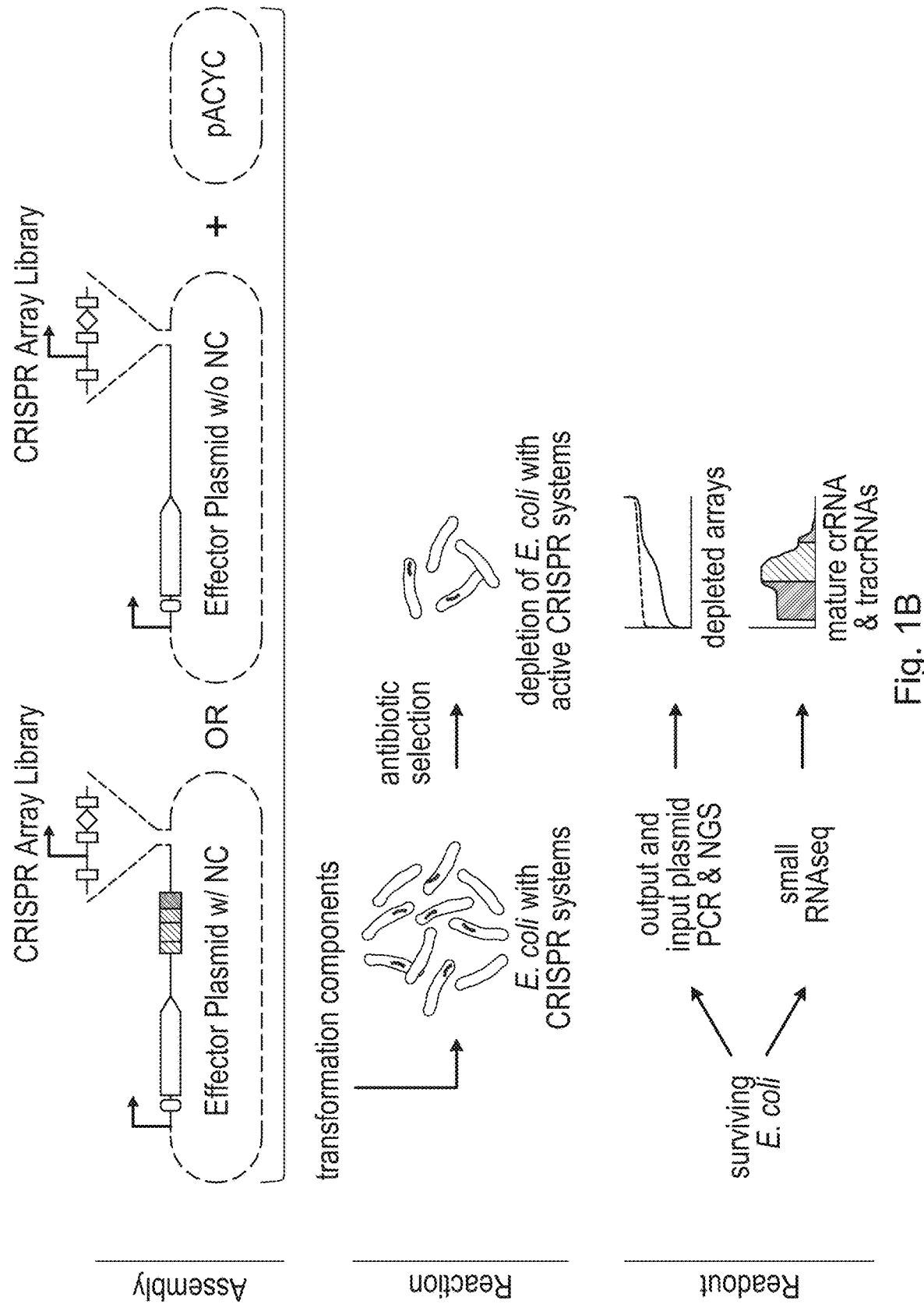

The plasmid library containing the distinct repeat-spacer-
repeat elements and CRISPR effectors was electroporated
into E. Cloni electrocompetent E. coli (Lucigen) using a
Gene Pulser Xcell® (Bio-rad) following the protocol rec-
ommended by Lucigen. The library was either co-trans-
formed with purified pACYC184 plasmid or directly trans-
formed into pACYC184-containing E. Cloni
electrocompetent E. coli (Lucigen), plated onto agar con-
taining chloramphenicol (Fisher), tetracycline (Alfa Aesar),
and kanamycin (Alfa Aesar) in BioAssay® dishes (Thermo
Fisher), and incubated for 10-12 hours at 37° C. After
estimation of approximate colony count to ensure sufficient
library representation on the bacterial plate, the bacteria
were harvested, and plasmid DNA WAS extracted using a
QIAprep Spin Miniprep® Kit (Qiagen) to create an "output library." By performing a PCR using custom primers containing barcodes and sites compatible with Illumina sequencing chemistry, a barcoded next generation sequencing library was generated from both the pre-transformation "input library" and the post-harvest "output library," which were then pooled and loaded onto a Nextseq 550 (Illumina) to evaluate the effectors. At least two independent biological replicates were performed for each screen to ensure consistency. See FIG. 1B.

Bacterial Screen Sequencing Analysis

Next generation sequencing data for screen input and output libraries were demultiplexed using Illumina bcl2fastq. Reads in resulting fastq files for each sample contained the CRISPR array elements for the screening plasmid library. The direct repeat sequence of the CRISPR array was used to determine the array orientation, and the spacer sequence was mapped to the source (pACYC184 or E. Cloni) or negative control sequence (GFP) to determine the corresponding target. For each sample, the total number of reads for each unique array element ($r_a$) in a given plasmid library was counted and normalized as follows: $(r_a+1)$/total reads for all library array elements. The depletion score was calculated by dividing normalized output reads for a given array element by normalized input reads.

To identify specific parameters resulting in enzymatic activity and bacterial cell death, next generation sequencing (NGS) was used to quantify and compare the representation of individual CRISPR arrays (i.e., repeat-spacer-repeat) in the PCR product of the input and output plasmid libraries. The array depletion ratio was defined as the normalized output read count divided by the normalized input read count. An array was considered to be "strongly depleted" if the depletion ratio was less than 0.3 (more than 3-fold depletion), depicted by the "hit threshold" dashed line in FIG. 3, FIG. 6, FIG. 9, FIG. 12, FIG. 15, FIG. 18, FIG. 21, FIG. 24, and FIG. 27. When calculating the array depletion ratio across biological replicates, the maximum depletion ratio value for a given CRISPR array was taken across all experiments (i.e. a strongly depleted array must be strongly depleted in all biological replicates). A matrix including array depletion ratios and the following features were generated for each spacer target: target strand, transcript targeting, ORI targeting, target sequence motifs, flanking sequence motifs, and target secondary structure. The degree to which different features in this matrix explained target depletion for CLUST.200916 systems was investigated.

FIG. 3, FIG. 9, FIG. 15, FIG. 21, and FIG. 27 show the degree of interference activity of the engineered composition, with a non-coding sequence, by plotting for a given target the normalized ratio of sequencing reads in the screen output versus the screen input. The results are plotted for each DR transcriptional orientation. In the functional screen for the composition, an active effector complexed with an active RNA guide will interfere with the ability of the pACYC184 to confer E. coli resistance to chloramphenicol and tetracycline, resulting in cell death and depletion of the spacer element within the pool. Comparison of the results of deep sequencing the initial DNA library (screen input) versus the surviving transformed E. coli (screen output) suggests specific target sequences and DR transcriptional orientations that enable an active, programmable CRISPR system. The screen also indicates that the effector complex is only active with one orientation of the DR. As such, the screen indicated that the CLUST.200916 3300013232 effector was active in the "forward" orientation (5'-CAAC . . . AGAC-[spacer]-3') of the DR (FIG. 3), that the CLUST.200916 SRR6837570 effector was active in the "reverse" orientation (5'-GCGC . . . GAAC-[spacer]-3') of the DR (FIG. 9), that the CLUST.200916 SRR6837575 effector was active in the "forward" orientation (5'-CCAT . . . ACAC-[spacer]-3') of the DR (FIG. 15), that the CLUST.200916 SRR6837577 effector was active in the "forward" orientation (5'-GTCG . . . CGAC-[spacer]-3') of the DR (FIG. 21), and that the CLUST.200916 SRR6837569 effector was active in the "reverse" orientation (5'-CCTG . . . AGAC-[spacer]-3') of the DR (FIG. 27).

FIG. 4A and FIG. 4B depict the location of strongly depleted targets for the CLUST.200916 3300013232 effector (plus non-coding sequence) targeting pACYC184 and E. coli E. Cloni essential genes, respectively. FIG. 10A and FIG. 10B depict the location of strongly depleted targets for the CLUST.200916 SRR6837570 effector (plus non-coding sequence) targeting pACYC184 and E. coli E. Cloni essential genes, respectively. FIG. 16A and FIG. 16B depict the location of strongly depleted targets for the CLUST.200916 SRR6837575 effector (plus non-coding sequence) targeting pACYC184 and E. coli E. Cloni essential genes, respectively. FIG. 22A and FIG. 22B depict the location of strongly depleted targets for the CLUST.200916 SRR6837577 effector (plus non-coding sequence) targeting pACYC184 and E. coli E. Cloni essential genes, respectively. FIG. 28A and FIG. 28B depict the location of strongly depleted targets for the CLUST.200916 SRR6837569 effector (plus non-coding sequence) targeting pACYC184 and E. coli E. Cloni essential genes, respectively.

Flanking sequences of depleted targets were analyzed to determine the PAM sequence for CLUST.200916 effectors with a non-coding sequence. WebLogo representations (Crooks et al., Genome Research 14: 1188-90, 2004) of the PAM sequences for CLUST.200916 effectors 3300013232, SRR6837570, SRR6837575, SRR6837577, and SRR6837569, with a non-coding sequence, are shown in FIG. 5, FIG. 11, FIG. 17, FIG. 23, and FIG. 29 respectively, where the "20" position corresponds to the nucleotide adjacent to the 5' end of the target.

Furthermore, FIG. 6, FIG. 12, FIG. 18, FIG. 24, and FIG. 30 show that the CLUST.200916 effectors retain activity in the absence of the non-coding sequence. In agreement with FIG. 3, the CLUST.200916 3300013232 effector, without the non-coding sequence, was active in the "forward" orientation (5'-CAAC . . . AGAC-[spacer]-3') of the DR (FIG. 6). In agreement with FIG. 9, the CLUST.200916 SRR6837570 effector was active in the "reverse" orientation (5'-GCGC . . . GAAC-[spacer]-3') of the DR (FIG. 12). In agreement with FIG. 15, the CLUST.200916 SRR6837575 effector was active in the "forward" orientation (5'-CCAT . . . AGAC-[spacer]-3') of the DR (FIG. 18). In agreement with FIG. 21, the CLUST.200916 SRR6837577 effector was active in the "forward" orientation (5'-GTCG . . . CGAC-[spacer]-3') of the DR (FIG. 24). In agreement with FIG. 27, the CLUST.200916 SRR6837569 effector was active in the "reverse" orientation (5'-CCTG . . . AGAC-[spacer]-3') of the DR (FIG. 30).

FIG. 7A and FIG. 7B depict the locations of the strongly depleted targets for the CLUST.200916 3300013232 effector, without the non-coding sequence, targeting pACYC184 and E. coli E. Cloni essential genes, respectively. FIG. 13A and FIG. 13B depict the location of strongly depleted targets for the CLUST.200916 SRR6837570 effector (plus non-coding sequence) targeting pACYC184 and E. coli E. Cloni essential genes, respectively. FIG. 19A and FIG. 19B depict the location of strongly depleted targets for the CLUST.200916 SRR6837575 effector (plus non-coding sequence) targeting pACYC184 and E. coli E. Cloni essential genes, respectively. FIG. 25A and FIG. 25B depict the location of strongly depleted targets for the CLUST.200916 SRR6837577 effector (plus non-coding sequence) targeting pACYC184 and *E. coli* E. Cloni essential genes, respectively. FIG. 31A and FIG. 31B depict the location of strongly depleted targets for the CLUST.200916 SRR6837569 effector (plus non-coding sequence) targeting pACYC184 and *E. coli* E. Cloni essential genes, respectively.

Flanking sequences of depleted targets were analyzed to determine the PAM sequence for CLUST.200916 effectors without a non-coding sequence. WebLogo representations of the PAM sequences for CLUST.200916 effectors 3300013232, SRR6837570, SRR6837575, SRR6837577, and SRR6837569, without a non-coding sequence, are shown in FIG. 8, FIG. 14, FIG. 20, FIG. 26, and FIG. 32 respectively, where the "20" position corresponds to the nucleotide adjacent to the 5' end of the target.

Example 3—Double-Stranded DNA Cleavage with CLUST.200916 Effectors

This Example demonstrates double-stranded DNA (dsDNA) cleavage by CLUST.200916 effectors.

RNA guide sequences comprising a DR-spacer-DR sequence were synthesized for five CLUST.200916 effectors: the effectors of SEQ ID NO: 1, SEQ ID NO: 28, SEQ ID NO: 26, SEQ ID NO: 27, and SEQ ID NO: 25. Each spacer of the RNA guide was generated to have complementarity to one strand of a DNA target sequence. For example, for the effector of SEQ ID NO: 1, the spacer sequence of the RNA guide of SEQ ID NO: 139 was designed to have complementary to Target A (SEQ ID NO: 57) but have no complementarity to Non-Target B (SEQ ID NO: 58), which was thus used as a negative control. The Target, Non-Target Control, and RNA guide sequences corresponding to the effectors of SEQ ID NO: 1, SEQ ID NO: 28, SEQ ID NO: 26, SEQ ID NO: 27, and SEQ ID NO: 25 are shown in Table 10. The bolded sequences in Table 10 (e.g., the bolded sequences in the target sequences of SEQ ID NO: 57, SEQ ID NO: 59, SEQ ID NO: 61, SEQ ID NO: 63, and SEQ ID NO: 65) correspond to the sequences to which the pre-crRNAs in Table 10 bind (e.g., the pre-crRNA sequences of SEQ ID NO: 139, SEQ ID NO: 140, SEQ ID NO: 141, SEQ ID NO: 142, and SEQ ID NO: 143, respectively).

TABLE 10

Target and RNA guide sequences for CLUST.200916 effectors.

| Effector | Target Sequence | pre-crRNA Sequence | Non-Target Control Sequence |
|---|---|---|---|
| SEQ ID NO: 1 | Target A: TCCATGTCTCGTTATACGC TGTGGTTCGCCAACAAATA CCTTACTACTCGTCACGCC ACG*CCATCGTGGTGCCAGA TCTGTCACAGGTAACT*GAA CACCTGGAAACTACTAATA CCTTTTGACAGCTAGCTCA GTCCTAGGTATAAT (SEQ ID NO: 57) | CAACCTAAACGATGGCTCG ATTCGTCGAGACAACGAAA GTGGCCTCTGGCGAAGCGG GCGGCACAACCAAAACGAT GGCTCGATTCGTCGAGACA GTTACCTGTGACAGATCTG GCACCACGATGGCAACCAA AACGATGGCTCGATTCGTC GAGAC (SEQ ID NO: 139) | Non-Target B: TCCATGTCTCGTTATACGC TGTGGTTCGCCAACGCAAG AATACTACTACTGCAACCT GTACTAACGTATGGTGACT TAACTCGTCTGGATCCTAC AACAGTAACGCACTACTAG AATACTTTGACAGCTAGCT CAGTCCTAGGTATAAT (SEQ ID NO: 58) |
| SEQ ID NO: 28 | Target C: TCCATGTCTCGTTATACGC TGTGGTTCGCCAACACTCT CATAACTACTGCGTGAAGT GCT*TTCCGAACGCTTCGCC ACGCTCTCCTTTGATGTAC A*GAAAACTCAGCGACTACT CTCTCATATTGACAGCTAG CTCAGTCCTAGGTATAAT (SEQ ID NO: 59) | CCATCAATGGATCCAAATT GCTCTGTACGCAGAGACAG CGCGCCGCGGTACATCTTC TTGTTAACTTTTTGACCAT CAATGGATCCAAATTGCTC TGTACGCAGAGACTGTACA TCAAAGGAGAGCGTGGCGA AGCGTTCGGAACCATCAAT GGATCCAAATTGCTCTGTA CGCAGAGAC (SEQ ID NO: 140) | Non-Target D: TCCATGTCTCGTTATACGC TGTGGTTCGCCAACGCACC CCCCCGACTACTCGGTAGC GTCGATGTTCTGCTGCCGT TGCCGGGGCGTCACAATAT TGCGAATGCGCTGGCACTA CTCCCCCCCGTTGACAGCT AGCTCAGTCCTAGGTATAA T (SEQ ID NO: 60) |
| SEQ ID NO: 26 | Target E: TCCATGTCTCGTTATACGC TGTGGTTCGCCAACACTGC ATACACTACTGTGACCGAC GGT*GTTGTAACTGACGAAA TTCACTACCTGTCTGCTAT C*GAAGAAGGCAACACTACT CTGCATACTTGACAGCTAG CTCAGTCCTAGGTATAAT (SEQ ID NO: 61) | GCGCCAACGACCTCTGATT GTCCGGTACGCCGGAACGA GGAGCGCAGTCACCAAAAC TTGTCCTTTCAGTTTGCGC CAACGACCTCTGATTGTCC GGTACGCCGGAACGATAGC AGACAGGTAGTGAATTTCG TCAGTTACAACGCGCCAAC GACCTCTGATTGTCCGGTA CGCCGGAAC (SEQ ID NO: 141) | Non-Target F: TCCATGTCTCGTTATACGC TGTGGTTCGCCAACGCAAG AAAGTCACTACTACTGAAA GCGATCATCTCTGATGTGA ACGCTTCCGACGAAGATCG TTGGAACGCTGTTCTACTA CTAGAAAGTCTTGACAGCT AGCTCAGTCCTAGGTATAA T (SEQ ID NO: 62) |
| SEQ ID NO: 27 | Target G: TCCATGTCTCGTTATACGC TGTGGTTCGCCAACATGAG ATGGACTACTTGTTTGGTC GTG*CTGCGCGTGAAAGCCG TATTGAAAGCCTCCATGCC GAGCGT*GAAGTGCTTTCCA CTACTTGAGATGGTTGACA GCTAGCTCAGTCCTAGGTA TAAT (SEQ ID NO: 63) | GTCGAGAGCGATGACGAGT GCGCGGTGCGCCGCGACGA ACCGAGGTAACTGGCTTGG AGGAGCGCAGTCACCAAAA CGTCGAGAGCGATGACGAG TGCGCGGTGCGCCGCGACA CGCTCGGCATGGAGGCTTT CAATACGGCTTTCACGCGC AGGTCGAGAGCGATGACGA GTGCGCGGTGCGCCGCGAC (SEQ ID NO: 142) | Non-Target H: TCCATGTCTCGTTATACGC TGTGGTTCGCCAACGCAGT GGGACCACTACTGAAGGTG ATCATGCCGTTTTCAGTTT CAACGTGGTATGCACCAAT GTGCTGGGTAATGCCGCCC GACTACTGTGGGACCTTGA CAGCTAGCTCAGTCCTAGG TATAAT (SEQ ID NO: 64) |

TABLE 10-continued

| | | Non-Target Control | |
|---|---|---|---|
| Effector | Target Sequence | pre-crRNA Sequence | Sequence |

| | | | |
|---|---|---|---|
| SEQ ID<br>NO: 25 | Target I:<br>TCCATGTCTCGTTATACGC<br>TGTGGTTCGCCAACATACT<br>GGCTACTACTATGGAAATA<br>CGCGGGTCCGTACCTGGAG<br>GAAATGAAGTCGCCGCATG<br>GCTAAAACGAAGACCGACT<br>ACTTACTGGCTTTGACAGC<br>TAGCTCAGTCCTAGGTATA<br>AT<br>(SEQ ID NO: 65) | CCTGCAAGGGATCCAAATT<br>GCTCTGTTCGCAGAGACTG<br>GCGCGCAAGCCGAATGCCA<br>AAGTGGTTTATATGCACTC<br>CTGCAAGGGATCCAAATTG<br>CTCTGTTCGCAGAGACTAG<br>CCATGCGGCGACTTCATTT<br>CCTCCAGGTACGGACCCCC<br>TGCAAGGGATCCAAATTGC<br>TCTGTTCGCAGAGAC<br>(SEQ ID NO: 143) | Non-Target J:<br>TCCATGTCTCGTTATACGC<br>TGTGGTTCGCCAACGCACA<br>ACGCTGACTACTCCGCGTC<br>CGGCAGTTTTGCCAGCCAG<br>CGGCGGCCCACTTCATCGT<br>CGGCGTTAATAATCGCCTA<br>CTACTCAACGCTGTTGACA<br>GCTAGCTCAGTCCTAGGTA<br>TAAT<br>(SEQ ID NO: 66) |

The RNA guide sequences for all effectors were prepared using in vitro transcription (IVT). Double-stranded DNA templates for the IVT reaction were prepared by PCR using a commercially synthesized oligo template having a T7 promoter (IDT). IVT was performed by incubating the double-stranded DNA templates with T7 RNA polymerase (HiScribe T7 Quick High Yield RNA synthesis kit NEB) followed by treatment with DNase (Thermo Fisher Scientific) to remove the DNA template. The IVT product was cleaned up using RNA prep kit (Zymo Research).

Labeled dsDNA target and non-target substrates were generated via PCR using an IR800-labeled forward primer and an unlabeled reverse primer. The resulting PCR product comprised an IR800 label on the spacer complementary strand as shown in FIG. 33. These substrates were purified using SPRI beads (Agilent), and concentrations were measured via a nanodrop spectrophotometer (Thermo Fisher Scientific).

Cleavage assays were conducted in a buffer comprising 25 mM Tris pH 8.0, 50 mM NaCl, 10 mM MgCl2, 1 mM DTT. Complexed RNPs (effector plus corresponding RNA guide) were formed by incubating each purified effector with the RNA guide from Table 1 at a ratio of 1:2. Complexed RNPs were then added to 100 nM dsDNA substrate and incubated. Reactions were treated with an RNase cocktail and incubated, followed by incubation with Proteinase K. To detect dsDNA cleavage, DNA products from the reactions were analyzed on 15% TBE-Urea gels. Gels were imaged on a fluorescent digital imaging system (LI-COR Biosciences) for IR800 fluorescence.

As shown in FIG. 34A, FIG. 34B, FIG. 34C, FIG. 34D and FIG. 34E, target-specific cleavage was observed for the dsDNA target with the effector RNPs of SEQ ID NO: 1, SEQ ID NO: 28, SEQ ID NO: 26, SEQ ID NO: 27, and SEQ ID NO: 25, respectively. The full-length target/non-target bands and cleavage bands are indicated. For each of the effector RNPs, cleavage was positively correlated with effector RNP concentration, as shown in lanes 5-7 of FIG. 34A, FIG. 34B, FIG. 34C, FIG. 34D and FIG. 34E. No detectable cleavage activity was observed in the absence of RNA guide (lanes 2-4 of FIG. 34A, FIG. 34B, FIG. 34C, FIG. 34D and FIG. 34E) or in the absence of effector RNP (lane 1 of FIG. 34A, FIG. 34B, FIG. 34C, FIG. 34D and FIG. 34E). Furthermore, no detectable cleavage activity was observed for effector RNPs incubated with a non-target dsDNA, as shown in lanes 12-14 of FIG. 34A, FIG. 34B, FIG. 34C, FIG. 34D and FIG. 34E. For example, no detectable cleavage was observed in Non-Target B with an RNA guide designed for Target A (lanes 12-14 of FIG. 34A).

This Example thus shows that the effectors of SEQ ID NO: 1, SEQ ID NO: 28, SEQ ID NO: 26, SEQ ID NO: 27, and SEQ ID NO: 25 have nuclease activity and catalyze target-specific dsDNA cleavage.

Example 4—Targeting of GFP by CLUST.200916 Effectors

This Example describes use of a fluorescence depletion assay (FDA) to measure activity of CLUST.200916 effectors.

In this assay, an active CRISPR system designed to target GFP binds and cleaves the double-stranded DNA region encoding GFP, resulting in depletion of GFP fluorescence. The FDA assay involves in vitro transcription and translation, allowing production of an RNP from a DNA template encoding a CLUST.200916 effector and a DNA template containing a pre-crRNA sequence under a T7 promoter with direct repeat (DR)-spacer-direct repeat (DR); the spacer targeted GFP. In the same one-pot reaction, GFP and RFP were also produced as both the target and the fluorescence reporter (FIG. 35). The target GFP plasmid sequence is set forth in SEQ ID NO: 144, and the RFP plasmid sequence is set forth in SEQ ID NO: 145. GFP and RFP fluorescence values were measured every 20 min at 37° C. for 12 hr, using a TECAN Infinite F Plex plate reader. Since RFP was not targeted, its fluorescence was not affected and was therefore used as an internal signal control.

```
                                            SEQ ID NO: 144
ccccttgtattactgtttatgtaagcagacaggat gcgtccggcgtagaggatcgagatctcCAAAAAAT

GGCTGTTTTTGAAAAAAATTCTAAAGGTTGTTTTA

CGACAGACGATAACAGGGTTgaaataattttgttt aactttaagaaggagATTTAAATatgAAAATCGAA

GAAGGTAAAGGTCACCATCACCATCACCACggatc catgacggcattgacggaaggtgcaaaactgtttg agaaagagatcccgtatatcaccgaactggaaggc gacgtcgaaggtatgaaatttatcattaaaggcga gggtaccggtgacgcgaccacgggtaccattaaag cgaaatacatctgcactacgggcgacctgccggtc
```

-continued ccgtgggcaaccctggtgagcaccctgagctacgg tgttcagtgtttcgccaagtacccgagccacatca aggatttctttaagagcgccatgccggaaggttat acccaagagcgtaccatcagcttcgaaggcgacgg cgtgtacaagacgcgtgctatggttacctacgaac gcggttctatctacaatcgtgtcacgctgactggt gagaactttaagaaagacggtcacattctgcgtaa gaacgttgcattccaatgcccgccaagcattctgt atattctgcctgacaccgttaacaatggcatccgc gttgagttcaaccaggcgtacgatattgaaggtgt gaccgaaaaactggttaccaaatgcagccaaatga atcgtccgttggcgggctccgcggcagtgcatatc ccgcgttatcatcacattacctaccacaccaaact gagcaaagaccgcgacgagcgccgtgatcacatgt gtctggtagaggtcgtgaaagcggttgatctggac acgtatcagTAATAAaaagcccgaaaggaagctga gttggctgctgccaccgctgagcaataactagcat aaccccttggggcctctaaacgggtcttgaggggt tttttgctgaaaggaggaactatatccggCTTCCT

CGCTCACTGACTCGCTGCGCTCGGTCGTTCGGCTG

CGGCGAGCGGTATCAGCTCACTCAAAGGCGGTAAT

ACGGTTATCCACAGAATCAGGGGATAACGCAGGAA

AGAACATGTGAGCAAAAGGCCAGCAAAAGGCCAGG

AACCGTAAAAAGGCCGCGTTGCTGGCGTTTTTCCA

TAGGCTCCGCCCCCCTGACGAGCATCACAAAAATC

GACGCTCAAGTCAGAGGTGGCGAAACCCGACAGGA

CTATAAAGATACCAGGCGTTTCCCCCTGGAAGCTC

CCTCGTGCGCTCTCCTGTTCCGACCCTGCCGCTTA

CCGGATACCTGTCCGCCTTTCTCCCTTCGGGAAGC

GTGGCGCTTTCTCATAGCTCACGCTGTAGGTATCT

CAGTTCGGTGTAGGTCGTTCGCTCCAAGCTGGGCT

GTGTGCACGAACCCCCCGTTCAGCCCGACCGCTGC

GCCTTATCCGGTAACTATCGTCTTGAGTCCAACCC

GGTAAGACACGACTTATCGCCACTGGCAGCAGCCA

CTGGTAACAGGATTAGCAGAGCGAGGTATGTAGGC

GGTGCTACAGAGTTCTTGAAGTGGTGGCCTAACTA

CGGCTACACTAGAAGAACAGTATTTGGTATCTGCG

CTCTGCTGAAGCCAGTTACCTTCGGAAAAAGAGTT

GGTAGCTCTTGATCCGGCAAACAAACCACCGCTGG

TAGCGGTGGTTTTTTTGTTTGCAAGCAGCAGATTA

-continued

CGCGCAGAAAAAAAGGATCTCAAGAAGATCCTTTG

ATCTTTTCTACGGGGTCTGACGCTCAGTGGAACGA

AAACTCACGggtggcacttttcggggaaatgtgcg cggaacccctatttgtttattttttctaaatacatt caaatatgtatccgctcatgaattaattcttagaa aaactcatcgagcatcaaatgaaactgcaatttat tcatatcaggattatcaataccatattttgaaaa agccgtttctgtaatgaaggagaaaactcaccgag gcagttccataggatggcaagatcctggtatcggt ctgcgattccgactcgtccaacatcaatacaacct attaatttcccctcgtcaaaaataaggttatcaag tgagaaatcaccatgagtgacgactgaatccggtg agaatggcaaaagtttatgcatttctttccagact tgttcaacaggccagccattacgctcgtcatcaaa atcactcgcatcaaccaaaccgttattcattcgtg attgcgcctgagcgagacgaaatacgcgatcgctg ttaaaaggacaattacaaacaggaatcgaatgcaa ccggcgcaggaacactgccagcgcatcaacaatat tttcacctgaatcaggatattcttctaatacctgg aatgctgttttcccggggatcgcagtggtgagtaa ccatgcatcatcaggagtacggataaaatgcttga tggtcggaagaggcataaaattccgtcagccagttt agtctgaccatctcatctgtaacatcattggcaac gctacctttgccatgtttcagaaacaactctggcg catcgggcttcccatacaatcgatagattgtcgca cctgattgcccgacattatcgcgagcccatttata cccatataaatcagcatccatgttggaatttaatc gcggcctagagcaagacgtttcccgttgaatatgg ctcataaca

SEQ ID NO: 145 cccccttgtattactgtttatgtaagcagacaggat gcgtccggcgtagaggatcgagatctcCAAAAAAT

GGCTGTTTTTGAAAAAAATTCTAAAGGTTGTTTTA

CGACAGACGATAACAGGGTTgaaataattttgttt aactttaagaaggagATTTAAATatgAAAATCGAA

GAAGGTAAAGGTCACCATCACCATCACCACGgatc caTGGTCAGCAAGGGGGAGGAAGACAATATGGCTA

TTATCAAGGAATTCATGCGCTTCAAGGTGCATATG

GAAGGAAGCGTGAATGGACACGAATTCGAGATCGA

AGGCGAGGGGGAGGGTCGCCCTTATGAAGGCACAC

AAACAGCTAAACTGAAAGTGACGAAGGGAGGGCCG

-continued

```
CTTCCCTTCGCTTGGGACATTCTTTCACCCCAGTT

CATGTATGGTTCAAAGGCTTATGTCAAGCACCCGG

CGGACATTCCAGACTACTTAAAATTGTCGTTCCCC

GAGGGGTTTAAATGGGAACGCGTTATGAATTTCGA

GGATGGGGGAGTCGTAACGGTTACCCAGGACAGTA

GCCTGCAGGATGGCGAGTTCATCTACAAAGTGAAA

TTGCGCGGGACGAACTTCCCTAGCGATGGGCCAGT

CATGCAGAAGAAAACGATGGGATGGGAAGCGTCAT

CCGAGCGCATGTATCCTGAAGATGGTGCTTTAAAA

GGTGAGATCAAGCAGCGTTTGAAACTGAAGGACGG

GGGCCATTATGATGCTGAAGTTAAAACGACATATA

AGGCCAAGAAGCCAGTTCAACTGCCAGGGGCTTAT

AATGTTAATATTAAATTAGACATTACGAGCCATAA

TGAAGATTACACGATTGTCGAGCAATACGAGCGCG

CAGAAGGACGCCACTCAACGGGGGGCATGGACGAG

CTGTACAAGTAAaaagcccgaaaggaagctgagtt ggctgctgccaccgctgagcaataactagcataac cccttggggcctctaaacgggtcttgaggggtttt ttgctgaaaggaggaactatatccggCTTCCTCGC

TCACTGACTCGCTGCGCTCGGTCGTTCGGCTGCGG

CGAGCGGTATCAGCTCACTCAAAGGCGGTAATACG

GTTATCCACAGAATCAGGGGATAACGCAGGAAAGA

ACATGTGAGCAAAAGGCCAGCAAAAGGCCAGGAAC

CGTAAAAAGGCCGCGTTGCTGGCGTTTTTCCATAG

GCTCCGCCCCCTGACGAGCATCACAAAAATCGAC

GCTCAAGTCAGAGGTGGCGAAACCCGACAGGACTA

TAAAGATACCAGGCGTTTCCCCCTGGAAGCTCCCT

CGTGCGCTCTCCTGTTCCGACCCTGCCGCTTACCG

GATACCTGTCCGCCTTTCTCCCTTCGGGAAGCGTG

GCGCTTTCTCATAGCTCACGCTGTAGGTATCTCAG

TTCGGTGTAGGTCGTTCGCTCCAAGCTGGGCTGTG

TGCACGAACCCCCCGTTCAGCCCGACCGCTGCGCC

TTATCCGGTAACTATCGTCTTGAGTCCAACCCGGT

AAGACACGACTTATCGCCACTGGCAGCAGCCACTG

GTAACAGGATTAGCAGAGCGAGGTATGTAGGCGGT

GCTACAGAGTTCTTGAAGTGGTGGCCTAACTACGG

CTACACTAGAAGAACAGTATTTGGTATCTGCGCTC

TGCTGAAGCCAGTTACCTTCGGAAAAAGAGTTGGT

AGCTCTTGATCCGGCAAACAAACCACCGCTGGTAG

CGGTGGTTTTTTTGTTTGCAAGCAGCAGATTACGC

GCAGAAAAAAAGGATCTCAAGAAGATCCTTTGATC
```

-continued

```
TTTTCTACGGGGTCTGACGCTCAGTGGAACGAAAA

CTCACGggtggcacttttcggggaaatgtgcgcgg aacccctatttgtttattttttctaaatacattcaa atatgtatccgctcatgaattaattcttagaaaaa ctcatcgagcatcaaatgaaactgcaatttattca tatcaggattatcaataccatatttttgaaaaagc cgtttctgtaatgaaggagaaaactcaccgaggca gttccataggatggcaagatcctggtatcggtctg cgattccgactcgtccaacatcaatacaacctatt aatttcccctcgtcaaaaataaggttatcaagtga gaaatcaccatgagtgacgactgaatccggtgaga atggcaaaagtttatgcatttctttccagacttgt tcaacaggccagccattacgctcgtcatcaaaatc actcgcatcaaccaaaccgttattcattcgtgatt gcgcctgagcgagacgaaatacgcgatcgctgtta aaaggacaattacaaacaggaatcgaatgcaaccg gcgcaggaacactgccagcgcatcaacaatatttt cacctgaatcaggatattcttctaatacctggaat gctgttttcccggggatcgcagtggtgagtaacca tgcatcatcaggagtacggataaaatgcttgatgg tcggaagaggcataaaattccgtcagccagtttagt ctgaccatctcatctgtaacatcattggcaacgct acctttgccatgtttcagaaacaactctggcgcat cgggcttcccatacaatcgatagattgtcgcacct gattgcccgacattatcgcgagcccatttataccc atataaatcagcatccatgttggaatttaatcgcg gcctagagcaagacgtttcccgttgaatatggctc ataaca
```

5 GFP targets (plus 1 non-target) were designed for each of the effectors of SEQ ID NO: 28 and SEQ ID NO: 25. The direct repeat (DR) sequence and spacer length varied for each effector. RNA guide sequences, target sequences, and the non-target control sequences used for the FDA assay are listed in Table 11. The pre-crRNA sequences shown in Table 11 further include a T7 promoter at the 5' end and a hairpin motif that caps the 3' end of the RNA to ensure that the RNA is not degraded by nucleases present in the in vitro transcription and translation mixture.

TABLE 11

RNA guide and Target Sequences for FDA Assay.

| Target | Effector Tested | PAM Sequence | pre-crRNA Sequence | Target Sequence |
|---|---|---|---|---|
| Target 1 | SEQ ID NO: 28 | TTG | gaaattaatacgactcactatagC CATCAATGGATCCAAATTGCTCTG TACGCAGAGACagaaagagatccc gtatatcaccgaactggaaggcgC CATCAATGGATCCAAATTGCTCTG TACGCAGAGACctaacccctctct aaacggaggggttt (SEQ ID NO: 146) | agaaagagatcccg tatatcaccgaact ggaaggcg (SEQ ID NO: 67) |
| Target 2 | SEQ ID NO: 28 | TTG | gaaattaatacgactcactatagC CATCAATGGATCCAAATTGCTCTG TACGCAGAGACgtgtggtaggtaa tgtgatgataacgcgggatatgcC CATCAATGGATCCAAATTGCTCTG TACGCAGAGACctaacccctctct aaacggaggggttt (SEQ ID NO: 147) | gtgtggtaggtaat gtgatgataacgcg ggatatgc (SEQ ID NO: 68) |
| Target 3 | SEQ ID NO: 28 | TTT | gaaattaatacgactcactatagC CATCAATGGATCCAAATTGCTCTG TACGCAGAGACaagagcgccatgc cggaaggttatacccaagagcgtC CATCAATGGATCCAAATTGCTCTG TACGCAGAGACctaacccctctct aaacggaggggttt (SEQ ID NO: 148) | aagagcgccatgcc ggaaggttataccc aagagcgt (SEQ ID NO: 69) |
| Target 4 | SEQ ID NO: 28 | TTT | gaaattaatacgactcactatagC CATCAATGGATCCAAATTGCTCTG TACGCAGAGACaagaaagacggtc acattctgcgtaagaacgttgcaC CATCAATGGATCCAAATTGCTCTG TACGCAGAGACctaacccctctct aaacggaggggttt (SEQ ID NO: 149) | aagaaagacggtca cattctgcgtaaga acgttgca (SEQ ID NO: 70) |
| Target 5 | SEQ ID NO: 28 | TTT | gaaattaatacgactcactatagC CATCAATGGATCCAAATTGCTCTG TACGCAGAGACgagaaagagatcc cgtatatcaccgaactggaaggcC CATCAATGGATCCAAATTGCTCTG TACGCAGAGACctaacccctctct aaacggaggggttt (SEQ ID NO: 150) | gagaaagagatccc gtatatcaccgaac tggaaggc (SEQ ID NO: 71) |
| Non-Target 6 | SEQ ID NO: 28 | | gaaattaatacgactcactatagC TATAACGACCCTGCGAAGTGGGGT GTAACTTCGACgtgattgcgcctg agcgagacgaaatacgcgatcgcG TATAACGACCCTGCGAAGTGGGGT GTAACTTCGACctaacccctctct aaacggaggggttt (SEQ ID NO: 151) | |
| Target 7 | SEQ ID NO: 25 | TTG | gaaattaatacgactcactatagC CTGCAAGGGATCCAAATTGCTCTG TTCGCAGAGACacggaaggtgcaa aactgtttgagaaagagatcccgt atCCTGCAAGGGATCCAAATTGCT CTGTTCGCAGAGACctaacccctc tctaaacggaggggttt (SEQ ID NO: 152) | acggaaggtgcaaa actgtttgagaaag agatcccgtat (SEQ ID NO: 72) |
| Target 8 | SEQ ID NO: 25 | TTG | gaaattaatacgactcactatagC CTGCAAGGGATCCAAATTGCTCTG TTCGCAGAGACagaaagagatccc gtatatcaccgaactggaaggcga cgCCTGCAAGGGATCCAAATTGCT CTGTTCGCAGAGACctaacccctc tctaaacggaggggttt (SEQ ID NO: 153) | agaaagagatcccg tatatcaccgaact ggaaggcgacg (SEQ ID NO: 73) |

TABLE 11-continued

RNA guide and Target Sequences for FDA Assay.

| Target | Effector Tested | PAM Sequence | pre-crRNA Sequence | Target Sequence |
|--------|-----------------|--------------|--------------------|-----------------|
| Target 9 | SEQ ID NO: 25 | TTT | gaaattaatacgactcactatagC CTGCAAGGGATCCAAATTGCTCTG TTCGCAGAGACaatgataaatttc ataccttcgacgtcgccttccagt tcCCTGCAAGGGATCCAAATTGCT CTGTTCGCAGAGACctaacccctc tctaaacggaggggttt (SEQ ID NO: 154) | aatgataaatttca taccttcgacgtcg ccttccagttc (SEQ ID NO: 74) |
| Target 10 | SEQ ID NO: 25 | TTT | gaaattaatacgactcactatagC CTGCAAGGGATCCAAATTGCTCTG TTCGCAGAGACaagagcgccatgc cggaaggttatacccaagagcgta ccCCTGCAAGGGATCCAAATTGCT CTGTTCGCAGAGACctaacccctc tctaaacggaggggttt (SEQ ID NO: 155) | aagagcgccatgcc ggaaggttataccc aagagcgtacc (SEQ ID NO: 75) |
| Target 11 | SEQ ID NO: 25 | TTT | gaaattaatacgactcactatagC CTGCAAGGGATCCAAATTGCTCTG TTCGCAGAGACgagaaagagatcc cgtatatcaccgaactggaaggcg acCCTGCAAGGGATCCAAATTGCT CTGTTCGCAGAGACctaacccctc tctaaacggaggggttt (SEQ ID NO: 156) | gagaaagagatccc gtatatcaccgaac tggaaggcgac (SEQ ID NO: 76) |
| Non-Target 12 | SEQ ID NO: 25 | | gaaattaatacgactcactatagC TATAACGACCCTGCGAAGTGGGGT GTAACTTCGACgtgattgcgcctg agcgagacgaaatacgcgatcgct gtGTATAACGACCCTGCGAAGTGG GGTGTAACTTCGACctaacccctc tctaaacggaggggttt (SEQ ID NO: 157) | |

GFP signal was normalized to RFP signal, then the average fluorescence of three technical replicates was taken at each time point. GFP fluorescence depletion was then calculated by dividing the GFP signal of an effector incubated with a non-GFP targeting RNA guide (which instead targets a kanamycin resistance gene and does not deplete GFP signal) by the GFP signal of an effector incubated with a GFP targeting RNA guide. The resulting value is referred to as "Depletion" in FIG. 36A and FIG. 36B.

A Depletion of one or approximately one indicated that there was little to no difference in GFP depletion with respect to a non-GFP targeting pre-crRNA and a GFP targeting pre-crRNA (e.g., 10 RFU/10 RFU=1). A Depletion of greater than one indicated that there was a difference in GFP depletion with respect to a non-GFP targeting pre-crRNA and a GFP targeting pre-crRNA (e.g., 10 RFU/5 RFU=2). Depletion of the GFP signal indicated that the effector formed a functional RNP and interfered with the production of GFP by introducing double-stranded DNA cleavage within the GFP coding region. The extent of the GFP depletion was largely correlated to the specific activity of a CLUST.200916 effector.

FIGS. 36A and 36B show depletion curves for RNPs formed by the effectors of SEQ ID NO: 28 and SEQ ID NO: 25, respectively, measured every 20 minutes for each of the GFP targets (Targets 1-5 for SEQ ID NO: 28 and Targets 7-11 for SEQ ID NO: 25. At each target, the depletion values for RNPs formed with the effector of SEQ ID NO: 28 or the effector of SEQ ID NO: 25 were greater than one.

This indicated that the CLUST.200916 effectors formed functional RNPs capable of interfering with the production of GFP.

Example 5—Targeting of Mammalian Genes by CLUST.200916 Effectors

This Example describes an indel assessment on a mammalian AAVS1 target by CLUST.200916 effectors introduced into mammalian cells by transient transfection.

The effectors of SEQ ID NO: 24, SEQ ID NO: 28, and SEQ ID NO: 25 were cloned into a pcda3.1 backbone (Invitrogen). The plasmids were then maxi-prepped and diluted to 1 μg/μL. For RNA guide preparation, a dsDNA fragment encoding an RNA guide was derived by ultramers containing the target sequence scaffold, and the U6 promoter. Ultramers were resuspended in 10 mM Tris.HCl at a pH of 7.5 to a final stock concentration of 100 μM. Working stocks were subsequently diluted to 10 μM, again using 10 mM Tris.HCl to serve as the template for the PCR reaction. The amplification of the RNA guide was done in 50 μL reactions with the following components: 0.02 μl of aforementioned template, 2.5 μl forward primer, 2.5 μl reverse primer, 25 μL NEB HiFi Polymerase, and 20 μl water. Cycling conditions were: 1× (30 s at 98° C.), 30× (10 s at 98° C., 15 s at 67° C.), 1× (2 min at 72° C.). PCR products were cleaned up with a 1.8× SPRI treatment and normalized to 25 ng/μL. The prepared RNA guide sequences for the AAVS1 target locus tested: TGGCCTGGGTCACCTCTACGGCTG (SEQ ID NO: 158) are shown in Table 12.

TABLE 12

| RNA Guides for Transient Transfection with CLUST.200916 Effectors. | |
| --- | --- |
| Effector | Pre-crRNA |
| SEQ ID NO: 24 | CCTGCAAGGGATCCAAA TTGCTCTGTTCGCAGAG ACTGGCCTGGGTCACCT CTACGGCTGCCTGCAAG GGATCCAAATTGCTCTG TTCGCAGAGAC (SEQ ID NO: 159) |
| SEQ ID NO: 28 | CCATCAATGGATCCAAA TTGCTCTGTACGCAGAG ACTGGCCTGGGTCACCT CTACGGCTGCCATCAAT GGATCCAAATTGCTCTG TACGCAGAGAC (SEQ ID NO: 160) |
| SEQ ID NO: 25 | CCTGCAAGGGATCCAAA TTGCTCTGTTCGCAGAG ACTGGCCTGGGTCACCT CTACGGCTGCCTGCAAG GGATCCAAATTGCTCTG TTCGCAGAGAC (SEQ ID NO: 161) |

Approximately 16 hours prior to transfection, 100 μl of 25,000 HEK293T cells in DMEM/10% FBS+Pen/Strep were plated into each well of a 96-well plate. On the day of transfection, the cells were 70-90% confluent. For each well to be transfected, a mixture of 0.5 μl of Lipofectamine 2000 and 9.5 μl of Opti-MEM was prepared and then incubated at room temperature for 5-20 minutes (Solution 1). After incubation, the lipofectamine:OptiMEM mixture was added to a separate mixture containing 182 ng of effector plasmid and 14 ng of RNA guide and water up to 10 μL (Solution 2). For the negative control, the RNA guide was not included in Solution 2. The solution 1 and solution 2 mixtures were mixed by pipetting up and down and then incubated at room temperature for 25 minutes. Following incubation, 20 L of the Solution 1 and Solution 2 mixture were added dropwise to each well of a 96 well plate containing the cells. 72 hours post transfection, cells are trypsinized by adding 10 μL of TrypLE to the center of each well and incubated for approximately 5 minutes. 100 μL of D10 media was then added to each well and mixed to resuspend cells. The cells were then spun down at 500 g for 10 minutes, and the supernatant was discarded. QuickExtract buffer was added to ⅕ the amount of the original cell suspension volume. Cells were incubated at 65° C. for 15 minutes, 68° C. for 15 minutes, and 98° C. for 10 minutes.

Samples for Next Generation Sequencing were prepared by two rounds of PCR. The first round (PCR1) was used to amplify specific genomic regions depending on the target. PCR1 products were purified by column purification. Round 2 PCR (PCR2) was done to add Illumina adapters and indexes. Reactions were then pooled and purified by column purification. Sequencing runs were done with a 150 cycle NextSeq v2.5 mid or high output kit.

FIG. 37 shows percent indels in the AAVS1 target locus in HEK293T cells following transfection with the effectors of SEQ ID NO: 24, SEQ ID NO: 28, and SEQ ID NO: 25. For each effector, the dots reflect percent indels measured in two bioreplicates, and the bars reflect the mean percent indels measured in the two bioreplicates. For each of the effectors of SEQ ID NO: 24, SEQ ID NO: 28, and SEQ ID NO: 25, the percent indels are higher than the percent indels of the negative control, which is indicated by the dotted line.

This Example suggests that CLUST.200916 effectors have nuclease activity in mammalian cells.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

---

What is claimed is:

1. An engineered, non-naturally occurring Clustered Regularly Interspaced Short Palindromic Repeat (CRISPR)-Cas system of CLUST.133120 comprising:

(a) a CRISPR-associated protein or a nucleic acid encoding the CRISPR-associated protein, wherein the CRISPR-associated protein comprises an amino acid sequence that is at least 80% identical to an amino acid sequence set forth in any one of SEQ ID NOs: 1, 4-11, 13-15, 18-20, or 23-29; and (b) an RNA guide, or a nucleic acid encoding the RNA guide, comprising a direct repeat sequence and a spacer sequence capable of hybridizing to a target nucleic acid in a eukaryotic cell;

wherein the CRISPR-associated protein is capable of binding to the RNA guide and of modifying the target nucleic acid sequence complementary to the spacer sequence.

2. The system of claim 1, wherein:

i) the CRISPR-associated protein comprises at least one RuvC domain or at least one split RuvC domain;

ii) the CRISPR-associated protein is capable of recognizing a protospacer adjacent motif (PAM) sequence in the target nucleic acid, wherein the PAM sequence comprises a nucleic acid sequence set forth as 5'-TTN-3', 5'-YYN-3', 5'-HHN-3', 5'-YKN-3', or 5'-HBN-3', wherein N is any nucleotide, Y is C or T, K is G or T, B is G, T, or C, and His A, C, or T;

iii) the CRISPR-associated protein further comprises a peptide tag, a fluorescent protein, a base-editing domain, a DNA methylation domain, a histone residue modification domain, a localization factor, a transcription modification factor, a light-gated control factor, a chemically inducible factor, or a chromatin visualization factor; or iv) the nucleic acid encoding the CRISPR-associated protein is:

a) codon-optimized for expression in a cell;

b) operably linked to a promoter; or c) in a vector.

3. The system of claim 2, wherein the vector comprises a retroviral vector, a lentiviral vector, a phage vector, an adenoviral vector, an adeno-associated vector, or a herpes simplex vector.

4. The system of claim 1, wherein the direct repeat sequence comprises a nucleotide sequence that is at least 80% identical to a nucleotide sequence set forth in any one of SEQ ID NOs: 30, 32-36, 38, 40-45, 77, 78, 81-94, 122, 124-128, 130, or 132-138.

5. The system of claim 1, wherein the spacer sequence of the RNA guide comprises between about 14 nucleotides to about 50 nucleotides or comprises between 20 and 35 nucleotides.

6. The system of claim 1, wherein the target nucleic acid is a DNA molecule and recognition of the target nucleic acid by the CRISPR-associated protein and RNA guide results in a modification of the target nucleic acid.

7. The system of claim 6, wherein the modification of the target nucleic acid:

i) is a double-stranded cleavage event;

ii) is a single-stranded cleavage event;

iii) results in an insertion event; or iv) results in a deletion event.

8. The system of claim 1, wherein the system does not comprise a tracrRNA.

9. The system of claim 1, wherein the system is present in a delivery composition comprising a nanoparticle, a liposome, an exosome, a microvesicle, or a gene-gun.

10. The system of claim 1, which is within an in vitro cell.

11. The system of claim 10, wherein the in vitro cell is a eukaryotic cell.

12. The system of claim 11, wherein the eukaryotic cell is a mammalian cell or a human cell.

13. The system of claim 1, wherein the CRISPR-associate protein comprises an amino acid sequence that is at least 90% identical to SEQ ID NO: 28.

14. The system of claim 1, wherein the CRISPR-associate protein comprises an amino acid sequence that is at least 95% identical to SEQ ID NO: 28.

15. A genetically modified in vitro cell, wherein the in vitro cell comprises:

(a) a CRISPR-associated protein or a nucleic acid encoding the CRISPR-associated protein, wherein the CRISPR-associated protein comprises an amino acid sequence that is at least 80% identical to an amino acid sequence set forth in any one of SEQ ID NOs: 1, 4-11, 13-15, 18-20, or 23-29; and (b) an RNA guide, or a nucleic acid encoding the RNA guide, comprising a direct repeat sequence and a spacer sequence capable of hybridizing to a target nucleic acid in an in vitro eukaryotic cell.

16. The genetically modified in vitro cell of claim 15, wherein:

i) the CRISPR-associated protein is capable of recognizing a PAM sequence comprising a nucleic acid sequence set forth as 5'-TTN-3', 5'-YYN-3', 5'-HHN-3', 5'-YKN-3', or 5'-HBN-3', wherein N is any nucleotide, Y is C or T, K is G or T, B is G, T, or C, and H is A, C, or T;

ii) the direct repeat sequence comprises a nucleotide sequence that is at least 80% identical to a nucleotide sequence set forth in any one of SEQ ID NOs: 30, 32-36, 38, 40-45, 77, 78, 81-94, 122, 124-128, 130, or 132-138;

iii) the spacer sequence comprises between about 14 nucleotides to about 50 nucleotides or between 20 and 35 nucleotides;

iv) the in vitro cell does not comprise a tracrRNA; or v) the in vitro cell is a eukaryotic cell.

17. The genetically modified in vitro cell of claim 16, wherein the eukaryotic cell is a mammalian cell or a human cell.

18. A method of binding the system of claim 1 to a target nucleic acid in a eukaryotic cell comprising:

(a) providing the system; and (b) delivering the system to the cell, wherein the cell comprises the target nucleic acid, wherein the CRISPR-associated protein binds to the RNA guide, and wherein the spacer sequence binds to the target nucleic acid.

19. A method of modifying a target nucleic acid in a eukaryotic cell, the method comprising delivering to the target nucleic acid an engineered, non-naturally occurring CRISPR-Cas system comprising:

(a) a CRISPR-associated protein or a nucleic acid encoding the CRISPR-associated protein, wherein the CRISPR-associated protein comprises an amino acid sequence that is at least 80% identical to an amino acid sequence set forth in any one of SEQ ID NOs: 1, 4-11, 13-15, 18-20, or 23-29; and (b) an RNA guide, or a nucleic acid encoding the RNA guide, comprising a direct repeat sequence and a spacer sequence capable of hybridizing to the target nucleic acid;

wherein the CRISPR-associated protein is capable of binding to the RNA guide; and wherein recognition of the target nucleic acid by the CRISPR-associated protein and RNA guide results in a modification of the target nucleic acid.

20. The method of claim 19, wherein:

i) the CRISPR-associated protein is capable of recognizing a PAM sequence comprising a nucleic acid sequence set forth as 5'-TTN-3', 5'-YYN-3', 5'-HHN-3', 5'-YKN-3', or 5'-HBN-3', wherein N is any nucleotide, Y is C or T, K is G or T, B is G, T, or C, and H is A, C, or T;

ii) the direct repeat sequence comprises a nucleotide sequence that is at least 80% identical to a nucleotide sequence set forth in any one of SEQ ID NOs: 30, 32-36, 38, 40-45, 77, 78, 81-94, 122, 124-128, 130, or 132-138;

iii) the spacer sequence comprises between about 14 nucleotides to about 50 nucleotides, optionally the spacer sequence comprises between 20 and 35 nucleotides; or iv) the system does not comprise a tracrRNA.

21. The method of claim 19, wherein the target nucleic acid:

a) is a DNA molecule; or b) comprises a PAM sequence.

22. The method of claim 19, wherein the modification of the target nucleic acid:

a) is a double-stranded cleavage event:

b) is a single-stranded cleavage event;

c) results in an insertion event; or d) results in a deletion event.

23. A method of editing a target nucleic acid, the method comprising contacting the target nucleic acid with the system of claim 1.

24. A method of modifying expression of a target nucleic acid, the method comprising contacting the target nucleic acid with the system of claim 1.

* * * * *

SEQUENCE LISTING

```
<160> NUMBER OF SEQ ID NOS: 164

<210> SEQ ID NO 1
<211> LENGTH: 830
<212> TYPE: PRT
<213> ORGANISM: Unknown
<220> FEATURE:
<223> OTHER INFORMATION: Description of Unknown:
      wastewater-industrial wastewater-sediment sequence

<400> SEQUENCE: 1

Met Pro Lys Ile Lys Lys Pro Thr Glu Ile Ser Leu Leu Arg Lys Glu
1               5                   10                  15

Val Phe Pro Asp Leu His Phe Ala Lys Asp Arg Met Arg Ala Ala Ser
            20                  25                  30

Leu Val Leu Lys Asn Glu Gly Arg Glu Ala Ala Ile Glu Tyr Leu Arg
        35                  40                  45

Val Asn His Glu Asp Lys Pro Pro Asn Phe Met Pro Pro Ala Lys Thr
    50                  55                  60

Pro Tyr Val Ala Leu Ser Arg Pro Leu Glu Gln Trp Pro Ile Ala Gln
65                  70                  75                  80
```

Ala Ser Ile Ala Ile Gln Lys Tyr Ile Phe Gly Leu Thr Lys Asp Glu
                    85                  90                  95

Phe Ser Ala Thr Lys Lys Leu Leu Tyr Gly Asp Lys Ser Thr Pro Asn
                100                 105                 110

Thr Glu Ser Arg Lys Arg Trp Phe Glu Val Thr Gly Val Pro Asn Phe
                115                 120                 125

Gly Tyr Met Ser Ala Gln Gly Leu Asn Ala Ile Phe Ser Gly Ala Leu
    130                 135                 140

Ala Arg Tyr Glu Gly Val Val Gln Lys Val Glu Asn Arg Asn Lys Lys
145                 150                 155                 160

Arg Phe Glu Lys Leu Ser Glu Lys Asn Gln Leu Leu Ile Glu Glu Gly
                165                 170                 175

Gln Pro Val Lys Asp Tyr Val Pro Asp Thr Ala Tyr His Thr Pro Glu
                180                 185                 190

Thr Leu Gln Lys Leu Ala Glu Asn Asn His Val Arg Val Glu Asp Leu
                195                 200                 205

Gly Asp Met Ile Asp Arg Leu Val His Pro Pro Gly Ile His Arg Ser
    210                 215                 220

Ile Tyr Gly Tyr Gln Gln Val Pro Pro Phe Ala Tyr Asp Pro Asp Asn
225                 230                 235                 240

Pro Lys Gly Ile Ile Leu Pro Lys Ala Tyr Ala Gly Tyr Thr Arg Lys
                245                 250                 255

Pro His Asp Ile Ile Glu Ala Met Pro Asn Arg Leu Asn Ile Pro Glu
                260                 265                 270

Gly Gln Ala Gly Tyr Ile Pro Glu His Gln Arg Asp Lys Leu Lys Lys
                275                 280                 285

Gly Gly Arg Val Lys Arg Leu Arg Thr Thr Arg Val Arg Val Asp Ala
    290                 295                 300

Thr Glu Thr Val Arg Ala Lys Ala Glu Ala Leu Asn Ala Glu Lys Ala
305                 310                 315                 320

Arg Leu Arg Gly Lys Glu Ala Ile Leu Ala Val Phe Gln Ile Glu Glu
                325                 330                 335

Asp Trp Ala Leu Ile Asp Met Arg Gly Leu Leu Arg Asn Val Tyr Met
                340                 345                 350

Arg Lys Leu Ile Ala Ala Gly Glu Leu Thr Pro Thr Thr Leu Leu Gly
                355                 360                 365

Tyr Phe Thr Glu Thr Leu Thr Leu Asp Pro Arg Arg Thr Glu Ala Thr
    370                 375                 380

Phe Cys Tyr His Leu Arg Ser Glu Gly Ala Leu His Ala Glu Tyr Val
385                 390                 395                 400

Arg His Gly Lys Asn Thr Arg Glu Leu Leu Leu Asp Leu Thr Lys Asp
                405                 410                 415

Asn Glu Lys Ile Ala Leu Val Thr Ile Asp Leu Gly Gln Arg Asn Pro
                420                 425                 430

Leu Ala Ala Ala Ile Phe Arg Val Gly Arg Asp Ala Ser Gly Asp Leu
                435                 440                 445

Thr Glu Asn Ser Leu Glu Pro Val Ser Arg Met Leu Leu Pro Gln Ala
    450                 455                 460

Tyr Leu Asp Gln Ile Lys Ala Tyr Arg Asp Ala Tyr Asp Ser Phe Arg
465                 470                 475                 480

Gln Asn Ile Trp Asp Thr Ala Leu Ala Ser Leu Thr Pro Glu Gln Gln
                485                 490                 495

Arg Gln Ile Leu Ala Tyr Glu Ala Tyr Thr Pro Asp Asp Ser Lys Glu

-continued

```
              500                505                510
Asn Val Leu Arg Leu Leu Leu Gly Gly Asn Val Met Pro Asp Asp Leu
          515                520                525
Pro Trp Glu Asp Met Thr Lys Asn Thr His Tyr Ile Ser Asp Arg Tyr
          530                535                540
Leu Ala Asp Gly Gly Asp Pro Ser Lys Val Trp Phe Val Pro Gly Pro
545                550                555                560
Arg Lys Arg Lys Lys Asn Ala Pro Pro Leu Lys Lys Pro Pro Lys Pro
                565                570                575
Arg Glu Leu Val Lys Arg Ser Asp His Asn Ile Ser His Leu Ser Glu
          580                585                590
Phe Arg Pro Gln Leu Leu Lys Glu Thr Arg Asp Ala Phe Glu Lys Ala
          595                600                605
Lys Ile Asp Thr Glu Arg Gly His Val Gly Tyr Gln Lys Leu Ser Thr
          610                615                620
Arg Lys Asp Gln Leu Cys Lys Glu Ile Leu Asn Trp Leu Glu Ala Glu
625                630                635                640
Ala Val Arg Leu Thr Arg Cys Lys Thr Met Val Leu Gly Leu Glu Asp
                645                650                655
Leu Asn Gly Pro Phe Phe Asn Gln Gly Lys Gly Lys Val Arg Gly Trp
                660                665                670
Val Ser Phe Phe Arg Gln Lys Gln Glu Asn Arg Trp Ile Val Asn Gly
          675                680                685
Phe Arg Lys Asn Ala Leu Ala Arg Ala His Asp Lys Gly Lys Tyr Ile
          690                695                700
Leu Glu Leu Trp Pro Ser Trp Thr Ser Gln Thr Cys Pro Lys Cys Lys
705                710                715                720
His Val His Ala Asp Asn Arg His Gly Asp Asp Phe Val Cys Leu Gln
                725                730                735
Cys Gly Ala Arg Leu His Ala Asp Ala Glu Val Ala Thr Trp Asn Leu
                740                745                750
Ala Val Val Ala Ile Gln Gly His Ser Leu Pro Gly Pro Val Arg Glu
                755                760                765
Lys Ser Asn Asp Arg Lys Lys Ser Gly Ser Ala Arg Lys Ser Lys Lys
          770                775                780
Ala Asn Glu Ser Gly Lys Val Val Gly Ala Trp Ala Ala Gln Ala Thr
785                790                795                800
Pro Lys Arg Ala Thr Ser Lys Lys Glu Thr Gly Thr Ala Arg Asn Pro
                805                810                815
Val Tyr Asn Pro Leu Glu Thr Gln Ala Ser Cys Pro Ala Pro
                820                825                830
```

<210> SEQ ID NO 2
<211> LENGTH: 781
<212> TYPE: PRT
<213> ORGANISM: Unknown
<220> FEATURE:
<223> OTHER INFORMATION: Description of Unknown:
     aquatic-freshwater-bog forest soil sequence

<400> SEQUENCE: 2

```
Met Arg Gln Pro Ala Glu Lys Thr Ala Phe Gln Val Phe Arg Gln Glu
1                5                10                15
Val Ile Gly Thr Gln Lys Leu Ser Gly Gly Asp Ala Lys Thr Ala Gly
          20                25                30
```

-continued

```
Arg Leu Tyr Lys Gln Gly Lys Met Glu Ala Ala Arg Glu Trp Leu Leu
        35              40              45

Lys Gly Ala Arg Asp Asp Val Pro Pro Asn Phe Gln Pro Pro Ala Lys
        50              55              60

Cys Leu Val Val Ala Val Ser His Pro Phe Glu Glu Trp Asp Ile Ser
65              70              75              80

Lys Thr Asn His Asp Val Gln Ala Tyr Ile Tyr Ala Gln Pro Leu Gln
                85              90              95

Ala Glu Gly His Leu Asn Gly Leu Ser Glu Lys Trp Glu Asp Thr Ser
                100             105             110

Ala Asp Gln His Lys Leu Trp Phe Glu Lys Thr Gly Val Pro Asp Arg
                115             120             125

Gly Leu Pro Val Gln Ala Ile Asn Lys Ile Ala Lys Ala Ala Val Asn
        130             135             140

Arg Ala Phe Gly Val Val Arg Lys Val Glu Asn Arg Asn Glu Lys Arg
145             150             155             160

Arg Ser Arg Asp Asn Arg Ile Ala Glu His Asn Arg Glu Asn Gly Leu
                165             170             175

Thr Glu Val Val Arg Glu Ala Pro Glu Val Ala Thr Asn Ala Asp Gly
                180             185             190

Phe Leu Leu His Pro Pro Gly Ile Asp Pro Ser Ile Leu Ser Tyr Ala
                195             200             205

Ser Val Ser Pro Val Pro Tyr Asn Ser Ser Lys His Ser Phe Val Arg
        210             215             220

Leu Pro Glu Glu Tyr Gln Ala Tyr Asn Val Glu Pro Asp Ala Pro Ile
225             230             235             240

Pro Gln Phe Val Val Glu Asp Arg Phe Ala Ile Pro Pro Gly Gln Pro
                245             250             255

Gly Tyr Val Pro Glu Trp Gln Arg Leu Lys Cys Ser Thr Asn Lys His
                260             265             270

Arg Arg Met Arg Gln Trp Ser Asn Gln Asp Tyr Lys Pro Lys Ala Gly
        275             280             285

Arg Arg Ala Lys Pro Leu Glu Phe Gln Ala His Leu Thr Arg Glu Arg
        290             295             300

Ala Lys Gly Ala Leu Leu Val Val Met Arg Ile Lys Glu Asp Trp Val
305             310             315             320

Val Phe Asp Val Arg Gly Leu Leu Arg Asn Val Glu Trp Arg Lys Val
                325             330             335

Leu Ser Glu Glu Ala Arg Glu Lys Leu Thr Leu Lys Gly Leu Leu Asp
                340             345             350

Leu Phe Thr Gly Asp Pro Val Ile Asp Thr Lys Arg Gly Ile Val Thr
                355             360             365

Phe Leu Tyr Lys Ala Glu Ile Thr Lys Ile Leu Ser Lys Arg Thr Val
        370             375             380

Lys Thr Lys Asn Ala Arg Asp Leu Leu Leu Arg Leu Thr Glu Pro Gly
385             390             395             400

Glu Asp Gly Leu Arg Arg Glu Val Gly Leu Val Ala Val Asp Leu Gly
                405             410             415

Gln Thr His Pro Ile Ala Ala Ala Ile Tyr Arg Ile Gly Arg Thr Ser
                420             425             430

Ala Gly Ala Leu Glu Ser Thr Val Leu His Arg Gln Gly Leu Arg Glu
        435             440             445

Asp Gln Lys Glu Lys Leu Lys Glu Tyr Arg Lys Arg His Thr Ala Leu
```

```
        450             455             460

Asp Ser Arg Leu Arg Lys Glu Ala Phe Glu Thr Leu Ser Val Glu Gln
465             470             475             480

Gln Lys Glu Ile Val Thr Val Ser Gly Ser Gly Ala Gln Ile Thr Lys
                485             490             495

Asp Lys Val Cys Asn Tyr Leu Gly Val Asp Pro Ser Thr Leu Pro Trp
            500             505             510

Glu Lys Met Gly Ser Tyr Thr His Phe Ile Ser Asp Asp Phe Leu Arg
        515             520             525

Arg Gly Gly Asp Pro Asn Ile Val His Phe Asp Arg Gln Pro Lys Lys
        530             535             540

Gly Lys Val Ser Lys Lys Ser Gln Arg Ile Lys Arg Ser Asp Ser Gln
545             550             555             560

Trp Val Gly Arg Met Arg Pro Arg Leu Ser Gln Glu Thr Ala Lys Ala
                565             570             575

Arg Met Glu Ala Asp Trp Ala Ala Gln Asn Glu Asn Glu Glu Tyr Lys
            580             585             590

Arg Leu Ala Arg Ser Lys Gln Glu Leu Ala Arg Trp Cys Val Asn Thr
        595             600             605

Leu Leu Gln Asn Thr Arg Cys Ile Thr Gln Cys Asp Glu Ile Val Val
        610             615             620

Val Ile Glu Asp Leu Asn Val Lys Ser Leu His Gly Lys Gly Ala Arg
625             630             635             640

Glu Pro Gly Trp Asp Asn Phe Phe Thr Pro Lys Thr Glu Asn Arg Trp
                645             650             655

Phe Ile Gln Ile Leu His Lys Thr Phe Ser Glu Leu Pro Lys His Arg
            660             665             670

Gly Glu His Val Ile Glu Gly Cys Pro Leu Arg Thr Ser Ile Thr Cys
            675             680             685

Pro Ala Cys Ser Tyr Cys Asp Lys Asn Ser Arg Asn Gly Glu Lys Phe
        690             695             700

Val Cys Val Ala Cys Gly Ala Thr Phe His Ala Asp Phe Glu Val Ala
705             710             715             720

Thr Tyr Asn Leu Val Arg Leu Ala Thr Thr Gly Met Pro Met Pro Lys
                725             730             735

Ser Leu Glu Arg Gln Gly Gly Gly Glu Lys Ala Gly Gly Ala Arg Lys
            740             745             750

Ala Arg Lys Lys Ala Lys Gln Val Glu Lys Ile Val Val Gln Ala Asn
            755             760             765

Ala Asn Val Thr Met Asn Gly Ala Ser Leu His Ser Pro
        770             775             780
```

<210> SEQ ID NO 3
<211> LENGTH: 781
<212> TYPE: PRT
<213> ORGANISM: Unknown
<220> FEATURE:
<223> OTHER INFORMATION: Description of Unknown:
     aquatic-freshwater-bog forest soil sequence

<400> SEQUENCE: 3

```
Met Arg Gln Pro Ala Glu Lys Thr Ala Phe Gln Val Phe Arg Gln Glu
1               5               10              15

Val Ile Gly Thr Gln Lys Leu Ser Gly Gly Asp Ala Lys Thr Ala Gly
            20              25              30
```

-continued

```
Arg Leu Tyr Lys Gln Gly Lys Met Glu Ala Ala Arg Glu Trp Leu Leu
        35              40              45

Lys Gly Ala Arg Asp Asp Val Pro Pro Asn Phe Gln Pro Pro Ala Lys
        50              55              60

Cys Leu Val Val Ala Val Ser His Pro Phe Glu Glu Trp Asp Ile Ser
65              70              75              80

Lys Thr Asn His Asp Val Gln Ala Tyr Ile Tyr Ala Gln Pro Leu Gln
                85              90              95

Ala Glu Gly His Leu Asn Gly Leu Ser Glu Lys Trp Glu Asp Thr Ser
                100             105             110

Ala Asp Gln His Lys Leu Trp Phe Glu Lys Thr Gly Val Pro Asp Arg
                115             120             125

Gly Leu Pro Val Gln Ala Ile Asn Lys Ile Ala Lys Ala Ala Val Asn
        130             135             140

Arg Ala Phe Gly Val Val Arg Lys Val Glu Asn Arg Asn Glu Lys Arg
145             150             155             160

Arg Ser Arg Asp Asn Arg Ile Ala Glu His Asn Arg Glu Asn Gly Leu
                165             170             175

Thr Glu Val Val Arg Glu Ala Pro Glu Val Ala Thr Asn Ala Asp Gly
                180             185             190

Phe Leu Leu His Pro Pro Gly Ile Asp Pro Ser Ile Leu Ser Tyr Ala
                195             200             205

Ser Val Ser Pro Val Pro Tyr Asn Ser Ser Lys His Ser Phe Val Arg
        210             215             220

Leu Pro Glu Glu Tyr Gln Ala Tyr Asn Val Glu Pro Asp Ala Pro Ile
225             230             235             240

Pro Gln Phe Val Val Glu Asp Arg Phe Ala Ile Pro Pro Gly Gln Pro
                245             250             255

Gly Tyr Val Pro Glu Trp Gln Arg Leu Lys Cys Ser Thr Asn Lys His
                260             265             270

Arg Arg Met Arg Gln Trp Ser Asn Gln Asp Tyr Lys Pro Lys Ala Gly
        275             280             285

Arg Arg Ala Lys Pro Leu Glu Phe Gln Ala His Leu Thr Arg Glu Arg
        290             295             300

Ala Lys Gly Ala Leu Leu Val Val Met Arg Ile Lys Glu Asp Trp Val
305             310             315             320

Val Phe Asp Val Arg Gly Leu Leu Arg Asn Val Glu Trp Arg Lys Val
                325             330             335

Leu Ser Glu Glu Ala Arg Glu Lys Leu Thr Leu Lys Gly Leu Leu Asp
                340             345             350

Leu Phe Thr Gly Asp Pro Val Ile Asp Thr Lys Arg Gly Ile Val Thr
                355             360             365

Phe Leu Tyr Lys Ala Glu Ile Thr Lys Ile Leu Ser Lys Arg Thr Val
        370             375             380

Lys Thr Lys Asn Ala Arg Asp Leu Leu Leu Arg Leu Thr Glu Pro Gly
385             390             395             400

Glu Asp Gly Leu Arg Arg Glu Val Gly Leu Val Ala Val Asp Leu Gly
                405             410             415

Gln Thr His Pro Ile Ala Ala Ile Tyr Arg Ile Gly Arg Thr Ser
                420             425             430

Ala Gly Ala Leu Glu Ser Thr Val Leu His Arg Gln Gly Leu Arg Glu
        435             440             445

Asp Gln Lys Glu Lys Leu Lys Glu Tyr Arg Lys Arg His Thr Ala Leu
```

-continued

```
        450             455             460

Asp Ser Arg Leu Arg Lys Glu Ala Phe Glu Thr Leu Ser Val Glu Gln
465                 470                 475                 480

Gln Lys Glu Ile Val Thr Val Ser Gly Ser Gly Ala Gln Ile Thr Lys
                485                 490                 495

Asp Lys Val Cys Asn Tyr Leu Gly Val Asp Pro Ser Thr Leu Pro Trp
                500                 505                 510

Glu Lys Met Gly Ser Tyr Thr His Phe Ile Ser Asp Asp Phe Leu Arg
            515                 520                 525

Arg Gly Gly Asp Pro Asn Ile Val His Phe Asp Arg Gln Pro Lys Lys
        530                 535                 540

Gly Lys Val Ser Lys Lys Ser Gln Arg Ile Lys Arg Ser Asp Ser Gln
545                 550                 555                 560

Trp Val Gly Arg Met Arg Pro Arg Leu Ser Gln Glu Thr Ala Lys Ala
                565                 570                 575

Arg Met Glu Ala Asp Trp Ala Ala Gln Asn Glu Asn Glu Glu Tyr Lys
                580                 585                 590

Arg Leu Ala Arg Ser Lys Gln Glu Leu Ala Arg Trp Cys Val Asn Thr
            595                 600                 605

Leu Leu Gln Asn Thr Arg Cys Ile Thr Gln Cys Asp Glu Ile Val Val
        610                 615                 620

Val Ile Glu Asp Leu Asn Val Lys Ser Leu His Gly Lys Gly Ala Arg
625                 630                 635                 640

Glu Pro Gly Trp Asp Asn Phe Phe Thr Pro Lys Thr Glu Asn Arg Trp
                645                 650                 655

Phe Ile Gln Ile Leu His Lys Thr Phe Ser Glu Leu Pro Lys His Arg
                660                 665                 670

Gly Glu His Val Ile Glu Gly Cys Pro Leu Arg Thr Ser Ile Thr Cys
            675                 680                 685

Pro Ala Cys Ser Tyr Cys Asp Lys Asn Ser Arg Asn Gly Glu Lys Phe
        690                 695                 700

Val Cys Val Ala Cys Gly Ala Thr Phe His Ala Asp Phe Glu Val Ala
705                 710                 715                 720

Thr Tyr Asn Leu Val Arg Leu Ala Thr Thr Gly Met Pro Met Pro Lys
                725                 730                 735

Ser Leu Glu Arg Gln Gly Gly Gly Glu Lys Ala Gly Gly Ala Arg Lys
            740                 745                 750

Ala Arg Lys Lys Ala Lys Gln Val Glu Lys Ile Val Val Gln Ala Asn
        755                 760                 765

Ala Asn Val Thr Met Asn Gly Ala Ser Leu His Ser Pro
        770                 775                 780
```

```
<210> SEQ ID NO 4
<211> LENGTH: 790
<212> TYPE: PRT
<213> ORGANISM: Unknown
<220> FEATURE:
<223> OTHER INFORMATION: Description of Unknown:
      aquatic-freshwater-sediment sequence

<400> SEQUENCE: 4

Met Thr Pro Ser Pro Gln Ile Ala Arg Leu Val Glu Thr Pro Leu Ala
1               5                   10                  15

Ala Ala Leu Lys Ala His His Pro Gly Lys Lys Phe Arg Ser Asp Tyr
            20                  25                  30
```

-continued

Leu Lys Lys Ala Gly Lys Ile Leu Lys Asp Gln Gly Val Glu Ala Ala
        35                  40                  45

Met Ala His Leu Asp Gly Lys Asp Gln Ala Glu Pro Pro Asn Phe Lys
    50                  55                  60

Pro Pro Ala Lys Cys Arg Ile Val Ala Arg Ser Arg Glu Phe Ser Glu
65                  70                  75                  80

Trp Pro Ile Val Lys Ala Ser Val Glu Ile Gln Lys Tyr Ile Tyr Gly
                85                  90                  95

Leu Thr Leu Glu Glu Arg Lys Ala Cys Asp Pro Gly Lys Ser Ser Ala
            100                 105                 110

Ser His Lys Ala Trp Phe Ala Lys Thr Gly Val Asn Thr Phe Gly Tyr
            115                 120                 125

Ser Ser Val Gln Gly Phe Asn Leu Ile Phe Gly His Thr Leu Gly Arg
    130                 135                 140

Tyr Asp Gly Val Leu Val Lys Thr Glu Asn Leu Asn Lys Lys Arg Ala
145                 150                 155                 160

Glu Lys Asn Glu Arg Phe Arg Ala Lys Ala Leu Ala Glu Gly Arg Ala
                165                 170                 175

Glu Pro Val Cys Pro Pro Leu Val Thr Ala Thr Asn Asp Thr Gly Gln
            180                 185                 190

Asp Val Thr Leu Glu Asp Gly Arg Val Val Arg Pro Gly Gln Leu Leu
            195                 200                 205

Gln Pro Pro Gly Ile Asn Pro Asn Ile Tyr Ala Tyr Gln Gln Val Ser
    210                 215                 220

Pro Lys Ala Tyr Val Pro Gly Ile Ile Glu Leu Pro Glu Glu Phe Gln
225                 230                 235                 240

Gly Tyr Ser Arg Asp Pro Asn Ala Val Ile Leu Pro Leu Val Pro Arg
                245                 250                 255

Asp Arg Leu Ser Ile Pro Lys Gly Gln Pro Gly Tyr Val Pro Glu Pro
            260                 265                 270

His Arg Glu Gly Leu Thr Gly Arg Lys Asp Arg Arg Met Arg Arg Tyr
            275                 280                 285

Tyr Glu Thr Glu Arg Gly Thr Lys Leu Lys Arg Pro Pro Leu Thr Ala
    290                 295                 300

Lys Gly Arg Ala Asp Lys Ala Asn Glu Ala Leu Leu Val Val Val Arg
305                 310                 315                 320

Ile Asp Ser Asp Trp Val Val Met Asp Val Arg Gly Leu Leu Arg Asn
                325                 330                 335

Ala Arg Trp Arg Arg Leu Val Ser Lys Glu Gly Ile Thr Leu Asn Gly
            340                 345                 350

Leu Leu Asp Leu Phe Thr Gly Asp Pro Val Leu Asn Pro Lys Asp Cys
            355                 360                 365

Ser Val Ser Arg Asp Thr Gly Asp Pro Val Asn Asp Pro Arg His Gly
    370                 375                 380

Val Val Thr Phe Cys Tyr Lys Leu Gly Val Val Asp Val Cys Ser Lys
385                 390                 395                 400

Asp Arg Pro Ile Lys Gly Phe Arg Thr Lys Glu Val Leu Glu Arg Leu
                405                 410                 415

Thr Ser Ser Gly Thr Val Gly Met Val Ser Ile Asp Leu Gly Gln Thr
            420                 425                 430

Asn Pro Val Ala Ala Ala Val Ser Arg Val Thr Lys Gly Leu Gln Ala
            435                 440                 445

Glu Thr Leu Glu Thr Phe Thr Leu Pro Asp Asp Leu Leu Gly Lys Val

-continued

```
              450                 455                 460

Arg Ala Tyr Arg Ala Lys Thr Asp Arg Met Glu Glu Gly Phe Arg Arg
465                 470                 475                 480

Asn Ala Leu Arg Lys Leu Thr Ala Glu Gln Gln Ala Glu Ile Thr Arg
                485                 490                 495

Tyr Asn Asp Ala Thr Glu Gln Gln Ala Lys Ala Leu Val Cys Ser Thr
                500                 505                 510

Tyr Gly Ile Gly Pro Glu Glu Val Pro Trp Glu Arg Met Thr Ser Asn
                515                 520                 525

Thr Thr Tyr Ile Ser Asp His Ile Leu Asp His Gly Gly Asp Pro Asp
        530                 535                 540

Thr Val Phe Phe Met Ala Thr Lys Arg Gly Gln Asn Lys Pro Thr Leu
545                 550                 555                 560

His Lys Arg Lys Asp Lys Ala Trp Gly Gln Lys Phe Arg Pro Ala Ile
                565                 570                 575

Ser Val Glu Thr Arg Leu Ala Arg Gln Ala Ala Glu Trp Glu Leu Arg
                580                 585                 590

Arg Ala Ser Leu Glu Phe Gln Lys Leu Ser Val Trp Lys Thr Glu Leu
                595                 600                 605

Cys Arg Gln Ala Val Asn Tyr Val Met Glu Arg Thr Lys Lys Arg Thr
        610                 615                 620

Gln Cys Asp Val Ile Ile Pro Val Ile Glu Asp Leu Pro Val Pro Leu
625                 630                 635                 640

Phe His Gly Ser Gly Lys Arg Asp Pro Gly Trp Ala Asn Phe Phe Val
                645                 650                 655

His Lys Arg Glu Asn Arg Trp Phe Ile Asp Gly Leu His Lys Ala Phe
                660                 665                 670

Ser Glu Leu Gly Lys His Arg Gly Ile Tyr Val Phe Glu Val Cys Pro
                675                 680                 685

Gln Arg Thr Ser Ile Thr Cys Pro Lys Cys Gly His Cys Asp Pro Asp
        690                 695                 700

Asn Arg Asp Gly Glu Lys Phe Val Cys Leu Ser Cys Gln Ala Thr Leu
705                 710                 715                 720

His Ala Asp Leu Asp Val Ala Thr Thr Asn Leu Val Arg Val Ala Leu
                725                 730                 735

Thr Gly Lys Val Met Pro Arg Ser Glu Arg Ser Gly Asp Ala Gln Thr
                740                 745                 750

Pro Gly Pro Ala Arg Lys Ala Arg Thr Gly Lys Ile Lys Gly Ser Lys
                755                 760                 765

Pro Thr Ser Ala Pro Gln Gly Ala Thr Gln Thr Asp Ala Lys Ala His
        770                 775                 780

Leu Ser Gln Thr Gly Val
785                 790

<210> SEQ ID NO 5
<211> LENGTH: 790
<212> TYPE: PRT
<213> ORGANISM: Unknown
<220> FEATURE:
<223> OTHER INFORMATION: Description of Unknown:
      aquatic-freshwater-sediment sequence

<400> SEQUENCE: 5

Met Thr Pro Ser Pro Gln Ile Ala Arg Leu Val Glu Thr Pro Leu Ala
1               5                   10                  15
```

```
Ala Ala Leu Lys Ala His His Pro Gly Lys Lys Phe Arg Ser Asp Tyr
            20              25                  30

Leu Lys Lys Ala Gly Lys Ile Leu Lys Asp Gln Gly Val Glu Ala Ala
            35              40                  45

Met Ala His Leu Asp Gly Lys Asp Gln Ala Glu Pro Pro Asn Phe Lys
        50              55                  60

Pro Pro Ala Lys Cys Arg Ile Val Ala Arg Ser Arg Glu Phe Ser Glu
65                  70                  75                  80

Trp Pro Ile Val Lys Ala Ser Val Glu Ile Gln Lys Tyr Ile Tyr Gly
                85                  90                  95

Leu Thr Leu Glu Glu Arg Lys Ala Cys Asp Pro Gly Lys Ser Ser Ala
            100                 105                 110

Ser His Lys Ala Trp Phe Ala Lys Thr Gly Val Asn Thr Phe Gly Tyr
            115                 120                 125

Ser Ser Val Gln Gly Phe Asn Leu Ile Phe Gly His Thr Leu Gly Arg
    130                 135                 140

Tyr Asp Gly Val Leu Val Lys Thr Glu Asn Leu Asn Lys Lys Arg Ala
145                 150                 155                 160

Glu Lys Asn Glu Arg Phe Arg Ala Lys Ala Leu Ala Glu Gly Arg Ala
                165                 170                 175

Glu Pro Val Cys Pro Pro Leu Val Thr Ala Thr Asn Asp Thr Gly Gln
                180                 185                 190

Asp Val Thr Leu Glu Asp Gly Arg Val Val Arg Pro Gly Gln Leu Leu
            195                 200                 205

Gln Pro Pro Gly Ile Asn Pro Asn Ile Tyr Ala Tyr Gln Gln Val Ser
    210                 215                 220

Pro Lys Ala Tyr Val Pro Gly Ile Ile Glu Leu Pro Glu Glu Phe Gln
225                 230                 235                 240

Gly Tyr Ser Arg Asp Pro Asn Ala Val Ile Leu Pro Leu Val Pro Arg
                245                 250                 255

Asp Arg Leu Ser Ile Pro Lys Gly Gln Pro Gly Tyr Val Pro Glu Pro
                260                 265                 270

His Arg Glu Gly Leu Thr Gly Arg Lys Asp Arg Arg Met Arg Arg Tyr
            275                 280                 285

Tyr Glu Thr Glu Arg Gly Thr Lys Leu Lys Arg Pro Pro Leu Thr Ala
    290                 295                 300

Lys Gly Arg Ala Asp Lys Ala Asn Glu Ala Leu Leu Val Val Val Arg
305                 310                 315                 320

Ile Asp Ser Asp Trp Val Val Met Asp Val Arg Gly Leu Leu Arg Asn
                325                 330                 335

Ala Arg Trp Arg Arg Leu Val Ser Lys Glu Gly Ile Thr Leu Asn Gly
            340                 345                 350

Leu Leu Asp Leu Phe Thr Gly Asp Pro Val Leu Asn Pro Lys Asp Cys
            355                 360                 365

Ser Val Ser Arg Asp Thr Gly Asp Pro Val Asn Asp Pro Arg His Gly
    370                 375                 380

Val Val Thr Phe Cys Tyr Lys Leu Gly Val Val Asp Val Cys Ser Lys
385                 390                 395                 400

Asp Arg Pro Ile Lys Gly Phe Arg Thr Lys Glu Val Leu Glu Arg Leu
                405                 410                 415

Thr Ser Ser Gly Thr Val Gly Met Val Ser Ile Asp Leu Gly Gln Thr
            420                 425                 430

Asn Pro Val Ala Ala Ala Val Ser Arg Val Thr Lys Gly Leu Gln Ala
```

-continued

```
              435                    440                     445
Glu Thr Leu Glu Thr Phe Thr Leu Pro Asp Asp Leu Leu Gly Lys Val
    450                     455                    460

Arg Ala Tyr Arg Ala Lys Thr Asp Arg Met Glu Glu Gly Phe Arg Arg
465                     470                    475                     480

Asn Ala Leu Arg Lys Leu Thr Ala Glu Gln Gln Ala Glu Ile Thr Arg
                    485                     490                    495

Tyr Asn Asp Ala Thr Glu Gln Gln Ala Lys Ala Leu Val Cys Ser Thr
                500                     505                    510

Tyr Gly Ile Gly Pro Glu Glu Val Pro Trp Glu Arg Met Thr Ser Asn
            515                     520                    525

Thr Thr Tyr Ile Ser Asp His Ile Leu Asp His Gly Gly Asp Pro Asp
    530                     535                    540

Thr Val Phe Phe Met Ala Thr Lys Arg Gly Gln Asn Lys Pro Thr Leu
545                     550                    555                     560

His Lys Arg Lys Asp Lys Ala Trp Gly Gln Lys Phe Arg Pro Ala Ile
                565                     570                    575

Ser Val Glu Thr Arg Leu Ala Arg Gln Ala Ala Glu Trp Glu Leu Arg
            580                     585                    590

Arg Ala Ser Leu Glu Phe Gln Lys Leu Ser Val Trp Lys Thr Glu Leu
            595                     600                    605

Cys Arg Gln Ala Val Asn Tyr Val Met Glu Arg Thr Lys Lys Arg Thr
    610                     615                    620

Gln Cys Asp Val Ile Ile Pro Val Ile Glu Asp Leu Pro Val Pro Leu
625                     630                    635                     640

Phe His Gly Ser Gly Lys Arg Asp Pro Gly Trp Ala Asn Phe Phe Val
                645                     650                    655

His Lys Arg Glu Asn Arg Trp Phe Ile Asp Gly Leu His Lys Ala Phe
            660                     665                    670

Ser Glu Leu Gly Lys His Arg Gly Ile Tyr Val Phe Glu Val Cys Pro
            675                     680                    685

Gln Arg Thr Ser Ile Thr Cys Pro Lys Cys Gly His Cys Asp Pro Asp
    690                     695                    700

Asn Arg Asp Gly Glu Lys Phe Val Cys Leu Ser Cys Gln Ala Thr Leu
705                     710                    715                     720

Asn Ala Asp Leu Asp Val Ala Thr Thr Asn Leu Val Arg Val Ala Leu
                725                     730                    735

Thr Gly Lys Val Met Pro Arg Ser Glu Arg Ser Gly Asp Ala Gln Thr
            740                     745                    750

Pro Gly Pro Ala Arg Lys Ala Arg Thr Gly Lys Ile Lys Gly Ser Lys
            755                     760                    765

Pro Thr Ser Ala Pro Gln Gly Ala Thr Gln Thr Asp Ala Lys Ala His
    770                     775                    780

Leu Ser Gln Thr Gly Val
785                     790
```

<210> SEQ ID NO 6
<211> LENGTH: 790
<212> TYPE: PRT
<213> ORGANISM: Unknown
<220> FEATURE:
<223> OTHER INFORMATION: Description of Unknown:
      aquatic-freshwater-sediment sequence

<400> SEQUENCE: 6

-continued

```
Met Thr Pro Ser Pro Gln Ile Ala Arg Leu Val Glu Thr Pro Leu Ala
1               5                   10                  15

Ala Ala Leu Lys Ala His His Pro Gly Lys Lys Phe Arg Ser Asp Tyr
            20                  25                  30

Leu Lys Lys Ala Gly Lys Ile Leu Lys Asp Gln Gly Val Glu Ala Ala
        35                  40                  45

Met Ala His Leu Asp Gly Lys Asp Gln Ala Glu Pro Pro Asn Phe Lys
    50                  55                  60

Pro Pro Ala Lys Cys Arg Ile Val Ala Arg Ser Arg Glu Phe Ser Glu
65                  70                  75                  80

Trp Pro Ile Val Lys Ala Ser Val Glu Ile Gln Lys Tyr Ile Tyr Gly
                85                  90                  95

Leu Thr Leu Glu Glu Arg Lys Ala Cys Asp Pro Gly Lys Ser Ser Ala
            100                 105                 110

Ser His Lys Ala Trp Phe Ala Lys Thr Gly Val Asn Thr Phe Gly Tyr
        115                 120                 125

Ser Ser Val Gln Gly Phe Asn Leu Ile Phe Gly His Thr Leu Gly Arg
    130                 135                 140

Tyr Asp Gly Val Leu Val Lys Thr Glu Asn Leu Asn Lys Lys Arg Ala
145                 150                 155                 160

Glu Lys Asn Glu Arg Phe Arg Ala Lys Ala Leu Ala Glu Gly Arg Ala
                165                 170                 175

Glu Pro Val Cys Pro Pro Leu Val Thr Ala Thr Asn Asp Thr Gly Gln
            180                 185                 190

Asp Val Thr Leu Glu Asp Gly Arg Val Val Arg Pro Gly Gln Leu Leu
        195                 200                 205

Gln Pro Pro Gly Ile Asn Pro Asn Ile Tyr Ala Tyr Gln Gln Val Ser
    210                 215                 220

Pro Lys Ala Tyr Val Pro Gly Ile Ile Glu Leu Pro Glu Glu Phe Gln
225                 230                 235                 240

Gly Tyr Ser Arg Asp Pro Asn Ala Val Ile Leu Pro Leu Val Pro Arg
                245                 250                 255

Asp Arg Leu Ser Ile Pro Lys Gly Gln Pro Gly Tyr Val Pro Glu Pro
            260                 265                 270

His Arg Glu Gly Leu Thr Gly Arg Lys Asp Arg Arg Met Arg Arg Tyr
        275                 280                 285

Tyr Glu Thr Glu Arg Gly Thr Lys Leu Lys Arg Pro Pro Leu Thr Ala
    290                 295                 300

Lys Gly Arg Ala Asp Lys Ala Asn Glu Ala Leu Leu Val Val Val Arg
305                 310                 315                 320

Ile Asp Ser Asp Trp Val Val Met Asp Val Arg Gly Leu Leu Arg Asn
                325                 330                 335

Ala Arg Trp Arg Arg Leu Val Ser Lys Glu Gly Ile Thr Leu Asn Gly
            340                 345                 350

Leu Leu Asp Leu Phe Thr Gly Asp Pro Val Leu Asn Pro Lys Asp Cys
        355                 360                 365

Ser Val Ser Arg Asp Thr Gly Asp Pro Val Asn Asp Pro Arg His Gly
    370                 375                 380

Val Val Thr Phe Cys Tyr Lys Leu Gly Val Val Asp Val Cys Ser Lys
385                 390                 395                 400

Asp Arg Pro Ile Lys Gly Phe Arg Thr Lys Glu Val Leu Glu Arg Leu
                405                 410                 415

Thr Ser Ser Gly Thr Val Gly Met Val Ser Ile Asp Leu Gly Gln Thr
```

-continued

```
                420             425             430

Asn Pro Val Ala Ala Ala Val Ser Arg Val Thr Lys Gly Leu Gln Ala
        435             440             445

Glu Thr Leu Glu Thr Phe Thr Leu Pro Asp Asp Leu Leu Gly Lys Val
        450             455             460

Arg Ala Tyr Arg Ala Lys Thr Asp Arg Met Glu Glu Gly Phe Arg Arg
465             470             475             480

Asn Ala Leu Arg Lys Leu Thr Ala Glu Gln Gln Ala Glu Ile Thr Arg
                485             490             495

Tyr Asn Asp Ala Thr Glu Gln Gln Ala Lys Ala Leu Val Cys Ser Thr
                500             505             510

Tyr Gly Ile Gly Pro Glu Glu Val Pro Trp Glu Arg Met Thr Ser Asn
                515             520             525

Thr Thr Tyr Ile Ser Asp His Ile Leu Asp His Gly Gly Asp Pro Asp
        530             535             540

Thr Val Phe Phe Met Ala Thr Lys Arg Gly Gln Asn Lys Pro Thr Leu
545             550             555             560

His Lys Arg Lys Asp Lys Ala Trp Gly Gln Lys Phe Arg Pro Ala Ile
                565             570             575

Ser Val Glu Thr Arg Leu Ala Arg Gln Ala Ala Glu Trp Glu Leu Arg
                580             585             590

Arg Ala Ser Leu Glu Phe Gln Lys Leu Ser Val Trp Lys Thr Glu Leu
                595             600             605

Cys Arg Gln Ala Val Asn Tyr Val Met Glu Arg Thr Lys Lys Arg Thr
        610             615             620

Gln Cys Asp Val Ile Ile Pro Val Ile Glu Asp Leu Pro Val Pro Leu
625             630             635             640

Phe His Gly Ser Gly Lys Arg Asp Pro Gly Trp Ala Asn Phe Phe Val
                645             650             655

His Lys Arg Glu Asn Arg Trp Phe Ile Asp Gly Leu His Lys Ala Phe
                660             665             670

Ser Glu Leu Gly Lys His Arg Gly Ile Tyr Val Phe Glu Val Cys Pro
                675             680             685

Gln Arg Thr Ser Ile Thr Cys Pro Lys Cys Gly His Cys Asp Pro Asp
        690             695             700

Asn Arg Asp Gly Glu Lys Phe Val Cys Leu Ser Cys Gln Ala Thr Leu
705             710             715             720

Asn Ala Asp Leu Asp Val Ala Thr Thr Asn Leu Val Arg Val Ala Leu
                725             730             735

Thr Gly Lys Val Met Pro Arg Ser Glu Arg Ser Gly Asp Ala Gln Thr
                740             745             750

Pro Gly Pro Ala Arg Lys Ala Arg Thr Gly Lys Ile Lys Gly Ser Lys
                755             760             765

Pro Thr Ser Ala Pro Gln Gly Ala Thr Gln Thr Asp Ala Lys Ala His
        770             775             780

Leu Ser Gln Thr Gly Val
785             790
```

<210> SEQ ID NO 7
<211> LENGTH: 782
<212> TYPE: PRT
<213> ORGANISM: Unknown
<220> FEATURE:
<223> OTHER INFORMATION: Description of Unknown:
    aquatic-freshwater-sediment sequence -continued

<400> SEQUENCE: 7

```
Met Lys Thr Glu Lys Pro Lys Thr Ala Leu Thr Leu Leu Arg Glu Glu
1               5                   10                  15

Val Phe Pro Gly Lys Lys Tyr Arg Leu Asp Val Leu Lys Glu Ala Gly
                20                  25                  30

Lys Lys Leu Ser Thr Lys Gly Arg Glu Ala Thr Ile Glu Phe Leu Thr
        35                  40                  45

Gly Lys Asp Glu Glu Arg Pro Gln Asn Phe Gln Pro Pro Ala Lys Thr
        50                  55                  60

Ser Ile Val Ala Gln Ser Arg Pro Phe Asp Gln Trp Pro Ile Val Gln
65                  70                  75                  80

Val Ser Leu Ala Val Gln Lys Tyr Ile Tyr Gly Leu Thr Gln Ser Glu
                85                  90                  95

Phe Glu Ala Asn Lys Lys Ala Leu Tyr Gly Glu Thr Gly Lys Ala Ile
                100                 105                 110

Ser Thr Glu Ser Arg Arg Ala Trp Phe Glu Ala Thr Gly Val Asp Asn
        115                 120                 125

Phe Gly Phe Thr Ala Ala Gln Gly Ile Asn Pro Ile Phe Ser Gln Ala
        130                 135                 140

Val Ala Arg Tyr Glu Gly Val Ile Lys Lys Val Glu Asn Arg Asn Glu
145                 150                 155                 160

Lys Lys Leu Lys Lys Leu Thr Lys Lys Asn Leu Leu Arg Leu Glu Ser
                165                 170                 175

Gly Glu Glu Ile Glu Asp Phe Glu Pro Glu Ala Thr Phe Asn Glu Glu
                180                 185                 190

Gly Arg Leu Leu Gln Pro Pro Gly Ala Asn Pro Asn Ile Tyr Cys Tyr
        195                 200                 205

Gln Gln Ile Ser Pro Arg Ile Tyr Asp Pro Ser Asp Pro Lys Gly Val
        210                 215                 220

Ile Leu Pro Gln Ile Tyr Ala Gly Tyr Asp Arg Lys Pro Glu Asp Ile
225                 230                 235                 240

Ile Ser Ala Gly Val Pro Asn Arg Leu Ala Ile Pro Glu Gly Gln Pro
                245                 250                 255

Gly Tyr Ile Pro Glu His Gln Arg Ala Gly Leu Lys Thr Gln Gly Arg
                260                 265                 270

Ile Arg Cys Arg Ala Ser Val Glu Ala Lys Ala Arg Ala Ala Ile Leu
        275                 280                 285

Ala Val Val His Leu Gly Glu Asp Trp Val Val Leu Asp Leu Arg Gly
        290                 295                 300

Leu Leu Arg Asn Val Tyr Trp Arg Lys Leu Ala Ser Pro Gly Thr Leu
305                 310                 315                 320

Thr Leu Lys Gly Leu Leu Asp Phe Phe Thr Gly Gly Pro Val Leu Asp
                325                 330                 335

Ala Arg Arg Gly Ile Ala Thr Phe Ser Tyr Thr Leu Lys Ser Ala Ala
                340                 345                 350

Ala Val His Ala Glu Asn Thr Tyr Lys Gly Lys Gly Thr Arg Glu Val
        355                 360                 365

Leu Leu Lys Leu Thr Glu Asn Asn Ser Val Ala Leu Val Thr Val Asp
        370                 375                 380

Leu Gly Gln Arg Asn Pro Leu Ala Ala Met Ile Ala Arg Val Ser Arg
385                 390                 395                 400

Thr Ser Gln Gly Asp Leu Thr Tyr Pro Glu Ser Val Glu Pro Leu Thr
```

-continued

```
              405                    410                    415

Arg Leu Phe Leu Pro Asp Pro Phe Leu Glu Glu Val Arg Lys Tyr Arg
            420                    425                    430

Ser Ser Tyr Asp Ala Leu Arg Leu Ser Ile Arg Glu Ala Ala Ile Ala
            435                    440                    445

Ser Leu Thr Pro Glu Gln Gln Ala Glu Ile Arg Tyr Ile Glu Lys Phe
        450                    455                    460

Ser Ala Gly Asp Ala Lys Lys Asn Val Ala Glu Val Phe Gly Ile Asp
    465                    470                    475                    480

Pro Thr Gln Leu Pro Trp Asp Ala Met Thr Pro Arg Thr Thr Tyr Ile
                485                    490                    495

Ser Asp Leu Phe Leu Arg Met Gly Gly Asp Arg Ser Arg Val Phe Phe
            500                    505                    510

Glu Val Pro Pro Lys Lys Ala Lys Lys Ala Pro Lys Lys Pro Pro Lys
            515                    520                    525

Lys Pro Ala Gly Pro Arg Ile Val Lys Arg Thr Asp Gly Met Ile Ala
        530                    535                    540

Arg Leu Arg Glu Ile Arg Pro Arg Leu Ser Ala Glu Thr Asn Lys Ala
    545                    550                    555                    560

Phe Gln Glu Ala Arg Trp Glu Gly Glu Arg Ser Asn Val Ala Phe Gln
                565                    570                    575

Lys Leu Ser Val Arg Arg Lys Gln Phe Ala Arg Thr Val Val Asn His
            580                    585                    590

Leu Val Gln Thr Ala Gln Lys Met Ser Arg Cys Asp Thr Val Val Leu
            595                    600                    605

Gly Ile Glu Asp Leu Asn Val Pro Phe Phe His Gly Arg Gly Lys Tyr
        610                    615                    620

Gln Pro Gly Trp Glu Gly Phe Phe Arg Gln Lys Lys Glu Asn Arg Trp
    625                    630                    635                    640

Leu Ile Asn Asp Met His Lys Ala Leu Ser Glu Arg Gly Pro His Arg
                645                    650                    655

Gly Gly Tyr Val Leu Glu Leu Thr Pro Phe Trp Thr Ser Leu Arg Cys
            660                    665                    670

Pro Lys Cys Gly His Thr Asp Ser Ala Asn Arg Asp Gly Asp Asp Phe
        675                    680                    685

Val Cys Val Lys Cys Gly Ala Lys Leu His Ser Asp Leu Glu Val Ala
    690                    695                    700

Thr Ala Asn Leu Ala Leu Val Ala Ile Thr Gly Gln Ser Ile Pro Arg
705                    710                    715                    720

Pro Pro Arg Glu Gln Ser Ser Gly Lys Lys Ser Thr Gly Thr Ala Arg
                725                    730                    735

Met Lys Lys Thr Ser Gly Glu Thr Gln Gly Lys Gly Ser Lys Ala Cys
            740                    745                    750

Val Ser Glu Ala Leu Asn Lys Ile Glu Gln Gly Thr Ala Arg Asp Pro
            755                    760                    765

Val Tyr Asn Pro Leu Asn Ser Gln Val Ser Cys Pro Ala Pro
    770                    775                    780
```

<210> SEQ ID NO 8
<211> LENGTH: 774
<212> TYPE: PRT
<213> ORGANISM: Unknown
<220> FEATURE:
<223> OTHER INFORMATION: Description of Unknown:
      aquatic-marine-worm burrow sequence

<400> SEQUENCE: 8

```
Met Tyr Asn Pro Asp Met Lys Lys Pro Asn Asn Ile Arg Arg Ile Arg
1               5                   10                  15

Glu Glu His Phe Glu Gly Leu Cys Phe Gly Lys Asp Val Leu Thr Lys
            20                  25                  30

Ala Gly Lys Ile Tyr Glu Lys Asp Gly Glu Glu Ala Ala Ile Asp Phe
        35                  40                  45

Leu Met Gly Lys Asp Glu Glu Asp Pro Pro Asn Phe Lys Pro Pro Ala
    50                  55                  60

Lys Thr Thr Ile Val Ala Gln Ser Arg Pro Phe Asp Gln Trp Pro Ile
65                  70                  75                  80

Tyr Gln Val Ser Gln Ala Val Gln Glu Arg Val Phe Ala Tyr Thr Glu
                85                  90                  95

Glu Glu Phe Asn Ala Ser Lys Glu Ala Leu Phe Ser Gly Asp Ile Ser
            100                 105                 110

Ser Lys Ser Arg Asp Phe Trp Phe Lys Thr Asn Asn Ile Ser Asp Gln
        115                 120                 125

Gly Ile Gly Ala Gln Gly Leu Asn Thr Ile Leu Ser His Ala Phe Ser
    130                 135                 140

Arg Tyr Ser Gly Val Ile Lys Lys Val Glu Asn Arg Asn Lys Lys Arg
145                 150                 155                 160

Leu Lys Lys Leu Ser Lys Lys Asn Gln Leu Lys Ile Glu Glu Gly Leu
                165                 170                 175

Glu Ile Leu Glu Phe Lys Pro Asp Ser Ala Phe Asn Glu Asn Gly Leu
            180                 185                 190

Leu Ala Gln Pro Pro Gly Ile Asn Pro Asn Ile Tyr Gly Tyr Gln Ala
        195                 200                 205

Val Thr Pro Phe Val Phe Asp Pro Asp Asn Pro Gly Asp Val Ile Leu
    210                 215                 220

Pro Lys Gln Tyr Glu Gly Tyr Ser Arg Lys Pro Asp Asp Ile Ile Glu
225                 230                 235                 240

Lys Gly Pro Ser Arg Leu Asp Ile Pro Lys Gly Gln Pro Gly Tyr Val
                245                 250                 255

Pro Glu His Gln Arg Lys Asn Leu Lys Lys Lys Gly Arg Val Arg Leu
            260                 265                 270

Tyr Arg Arg Thr Pro Pro Lys Thr Lys Ala Leu Ala Ser Ile Leu Ala
        275                 280                 285

Val Leu Gln Ile Gly Lys Asp Trp Val Leu Phe Asp Met Arg Gly Leu
    290                 295                 300

Leu Arg Ser Val Tyr Met Arg Glu Ala Ala Thr Pro Gly Gln Ile Ser
305                 310                 315                 320

Ala Lys Asp Leu Leu Asp Thr Phe Thr Gly Cys Pro Val Leu Asn Thr
                325                 330                 335

Arg Thr Gly Glu Phe Thr Phe Cys Tyr Lys Leu Arg Ser Glu Gly Ala
            340                 345                 350

Leu His Ala Arg Lys Ile Tyr Thr Lys Gly Glu Thr Arg Thr Leu Leu
        355                 360                 365

Thr Ser Leu Thr Ser Glu Asn Asn Thr Ile Ala Leu Val Thr Val Asp
    370                 375                 380

Leu Gly Gln Arg Asn Pro Ala Ala Ile Met Ile Ser Arg Leu Ser Arg
385                 390                 395                 400

Lys Glu Glu Leu Ser Glu Lys Asp Ile Gln Pro Val Ser Arg Arg Leu
```

-continued

```
                       405                    410                    415

Leu Pro Asp Arg Tyr Leu Asn Glu Leu Lys Arg Tyr Arg Asp Ala Tyr
            420                    425                    430

Asp Ala Phe Arg Gln Glu Val Arg Asp Glu Ala Phe Thr Ser Leu Cys
            435                    440                    445

Pro Glu His Gln Glu Gln Val Gln Gln Tyr Glu Ala Leu Thr Pro Glu
            450                    455                    460

Lys Ala Lys Asn Leu Val Leu Lys His Phe Phe Gly Thr His Asp Pro
465                    470                    475                    480

Asp Leu Pro Trp Asp Asp Met Thr Ser Asn Thr His Tyr Ile Ala Asn
            485                    490                    495

Leu Tyr Leu Glu Arg Gly Gly Asp Pro Ser Lys Val Phe Phe Thr Arg
            500                    505                    510

Pro Leu Lys Lys Asp Ser Lys Ser Lys Lys Pro Arg Lys Pro Thr Lys
            515                    520                    525

Arg Thr Asp Ala Ser Ile Ser Arg Leu Pro Glu Ile Arg Pro Lys Met
            530                    535                    540

Pro Glu Asp Ala Arg Lys Ala Phe Glu Lys Ala Lys Trp Glu Ile Tyr
545                    550                    555                    560

Thr Gly His Glu Lys Phe Pro Lys Leu Ala Lys Arg Val Asn Gln Leu
            565                    570                    575

Cys Arg Glu Ile Ala Asn Trp Ile Glu Lys Glu Ala Lys Arg Leu Thr
            580                    585                    590

Leu Cys Asp Thr Val Val Val Gly Ile Glu Asp Leu Ser Leu Pro Pro
            595                    600                    605

Lys Arg Gly Lys Gly Lys Phe Gln Glu Thr Trp Gln Gly Phe Phe Arg
            610                    615                    620

Gln Lys Phe Glu Asn Arg Trp Val Ile Asp Thr Leu Lys Lys Ala Ile
625                    630                    635                    640

Gln Asn Arg Ala His Asp Lys Gly Lys Tyr Val Leu Gly Leu Ala Pro
            645                    650                    655

Tyr Trp Thr Ser Gln Arg Cys Pro Ala Cys Gly Phe Ile His Lys Ser
            660                    665                    670

Asn Arg Asn Gly Asp His Phe Lys Cys Leu Lys Cys Glu Ala Leu Phe
            675                    680                    685

His Ala Asp Ser Glu Val Ala Thr Trp Asn Leu Ala Leu Val Ala Val
            690                    695                    700

Leu Gly Lys Gly Ile Thr Asn Pro Asp Ser Lys Lys Pro Ser Gly Gln
705                    710                    715                    720

Lys Lys Thr Gly Thr Thr Arg Lys Lys Gln Ile Lys Gly Lys Asn Lys
            725                    730                    735

Gly Lys Glu Thr Val Asn Val Pro Pro Thr Thr Gln Glu Val Glu Asp
            740                    745                    750

Ile Ile Ala Phe Phe Glu Lys Asp Asp Glu Thr Val Arg Asn Pro Val
            755                    760                    765

Tyr Lys Pro Thr Gly Thr
    770
```

<210> SEQ ID NO 9
<211> LENGTH: 769
<212> TYPE: PRT
<213> ORGANISM: Unknown
<220> FEATURE:
<223> OTHER INFORMATION: Description of Unknown:
    aquatic-marine-worm burrow sequence -continued

```
<400> SEQUENCE: 9

Met Lys Lys Pro Asn Asn Ile Arg Arg Ile Arg Glu Glu His Phe Glu
1               5                  10                  15

Gly Leu Cys Phe Gly Lys Asp Val Leu Thr Lys Ala Gly Lys Ile Tyr
            20                  25                  30

Glu Lys Asp Gly Glu Glu Ala Ala Ile Asp Phe Leu Met Gly Lys Asp
        35                  40                  45

Glu Glu Asp Pro Pro Asn Phe Lys Pro Pro Ala Lys Thr Thr Ile Val
    50                  55                  60

Ala Gln Ser Arg Pro Phe Asp Gln Trp Pro Ile Tyr Gln Val Ser Gln
65                  70                  75                  80

Ala Val Gln Glu Arg Val Phe Ala Tyr Thr Glu Glu Glu Phe Asn Ala
                85                  90                  95

Ser Lys Glu Ala Leu Phe Ser Gly Asp Ile Ser Ser Lys Ser Arg Asp
            100                 105                 110

Phe Trp Phe Lys Thr Asn Asn Ile Ser Asp Gln Gly Ile Gly Ala Gln
            115                 120                 125

Gly Leu Asn Thr Ile Leu Ser His Ala Phe Ser Arg Tyr Ser Gly Val
    130                 135                 140

Ile Lys Lys Val Glu Asn Arg Asn Lys Lys Arg Leu Lys Lys Leu Ser
145                 150                 155                 160

Lys Lys Asn Gln Leu Lys Ile Glu Glu Gly Leu Glu Ile Leu Glu Phe
            165                 170                 175

Lys Pro Asp Ser Ala Phe Asn Glu Asn Gly Leu Leu Ala Gln Pro Pro
            180                 185                 190

Gly Ile Asn Pro Asn Ile Tyr Gly Tyr Gln Ala Val Thr Pro Phe Val
    195                 200                 205

Phe Asp Pro Asp Asn Pro Gly Asp Val Ile Leu Pro Lys Gln Tyr Glu
    210                 215                 220

Gly Tyr Ser Arg Lys Pro Asp Asp Ile Ile Glu Lys Gly Pro Ser Arg
225                 230                 235                 240

Leu Asp Ile Pro Lys Gly Gln Pro Gly Tyr Val Pro Glu His Gln Arg
            245                 250                 255

Lys Asn Leu Lys Lys Lys Gly Arg Val Arg Leu Tyr Arg Arg Thr Pro
            260                 265                 270

Pro Lys Thr Lys Ala Leu Ala Ser Ile Leu Ala Val Leu Gln Ile Gly
            275                 280                 285

Lys Asp Trp Val Leu Phe Asp Met Arg Gly Leu Leu Arg Ser Val Tyr
    290                 295                 300

Met Arg Glu Ala Ala Thr Pro Gly Gln Ile Ser Ala Lys Asp Leu Leu
305                 310                 315                 320

Asp Thr Phe Thr Gly Cys Pro Val Leu Asn Thr Arg Thr Gly Glu Phe
            325                 330                 335

Thr Phe Cys Tyr Lys Leu Arg Ser Glu Gly Ala Leu His Ala Arg Lys
            340                 345                 350

Ile Tyr Thr Lys Gly Glu Thr Arg Thr Leu Leu Thr Ser Leu Thr Ser
            355                 360                 365

Glu Asn Asn Thr Ile Ala Leu Val Thr Val Asp Leu Gly Gln Arg Asn
    370                 375                 380

Pro Ala Ala Ile Met Ile Ser Arg Leu Ser Arg Lys Glu Glu Leu Ser
385                 390                 395                 400

Glu Lys Asp Ile Gln Pro Val Ser Arg Arg Leu Leu Pro Asp Arg Tyr
```

-continued

```
                    405              410              415

Leu Asn Glu Leu Lys Arg Tyr Arg Asp Ala Tyr Asp Ala Phe Arg Gln
                420              425              430

Glu Val Arg Asp Glu Ala Phe Thr Ser Leu Cys Pro Glu His Gln Glu
                435              440              445

Gln Val Gln Gln Tyr Glu Ala Leu Thr Pro Glu Lys Ala Lys Asn Leu
            450              455              460

Val Leu Lys His Phe Phe Gly Thr His Asp Pro Asp Leu Pro Trp Asp
465              470              475              480

Asp Met Thr Ser Asn Thr His Tyr Ile Ala Asn Leu Tyr Leu Glu Arg
                485              490              495

Gly Gly Asp Pro Ser Lys Val Phe Phe Thr Arg Pro Leu Lys Lys Asp
                500              505              510

Ser Lys Ser Lys Lys Pro Arg Lys Pro Thr Lys Arg Thr Asp Ala Ser
            515              520              525

Ile Ser Arg Leu Pro Glu Ile Arg Pro Lys Met Pro Glu Asp Ala Arg
            530              535              540

Lys Ala Phe Glu Lys Ala Lys Trp Glu Ile Tyr Thr Gly His Glu Lys
545              550              555              560

Phe Pro Lys Leu Ala Lys Arg Val Asn Gln Leu Cys Arg Glu Ile Ala
                565              570              575

Asn Trp Ile Glu Lys Glu Ala Lys Arg Leu Thr Leu Cys Asp Thr Val
                580              585              590

Val Val Gly Ile Glu Asp Leu Ser Leu Pro Pro Lys Arg Gly Lys Gly
                595              600              605

Lys Phe Gln Glu Thr Trp Gln Gly Phe Phe Arg Gln Lys Phe Glu Asn
            610              615              620

Arg Trp Val Ile Asp Thr Leu Lys Lys Ala Ile Gln Asn Arg Ala His
625              630              635              640

Asp Lys Gly Lys Tyr Val Leu Gly Leu Ala Pro Tyr Trp Thr Ser Gln
                645              650              655

Arg Cys Pro Ala Cys Gly Phe Ile His Lys Ser Asn Arg Asn Gly Asp
                660              665              670

His Phe Lys Cys Leu Lys Cys Glu Ala Leu Phe His Ala Asp Ser Glu
                675              680              685

Val Ala Thr Trp Asn Leu Ala Leu Val Ala Val Leu Gly Lys Gly Ile
            690              695              700

Thr Asn Pro Asp Ser Lys Lys Pro Ser Gly Gln Lys Lys Thr Gly Thr
705              710              715              720

Thr Arg Lys Lys Gln Ile Lys Gly Lys Asn Lys Gly Lys Glu Thr Val
                725              730              735

Asn Val Pro Pro Thr Thr Gln Glu Val Glu Asp Ile Ile Ala Phe Phe
                740              745              750

Glu Lys Asp Asp Glu Thr Val Arg Asn Pro Val Tyr Lys Pro Thr Gly
                755              760              765

Thr
```

```
<210> SEQ ID NO 10
<211> LENGTH: 769
<212> TYPE: PRT
<213> ORGANISM: Unknown
<220> FEATURE:
<223> OTHER INFORMATION: Description of Unknown:
      crustacean metagenome sequence
```

-continued

<400> SEQUENCE: 10

```
Met Glu Lys Ser Asn Thr Arg Lys Val Ile Asp Glu His Phe Lys Gly
1               5                   10                  15

Leu Leu Phe Arg Lys Asp Ile Leu Gln Lys Ala Gly Lys Ile Tyr Lys
            20                  25                  30

Lys Glu Gly Glu Glu Ala Thr Ile Ser Phe Leu Met Gly Lys Asp Glu
        35                  40                  45

Glu Ala Pro Pro Asn Phe Gln Pro Pro Ala Lys Thr Ser Ile Val Ala
    50                  55                  60

Gln Ser Arg Pro Phe Asn Gln Trp Pro Ile Tyr Gln Val Ser Glu Ala
65                  70                  75                  80

Ile Gln Lys Arg Val Phe Gly Tyr Thr Glu Asp Glu Phe Tyr Ala Gln
                85                  90                  95

Lys Lys Ala Leu Phe Gly Glu Gly Gly Ala Ser Ser Lys Ser Arg Asp
            100                 105                 110

Ala Trp Phe Lys Ala Asn Gly Ile Ser Asp Arg Gly Ile Val Ala Gln
            115                 120                 125

Gly Leu Asn Met Ile Leu Gly His Ala Phe Ala Arg Tyr Glu Gly Val
        130                 135                 140

Ile Gln Lys Val Glu Asn Arg Asn Lys Lys Arg Leu Asp Lys Leu Ser
145                 150                 155                 160

Lys Lys Asn Gln Leu Arg Val Lys Glu Gly Leu Glu Val Tyr Glu Phe
                165                 170                 175

Thr Pro Glu Ser Ala Phe Ile Asp Gly Ser Gly Leu Leu Ala Gln Pro
            180                 185                 190

Pro Gly Ile Ser Pro Asn Ile Tyr Gly Tyr Gln Ala Ile Ala Pro Phe
            195                 200                 205

Val Phe Asp Pro Asp Asp Pro Arg Asp Ile Val Leu Pro Lys Glu Tyr
    210                 215                 220

Glu Gly Tyr Ser Arg Lys Pro Asp Asp Ile Ile Glu Lys Gly Pro Asn
225                 230                 235                 240

Arg Leu Asp Ile Pro Lys Gly Gln Pro Gly Tyr Val Pro Glu His Gln
            245                 250                 255

Arg Ser Gly Leu Lys Lys Gly Gly Arg Val Trp Leu Tyr Arg Arg Ala
            260                 265                 270

Thr Thr Arg Ala Lys Ala Leu Ala Ser Ile Leu Gly Val Leu Gln Ile
        275                 280                 285

Gly Glu Asp Trp Val Leu Phe Asp Met Arg Gly Leu Leu Arg Asn Ala
        290                 295                 300

Tyr Met Arg Lys Ala Leu Thr Pro Gly Lys Ala Ser Ala Arg Asp Leu
305                 310                 315                 320

Leu Gly Thr Phe Thr Glu Tyr Pro Val Leu Asn Ala Arg Thr Gly Glu
            325                 330                 335

Phe Thr Phe Cys Tyr Lys Leu Arg Ser Gly Gly Ser Leu Tyr Ala Arg
            340                 345                 350

Gln Val Tyr Lys Lys Gly Lys Thr Arg Glu Ile Leu Thr Glu Leu Thr
            355                 360                 365

Ser Glu Gly Lys Thr Ile Ala Leu Val Thr Val Asp Leu Gly Gln Arg
        370                 375                 380

Asn Pro Val Ala Ala Met Val Ala Arg Val Ser Arg Asp Gly Glu Leu
385                 390                 395                 400

Ser Glu Ser Cys Ile Asp Pro Val Ser Arg Phe Leu Leu Pro Glu Tyr
            405                 410                 415
```

```
Tyr Ala Arg Gln Ile Gln Lys Tyr Arg Asp Asp Phe Asp Ala Phe Arg
        420             425             430

Gln Glu Val Trp Asp Glu Ala Phe Ala Ser Met Pro Pro Glu Tyr Gln
        435             440             445

Glu Gln Ile Arg Gln Tyr Glu Ala Tyr Thr Pro Asp Gln Ala Lys Ser
        450             455             460

Leu Val Leu Lys His Phe Phe Gly Asp Glu Val Ser Leu Asp Asp Leu
465             470             475             480

Pro Trp Glu Lys Met Thr Ser Asn Thr Cys Tyr Ile Ser Asn Leu Tyr
                485             490             495

Ile Lys Arg Gly Gly Asp Pro Ser Arg Val Thr Phe Thr Pro Ser Pro
        500             505             510

Gly Lys Asn Ser Lys Lys Pro Arg Lys Pro Val Lys Arg Thr Asp Ser
        515             520             525

Gly Ile Ser Arg Leu Pro Glu Val Arg Pro Gly Leu Pro Lys Asp Thr
        530             535             540

Arg Asp Ala Phe Glu Glu Ala Lys Trp Asp Val Tyr Arg Gly His Glu
545             550             555             560

Lys Phe Pro Lys Leu Ala Lys Arg Val Asn Gln Leu Cys Arg Glu Ile
                565             570             575

Ala Asn Trp Leu Glu Lys Glu Ala Gly Arg Ile Thr Leu Cys Asp Thr
                580             585             590

Val Val Phe Gly Ile Glu Asp Met Gly Ala Lys Phe Cys Gly Lys Gly
        595             600             605

Lys Gly Lys Phe Gln Glu Thr Trp Glu Gly Phe Phe Arg Gln Lys Ser
        610             615             620

Glu Asn Arg Trp Val Met Asn Leu Leu Lys Ser Ser Ile His Met Arg
625             630             635             640

Ala His Asp Lys Gly Arg Tyr Val Leu Glu Leu Ala Pro Phe Tyr Thr
                645             650             655

Ser Gln Arg Cys Pro Lys Cys Gly Tyr Ile His Lys Asn Asn Arg Lys
                660             665             670

Gly Asp Arg Phe Glu Cys Leu Ser Cys Gly Ala Leu Leu His Ala Asp
        675             680             685

Ser Glu Val Ala Thr Trp Asn Leu Ala Val Val Ala Ile Leu Gly Lys
        690             695             700

Ala Leu Lys Lys Pro Ser Leu Lys Cys Glu Lys Ser Ser Gly Gln Lys
705             710             715             720

Lys Ala Arg Thr Ser Arg Lys Ile Gln Ile Lys Val Gly Asn Lys Ala
                725             730             735

Glu Thr Ser Ser Ser Pro Gln Glu Asn Gly Glu Val Leu Ala Pro Pro
        740             745             750

Glu Glu Asn Ser Gly Thr Ser Arg Asp Pro Val Tyr Asn Pro Ser Gly
        755             760             765

Thr
```

<210> SEQ ID NO 11
<211> LENGTH: 769
<212> TYPE: PRT
<213> ORGANISM: Unknown
<220> FEATURE:
<223> OTHER INFORMATION: Description of Unknown:
      crustacean metagenome sequence

<400> SEQUENCE: 11

```
Met Glu Lys Ser Asn Thr Arg Lys Val Ile Asp Glu His Phe Lys Gly
1               5                   10                  15

Leu Leu Phe Arg Lys Asp Ile Leu Gln Lys Ala Gly Lys Ile Tyr Lys
            20                  25                  30

Lys Glu Gly Glu Glu Ala Thr Ile Ser Phe Leu Met Gly Lys Asp Glu
        35                  40                  45

Glu Ala Pro Pro Asn Phe Gln Pro Pro Ala Lys Thr Ser Ile Val Ala
    50                  55                  60

Gln Ser Arg Pro Phe Asn Gln Trp Pro Ile Tyr Gln Val Ser Glu Ala
65                  70                  75                  80

Ile Gln Lys Arg Val Phe Gly Tyr Thr Glu Asp Glu Phe Tyr Ala Gln
                85                  90                  95

Lys Lys Ala Leu Phe Gly Glu Gly Gly Ala Ser Ser Lys Ser Arg Asp
            100                 105                 110

Ala Trp Phe Lys Ala Asn Gly Ile Ser Asp Arg Gly Ile Val Ala Gln
            115                 120                 125

Gly Leu Asn Met Ile Leu Gly His Ala Phe Ala Arg Tyr Glu Gly Val
        130                 135                 140

Ile Gln Lys Val Glu Asn Arg Asn Lys Lys Arg Leu Asp Lys Leu Ser
145                 150                 155                 160

Lys Lys Asn Gln Leu Arg Val Lys Glu Gly Leu Glu Val Tyr Glu Phe
                165                 170                 175

Thr Pro Glu Ser Ala Phe Ile Asp Gly Ser Gly Leu Leu Ala Gln Pro
            180                 185                 190

Pro Gly Ile Ser Pro Asn Ile Tyr Gly Tyr Gln Ala Ile Ala Pro Phe
            195                 200                 205

Val Phe Asp Pro Asp Asp Pro Arg Asp Ile Val Leu Pro Lys Glu Tyr
        210                 215                 220

Glu Gly Tyr Ser Arg Lys Pro Asp Asp Ile Ile Glu Lys Gly Pro Asn
225                 230                 235                 240

Arg Leu Asp Ile Pro Lys Gly Gln Pro Gly Tyr Val Pro Glu His Gln
                245                 250                 255

Arg Ser Gly Leu Lys Lys Gly Gly Arg Val Trp Leu Tyr Arg Arg Ala
            260                 265                 270

Thr Thr Arg Ala Lys Ala Leu Ala Ser Ile Leu Gly Val Leu Gln Ile
        275                 280                 285

Gly Glu Asp Trp Val Leu Phe Asp Met Arg Gly Leu Leu Arg Asn Ala
        290                 295                 300

Tyr Met Arg Lys Ala Leu Thr Pro Gly Lys Ala Ser Ala Arg Asp Leu
305                 310                 315                 320

Leu Gly Thr Phe Thr Glu Tyr Pro Val Leu Asn Ala Arg Thr Gly Glu
            325                 330                 335

Phe Thr Phe Cys Tyr Lys Leu Arg Ser Gly Gly Ser Leu Tyr Ala Arg
            340                 345                 350

Gln Val Tyr Lys Lys Gly Lys Thr Arg Glu Ile Leu Thr Glu Leu Thr
        355                 360                 365

Ser Glu Gly Lys Thr Ile Ala Leu Val Thr Val Asp Leu Gly Gln Arg
    370                 375                 380

Asn Pro Val Ala Ala Met Val Ala Arg Val Ser Arg Asp Gly Glu Leu
385                 390                 395                 400

Ser Glu Ser Cys Ile Asp Pro Val Ser Arg Phe Leu Leu Pro Glu Tyr
            405                 410                 415
```

```
Tyr Ala Arg Gln Ile Gln Lys Tyr Arg Asp Asp Phe Asp Ala Phe Arg
            420                 425                 430

Gln Glu Val Trp Asp Glu Ala Phe Ala Ser Met Pro Pro Glu Tyr Gln
            435                 440                 445

Glu Gln Ile Arg Gln Tyr Glu Ala Tyr Thr Pro Asp Gln Ala Lys Ser
    450                 455                 460

Leu Val Leu Lys His Phe Phe Gly Asp Glu Val Ser Leu Asp Asp Leu
465                 470                 475                 480

Pro Trp Glu Lys Met Thr Ser Asn Thr Cys Tyr Ile Ser Asn Leu Tyr
                485                 490                 495

Ile Lys Arg Gly Gly Asp Pro Ser Arg Val Thr Phe Thr Pro Ser Pro
            500                 505                 510

Gly Lys Asn Ser Lys Lys Pro Arg Lys Pro Val Lys Arg Thr Asp Ser
            515                 520                 525

Gly Ile Ser Arg Leu Pro Glu Val Arg Pro Gly Leu Pro Lys Asp Thr
    530                 535                 540

Arg Asp Ala Phe Glu Glu Ala Lys Trp Asp Val Tyr Arg Gly His Glu
545                 550                 555                 560

Lys Phe Pro Lys Leu Ala Lys Arg Val Asn Gln Leu Cys Arg Glu Ile
                565                 570                 575

Ala Asn Trp Leu Glu Lys Glu Ala Gly Arg Ile Thr Leu Cys Asp Thr
            580                 585                 590

Val Val Phe Gly Ile Glu Asp Met Gly Ala Lys Phe Cys Gly Lys Gly
            595                 600                 605

Lys Gly Lys Phe Gln Glu Thr Trp Glu Gly Phe Phe Arg Gln Lys Ser
    610                 615                 620

Glu Asn Arg Trp Val Met Asn Leu Leu Lys Ser Ser Ile His Met Arg
625                 630                 635                 640

Ala His Asp Lys Gly Arg Tyr Val Leu Glu Leu Ala Pro Phe Tyr Thr
                645                 650                 655

Ser Gln Arg Cys Pro Lys Cys Gly Tyr Ile His Lys Asn Asn Arg Lys
            660                 665                 670

Gly Asp Arg Phe Glu Cys Leu Ser Cys Gly Ala Leu Leu His Ala Asp
            675                 680                 685

Ser Glu Val Ala Thr Trp Asn Leu Ala Val Val Ala Ile Leu Gly Lys
    690                 695                 700

Ala Leu Lys Lys Pro Ser Leu Lys Cys Glu Lys Ser Ser Gly Gln Lys
705                 710                 715                 720

Lys Ala Arg Thr Ser Arg Lys Ile Gln Ile Lys Val Gly Asn Lys Ala
                725                 730                 735

Glu Thr Ser Ser Ser Pro Gln Glu Asn Gly Glu Val Leu Ala Pro Pro
                740                 745                 750

Glu Glu Asn Ser Gly Thr Ser Arg Asp Pro Val Tyr Asn Pro Ser Gly
            755                 760                 765

Thr
```

```
<210> SEQ ID NO 12
<211> LENGTH: 812
<212> TYPE: PRT
<213> ORGANISM: Unknown
<220> FEATURE:
<223> OTHER INFORMATION: Description of Unknown:
      microbial mat metagenome sequence

<400> SEQUENCE: 12
```

-continued

```
Met Asp Met Leu Asp Thr Glu Thr Asn Tyr Ala Thr Glu Thr Pro Ser
1               5                   10                  15

Gln Gln Gln Asp Tyr Ser Pro Lys Pro Pro Lys Lys Asp Arg Arg Ala
            20                  25                  30

Pro Lys Gly Phe Ser Lys Lys Ala Arg Pro Glu Lys Lys Pro Pro Lys
        35                  40                  45

Pro Ile Thr Leu Phe Thr Gln Lys His Phe Ser Gly Val Arg Phe Leu
    50                  55                  60

Lys Arg Val Ile Arg Asp Ala Ser Lys Ile Leu Lys Leu Ser Glu Ser
65                  70                  75                  80

Arg Thr Ile Thr Phe Leu Glu Gln Ala Ile Glu Arg Asp Gly Ser Ala
                85                  90                  95

Pro Pro Asp Val Thr Pro Pro Val His Asn Thr Ile Met Ala Val Thr
            100                 105                 110

Arg Pro Phe Glu Glu Trp Pro Glu Val Ile Leu Ser Lys Ala Leu Gln
        115                 120                 125

Lys His Cys Tyr Ala Leu Thr Lys Lys Ile Lys Ile Lys Thr Trp Pro
    130                 135                 140

Lys Lys Gly Pro Gly Lys Lys Cys Leu Ala Ala Trp Ser Ala Arg Thr
145                 150                 155                 160

Lys Ile Pro Leu Ile Pro Gly Gln Val Gln Ala Thr Asn Gly Leu Phe
                165                 170                 175

Asp Arg Ile Gly Ser Ile Tyr Asp Gly Val Glu Lys Lys Val Thr Asn
            180                 185                 190

Arg Asn Ala Asn Lys Lys Leu Glu Tyr Asp Glu Ala Ile Lys Glu Gly
        195                 200                 205

Arg Asn Pro Ala Val Pro Glu Tyr Glu Thr Ala Tyr Asn Ile Asp Gly
    210                 215                 220

Thr Leu Ile Asn Lys Pro Gly Tyr Asn Pro Asn Leu Tyr Ile Thr Gln
225                 230                 235                 240

Ser Arg Thr Pro Arg Leu Ile Thr Glu Ala Asp Arg Pro Leu Val Glu
                245                 250                 255

Lys Ile Leu Trp Gln Met Val Glu Lys Lys Thr Gln Ser Arg Asn Gln
            260                 265                 270

Ala Arg Arg Ala Arg Leu Glu Lys Ala Ala His Leu Gln Gly Leu Pro
        275                 280                 285

Val Pro Lys Phe Val Pro Glu Lys Val Asp Arg Ser Gln Lys Ile Glu
    290                 295                 300

Ile Arg Ile Ile Asp Pro Leu Asp Lys Ile Glu Pro Tyr Met Pro Gln
305                 310                 315                 320

Asp Arg Met Ala Ile Lys Ala Ser Gln Asp Gly His Val Pro Tyr Trp
                325                 330                 335

Gln Arg Pro Phe Leu Ser Lys Arg Arg Asn Arg Arg Val Arg Ala Gly
            340                 345                 350

Trp Gly Lys Gln Val Ser Ser Ile Gln Ala Trp Leu Thr Gly Ala Leu
        355                 360                 365

Leu Val Ile Val Arg Leu Gly Asn Glu Ala Phe Leu Ala Asp Ile Arg
    370                 375                 380

Gly Ala Leu Arg Asn Ala Gln Trp Arg Lys Leu Leu Lys Pro Asp Ala
385                 390                 395                 400

Thr Tyr Gln Ser Leu Phe Asn Leu Phe Thr Gly Asp Pro Val Val Asn
                405                 410                 415

Thr Arg Thr Asn His Leu Thr Met Ala Tyr Arg Glu Gly Val Val Asp
```

-continued

```
                420             425             430
Ile Val Lys Ser Arg Ser Phe Lys Gly Arg Gln Thr Arg Glu His Leu
        435             440             445
Leu Thr Leu Leu Gly Gln Gly Lys Thr Val Ala Gly Val Ser Phe Asp
        450             455             460
Leu Gly Gln Lys His Ala Ala Gly Leu Leu Ala Ala His Phe Gly Leu
465             470             475             480
Gly Glu Asp Gly Asn Pro Val Phe Thr Pro Ile Gln Ala Cys Phe Leu
                485             490             495
Pro Gln Arg Tyr Leu Asp Ser Leu Thr Asn Tyr Arg Asn Arg Tyr Asp
                500             505             510
Ala Leu Thr Leu Asp Met Arg Arg Gln Ser Leu Leu Ala Leu Thr Pro
                515             520             525
Ala Gln Gln Gln Glu Phe Ala Asp Ala Gln Arg Asp Pro Gly Gly Gln
        530             535             540
Ala Lys Arg Ala Cys Cys Leu Lys Leu Asn Leu Asn Pro Asp Glu Ile
545             550             555             560
Arg Trp Asp Leu Val Ser Gly Ile Ser Thr Met Ile Ser Asp Leu Tyr
                565             570             575
Ile Glu Arg Gly Gly Asp Pro Arg Asp Val His Gln Gln Val Glu Thr
                580             585             590
Lys Pro Lys Gly Lys Arg Lys Ser Glu Ile Arg Ile Leu Lys Ile Arg
                595             600             605
Asp Gly Lys Trp Ala Tyr Asp Phe Arg Pro Lys Ile Ala Asp Glu Thr
        610             615             620
Arg Lys Ala Gln Arg Glu Gln Leu Trp Lys Leu Gln Lys Ala Ser Ser
625             630             635             640
Glu Phe Glu Arg Leu Ser Arg Tyr Lys Ile Asn Ile Ala Arg Ala Ile
                645             650             655
Ala Asn Trp Ala Leu Gln Trp Gly Arg Glu Leu Ser Gly Cys Asp Ile
                660             665             670
Val Ile Pro Val Leu Glu Asp Leu Asn Val Gly Ser Lys Phe Phe Asp
        675             680             685
Gly Lys Gly Lys Trp Leu Leu Gly Trp Asp Asn Arg Phe Thr Pro Lys
        690             695             700
Lys Glu Asn Arg Trp Phe Ile Lys Val Leu His Lys Ala Val Ala Glu
705             710             715             720
Leu Ala Pro His Arg Gly Val Pro Val Tyr Glu Val Met Pro His Arg
                725             730             735
Thr Ser Met Thr Cys Pro Ala Cys His Tyr Cys His Pro Thr Asn Arg
                740             745             750
Glu Gly Asp Arg Phe Glu Cys Gln Ser Cys His Val Val Lys Asn Thr
                755             760             765
Asp Arg Asp Val Ala Pro Tyr Asn Ile Leu Arg Val Ala Val Glu Gly
        770             775             780
Lys Thr Leu Asp Arg Trp Gln Ala Glu Lys Lys Pro Gln Ala Glu Pro
785             790             795             800
Asp Arg Pro Met Ile Leu Ile Asp Asn Gln Glu Ser
                805             810
```

<210> SEQ ID NO 13
<211> LENGTH: 708
<212> TYPE: PRT
<213> ORGANISM: Unknown

<220> FEATURE:
<223> OTHER INFORMATION: Description of Unknown:
      plants-rhizoplane-switchgrass rhizosphere sequence

<400> SEQUENCE: 13

```
Met Ser Lys Thr Lys Glu Leu Asn Asp Tyr Gln Glu Ala Leu Ala Arg
1               5                   10                  15

Arg Leu Pro Gly Val Arg His Gln Lys Ser Val Arg Arg Ala Ala Arg
                20                  25                  30

Leu Val Tyr Asp Arg Gln Gly Glu Asp Ala Met Val Ala Phe Leu Asp
            35                  40                  45

Gly Lys Glu Val Asp Glu Pro Tyr Thr Leu Gln Pro Pro Ala Lys Cys
    50                  55                  60

His Ile Leu Ala Val Ser Arg Pro Ile Glu Glu Trp Pro Ile Ala Arg
65                  70                  75                  80

Val Thr Met Ala Val Gln Glu His Val Tyr Ala Leu Pro Val His Glu
                85                  90                  95

Val Glu Lys Ser Arg Pro Glu Thr Thr Glu Gly Ser Arg Ser Ala Trp
            100                 105                 110

Phe Lys Asn Ser Gly Val Ser Asn His Gly Val Thr His Ala Gln Thr
            115                 120                 125

Leu Asn Ala Ile Leu Lys Asn Ala Tyr Asn Val Tyr Asn Gly Val Ile
    130                 135                 140

Lys Lys Val Glu Asn Arg Asn Ala Lys Lys Arg Asp Ser Leu Ala Ala
145                 150                 155                 160

Lys Asn Lys Ser Arg Glu Arg Lys Gly Leu Pro His Phe Lys Ala Asp
            165                 170                 175

Pro Pro Glu Leu Ala Thr Asp Glu Gln Gly Tyr Leu Leu Gln Pro Pro
            180                 185                 190

Ser Pro Asn Ser Ser Val Tyr Leu Val Gln Gln His Leu Arg Thr Pro
            195                 200                 205

Gln Ile Asp Leu Pro Ser Gly Tyr Thr Gly Pro Val Val Asp Pro Arg
    210                 215                 220

Ser Pro Ile Pro Ser Leu Ile Pro Ile Asp Arg Leu Ala Ile Pro Pro
225                 230                 235                 240

Gly Gln Pro Gly Tyr Val Pro Leu His Asp Arg Glu Lys Leu Thr Ser
            245                 250                 255

Asn Lys His Arg Arg Met Lys Leu Pro Lys Ser Leu Arg Ala Gln Gly
            260                 265                 270

Ala Leu Pro Val Cys Phe Arg Val Phe Asp Asp Trp Ala Val Val Asp
            275                 280                 285

Gly Arg Gly Leu Leu Arg His Ala Gln Tyr Arg Arg Leu Ala Pro Lys
    290                 295                 300

Asn Val Ser Ile Ala Glu Leu Leu Glu Leu Tyr Thr Gly Asp Pro Val
305                 310                 315                 320

Ile Asp Ile Lys Arg Asn Leu Met Thr Phe Arg Phe Ala Glu Ala Val
            325                 330                 335

Val Glu Val Thr Ala Arg Lys Ile Val Glu Lys Tyr His Asn Lys Tyr
            340                 345                 350

Leu Leu Lys Leu Thr Glu Pro Lys Gly Lys Pro Val Arg Glu Ile Gly
            355                 360                 365

Leu Val Ser Ile Asp Leu Asn Val Gln Arg Leu Ile Ala Leu Ala Ile
    370                 375                 380

Tyr Arg Val His Gln Thr Gly Glu Ser Gln Leu Ala Leu Ser Pro Cys
```

-continued

```
385                 390                 395                 400

Leu His Arg Glu Ile Leu Pro Ala Lys Gly Leu Gly Asp Phe Asp Lys
                405             410             415

Tyr Lys Ser Lys Phe Asn Gln Leu Thr Glu Glu Ile Leu Thr Ala Ala
                420             425             430

Val Gln Thr Leu Thr Ser Ala Gln Gln Glu Glu Tyr Gln Arg Tyr Val
                435             440             445

Glu Glu Ser Ser His Glu Ala Lys Ala Asp Leu Cys Leu Lys Tyr Ser
        450             455             460

Ile Thr Pro His Glu Leu Ala Trp Asp Lys Met Thr Ser Ser Thr Gln
465             470             475             480

Tyr Ile Ser Arg Trp Leu Arg Asp His Gly Trp Asn Ala Ser Asp Phe
                485             490             495

Thr Gln Ile Thr Lys Gly Arg Lys Lys Val Glu Arg Leu Trp Ser Asp
                500             505             510

Ser Arg Trp Ala Gln Glu Leu Lys Pro Lys Leu Ser Asn Glu Thr Arg
                515             520             525

Arg Lys Leu Glu Asp Ala Lys His Asp Leu Gln Arg Ala Asn Pro Glu
        530             535             540

Trp Gln Arg Leu Ala Lys Arg Lys Gln Glu Tyr Ser Arg His Leu Ala
545             550             555             560

Asn Thr Val Leu Ser Met Ala Arg Glu Tyr Thr Ala Cys Glu Thr Val
                565             570             575

Val Ile Ala Ile Glu Asn Leu Pro Met Lys Gly Gly Phe Val Asp Gly
                580             585             590

Asn Gly Ser Arg Glu Ser Gly Trp Asp Asn Phe Phe Thr His Lys Lys
                595             600             605

Glu Asn Arg Trp Met Ile Lys Asp Ile His Lys Ala Leu Ser Asp Leu
        610             615             620

Ala Pro Asn Arg Gly Val His Val Leu Glu Val Asn Pro Gln Tyr Thr
625             630             635             640

Ser Gln Thr Cys Pro Glu Cys Gly His Arg Asp Lys Ala Asn Arg Asp
                645             650             655

Pro Ile Gln Arg Glu Arg Phe Cys Cys Thr His Cys Gly Ala Gln Arg
                660             665             670

His Ala Asp Leu Glu Val Ala Thr His Asn Ile Ala Met Val Ala Thr
                675             680             685

Thr Gly Lys Ser Leu Thr Gly Lys Ser Leu Ala Pro Gln Arg Leu Gln
        690             695             700

Glu Ala Ala Glu
705
```

<210> SEQ ID NO 14
<211> LENGTH: 666
<212> TYPE: PRT
<213> ORGANISM: Unknown
<220> FEATURE:
<223> OTHER INFORMATION: Description of Unknown:
      rhizosphere metagenome sequence

<400> SEQUENCE: 14

```
Met Val Ala Phe Leu Asp Gly Lys Glu Val Asp Glu Pro Tyr Thr Leu
1               5               10              15

Gln Pro Pro Ala Lys Cys His Ile Leu Ala Val Ser Arg Pro Ile Glu
                20              25              30
```

```
Glu Trp Pro Ile Ala Arg Val Thr Met Ala Val Gln Glu His Val Tyr
    35                  40                  45

Ala Leu Pro Val His Glu Val Glu Lys Ser Arg Pro Glu Thr Thr Glu
    50                  55                  60

Gly Ser Arg Ser Ala Trp Phe Lys Asn Ser Gly Val Ser Asn His Gly
65                  70                  75                  80

Val Thr His Ala Gln Thr Leu Asn Ala Ile Leu Lys Asn Ala Tyr Asn
                85                  90                  95

Val Tyr Asn Gly Val Ile Lys Lys Val Glu Asn Arg Asn Ala Lys Lys
                100                 105                 110

Arg Asp Ser Leu Ala Ala Lys Asn Lys Ser Arg Glu Arg Lys Gly Leu
                115                 120                 125

Pro His Phe Lys Ala Asp Pro Pro Glu Leu Ala Thr Asp Glu Gln Gly
    130                 135                 140

Tyr Leu Leu Gln Pro Pro Ser Pro Asn Ser Ser Val Tyr Leu Val Gln
145                 150                 155                 160

Gln His Leu Arg Thr Pro Gln Ile Asp Leu Pro Ser Gly Tyr Thr Gly
                165                 170                 175

Pro Val Val Asp Pro Arg Ser Pro Ile Pro Ser Leu Ile Pro Ile Asp
                180                 185                 190

Arg Leu Ala Ile Pro Pro Gly Gln Pro Gly Tyr Val Pro Leu His Asp
                195                 200                 205

Arg Glu Lys Leu Thr Ser Asn Lys His Arg Arg Met Lys Leu Pro Lys
    210                 215                 220

Ser Leu Arg Ala Gln Gly Ala Leu Pro Val Cys Phe Arg Val Phe Asp
225                 230                 235                 240

Asp Trp Ala Val Val Asp Gly Arg Gly Leu Leu Arg His Ala Gln Tyr
                245                 250                 255

Arg Arg Leu Ala Pro Lys Asn Val Ser Ile Ala Glu Leu Leu Glu Leu
                260                 265                 270

Tyr Thr Gly Asp Pro Val Ile Asp Ile Lys Arg Asn Leu Met Thr Phe
    275                 280                 285

Arg Phe Ala Glu Ala Val Val Glu Val Thr Ala Arg Lys Ile Val Glu
    290                 295                 300

Lys Tyr His Asn Lys Tyr Leu Leu Lys Leu Thr Glu Pro Lys Gly Lys
305                 310                 315                 320

Pro Val Arg Glu Ile Gly Leu Val Ser Ile Asp Leu Asn Val Gln Arg
                325                 330                 335

Leu Ile Ala Leu Ala Ile Tyr Arg Val His Gln Thr Gly Glu Ser Gln
                340                 345                 350

Leu Ala Leu Ser Pro Cys Leu His Arg Glu Ile Leu Pro Ala Lys Gly
                355                 360                 365

Leu Gly Asp Phe Asp Lys Tyr Lys Ser Lys Phe Asn Gln Leu Thr Glu
    370                 375                 380

Glu Ile Leu Thr Ala Ala Val Gln Thr Leu Thr Ser Ala Gln Gln Glu
385                 390                 395                 400

Glu Tyr Gln Arg Tyr Val Glu Glu Ser His Glu Ala Lys Ala Asp
                405                 410                 415

Leu Cys Leu Lys Tyr Ser Ile Thr Pro His Glu Leu Ala Trp Asp Lys
                420                 425                 430

Met Thr Ser Ser Thr Gln Tyr Ile Ser Arg Trp Leu Arg Asp His Gly
    435                 440                 445

Trp Asn Ala Ser Asp Phe Thr Gln Ile Thr Lys Gly Arg Lys Lys Val
```

-continued

```
        450             455             460

Glu Arg Leu Trp Ser Asp Ser Arg Trp Ala Gln Glu Leu Lys Pro Lys
465             470             475             480

Leu Ser Asn Glu Thr Arg Arg Lys Leu Glu Asp Ala Lys His Asp Leu
                485             490             495

Gln Arg Ala Asn Pro Glu Trp Gln Arg Leu Ala Lys Arg Lys Gln Glu
                500             505             510

Tyr Ser Arg His Leu Ala Asn Thr Val Leu Ser Met Ala Arg Glu Tyr
                515             520             525

Thr Ala Cys Glu Thr Val Val Ile Ala Ile Glu Asn Leu Pro Met Lys
        530             535             540

Gly Gly Phe Val Asp Gly Asn Gly Ser Arg Glu Ser Gly Trp Asp Asn
545             550             555             560

Phe Phe Thr His Lys Lys Glu Asn Arg Trp Met Ile Lys Asp Ile His
                565             570             575

Lys Ala Leu Ser Asp Leu Ala Pro Asn Arg Gly Val His Val Leu Glu
                580             585             590

Val Asn Pro Gln Tyr Thr Ser Gln Thr Cys Pro Glu Cys Gly His Arg
                595             600             605

Asp Lys Ala Asn Arg Asp Pro Ile Gln Arg Glu Arg Phe Cys Cys Thr
        610             615             620

His Cys Gly Ala Gln Arg His Ala Asp Leu Glu Val Ala Thr His Asn
625             630             635             640

Ile Ala Met Val Ala Thr Thr Gly Lys Ser Leu Thr Gly Lys Ser Leu
                645             650             655

Ala Pro Gln Arg Leu Gln Glu Ala Ala Glu
                660             665
```

<210> SEQ ID NO 15
<211> LENGTH: 708
<212> TYPE: PRT
<213> ORGANISM: Unknown
<220> FEATURE:
<223> OTHER INFORMATION: Description of Unknown:
      rhizosphere metagenome sequence

<400> SEQUENCE: 15

```
Met Ser Lys Thr Lys Glu Leu Asn Asp Tyr Gln Glu Ala Leu Ala Arg
1               5               10              15

Arg Leu Pro Gly Val Arg His Gln Lys Ser Val Arg Arg Ala Ala Arg
                20              25              30

Leu Val Tyr Asp Arg Gln Gly Glu Asp Ala Met Val Ala Phe Leu Asp
                35              40              45

Gly Lys Glu Val Asp Glu Pro Tyr Thr Leu Gln Pro Pro Ala Lys Cys
        50              55              60

His Ile Leu Ala Val Ser Arg Pro Ile Glu Glu Trp Pro Ile Ala Arg
65              70              75              80

Val Thr Met Ala Val Gln Glu His Val Tyr Ala Leu Pro Val His Glu
                85              90              95

Val Glu Lys Ser Arg Pro Glu Thr Thr Glu Gly Ser Arg Ser Ala Trp
                100             105             110

Phe Lys Asn Ser Gly Val Ser Asn His Gly Val Thr His Ala Gln Thr
                115             120             125

Leu Asn Ala Ile Leu Lys Asn Ala Tyr Asn Val Tyr Asn Gly Val Ile
        130             135             140
```

```
Lys Lys Val Glu Asn Arg Asn Ala Lys Lys Arg Asp Ser Leu Ala Ala
145                 150                 155                 160

Lys Asn Lys Ser Arg Glu Arg Lys Gly Leu Pro His Phe Lys Ala Asp
                165                 170                 175

Pro Pro Glu Leu Ala Thr Asp Glu Gln Gly Tyr Leu Leu Gln Pro Pro
                180                 185                 190

Ser Pro Asn Ser Ser Val Tyr Leu Val Gln Gln His Leu Arg Thr Pro
                195                 200                 205

Gln Ile Asp Leu Pro Ser Gly Tyr Thr Gly Pro Val Val Asp Pro Arg
        210                 215                 220

Ser Pro Ile Pro Ser Leu Ile Pro Ile Asp Arg Leu Ala Ile Pro Pro
225                 230                 235                 240

Gly Gln Pro Gly Tyr Val Pro Leu His Asp Arg Glu Lys Leu Thr Ser
                245                 250                 255

Asn Lys His Arg Arg Met Lys Leu Pro Lys Ser Leu Arg Ala Gln Gly
                260                 265                 270

Ala Leu Pro Val Cys Phe Arg Val Phe Asp Asp Trp Ala Val Val Asp
                275                 280                 285

Gly Arg Gly Leu Leu Arg His Ala Gln Tyr Arg Arg Leu Ala Pro Lys
        290                 295                 300

Asn Val Ser Ile Ala Glu Leu Leu Glu Leu Tyr Thr Gly Asp Pro Val
305                 310                 315                 320

Ile Asp Ile Lys Arg Asn Leu Met Thr Phe Arg Phe Ala Glu Ala Val
                325                 330                 335

Val Glu Val Thr Ala Arg Lys Ile Val Glu Lys Tyr His Asn Lys Tyr
                340                 345                 350

Leu Leu Lys Leu Thr Glu Pro Lys Gly Lys Pro Val Arg Glu Ile Gly
                355                 360                 365

Leu Val Ser Ile Asp Leu Asn Val Gln Arg Leu Ile Ala Leu Ala Ile
        370                 375                 380

Tyr Arg Val His Gln Thr Gly Glu Ser Gln Leu Ala Leu Ser Pro Cys
385                 390                 395                 400

Leu His Arg Glu Ile Leu Pro Ala Lys Gly Leu Gly Asp Phe Asp Lys
                405                 410                 415

Tyr Lys Ser Lys Phe Asn Gln Leu Thr Glu Glu Ile Leu Thr Ala Ala
                420                 425                 430

Val Gln Thr Leu Thr Ser Ala Gln Gln Glu Glu Tyr Gln Arg Tyr Val
                435                 440                 445

Glu Glu Ser Ser His Glu Ala Lys Ala Asp Leu Cys Leu Lys Tyr Ser
        450                 455                 460

Ile Thr Pro His Glu Leu Ala Trp Asp Lys Met Thr Ser Ser Thr Gln
465                 470                 475                 480

Tyr Ile Ser Arg Trp Leu Arg Asp His Gly Trp Asn Ala Ser Asp Phe
                485                 490                 495

Thr Gln Ile Thr Lys Gly Arg Lys Lys Val Glu Arg Leu Trp Ser Asp
                500                 505                 510

Ser Arg Trp Ala Gln Glu Leu Lys Pro Lys Leu Ser Asn Glu Thr Arg
                515                 520                 525

Arg Lys Leu Glu Asp Ala Lys His Asp Leu Gln Arg Ala Asn Pro Glu
        530                 535                 540

Trp Gln Arg Leu Ala Lys Arg Lys Gln Glu Tyr Ser Arg His Leu Ala
545                 550                 555                 560

Asn Thr Val Leu Ser Met Ala Arg Glu Tyr Thr Ala Cys Glu Thr Val
```

```
                    565                   570                   575

Val Ile Ala Ile Glu Asn Leu Pro Met Lys Gly Gly Phe Val Asp Gly
                580                   585                   590

Asn Gly Ser Arg Glu Ser Gly Trp Asp Asn Phe Phe Thr His Lys Lys
                595                   600                   605

Glu Asn Arg Trp Met Ile Lys Asp Ile His Lys Ala Leu Ser Asp Leu
    610                   615                   620

Ala Pro Asn Arg Gly Val His Val Leu Glu Val Asn Pro Gln Tyr Thr
625                   630                   635                   640

Ser Gln Thr Cys Pro Glu Cys Gly His Arg Asp Lys Ala Asn Arg Asp
                645                   650                   655

Pro Ile Gln Arg Glu Arg Phe Cys Cys Thr His Cys Gly Ala Gln Arg
                660                   665                   670

His Ala Asp Leu Glu Val Ala Thr His Asn Ile Ala Met Val Ala Thr
                675                   680                   685

Thr Gly Lys Ser Leu Thr Gly Lys Ser Leu Ala Pro Gln Arg Leu Gln
    690                   695                   700

Glu Ala Ala Glu
705

<210> SEQ ID NO 16
<211> LENGTH: 717
<212> TYPE: PRT
<213> ORGANISM: Unknown
<220> FEATURE:
<223> OTHER INFORMATION: Description of Unknown:
      soil metagenome sequence

<400> SEQUENCE: 16

Met Ile Lys Pro Thr Val Ser Gln Phe Leu Thr Pro Gly Phe Lys Leu
1               5                   10                  15

Ile Arg Asn His Ser Arg Thr Ala Gly Leu Lys Leu Lys Asn Glu Gly
                20                  25                  30

Glu Glu Ala Cys Lys Lys Phe Val Arg Glu Asn Glu Ile Pro Lys Asp
            35                  40                  45

Glu Cys Pro Asn Phe Gln Gly Gly Pro Ala Ile Ala Asn Ile Ile Ala
    50                  55                  60

Lys Ser Arg Glu Phe Thr Glu Trp Glu Ile Tyr Gln Ser Ser Leu Ala
65                  70                  75                  80

Ile Gln Glu Val Ile Phe Thr Leu Pro Lys Asp Lys Leu Pro Glu Pro
                85                  90                  95

Ile Leu Lys Glu Glu Trp Arg Ala Gln Trp Leu Ser Glu His Gly Leu
            100                 105                 110

Asp Thr Val Pro Tyr Lys Glu Ala Ala Gly Leu Asn Leu Ile Ile Lys
        115                 120                 125

Asn Ala Val Asn Thr Tyr Lys Gly Val Gln Val Lys Val Asp Asn Lys
    130                 135                 140

Asn Lys Asn Asn Leu Ala Lys Ile Asn Arg Lys Asn Glu Ile Ala Lys
145                 150                 155                 160

Leu Asn Gly Glu Gln Glu Ile Ser Phe Glu Glu Ile Lys Ala Phe Asp
                165                 170                 175

Asp Lys Gly Tyr Leu Leu Gln Lys Pro Ser Pro Asn Lys Ser Ile Tyr
            180                 185                 190

Cys Tyr Gln Ser Val Ser Pro Lys Pro Phe Ile Thr Ser Lys Tyr His
        195                 200                 205
```

-continued

```
Asn Val Asn Leu Pro Glu Glu Tyr Ile Gly Tyr Tyr Arg Lys Ser Asn
    210                 215                 220

Glu Pro Ile Val Ser Pro Tyr Gln Phe Asp Arg Leu Arg Ile Pro Ile
225                 230                 235                 240

Gly Glu Pro Gly Tyr Val Pro Lys Trp Gln Tyr Thr Phe Leu Ser Lys
                245                 250                 255

Lys Glu Asn Lys Arg Arg Lys Leu Ser Lys Arg Ile Lys Asn Val Ser
                260                 265                 270

Pro Ile Leu Gly Ile Ile Cys Ile Lys Lys Asp Trp Cys Val Phe Asp
        275                 280                 285

Met Arg Gly Leu Leu Arg Thr Asn His Trp Lys Lys Tyr His Lys Pro
    290                 295                 300

Thr Asp Ser Ile Asn Asp Leu Phe Asp Tyr Phe Thr Gly Asp Pro Val
305                 310                 315                 320

Ile Asp Thr Lys Ala Asn Val Val Arg Phe Arg Tyr Lys Met Glu Asn
                325                 330                 335

Gly Ile Val Asn Tyr Lys Pro Val Arg Glu Lys Lys Gly Lys Glu Leu
                340                 345                 350

Leu Glu Asn Ile Cys Asp Gln Asn Gly Ser Cys Lys Leu Ala Thr Val
                355                 360                 365

Asp Val Gly Gln Asn Asn Pro Val Ala Ile Gly Leu Phe Glu Leu Lys
    370                 375                 380

Lys Val Asn Gly Glu Leu Thr Lys Thr Leu Ile Ser Arg His Pro Thr
385                 390                 395                 400

Pro Ile Asp Phe Cys Asn Lys Ile Thr Ala Tyr Arg Glu Arg Tyr Asp
                405                 410                 415

Lys Leu Glu Ser Ser Ile Lys Leu Asp Ala Ile Lys Gln Leu Thr Ser
                420                 425                 430

Glu Gln Lys Ile Glu Val Asp Asn Tyr Asn Asn Asn Phe Thr Pro Gln
        435                 440                 445

Asn Thr Lys Gln Ile Val Cys Ser Lys Leu Asn Ile Asn Pro Asn Asp
    450                 455                 460

Leu Pro Trp Asp Lys Met Ile Ser Gly Thr His Phe Ile Ser Glu Lys
465                 470                 475                 480

Ala Gln Val Ser Asn Lys Ser Glu Ile Tyr Phe Thr Ser Thr Asp Lys
                485                 490                 495

Gly Lys Thr Lys Asp Val Met Lys Ser Asp Tyr Lys Trp Phe Gln Asp
                500                 505                 510

Tyr Lys Pro Lys Leu Ser Lys Glu Val Arg Asp Ala Leu Ser Asp Ile
        515                 520                 525

Glu Trp Arg Leu Arg Arg Glu Ser Leu Glu Phe Asn Lys Leu Ser Lys
    530                 535                 540

Ser Arg Glu Gln Asp Ala Arg Gln Leu Ala Asn Trp Ile Ser Ser Met
545                 550                 555                 560

Cys Asp Val Ile Gly Ile Glu Asn Leu Val Lys Lys Asn Asn Phe Phe
                565                 570                 575

Gly Gly Ser Gly Lys Arg Glu Pro Gly Trp Asp Asn Phe Tyr Lys Pro
                580                 585                 590

Lys Lys Glu Asn Arg Trp Trp Ile Asn Ala Ile His Lys Ala Leu Thr
                595                 600                 605

Glu Leu Ser Gln Asn Lys Gly Lys Arg Val Ile Leu Leu Pro Ala Met
    610                 615                 620

Arg Thr Ser Ile Thr Cys Pro Lys Cys Lys Tyr Cys Asp Ser Lys Asn
```

-continued

```
625              630              635              640

Arg Asn Gly Glu Lys Phe Asn Cys Leu Lys Cys Gly Ile Glu Leu Asn
                645              650              655

Ala Asp Ile Asp Val Ala Thr Glu Asn Leu Ala Thr Val Ala Ile Thr
                660              665              670

Ala Gln Ser Met Pro Lys Pro Thr Cys Glu Arg Ser Gly Asp Ala Lys
                675              680              685

Lys Pro Val Arg Ala Arg Lys Ala Lys Ala Pro Glu Phe His Asp Lys
                690              695              700

Leu Ala Pro Ser Tyr Thr Val Val Leu Arg Glu Ala Val
705              710              715

<210> SEQ ID NO 17
<211> LENGTH: 781
<212> TYPE: PRT
<213> ORGANISM: Unknown
<220> FEATURE:
<223> OTHER INFORMATION: Description of Unknown:
      soil metagenome sequence

<400> SEQUENCE: 17

Met Arg Gln Pro Ala Glu Lys Thr Ala Phe Gln Val Phe Arg Gln Glu
1               5               10              15

Val Ile Gly Thr Gln Lys Leu Ser Gly Gly Asp Ala Lys Thr Ala Gly
                20              25              30

Arg Leu Tyr Lys Gln Gly Lys Met Glu Ala Ala Arg Glu Trp Leu Leu
                35              40              45

Lys Gly Ala Arg Asp Asp Val Pro Pro Asn Phe Gln Pro Pro Ala Lys
                50              55              60

Cys Leu Val Val Ala Val Ser His Pro Phe Glu Glu Trp Asp Ile Ser
65              70              75              80

Lys Thr Asn His Asp Val Gln Ala Tyr Ile Tyr Ala Gln Pro Leu Gln
                85              90              95

Ala Glu Gly His Leu Asn Gly Leu Ser Glu Lys Trp Glu Asp Thr Ser
                100             105             110

Ala Asp Gln His Lys Leu Trp Phe Glu Lys Thr Gly Val Pro Asp Arg
                115             120             125

Gly Leu Pro Val Gln Ala Ile Asn Lys Ile Ala Lys Ala Ala Val Asn
                130             135             140

Arg Ala Phe Gly Val Val Arg Lys Val Glu Asn Arg Asn Glu Lys Arg
145             150             155             160

Arg Ser Arg Asp Asn Arg Ile Ala Glu His Asn Arg Glu Asn Gly Leu
                165             170             175

Thr Glu Val Val Arg Glu Ala Pro Glu Val Ala Thr Asn Ala Asp Gly
                180             185             190

Phe Leu Leu His Pro Pro Gly Ile Asp Pro Ser Ile Leu Ser Tyr Ala
                195             200             205

Ser Val Ser Pro Val Pro Tyr Asn Ser Ser Lys His Ser Phe Val Arg
                210             215             220

Leu Pro Glu Glu Tyr Gln Ala Tyr Asn Val Glu Pro Asp Ala Pro Ile
225             230             235             240

Pro Gln Phe Val Val Glu Asp Arg Phe Ala Ile Pro Pro Gly Gln Pro
                245             250             255

Gly Tyr Val Pro Glu Trp Gln Arg Leu Lys Cys Ser Thr Asn Lys His
                260             265             270
```

-continued

```
Arg Arg Met Arg Gln Trp Ser Asn Gln Asp Tyr Lys Pro Lys Ala Gly
        275             280             285

Arg Arg Ala Lys Pro Leu Glu Phe Gln Ala His Leu Thr Arg Glu Arg
    290             295             300

Ala Lys Gly Ala Leu Leu Val Val Met Arg Ile Lys Glu Asp Trp Val
305             310             315             320

Val Phe Asp Val Arg Gly Leu Leu Arg Asn Val Glu Trp Arg Lys Val
                325             330             335

Leu Ser Glu Glu Ala Arg Glu Lys Leu Thr Leu Lys Gly Leu Leu Asp
            340             345             350

Leu Phe Thr Gly Asp Pro Val Ile Asp Thr Lys Arg Gly Ile Val Thr
            355             360             365

Phe Leu Tyr Lys Ala Glu Ile Thr Lys Ile Leu Ser Lys Arg Thr Val
        370             375             380

Lys Thr Lys Asn Ala Arg Asp Leu Leu Leu Arg Leu Thr Glu Pro Gly
385             390             395             400

Glu Asp Gly Leu Arg Arg Glu Val Gly Leu Val Ala Val Asp Leu Gly
                405             410             415

Gln Thr His Pro Ile Ala Ala Ala Ile Tyr Arg Ile Gly Arg Thr Ser
            420             425             430

Ala Gly Ala Leu Glu Ser Thr Val Leu His Arg Gln Gly Leu Arg Glu
            435             440             445

Asp Gln Lys Glu Lys Leu Lys Glu Tyr Arg Lys Arg His Thr Ala Leu
        450             455             460

Asp Ser Arg Leu Arg Lys Glu Ala Phe Glu Thr Leu Ser Val Glu Gln
465             470             475             480

Gln Lys Glu Ile Val Thr Val Ser Gly Ser Gly Ala Gln Ile Thr Lys
                485             490             495

Asp Lys Val Cys Asn Tyr Leu Gly Val Asp Pro Ser Thr Leu Pro Trp
            500             505             510

Glu Lys Met Gly Ser Tyr Thr His Phe Ile Ser Asp Asp Phe Leu Arg
            515             520             525

Arg Gly Gly Asp Pro Asn Ile Val His Phe Asp Arg Gln Pro Lys Lys
        530             535             540

Gly Lys Val Ser Lys Lys Ser Gln Arg Ile Lys Arg Ser Asp Ser Gln
545             550             555             560

Trp Val Gly Arg Met Arg Pro Arg Leu Ser Gln Glu Thr Ala Lys Ala
                565             570             575

Arg Met Glu Ala Asp Trp Ala Ala Gln Asn Glu Asn Glu Glu Tyr Lys
            580             585             590

Arg Leu Ala Arg Ser Lys Gln Glu Leu Ala Arg Trp Cys Val Asn Thr
        595             600             605

Leu Leu Gln Asn Thr Arg Cys Ile Thr Gln Cys Asp Glu Ile Val Val
        610             615             620

Val Ile Glu Asp Leu Asn Val Lys Ser Leu His Gly Lys Gly Ala Arg
625             630             635             640

Glu Pro Gly Trp Asp Asn Phe Phe Thr Pro Lys Thr Glu Asn Arg Trp
                645             650             655

Phe Ile Gln Ile Leu His Lys Thr Phe Ser Glu Leu Pro Lys His Arg
            660             665             670

Gly Glu His Val Ile Glu Gly Cys Pro Leu Arg Thr Ser Ile Thr Cys
            675             680             685

Pro Ala Cys Ser Tyr Cys Asp Lys Asn Ser Arg Asn Gly Glu Lys Phe
```

-continued

```
              690                    695                    700

Val Cys Val Ala Cys Gly Ala Thr Phe His Ala Asp Phe Glu Val Ala
705                    710                    715                    720

Thr Tyr Asn Leu Val Arg Leu Ala Thr Thr Gly Met Pro Met Pro Lys
                   725                    730                    735

Ser Leu Glu Arg Gln Gly Gly Gly Glu Lys Ala Gly Gly Ala Arg Lys
                   740                    745                    750

Ala Arg Lys Lys Ala Lys Gln Val Glu Lys Ile Val Val Gln Ala Asn
              755                    760                    765

Ala Asn Val Thr Met Asn Gly Ala Ser Leu His Ser Pro
              770                    775                    780

<210> SEQ ID NO 18
<211> LENGTH: 769
<212> TYPE: PRT
<213> ORGANISM: Unknown
<220> FEATURE:
<223> OTHER INFORMATION: Description of Unknown:
      soil metagenome sequence

<400> SEQUENCE: 18

Met Glu Lys His Lys Thr Lys Leu Ser Ile Ile Met Lys Glu Phe Phe
1                   5                    10                    15

Pro Gly Glu Arg Phe Pro Lys Asn Val Leu Met Gln Ile Gly Lys Lys
                   20                    25                    30

Ile Thr Asn Asn Lys Asp Gly Lys Glu Thr Ile Asp Val Lys Glu Lys
              35                    40                    45

Glu Asp Val Val Ser Phe Leu Thr Gly Lys Gly Ser Lys Lys Leu Leu
              50                    55                    60

Asp Phe Gln Pro Pro Ala Lys Ala Leu Ile Val Ala Lys Ser Arg Pro
65                    70                    75                    80

Phe Glu Glu Trp Pro Ile Tyr Gln Ala Ser Lys Ile Phe Gln Glu Tyr
                   85                    90                    95

Ile Tyr Gly Leu Pro His Asn Gln Leu Ser Ile Pro Gly Thr Ser Lys
                   100                   105                   110

Ser Glu His Lys Leu Trp Leu Glu Lys Ile Gly Leu Asn Ile Gly Thr
              115                   120                   125

Tyr Lys Asp Val Gln Gly Leu Asn Leu Ile Phe Arg His Thr Lys Asn
              130                   135                   140

Ile Tyr Glu Gly Val Ile Lys Lys Val Glu Asn Lys Asn Lys Lys Asn
145                   150                   155                   160

Lys Glu Lys Ile Glu Ile Lys Asn Lys Phe Glu Lys Glu His Gly Phe
                   165                   170                   175

Leu Leu Thr Pro Phe Glu Glu Glu Thr Ala Phe Asp Asp Asn Gly Lys
                   180                   185                   190

Leu Lys Asn Pro Pro Gly Ile Asn Asn Ser Ile Tyr Cys Tyr Ser Gln
              195                   200                   205

Val Ser Pro Glu Ala Thr Lys Ser Thr Thr Lys Leu Asp Asn Val Pro
              210                   215                   220

Ser Ile Tyr Leu Gly Tyr Tyr Arg Asp Ile Asp Thr Asn Ile Lys Ile
225                   230                   235                   240

Glu Tyr Ile Asn Arg Leu Ser Ile Pro Lys Gly Asp Pro Gly Tyr Ile
                   245                   250                   255

Pro Leu Trp Gln His Glu Leu Leu Ser Lys Lys Glu Asn Asn Thr Arg
                   260                   265                   270
```

-continued

```
Arg Gln Arg Lys Trp Tyr Ser Asn Asn Arg Met Lys Arg Val Lys Arg
        275                 280                 285

Lys Gly Val Ser Lys Tyr Ser Asp Glu Gln Ile Asn Gln Ala Arg Leu
        290                 295                 300

Gln Asp Ala Ile Leu Gly Lys Ile Ser Ile Gly Glu Asp Trp Val Leu
305                 310                 315                 320

Phe Asp Met Arg Gly Leu Leu Arg Asn Leu His Trp Arg Lys Leu Val
                325                 330                 335

Pro Ser Gln Gly Phe Ser Pro Lys Glu Ile Leu Glu Gln Phe Thr Gly
                340                 345                 350

Asp Pro Val Ile Asp Pro Val Arg Asn Val Ile Thr Phe Ile Tyr Lys
                355                 360                 365

Asp Gly Leu Ala His Lys Glu Glu Ile Val Leu Thr Lys Lys Ala Pro
        370                 375                 380

Asp Leu Leu Cys Lys Leu Thr Leu Asn Asn Pro Ile Gly Ile Val Ser
385                 390                 395                 400

Ile Asp Val Gly Gln Thr His Pro Gln Ser Ala Lys Phe Ser Leu Leu
                405                 410                 415

Lys Leu Glu Asp Asp Lys Leu Val Ala Glu Cys Lys Asp Arg Gln Phe
                420                 425                 430

Leu Pro Asp Tyr Leu Leu Asn Lys Leu Phe Ala Tyr Arg Glu Arg Ser
                435                 440                 445

Asp Gln Leu Arg Gly Glu Ile Asn Gln Leu Ala Met Gln Ser Leu Ser
        450                 455                 460

Glu Glu His Gln Lys Glu Phe Asn Asp Leu Lys Ile Glu Asn Asp Pro
465                 470                 475                 480

Thr Ala Val Arg Ile Arg Ile Glu Lys Gln Leu Gly Ile Asp Phe Asn
                485                 490                 495

Asn Leu Pro Ile Asn Asp Met Ile Tyr Asp Arg Thr Thr Tyr Ile Ala
                500                 505                 510

Asp Ala Tyr Leu Ser Ile Pro Gly Val Asp Lys Leu Leu Val Met Leu
                515                 520                 525

Gly Thr Ser Ser Lys Lys Lys Tyr Asp Ser Arg Ile Val Lys Asp Phe
        530                 535                 540

Phe Lys Lys Val Ser Lys Glu Ala Arg Glu Ala Leu Lys Val Ala Phe
545                 550                 555                 560

Gly Glu Ile Gln Lys Leu His Pro Gly Tyr Lys Lys Leu Ser Lys Ser
                565                 570                 575

Leu Gln Gln Trp Ala Arg Glu Cys Val Asn Phe Thr His Lys Tyr Ala
                580                 585                 590

Asn Lys Ile Thr Gly Cys Thr Asn Ile Val Phe Val Ile Glu Asn Leu
        595                 600                 605

Lys Asn Ile Arg Lys Arg Asn Gly Ser Gly Lys Arg Ala Lys Gly Tyr
        610                 615                 620

Asp Asn Phe Phe Val Tyr Lys Lys Glu Asn Arg Trp Val Met Asn Ala
625                 630                 635                 640

Leu Gln Lys Ala Tyr Ile Asp Leu Ala Thr His Lys Gly Ile Asn Ile
                645                 650                 655

Ile Glu Ile Gln Ala Ala Arg Thr Ser Ile Thr Cys Pro Lys Cys Asn
                660                 665                 670

Cys Gln Asp Lys Asn Asn Arg Lys Gly Asp Gln Phe Asn Cys Val Lys
        675                 680                 685

Cys Asn His Gln Ala Asn Thr Asp Leu Glu Ile Ala Thr Asp Asn Ile
```

-continued

```
              690               695               700
Glu Leu Val Ala Leu Asn Gly Lys Gly Met Pro Lys Ile Asp Cys Glu
705               710               715               720

Arg Ser Ser Gly Glu Glu Asn Ala Val Gly Ala Arg Lys Gly Lys Lys
              725               730               735

Thr Arg Lys Ile Lys Glu Ile Gln Glu Thr Asp Lys Asn Ile Lys Met
              740               745               750

Asp Asn Ala Gly Gly Asp Leu Leu Lys Asn Asn Arg Ser Gln Thr Ala
              755               760               765

Ala

<210> SEQ ID NO 19
<211> LENGTH: 805
<212> TYPE: PRT
<213> ORGANISM: Unknown
<220> FEATURE:
<223> OTHER INFORMATION: Description of Unknown:
      soil metagenome sequence

<400> SEQUENCE: 19

Met Asp Pro Gly Met Thr Ile Thr Glu Gly Lys Pro Gln Glu Glu Pro
1               5                 10                15

Thr Glu Leu Ala Lys Leu Leu Arg Glu His Tyr Pro Gly Lys Lys Leu
              20                25                30

Ser Lys Lys Asp Leu Leu Met Ala Gly Lys Ile Leu Ala Gly Lys Val
              35                40                45

Ala Lys Thr Arg Pro Glu Gly Leu Val Glu Trp Leu Ala Asp Lys Val
      50                55                60

Val Asp Glu Pro Pro Asn Phe Ser Pro Pro Ala Lys Ala Asn Ile Val
65                70                75                80

Ala Met Ser Arg Pro Phe Glu Glu Trp Pro Ile Ala Lys Ala Thr Leu
              85                90                95

Ala Ile Glu Ser Tyr Val Phe Gly Met Thr Val Asp Glu Arg Asn Arg
              100               105               110

Leu Cys Pro Lys Glu Thr Glu Glu Asp Arg Asp Glu Trp Phe Arg Val
              115               120               125

Thr Gly Val Ser Asn Tyr Gly Phe Thr Ser Ala Gln Gly Leu Asn His
      130               135               140

Ile Phe Lys Asn Ala Phe Asn Thr Phe Asp Gly Val Val Thr Arg Gly
145               150               155               160

Ser Asn Ala Asn Glu Lys Lys Arg Lys Glu Ile Glu Ala Gln Asn Glu
              165               170               175

Lys Arg Ala Glu Arg Gly Glu Ala Pro Val Pro Phe Glu Pro Arg Pro
              180               185               190

Val Leu Thr Glu Asp Gly His Leu Val His Pro Pro Gly Ser Lys Ser
              195               200               205

Gly Leu Arg Leu Asn Lys Ile Gln Leu Tyr Gln Val Thr Asp Lys
      210               215               220

Gly Arg Gly Phe Arg Gly Gln Val Glu Leu Pro Leu Glu Tyr Glu Asp
225               230               235               240

Tyr Val Arg Asp Pro Glu Ala Pro Ile Pro Phe Gly Val Pro Arg Asp
              245               250               255

Arg Leu Cys Ile Pro Glu Gly Glu Pro Gly Tyr Val Pro Glu Trp Gln
              260               265               270

Arg Pro Leu Leu Ser Thr Lys Lys Lys Arg Arg Arg Arg Gly Trp Gly
```

-continued

```
                275                 280                 285

Pro Ala Gly Pro Glu Gln Val Arg Ala Lys Ala Lys Ala Ala Leu Leu
    290                 295                 300

Trp Tyr Leu Pro Leu Gly Asp Asp Trp Val Val Leu Asp Val Arg Gly
305                 310                 315                 320

Leu Leu Arg Asn Val Arg Trp Arg Gly Leu Ala Pro Glu Gly Leu Ser
                325                 330                 335

Leu Asn Gly Leu Met Glu Leu Phe Thr Gly Tyr Pro Ile Ile His Asn
                340                 345                 350

Lys Thr Gly Asp Val Thr Phe Lys Phe Cys Pro Glu Val Ala Gly Val
                355                 360                 365

Arg Ser His Glu Pro Leu Lys Lys Ala Glu Gly Arg Lys Leu Leu Leu
    370                 375                 380

His Leu Thr Lys Pro Arg Gly Glu Phe His Pro Arg Val Gly Met Val
385                 390                 395                 400

Ala Ile Asp Leu Gly Gln Thr Asn Pro Ala Ala Phe Ser Val Ser Arg
                405                 410                 415

Leu His Gln Val Glu Val Glu Arg Glu Val Glu Val Lys Arg Lys Leu
                420                 425                 430

Pro Asp Gly Glu Thr Glu Lys Val Thr Glu Leu Arg Met Val Gly Glu
                435                 440                 445

Val Arg Gln Thr Ile Leu Ser Thr His Phe Leu Pro Asp Glu Leu Val
    450                 455                 460

Ala Glu Ile Lys Arg Tyr Arg Asn Leu Tyr Ser Ala Met Asn Glu Arg
465                 470                 475                 480

His His Ala Glu Ala Val Leu Arg Leu Pro Lys Glu Ala Gln Asp Val
                485                 490                 495

Tyr His Ala Trp Gln Asn Phe Ser Ala Asp Glu Ala Lys Arg Gln Leu
                500                 505                 510

Cys Ala Lys Tyr Gly Leu Asp Pro Ala Lys Met Pro Trp Asp Gln Met
                515                 520                 525

Thr Ser Ser Thr Met His Ile Ser Lys Ala Val Leu Ala Ala Gly His
    530                 535                 540

Asp Arg Ser Glu Val His Arg Met Val Lys Lys Gly Lys Lys Glu
545                 550                 555                 560

Arg Glu Val Lys Lys Arg Asp Arg Ala Trp Val Ser Asp Phe Lys Pro
                565                 570                 575

Thr Leu Pro Glu Glu Val Trp Arg Pro Lys Arg Glu His Leu Leu Asp
                580                 585                 590

Ile Gln Arg Glu Ser Glu Glu Tyr Arg Arg Leu Thr Ile Phe Lys Gln
                595                 600                 605

Gln Leu Val Arg Arg Cys Val Asn His Val Val Lys Val Gly Glu Arg
    610                 615                 620

Glu Ser Gln Cys Glu Lys Leu Val Phe Ala Ile Glu Asp Leu Asn Val
625                 630                 635                 640

Lys Gly Phe Phe Phe Gly Lys Gly Lys Asn Leu Pro Gly Trp Glu Gly
                645                 650                 655

Phe Phe Gln His Lys Arg Glu Asn Arg Phe Ile Ile Arg Glu Phe His
                660                 665                 670

Arg Ala Phe Ser Glu Leu Gly Pro His Arg Gly Tyr Tyr Val Leu Glu
                675                 680                 685

Ala Asn Pro Gly Tyr Thr Ser Cys Thr Cys Pro Asp Cys Arg His Pro
    690                 695                 700
```

-continued

```
Asp Pro Val Ser Arg Asn Gly Glu Arg Phe Lys Cys Thr Arg Cys Gly
705                 710                 715                 720

Ala Thr His His Ala Asp Ser Glu Val Ala Thr Tyr Asn Ile Ala Gln
                725                 730                 735

Val Ala Ile Met Gly Lys Ala Leu Pro Arg Pro Lys Lys Gln Lys Lys
            740                 745                 750

Pro Lys Arg Glu Arg Ser Gly Ala Val Lys Lys Ala Glu Thr Ala Arg
            755                 760                 765

Lys Arg Asn Gly Arg Lys Ser Asn Gly Lys Gly Gly Gln Arg Gln Glu
        770                 775                 780

Ala Pro Leu Leu Arg Pro Pro Val Arg Gly Thr Ala Arg Glu Pro Val
785                 790                 795                 800

Ala Asn Ala Ser Cys
                805
```

```
<210> SEQ ID NO 20
<211> LENGTH: 801
<212> TYPE: PRT
<213> ORGANISM: Unknown
<220> FEATURE:
<223> OTHER INFORMATION: Description of Unknown:
      soil metagenome sequence

<400> SEQUENCE: 20
```

```
Met Thr Ile Thr Glu Gly Lys Pro Gln Glu Glu Pro Thr Glu Leu Ala
1               5                   10                  15

Lys Leu Leu Arg Glu His Tyr Pro Gly Lys Lys Leu Ser Lys Lys Asp
            20                  25                  30

Leu Leu Met Ala Gly Lys Ile Leu Ala Gly Lys Val Ala Lys Thr Arg
            35                  40                  45

Pro Glu Gly Leu Val Glu Trp Leu Ala Asp Lys Val Val Asp Glu Pro
    50                  55                  60

Pro Asn Phe Ser Pro Pro Ala Lys Ala Asn Ile Val Ala Met Ser Arg
65                  70                  75                  80

Pro Phe Glu Glu Trp Pro Ile Ala Lys Ala Thr Leu Ala Ile Glu Ser
                85                  90                  95

Tyr Val Phe Gly Met Thr Val Asp Glu Arg Asn Arg Leu Cys Pro Lys
            100                 105                 110

Glu Thr Glu Glu Asp Arg Asp Glu Trp Phe Arg Val Thr Gly Val Ser
            115                 120                 125

Asn Tyr Gly Phe Thr Ser Ala Gln Gly Leu Asn His Ile Phe Lys Asn
        130                 135                 140

Ala Phe Asn Thr Phe Asp Gly Val Val Thr Arg Gly Ser Asn Ala Asn
145                 150                 155                 160

Glu Lys Lys Arg Lys Glu Ile Glu Ala Gln Asn Glu Lys Arg Ala Glu
                165                 170                 175

Arg Gly Glu Ala Pro Val Pro Phe Glu Pro Arg Pro Val Leu Thr Glu
            180                 185                 190

Asp Gly His Leu Val His Pro Pro Gly Ser Lys Ser Gly Leu Arg Leu
            195                 200                 205

Asn Lys Ile Gln Leu Tyr Gln Gln Val Thr Asp Lys Gly Arg Gly Phe
        210                 215                 220

Arg Gly Gln Val Glu Leu Pro Leu Glu Tyr Glu Asp Tyr Val Arg Asp
225                 230                 235                 240

Pro Glu Ala Pro Ile Pro Phe Gly Val Pro Arg Asp Arg Leu Cys Ile
```

-continued

```
                    245                 250                 255
Pro Glu Gly Glu Pro Gly Tyr Val Pro Glu Trp Gln Arg Pro Leu Leu
            260                 265                 270
Ser Thr Lys Lys Lys Arg Arg Arg Arg Gly Trp Gly Pro Ala Gly Pro
            275                 280                 285
Glu Gln Val Arg Ala Lys Ala Lys Ala Ala Leu Leu Trp Tyr Leu Pro
    290                 295                 300
Leu Gly Asp Asp Trp Val Val Leu Asp Val Arg Gly Leu Leu Arg Asn
305                 310                 315                 320
Val Arg Trp Arg Gly Leu Ala Pro Glu Gly Leu Ser Leu Asn Gly Leu
                325                 330                 335
Met Glu Leu Phe Thr Gly Tyr Pro Ile Ile His Asn Lys Thr Gly Asp
                340                 345                 350
Val Thr Phe Lys Phe Cys Pro Glu Val Ala Gly Val Arg Ser His Glu
                355                 360                 365
Pro Leu Lys Lys Ala Glu Gly Arg Lys Leu Leu Leu His Leu Thr Lys
    370                 375                 380
Pro Arg Gly Glu Phe His Pro Arg Val Gly Met Val Ala Ile Asp Leu
385                 390                 395                 400
Gly Gln Thr Asn Pro Ala Ala Phe Ser Val Ser Arg Leu His Gln Val
                405                 410                 415
Glu Val Glu Arg Glu Val Glu Val Lys Arg Lys Leu Pro Asp Gly Glu
                420                 425                 430
Thr Glu Lys Val Thr Glu Leu Arg Met Val Gly Glu Val Arg Gln Thr
                435                 440                 445
Ile Leu Ser Thr His Phe Leu Pro Asp Glu Leu Val Ala Glu Ile Lys
    450                 455                 460
Arg Tyr Arg Asn Leu Tyr Ser Ala Met Asn Glu Arg His His Ala Glu
465                 470                 475                 480
Ala Val Leu Arg Leu Pro Lys Glu Ala Gln Asp Val Tyr His Ala Trp
                485                 490                 495
Gln Asn Phe Ser Ala Asp Glu Ala Lys Arg Gln Leu Cys Ala Lys Tyr
                500                 505                 510
Gly Leu Asp Pro Ala Lys Met Pro Trp Asp Gln Met Thr Ser Ser Thr
                515                 520                 525
Met His Ile Ser Lys Ala Val Leu Ala Ala Gly His Asp Arg Ser Glu
    530                 535                 540
Val His Arg Met Val Lys Lys Lys Gly Lys Lys Glu Arg Glu Val Lys
545                 550                 555                 560
Lys Arg Asp Arg Ala Trp Val Ser Asp Phe Lys Pro Thr Leu Pro Glu
                565                 570                 575
Glu Val Trp Arg Pro Lys Arg Glu His Leu Leu Asp Ile Gln Arg Glu
                580                 585                 590
Ser Glu Glu Tyr Arg Arg Leu Thr Ile Phe Lys Gln Gln Leu Val Arg
                595                 600                 605
Arg Cys Val Asn His Val Val Lys Val Gly Glu Arg Glu Ser Gln Cys
    610                 615                 620
Glu Lys Leu Val Phe Ala Ile Glu Asp Leu Asn Val Lys Gly Phe Phe
625                 630                 635                 640
Phe Gly Lys Gly Lys Asn Leu Pro Gly Trp Glu Gly Phe Phe Gln His
                645                 650                 655
Lys Arg Glu Asn Arg Phe Ile Ile Arg Glu Phe His Arg Ala Phe Ser
                660                 665                 670
```

-continued

```
Glu Leu Gly Pro His Arg Gly Tyr Tyr Val Leu Glu Ala Asn Pro Gly
        675             680             685

Tyr Thr Ser Cys Thr Cys Pro Asp Cys Arg His Pro Asp Pro Val Ser
    690             695             700

Arg Asn Gly Glu Arg Phe Lys Cys Thr Arg Cys Gly Ala Thr His His
705             710             715             720

Ala Asp Ser Glu Val Ala Thr Tyr Asn Ile Ala Gln Val Ala Ile Met
        725             730             735

Gly Lys Ala Leu Pro Arg Pro Lys Lys Gln Lys Lys Pro Lys Arg Glu
        740             745             750

Arg Ser Gly Ala Val Lys Lys Ala Glu Thr Ala Arg Lys Arg Asn Gly
        755             760             765

Arg Lys Ser Asn Gly Lys Gly Gly Gln Arg Gln Glu Ala Pro Leu Leu
    770             775             780

Arg Pro Pro Val Arg Gly Thr Ala Arg Glu Pro Val Ala Asn Ala Ser
785             790             795             800

Cys
```

```
<210> SEQ ID NO 21
<211> LENGTH: 717
<212> TYPE: PRT
<213> ORGANISM: Unknown
<220> FEATURE:
<223> OTHER INFORMATION: Description of Unknown:
      terrestrial-soil-forest soil sequence

<400> SEQUENCE: 21

Met Ile Lys Pro Thr Val Ser Gln Phe Leu Thr Pro Gly Phe Lys Leu
1               5               10              15

Ile Arg Asn His Ser Arg Thr Ala Gly Leu Lys Leu Lys Asn Glu Gly
        20              25              30

Glu Glu Ala Cys Lys Lys Phe Val Arg Glu Asn Glu Ile Pro Lys Asp
        35              40              45

Glu Cys Pro Asn Phe Gln Gly Gly Pro Ala Ile Ala Asn Ile Ile Ala
    50              55              60

Lys Ser Arg Glu Phe Thr Glu Trp Glu Ile Tyr Gln Ser Ser Leu Ala
65              70              75              80

Ile Gln Glu Val Ile Phe Thr Leu Pro Lys Asp Lys Leu Pro Glu Pro
                85              90              95

Ile Leu Lys Glu Glu Trp Arg Ala Gln Trp Leu Ser Glu His Gly Leu
        100             105             110

Asp Thr Val Pro Tyr Lys Glu Ala Ala Gly Leu Asn Leu Ile Ile Lys
        115             120             125

Asn Ala Val Asn Thr Tyr Lys Gly Val Gln Val Lys Val Asp Asn Lys
        130             135             140

Asn Lys Asn Asn Leu Ala Lys Ile Asn Arg Lys Asn Glu Ile Ala Lys
145             150             155             160

Leu Asn Gly Glu Gln Glu Ile Ser Phe Glu Glu Ile Lys Ala Phe Asp
                165             170             175

Asp Lys Gly Tyr Leu Leu Gln Lys Pro Ser Pro Asn Lys Ser Ile Tyr
        180             185             190

Cys Tyr Gln Ser Val Ser Pro Lys Pro Phe Ile Thr Ser Lys Tyr His
        195             200             205

Asn Val Asn Leu Pro Glu Glu Tyr Ile Gly Tyr Tyr Arg Lys Ser Asn
        210             215             220
```

-continued

```
Glu Pro Ile Val Ser Pro Tyr Gln Phe Asp Arg Leu Arg Ile Pro Ile
225                 230                 235                 240

Gly Glu Pro Gly Tyr Val Pro Lys Trp Gln Tyr Thr Phe Leu Ser Lys
                245                 250                 255

Lys Glu Asn Lys Arg Arg Lys Leu Ser Lys Arg Ile Lys Asn Val Ser
                260                 265                 270

Pro Ile Leu Gly Ile Ile Cys Ile Lys Lys Asp Trp Cys Val Phe Asp
                275                 280                 285

Met Arg Gly Leu Leu Arg Thr Asn His Trp Lys Lys Tyr His Lys Pro
                290                 295                 300

Thr Asp Ser Ile Asn Asp Leu Phe Asp Tyr Phe Thr Gly Asp Pro Val
305                 310                 315                 320

Ile Asp Thr Lys Ala Asn Val Val Arg Phe Arg Tyr Lys Met Glu Asn
                325                 330                 335

Gly Ile Val Asn Tyr Lys Pro Val Arg Glu Lys Lys Gly Lys Glu Leu
                340                 345                 350

Leu Glu Asn Ile Cys Asp Gln Asn Gly Ser Cys Lys Leu Ala Thr Val
                355                 360                 365

Asp Val Gly Gln Asn Asn Pro Val Ala Ile Gly Leu Phe Glu Leu Lys
                370                 375                 380

Lys Val Asn Gly Glu Leu Thr Lys Thr Leu Ile Ser Arg His Pro Thr
385                 390                 395                 400

Pro Ile Asp Phe Cys Asn Lys Ile Thr Ala Tyr Arg Glu Arg Tyr Asp
                405                 410                 415

Lys Leu Glu Ser Ser Ile Lys Leu Asp Ala Ile Lys Gln Leu Thr Ser
                420                 425                 430

Glu Gln Lys Ile Glu Val Asp Asn Tyr Asn Asn Asn Phe Thr Pro Gln
                435                 440                 445

Asn Thr Lys Gln Ile Val Cys Ser Lys Leu Asn Ile Asn Pro Asn Asp
                450                 455                 460

Leu Pro Trp Asp Lys Met Ile Ser Gly Thr His Phe Ile Ser Glu Lys
465                 470                 475                 480

Ala Gln Val Ser Asn Lys Ser Glu Ile Tyr Phe Thr Ser Thr Asp Lys
                485                 490                 495

Gly Lys Thr Lys Asp Val Met Lys Ser Asp Tyr Lys Trp Phe Gln Asp
                500                 505                 510

Tyr Lys Pro Lys Leu Ser Lys Glu Val Arg Asp Ala Leu Ser Asp Ile
                515                 520                 525

Glu Trp Arg Leu Arg Arg Glu Ser Leu Glu Phe Asn Lys Leu Ser Lys
                530                 535                 540

Ser Arg Glu Gln Asp Ala Arg Gln Leu Ala Asn Trp Ile Ser Ser Met
545                 550                 555                 560

Cys Asp Val Ile Gly Ile Glu Asn Leu Val Lys Lys Asn Asn Phe Phe
                565                 570                 575

Gly Gly Ser Gly Lys Arg Glu Pro Gly Trp Asp Asn Phe Tyr Lys Pro
                580                 585                 590

Lys Lys Glu Asn Arg Trp Trp Ile Asn Ala Ile His Lys Ala Leu Thr
                595                 600                 605

Glu Leu Ser Gln Asn Lys Gly Lys Arg Val Ile Leu Leu Pro Ala Met
                610                 615                 620

Arg Thr Ser Ile Thr Cys Pro Lys Cys Lys Tyr Cys Asp Ser Lys Asn
625                 630                 635                 640
```

-continued

```
Arg Asn Gly Glu Lys Phe Asn Cys Leu Lys Cys Gly Ile Glu Leu Asn
            645             650             655

Ala Asp Ile Asp Val Ala Thr Glu Asn Leu Ala Thr Val Ala Ile Thr
            660             665             670

Ala Gln Ser Met Pro Lys Pro Thr Cys Glu Arg Ser Gly Asp Ala Lys
            675             680             685

Lys Pro Val Arg Ala Arg Lys Ala Lys Ala Pro Glu Phe His Asp Lys
        690             695             700

Leu Ala Pro Ser Tyr Thr Val Val Leu Arg Glu Ala Val
705             710             715

<210> SEQ ID NO 22
<211> LENGTH: 717
<212> TYPE: PRT
<213> ORGANISM: Unknown
<220> FEATURE:
<223> OTHER INFORMATION: Description of Unknown:
      terrestrial-soil-forest soil sequence

<400> SEQUENCE: 22

Met Ile Lys Pro Thr Val Ser Gln Phe Leu Thr Pro Gly Phe Lys Leu
1               5               10              15

Ile Arg Asn His Ser Arg Thr Ala Gly Leu Lys Leu Lys Asn Glu Gly
            20              25              30

Glu Glu Ala Cys Lys Lys Phe Val Arg Glu Asn Glu Ile Pro Lys Asp
            35              40              45

Glu Cys Pro Asn Phe Gln Gly Gly Pro Ala Ile Ala Asn Ile Ile Ala
        50              55              60

Lys Ser Arg Glu Phe Thr Glu Trp Glu Ile Tyr Gln Ser Ser Leu Ala
65              70              75              80

Ile Gln Glu Val Ile Phe Thr Leu Pro Lys Asp Lys Leu Pro Glu Pro
                85              90              95

Ile Leu Lys Glu Glu Trp Arg Ala Gln Trp Leu Ser Glu His Gly Leu
            100             105             110

Asp Thr Val Pro Tyr Lys Glu Ala Ala Gly Leu Asn Leu Ile Ile Lys
            115             120             125

Asn Ala Val Asn Thr Tyr Lys Gly Val Gln Val Lys Val Asp Asn Lys
        130             135             140

Asn Lys Asn Asn Leu Ala Lys Ile Asn Arg Lys Asn Glu Ile Ala Lys
145             150             155             160

Leu Asn Gly Glu Gln Glu Ile Ser Phe Glu Glu Ile Lys Ala Phe Asp
            165             170             175

Asp Lys Gly Tyr Leu Leu Gln Lys Pro Ser Pro Asn Lys Ser Ile Tyr
            180             185             190

Cys Tyr Gln Ser Val Ser Pro Lys Pro Phe Ile Thr Ser Lys Tyr His
            195             200             205

Asn Val Asn Leu Pro Glu Glu Tyr Ile Gly Tyr Tyr Arg Lys Ser Asn
        210             215             220

Glu Pro Ile Val Ser Pro Tyr Gln Phe Asp Arg Leu Arg Ile Pro Ile
225             230             235             240

Gly Glu Pro Gly Tyr Val Pro Lys Trp Gln Tyr Thr Phe Leu Ser Lys
                245             250             255

Lys Glu Asn Lys Arg Arg Lys Leu Ser Lys Arg Ile Lys Asn Val Ser
            260             265             270

Pro Ile Leu Gly Ile Ile Cys Ile Lys Lys Asp Trp Cys Val Phe Asp
            275             280             285
```

```
Met Arg Gly Leu Leu Arg Thr Asn His Trp Lys Lys Tyr His Lys Pro
    290                 295                 300

Thr Asp Ser Ile Asn Asp Leu Phe Asp Tyr Phe Thr Gly Asp Pro Val
305                 310                 315                 320

Ile Asp Thr Lys Ala Asn Val Val Arg Phe Arg Tyr Lys Met Glu Asn
                325                 330                 335

Gly Ile Val Asn Tyr Lys Pro Val Arg Glu Lys Lys Gly Lys Glu Leu
                340                 345                 350

Leu Glu Asn Ile Cys Asp Gln Asn Gly Ser Cys Lys Leu Ala Thr Val
                355                 360                 365

Asp Val Gly Gln Asn Asn Pro Val Ala Ile Gly Leu Phe Glu Leu Lys
    370                 375                 380

Lys Val Asn Gly Glu Leu Thr Lys Thr Leu Ile Ser Arg His Pro Thr
385                 390                 395                 400

Pro Ile Asp Phe Cys Asn Lys Ile Thr Ala Tyr Arg Glu Arg Tyr Asp
                405                 410                 415

Lys Leu Glu Ser Ser Ile Lys Leu Asp Ala Ile Lys Gln Leu Thr Ser
                420                 425                 430

Glu Gln Lys Ile Glu Val Asp Asn Tyr Asn Asn Asn Phe Thr Pro Gln
                435                 440                 445

Asn Thr Lys Gln Ile Val Cys Ser Lys Leu Asn Ile Asn Pro Asn Asp
    450                 455                 460

Leu Pro Trp Asp Lys Met Ile Ser Gly Thr His Phe Ile Ser Glu Lys
465                 470                 475                 480

Ala Gln Val Ser Asn Lys Ser Glu Ile Tyr Phe Thr Ser Thr Asp Lys
                485                 490                 495

Gly Lys Thr Lys Asp Val Met Lys Ser Asp Tyr Lys Trp Phe Gln Asp
                500                 505                 510

Tyr Lys Pro Lys Leu Ser Lys Glu Val Arg Asp Ala Leu Ser Asp Ile
                515                 520                 525

Glu Trp Arg Leu Arg Arg Glu Ser Leu Glu Phe Asn Lys Leu Ser Lys
    530                 535                 540

Ser Arg Glu Gln Asp Ala Arg Gln Leu Ala Asn Trp Ile Ser Ser Met
545                 550                 555                 560

Cys Asp Val Ile Gly Ile Glu Asn Leu Val Lys Lys Asn Asn Phe Phe
                565                 570                 575

Gly Gly Ser Gly Lys Arg Glu Pro Gly Trp Asp Asn Phe Tyr Lys Pro
                580                 585                 590

Lys Lys Glu Asn Arg Trp Trp Ile Asn Ala Ile His Lys Ala Leu Thr
                595                 600                 605

Glu Leu Ser Gln Asn Lys Gly Lys Arg Val Ile Leu Leu Pro Ala Met
    610                 615                 620

Arg Thr Ser Ile Thr Cys Pro Lys Cys Lys Tyr Cys Asp Ser Lys Asn
625                 630                 635                 640

Arg Asn Gly Glu Lys Phe Asn Cys Leu Lys Cys Gly Ile Glu Leu Asn
                645                 650                 655

Ala Asp Ile Asp Val Ala Thr Glu Asn Leu Ala Thr Val Ala Ile Thr
                660                 665                 670

Ala Gln Ser Met Pro Lys Pro Thr Cys Glu Arg Ser Gly Asp Ala Lys
                675                 680                 685

Lys Pro Val Arg Ala Arg Lys Ala Lys Ala Pro Glu Phe His Asp Lys
    690                 695                 700
```

-continued

```
Leu Ala Pro Ser Tyr Thr Val Val Leu Arg Glu Ala Val
705                 710             715
```

```
<210> SEQ ID NO 23
<211> LENGTH: 749
<212> TYPE: PRT
<213> ORGANISM: Unknown
<220> FEATURE:
<223> OTHER INFORMATION: Description of Unknown:
      wastewater metagenome sequence
```

```
<400> SEQUENCE: 23
```

```
Met Pro Asp Lys Gln Thr Pro Lys Asp Thr Lys Asp Lys Pro Glu Ser
1               5                   10                  15
```

```
Pro Val Ser Ala Phe Leu Lys Lys His Phe Pro Gly Lys His Phe Phe
                20                  25                  30
```

```
Gly His Ala Gly Thr Leu Ala Arg Leu Leu Lys Thr Lys Gly Glu Glu
            35                  40                  45
```

```
Val Ala Arg Asp Tyr Ala Ala Lys Lys Val Arg Asp Glu Lys Leu Asp
        50                  55                  60
```

```
Phe Arg Pro Pro Ala Lys Cys Gln Ile Val Ala Trp Ser Arg Asp Phe
65                  70                  75                  80
```

```
Ser Glu Trp Pro Ile Ala Arg Ala Ser Ala Thr Ile Gln Gln His Val
                85                  90                  95
```

```
Ser Gly Leu Thr Lys Glu Asp Phe Glu Arg Phe Asp Pro Gly Lys Ser
            100                 105                 110
```

```
Lys Ala Ala His Asp Ala Trp Phe Gln Glu Ser Gly Val Asp Cys His
            115                 120                 125
```

```
Gly Tyr Arg His Val Gln Gly Leu Asn Leu Ile Phe Ala Asn Ala Arg
            130                 135                 140
```

```
Asp Tyr Tyr Glu Gly Val Val Lys Lys Val Glu Asn Lys Asn Ala Gln
145                 150                 155                 160
```

```
Arg Arg Arg Arg Val Glu Ala Leu Asn Ala Arg Arg Ala Glu Glu Gly
                165                 170                 175
```

```
Glu Glu Pro Ile Pro Leu Asp Val Glu Glu Ser Pro Phe Gly Glu Asp
            180                 185                 190
```

```
Gly Arg Leu Ala His Pro Pro Gly Val Asn Pro Ser Ile Tyr Val Tyr
            195                 200                 205
```

```
Gln Ala Val Ser Pro Arg Pro Leu Lys Lys Ser Asp Leu Glu Thr Val
        210                 215                 220
```

```
Val Leu Pro Pro Ala Tyr Ala Gly Tyr Asp Arg Asp Pro Ser Ala Pro
225                 230                 235                 240
```

```
Ile Pro Val Met Gly Asp Arg Leu Ser Ile Pro Glu Gly Gln Arg Gly
                245                 250                 255
```

```
His Val Pro Ala Trp Gln Arg Asp Gln Leu Ser Pro Asp Lys His Arg
            260                 265                 270
```

```
Arg Met Arg Ala Trp Tyr Ser Ala Ala Asn Thr Lys Pro Lys Pro Gly
            275                 280                 285
```

```
Arg Thr Ser Val Pro Asp Ala Ala Ala Ile Glu Arg Ala Arg Ala Glu
        290                 295                 300
```

```
Gly Ala Leu Leu Val Val Ile Arg Ile Gly Glu Asp Trp Val Val Leu
305                 310                 315                 320
```

```
Asp Ala Arg Gly Leu Leu Arg Asn Ala Arg Trp Arg Arg Ile Ala Asp
                325                 330                 335
```

```
Lys Glu Ile Ser Leu Asp Gly Leu Leu Asp Leu Phe Thr Gly Asp Pro
            340                 345                 350
```

-continued

```
Val Ile Asp Ser Lys Arg Asn Val Val Thr Phe Ile Tyr Lys Ala Glu
        355             360             365

His Ala Thr Ala Thr Ser Arg Lys Val Val His Arg Lys Ala Ser Arg
        370             375             380

Lys Ala Leu Leu Asp Met Thr Ser Pro Gly Glu Asp Gly Leu Pro Arg
385             390             395             400

Glu Val Ala Leu Ala Ser Val Asp Leu Gly Gln Thr Asn Ala Ala Ala
                405             410             415

Val Arg Tyr Ala Arg Val His Arg Glu Gly Asp Asp Ile Thr Ser Glu
                420             425             430

Cys Leu Val Arg Glu Leu Leu Pro Asp Glu Ile Ser Arg Asp Ile Ala
        435             440             445

Arg Tyr Arg Ala Ala Ser Asp Arg Met Glu Ala Glu Ile Arg Glu Ala
        450             455             460

Ala Ile Ala Gly Leu Pro Glu Pro Met Gln Ala Glu Val Arg Ala Ala
465             470             475             480

Asp Ala Ser Ser Pro Glu Ala Ala Arg Ala Ala Val Val Ala Leu Val
                485             490             495

Gly Asp Gly Leu Pro Trp Glu Lys Met Ser Ser Ala Thr Tyr His Ile
                500             505             510

Ser Asp Ala Leu Val Ala Leu Gly Arg Gly Arg Glu Ala Tyr Leu Leu
        515             520             525

Ser Lys Ser Lys Asp Gly Glu Glu Lys Ser Val Gln Arg Ser Asp Tyr
        530             535             540

Gly Trp Ser Arg His Leu Arg Pro Arg Leu Ser Glu Glu Thr Arg Lys
545             550             555             560

Ala Met Asn Glu Ala Val Trp Ser Ile Lys Asp Ala His Glu Gly Tyr
                565             570             575

Gln Lys Leu Ser Arg Arg Lys Thr Glu Ile Gly Arg Arg Ala Ala Asn
                580             585             590

His Val Val Arg Arg Leu Arg Lys Leu Ala Lys Thr Asp Lys Val Ala
        595             600             605

Ile Ala Val Glu Asp Leu Asn Val Arg Met Phe His Gly Gly Gly Ser
        610             615             620

Arg Ser Thr Gly Trp Asp Asn Phe Phe Val Ala Lys Arg Glu Asn Leu
625             630             635             640

Trp Phe Val Gln Val Leu His Lys Ser Phe Cys Asp Leu Ala Leu His
                645             650             655

Arg Gly Glu Val Val Ile Glu Val Asp Thr Ala Arg Thr Ser Gln Thr
                660             665             670

Cys Pro Ala Cys Gly His Cys Asp Pro Lys Asn Arg Ser Ser Val Asp
        675             680             685

Arg Glu Val Phe Arg Cys Val Val Cys Gly Arg Thr Phe His Ala Asp
        690             695             700

Leu Glu Val Ala Thr Phe Asn Ile Glu Arg Val Ala Leu Thr Gly Glu
705             710             715             720

Ser Met Pro Lys Gly Glu Glu Gly Ala Arg Glu Arg Gly Gly Gly Gly
                725             730             735

Lys Ser Arg Gly Gly Ala Arg Gly Arg Asn Lys Leu Lys
                740             745
```

<210> SEQ ID NO 24
<211> LENGTH: 773

<212> TYPE: PRT
<213> ORGANISM: Unknown
<220> FEATURE:
<223> OTHER INFORMATION: Description of Unknown:
      wastewater metagenome sequence

<400> SEQUENCE: 24

```
Met Ser Glu Ile Thr Asp Leu Leu Lys Ala Asn Phe Lys Gly Lys Thr
1               5                   10                  15

Phe Lys Ser Ala Asp Met Arg Met Ala Gly Arg Ile Leu Lys Lys Ser
            20                  25                  30

Gly Ala Gln Ala Val Ile Lys Tyr Leu Ser Asp Lys Gly Ala Val Asp
        35                  40                  45

Pro Pro Asp Phe Arg Pro Pro Ala Lys Cys Asn Ile Ile Ala Gln Ser
    50                  55                  60

Arg Pro Phe Asp Glu Trp Pro Ile Cys Lys Ala Ser Met Ala Ile Gln
65                  70                  75                  80

Gln His Ile Tyr Gly Leu Thr Lys Asn Glu Phe Asp Glu Ser Ser Pro
                85                  90                  95

Gly Thr Ser Ser Ala Ser His Glu Gln Trp Phe Ala Lys Thr Gly Val
            100                 105                 110

Asp Thr His Gly Phe Thr His Val Gln Gly Leu Asn Leu Ile Phe Gln
        115                 120                 125

His Ala Lys Lys Arg Tyr Glu Gly Val Ile Lys Lys Val Glu Asn Tyr
    130                 135                 140

Asn Glu Lys Glu Arg Lys Lys Phe Glu Gly Ile Asn Glu Arg Arg Ser
145                 150                 155                 160

Lys Glu Gly Met Pro Leu Leu Glu Pro Arg Leu Arg Thr Ala Phe Gly
                165                 170                 175

Asp Asp Gly Lys Phe Ala Glu Lys Pro Gly Val Asn Pro Ser Ile Tyr
            180                 185                 190

Leu Tyr Gln Gln Thr Ser Pro Arg Pro Tyr Asp Lys Thr Lys His Pro
            195                 200                 205

Tyr Val His Ala Pro Phe Glu Leu Lys Glu Ile Thr Thr Ile Pro Thr
    210                 215                 220

Gln Asp Asp Arg Leu Lys Ile Pro Phe Gly Ala Pro Gly His Val Pro
225                 230                 235                 240

Glu Lys His Arg Ser Gln Leu Ser Met Ala Lys His Lys Arg Arg Arg
                245                 250                 255

Ala Trp Tyr Ala Leu Ser Gln Asn Lys Pro Arg Pro Pro Lys Asp Gly
            260                 265                 270

Ser Lys Gly Arg Arg Ser Val Arg Asp Leu Ala Asp Leu Lys Ala Ala
        275                 280                 285

Ser Leu Ala Asp Ala Ile Pro Leu Val Ser Arg Val Gly Phe Asp Trp
    290                 295                 300

Val Val Ile Asp Gly Arg Gly Leu Leu Arg Asn Leu Arg Trp Arg Lys
305                 310                 315                 320

Leu Ala His Glu Gly Met Thr Val Glu Glu Met Leu Gly Phe Phe Ser
                325                 330                 335

Gly Asp Pro Val Ile Asp Pro Arg Arg Asn Val Ala Thr Phe Ile Tyr
            340                 345                 350

Lys Ala Glu His Ala Thr Val Lys Ser Arg Lys Pro Ile Gly Gly Ala
        355                 360                 365

Lys Arg Ala Arg Glu Glu Leu Leu Lys Ala Thr Ala Ser Ser Asp Gly
    370                 375                 380
```

```
Val Ile Arg Gln Val Gly Leu Ile Ser Val Asp Leu Gly Gln Thr Asn
385                 390                 395                 400

Pro Val Ala Tyr Glu Ile Ser Arg Met His Gln Ala Asn Gly Glu Leu
                405                 410                 415

Val Ala Glu His Leu Glu Tyr Gly Leu Leu Asn Asp Glu Gln Val Asn
            420                 425                 430

Ser Ile Gln Arg Tyr Arg Ala Ala Trp Asp Ser Met Asn Glu Ser Phe
            435                 440                 445

Arg Gln Lys Ala Ile Glu Ser Leu Ser Met Glu Ala Gln Asp Glu Ile
        450                 455                 460

Met Gln Ala Ser Thr Gly Ala Ala Lys Arg Thr Arg Glu Ala Val Leu
465                 470                 475                 480

Thr Met Phe Gly Pro Asn Ala Thr Leu Pro Trp Ser Arg Met Ser Ser
                485                 490                 495

Asn Thr Thr Cys Ile Ser Asp Ala Leu Ile Glu Val Gly Lys Glu Glu
            500                 505                 510

Glu Thr Asn Phe Val Thr Ser Asn Gly Pro Arg Lys Arg Thr Asp Ala
            515                 520                 525

Gln Trp Ala Ala Tyr Leu Arg Pro Arg Val Asn Pro Glu Thr Arg Ala
        530                 535                 540

Leu Leu Asn Gln Ala Val Trp Asp Leu Met Lys Arg Ser Asp Glu Tyr
545                 550                 555                 560

Glu Arg Leu Ser Lys Arg Lys Leu Glu Met Ala Arg Gln Cys Val Asn
                565                 570                 575

Phe Val Val Ala Arg Ala Glu Lys Leu Thr Gln Cys Asn Asn Ile Gly
                580                 585                 590

Ile Val Leu Glu Asn Leu Val Val Arg Asn Phe His Gly Ser Gly Arg
            595                 600                 605

Arg Glu Ser Gly Trp Glu Gly Phe Phe Glu Pro Lys Arg Glu Asn Arg
        610                 615                 620

Trp Phe Met Gln Val Leu His Lys Ala Phe Ser Asp Leu Ala Gln His
625                 630                 635                 640

Arg Gly Val Met Val Phe Glu Val His Pro Ala Tyr Ser Ser Gln Thr
                645                 650                 655

Cys Pro Ala Cys Arg Tyr Val Asp Pro Lys Asn Arg Ser Ser Glu Asp
            660                 665                 670

Arg Glu Arg Phe Lys Cys Leu Lys Cys Gly Arg Ser Phe Asn Ala Asp
        675                 680                 685

Arg Glu Val Ala Thr Phe Asn Ile Arg Glu Ile Ala Arg Thr Gly Val
        690                 695                 700

Gly Leu Pro Lys Pro Asp Cys Glu Arg Ser Arg Asp Val Gln Thr Pro
705                 710                 715                 720

Gly Thr Ala Arg Lys Ser Gly Arg Ser Leu Lys Ser Asn Lys Asn Pro
                725                 730                 735

Ser Glu Pro Lys His Val Leu Arg Ser Lys Thr Arg Ser Asn Ile Thr
            740                 745                 750

Ser Thr Leu Ser Gln Asn Glu Pro Leu Ala Thr Asp Gln Lys Thr Ala
            755                 760                 765

Pro Lys Thr Gly Pro
    770
```

<210> SEQ ID NO 25
<211> LENGTH: 773

```
<212> TYPE: PRT
<213> ORGANISM: Unknown
<220> FEATURE:
<223> OTHER INFORMATION: Description of Unknown:
      wastewater metagenome sequence

<400> SEQUENCE: 25

Met Ser Glu Ile Thr Asp Leu Leu Lys Ala Asn Phe Lys Gly Lys Thr
1               5                   10                  15

Phe Lys Ser Ala Asp Met Arg Met Ala Gly Arg Ile Leu Lys Lys Ser
            20                  25                  30

Gly Ala Gln Ala Val Ile Lys Tyr Leu Ser Asp Lys Gly Ala Val Asp
        35                  40                  45

Pro Pro Asp Phe Arg Pro Pro Ala Lys Cys Asn Ile Ile Ala Gln Ser
    50                  55                  60

Arg Pro Phe Asp Glu Trp Pro Ile Cys Lys Ala Ser Met Ala Ile Gln
65                  70                  75                  80

Gln His Ile Tyr Gly Leu Thr Lys Asn Glu Phe Asp Glu Ser Ser Pro
                85                  90                  95

Gly Thr Ser Ser Ala Ser His Glu Gln Trp Phe Ala Lys Thr Gly Val
                100                 105                 110

Asp Thr His Gly Phe Thr His Val Gln Gly Leu Asn Leu Ile Phe Gln
            115                 120                 125

His Ala Lys Lys Arg Tyr Glu Gly Val Ile Lys Lys Val Glu Asn Tyr
    130                 135                 140

Asn Glu Lys Glu Arg Lys Lys Phe Glu Gly Ile Asn Glu Arg Arg Ser
145                 150                 155                 160

Lys Glu Gly Met Pro Leu Leu Glu Pro Arg Leu Arg Thr Ala Phe Gly
                165                 170                 175

Asp Asp Gly Lys Phe Ala Glu Lys Pro Gly Val Asn Pro Ser Ile Tyr
            180                 185                 190

Leu Tyr Gln Gln Thr Ser Pro Arg Pro Tyr Asp Lys Thr Lys His Pro
            195                 200                 205

Tyr Val His Ala Pro Phe Glu Leu Lys Glu Ile Thr Thr Ile Pro Thr
    210                 215                 220

Gln Asp Asp Arg Leu Lys Ile Pro Phe Gly Ala Pro Gly His Val Pro
225                 230                 235                 240

Glu Lys His Arg Ser Gln Leu Ser Met Ala Lys His Lys Arg Arg Arg
                245                 250                 255

Ala Trp Tyr Ala Leu Ser Gln Asn Lys Pro Arg Pro Pro Lys Asp Gly
            260                 265                 270

Ser Lys Gly Arg Arg Ser Val Arg Asp Leu Ala Asp Leu Lys Ala Ala
            275                 280                 285

Ser Leu Ala Asp Ala Ile Pro Leu Val Ser Arg Val Gly Phe Asp Trp
    290                 295                 300

Val Val Ile Asp Gly Arg Gly Leu Leu Arg Asn Leu Arg Trp Arg Lys
305                 310                 315                 320

Leu Ala His Glu Gly Met Thr Val Glu Glu Met Leu Gly Phe Phe Ser
                325                 330                 335

Gly Asp Pro Val Ile Asp Pro Arg Arg Asn Val Ala Thr Phe Ile Tyr
            340                 345                 350

Lys Ala Glu His Ala Thr Val Lys Ser Arg Lys Pro Ile Gly Gly Ala
            355                 360                 365

Lys Arg Ala Arg Glu Glu Leu Leu Lys Ala Thr Ala Ser Ser Asp Gly
    370                 375                 380
```

```
Val Ile Arg Gln Val Gly Leu Ile Ser Val Asp Leu Gly Gln Thr Asn
385                 390                 395                 400

Pro Val Ala Tyr Glu Ile Ser Arg Met His Gln Ala Asn Gly Glu Leu
                405                 410                 415

Val Ala Glu His Leu Glu Tyr Gly Leu Leu Asn Asp Glu Gln Val Asn
            420                 425                 430

Ser Ile Gln Arg Tyr Arg Ala Ala Trp Asp Ser Met Asn Glu Ser Phe
            435                 440                 445

Arg Gln Lys Ala Ile Glu Ser Leu Ser Met Glu Ala Gln Asp Glu Ile
        450                 455                 460

Met Gln Ala Ser Thr Gly Ala Ala Lys Arg Thr Arg Glu Ala Val Leu
465                 470                 475                 480

Thr Met Phe Gly Pro Asn Ala Thr Leu Pro Trp Ser Arg Met Ser Ser
                485                 490                 495

Asn Thr Thr Cys Ile Ser Asp Ala Leu Ile Glu Val Gly Lys Glu Glu
            500                 505                 510

Glu Thr Asn Phe Val Thr Ser Asn Gly Pro Arg Lys Arg Thr Asp Ala
            515                 520                 525

Gln Trp Ala Ala Tyr Leu Arg Pro Arg Val Asn Pro Glu Thr Arg Ala
        530                 535                 540

Leu Leu Asn Gln Ala Val Trp Asp Leu Met Lys Arg Ser Asp Glu Tyr
545                 550                 555                 560

Glu Arg Leu Ser Lys Arg Lys Leu Glu Met Ala Arg Gln Cys Val Asn
                565                 570                 575

Phe Val Val Ala Arg Ala Glu Lys Leu Thr Gln Cys Asn Asn Ile Gly
            580                 585                 590

Ile Val Leu Glu Asn Leu Val Val Arg Asn Phe His Gly Ser Gly Arg
            595                 600                 605

Arg Glu Ser Gly Trp Glu Gly Phe Phe Glu Pro Lys Arg Glu Asn Arg
        610                 615                 620

Trp Phe Met Gln Val Leu His Lys Ala Phe Ser Asp Leu Ala Gln His
625                 630                 635                 640

Arg Gly Val Met Val Phe Glu Val His Pro Ala Tyr Ser Ser Gln Thr
                645                 650                 655

Cys Pro Ala Cys Arg Tyr Val Asp Pro Lys Asn Arg Ser Ser Glu Asp
            660                 665                 670

Arg Glu Arg Phe Lys Cys Leu Lys Cys Gly Arg Ser Phe Asn Ala Asp
            675                 680                 685

Arg Glu Val Ala Thr Phe Asn Ile Arg Glu Ile Ala Arg Thr Gly Val
        690                 695                 700

Gly Leu Pro Lys Pro Asp Cys Glu Arg Ser Arg Gly Val Gln Thr Thr
705                 710                 715                 720

Gly Thr Ala Arg Asn Pro Gly Arg Ser Leu Lys Ser Asn Lys Asn Pro
                725                 730                 735

Ser Glu Pro Lys His Val Leu Arg Ser Lys Thr Arg Ser Asn Ile Thr
            740                 745                 750

Ser Thr Leu Ser Gln Asn Glu Pro Leu Ala Thr Asp Gln Lys Thr Ala
            755                 760                 765

Pro Lys Thr Gly Pro
    770
```

```
<210> SEQ ID NO 26
<211> LENGTH: 774
```

-continued

```
<212> TYPE: PRT
<213> ORGANISM: Unknown
<220> FEATURE:
<223> OTHER INFORMATION: Description of Unknown:
      wastewater metagenome sequence

<400> SEQUENCE: 26

Met Thr Leu Ala Glu Leu Arg Asp Lys Tyr Phe Tyr Lys Ile Lys Phe
1               5                   10                  15

Arg Lys Ile Asp Leu Arg Gln Ala Gly Lys Ile Leu Lys Arg Glu Gly
            20                  25                  30

Glu Glu Ala Ala Arg Arg Tyr Leu Asp Glu Gln Arg Glu Ser Pro Pro
        35                  40                  45

Glu Gly Asn Phe Cys Pro Pro Ala Lys Cys Gln Ile Val Gly Trp Ser
    50                  55                  60

Arg Pro Val Gly Glu Trp Pro Ile Ser Ile Ala Ser Ala Asn Met Gln
65                  70                  75                  80

Gln Tyr Val Tyr Asp Leu Pro Lys Val Glu Arg Asp Lys Met Thr Lys
                85                  90                  95

Phe Asp Leu Thr Ser Glu Glu Tyr Ala Val Trp Phe Ala Gln Thr Gly
            100                 105                 110

Ile Asp Asn Ala Gly Tyr Thr His Val Gln Gly Leu Asn Lys Ala Phe
        115                 120                 125

Lys Asn Ala Phe Arg Thr Tyr Asp Gly Val Ile Lys Lys Val Ala Asn
    130                 135                 140

Arg Asn Glu Lys Arg Lys Leu Lys Ala Glu Lys Ala Ala Glu Arg Ala
145                 150                 155                 160

Leu Leu Arg Gly Arg Glu Pro Glu Val Phe Val Pro Glu Glu Ala Leu
                165                 170                 175

Asp Glu Arg Gly Phe Leu Lys Glu Lys Pro Gly Ile Asn Arg Ser Ile
            180                 185                 190

Trp Thr Tyr Gln Gln Val Ser Pro Arg Pro Tyr Asp Pro Thr Arg Asp
            195                 200                 205

Leu Lys Ile Lys Glu Lys Leu Ala Gln Arg Arg Gly Arg Ser Glu Pro
    210                 215                 220

Val Ala Tyr Ala Asp Arg Leu Ala Ile Pro Glu Gly Gln Pro Gly His
225                 230                 235                 240

Val Pro Gln Trp Gln Arg Asp Ala Gly Leu Leu Ser Ala Asn Lys His
                245                 250                 255

Arg Arg Met Arg Ala His Tyr Ser Trp His Asn Asn Lys Pro Arg Pro
                260                 265                 270

Asn Arg Lys Thr Ser Arg Thr Ala Glu Glu Cys Arg Asp Leu Gly Ala
        275                 280                 285

Pro Glu Ala Ile Leu Ala Val Ile Glu Ile Gly Glu Asp Trp Leu Ala
    290                 295                 300

Val Asp Leu Arg Gly Leu Leu Arg Ser Ala Tyr Tyr Arg Arg Ile Leu
305                 310                 315                 320

Ser Pro Lys Glu Val Pro Thr Ala Ala Glu Leu Leu Lys Leu Phe Thr
                325                 330                 335

Gly Asp Pro Thr Ile Asp Pro Val Arg Glu Val Val Thr Phe Ile Tyr
            340                 345                 350

Lys Glu Asp Val Val Pro Val Leu Ser Thr Lys Pro Leu Arg Glu Arg
        355                 360                 365

Gln Gly Leu Lys Lys Ile Leu Asp Leu Thr Ala Pro Val Asn Gly Val
    370                 375                 380
```

```
Arg Asp Phe Ile Ala Ile Ala Ser Ile Asp Leu Gly Val Thr Asn Pro
385                 390                 395                 400

Ala Ala Met Ala Tyr Ser Arg Val Arg Gln Thr Ala Ala Gly Gly Phe
                405                 410                 415

Asp Ile Glu Glu Leu Ala Arg Glu Phe Leu Pro Ala Ala Val Leu Asp
            420                 425                 430

Gln Leu Ala His His Arg Gln Gln Trp Asp Glu Met Glu Asp Arg Phe
            435                 440                 445

Arg Gln Gln Ala Val Arg Ala Leu Pro Glu Ala Asp Gln Ala Glu Cys
        450                 455                 460

Glu Ala Val Phe Gly His Thr Gly Asp Gln Tyr Ala Ala Asp Ile Ala
465                 470                 475                 480

Arg Ala Leu Gln Leu Asp Gly Ala Ala Leu Pro Trp Ala Gln Met Ser
                485                 490                 495

Ser Arg Thr Thr Tyr Ile Thr Asp Ala Leu Leu Ala Arg Gly Gly Ser
            500                 505                 510

Pro Ala Thr Tyr His Thr Phe Val His Ser Glu Arg Lys Lys Gly Lys
            515                 520                 525

Lys Lys Lys Gly Lys Lys Lys Lys Gly Gln Glu Gly Ala Lys Pro Glu
        530                 535                 540

Leu Lys Ile Lys Glu Lys Pro Ser Asp Phe Asp Trp Ala Tyr Asp Phe
545                 550                 555                 560

Ala Arg Lys Gln Leu Ser Lys Glu Val Arg Glu Arg Phe Asn Lys Ala
                565                 570                 575

Leu Trp Glu Ile Lys Arg Thr Ser Pro Asp Tyr Ala Arg Met Ser Lys
            580                 585                 590

Gln Lys Arg Asp Leu Gly Arg Gln Val Ala Asn His Val Val Lys Gln
            595                 600                 605

Ala Arg Lys Leu Ala Gly Thr Gln Thr Leu Val Val Val Val Glu Asn
        610                 615                 620

Ile Asn Val Val Phe Phe His Gly Thr Gly Lys Arg Pro Val Gly Trp
625                 630                 635                 640

His Gln Cys Phe Leu Pro Lys Lys Glu Asn Arg Trp Phe Val Gln Thr
                645                 650                 655

Ile His Lys Ala Leu Thr Glu Ile Ala Met His Lys Gly Ile Tyr Val
            660                 665                 670

Ile Glu Val Ser Pro Tyr Tyr Thr Ser Leu His Cys Pro Lys Cys Glu
            675                 680                 685

His Ile Asp Ser Gly Asn Arg Cys Gly Glu Gln Phe Arg Cys Leu Lys
        690                 695                 700

Cys Gly Tyr Thr Ala His Ala Asp Leu Glu Val Ala Pro Tyr Asn Ile
705                 710                 715                 720

Arg Leu Val Ala Leu Arg Gly Ala Gly Leu Arg Lys Val Glu Thr Glu
                725                 730                 735

Ala Glu Val Glu Ala Val Asp Glu Ala Pro Ala Ala Ala Ser Val Glu
            740                 745                 750

Lys Pro Arg Lys Arg Arg Lys Ser Ala Ser Gly Glu Ala Ala Thr Phe
            755                 760                 765

Glu Ala Ala Pro Leu Ala
    770
```

<210> SEQ ID NO 27
<211> LENGTH: 749

```
<212> TYPE: PRT
<213> ORGANISM: Unknown
<220> FEATURE:
<223> OTHER INFORMATION: Description of Unknown:
      wastewater metagenome sequence

<400> SEQUENCE: 27

Met Pro Asp Lys Gln Thr Pro Lys Asp Thr Lys Asp Lys Pro Glu Ser
1               5                   10                  15

Pro Val Ser Ala Phe Leu Lys Lys His Phe Pro Gly Lys His Phe Phe
                20                  25                  30

Gly His Ala Gly Thr Leu Ala Arg Leu Leu Lys Thr Lys Gly Glu Glu
            35                  40                  45

Val Ala Arg Asp Tyr Ala Ala Lys Lys Val Arg Asp Glu Lys Leu Asp
        50                  55                  60

Phe Arg Pro Pro Ala Lys Cys Gln Ile Val Ala Trp Ser Arg Asp Phe
65                  70                  75                  80

Ser Glu Trp Pro Ile Ala Arg Ala Ser Ala Thr Ile Gln Gln His Val
                85                  90                  95

Ser Gly Leu Thr Lys Glu Asp Phe Glu Arg Phe Asp Pro Gly Lys Ser
                100                 105                 110

Lys Ala Ala His Asp Ala Trp Phe Gln Glu Ser Gly Val Asp Cys His
            115                 120                 125

Gly Tyr Arg His Val Gln Gly Leu Asn Leu Ile Phe Ala Asn Ala Arg
        130                 135                 140

Asp Tyr Tyr Glu Gly Val Val Lys Lys Val Glu Asn Lys Asn Ala Gln
145                 150                 155                 160

Arg Arg Arg Arg Val Glu Ala Leu Asn Ala Arg Arg Ala Glu Glu Gly
                165                 170                 175

Glu Glu Pro Ile Pro Leu Asp Val Glu Glu Ser Pro Phe Gly Glu Asp
                180                 185                 190

Gly Arg Leu Ala His Pro Pro Gly Val Asn Pro Ser Ile Tyr Val Tyr
            195                 200                 205

Gln Ala Val Ser Pro Arg Pro Leu Lys Lys Ser Asp Leu Glu Thr Val
        210                 215                 220

Val Leu Pro Pro Ala Tyr Ala Gly Tyr Asp Arg Asp Pro Ser Ala Pro
225                 230                 235                 240

Ile Pro Val Met Gly Asp Arg Leu Ser Ile Pro Glu Gly Gln Arg Gly
                245                 250                 255

His Val Pro Ala Trp Gln Arg Asp Gln Leu Ser Pro Asp Lys His Arg
            260                 265                 270

Arg Met Arg Ala Trp Tyr Ser Ala Ala Asn Thr Lys Pro Lys Pro Gly
        275                 280                 285

Arg Thr Ser Val Pro Asp Ala Ala Ile Glu Arg Ala Arg Ala Glu
    290                 295                 300

Gly Ala Leu Leu Val Val Ile Arg Ile Gly Glu Asp Trp Val Val Leu
305                 310                 315                 320

Asp Ala Arg Gly Leu Leu Arg Asn Ala Arg Trp Arg Arg Ile Ala Asp
                325                 330                 335

Lys Glu Ile Ser Leu Asp Gly Leu Leu Asp Leu Phe Thr Gly Asp Pro
            340                 345                 350

Val Ile Asp Ser Lys Arg Asn Val Val Thr Phe Ile Tyr Lys Ala Glu
        355                 360                 365

His Ala Thr Ala Thr Ser Arg Lys Val Val His Arg Lys Ala Ser Arg
    370                 375                 380
```

-continued

```
Lys Ala Leu Leu Asp Met Thr Ser Pro Gly Glu Asp Gly Leu Pro Arg
385                 390                 395                 400

Glu Val Ala Leu Ala Ser Val Asp Leu Gly Gln Thr Asn Ala Ala Ala
                405                 410                 415

Val Arg Tyr Ala Arg Val His Arg Glu Gly Asp Asp Ile Thr Ser Glu
            420                 425                 430

Cys Leu Val Arg Glu Leu Leu Pro Asp Glu Ile Ser Arg Asp Ile Ala
            435                 440                 445

Arg Tyr Arg Ala Ala Ser Asp Arg Met Glu Ala Glu Ile Arg Glu Ala
        450                 455                 460

Ala Ile Ala Gly Leu Pro Glu Pro Met Gln Ala Glu Val Arg Ala Ala
465                 470                 475                 480

Asp Ala Ser Ser Pro Glu Ala Ala Arg Ala Ala Val Val Ala Leu Val
                485                 490                 495

Gly Asp Gly Leu Pro Trp Glu Lys Met Ser Ser Ala Thr Tyr His Ile
            500                 505                 510

Ser Asp Ala Leu Val Ala Leu Gly Arg Gly Arg Glu Ala Tyr Leu Leu
            515                 520                 525

Ser Lys Ser Lys Asp Gly Glu Glu Lys Ser Val Gln Arg Ser Asp Tyr
        530                 535                 540

Gly Trp Ser Arg His Leu Arg Pro Arg Leu Ser Glu Glu Thr Arg Lys
545                 550                 555                 560

Ala Met Asn Glu Ala Val Trp Ser Ile Lys Asp Ala His Glu Gly Tyr
                565                 570                 575

Gln Lys Leu Ser Arg Arg Lys Thr Glu Ile Gly Arg Arg Ala Ala Asn
            580                 585                 590

His Val Val Arg Arg Leu Arg Lys Leu Ala Lys Thr Asp Lys Val Ala
            595                 600                 605

Ile Ala Val Glu Asp Leu Asn Val Arg Met Phe His Gly Gly Gly Ser
        610                 615                 620

Arg Ser Thr Gly Trp Asp Asn Phe Phe Val Ala Lys Arg Glu Asn Arg
625                 630                 635                 640

Trp Phe Val Gln Val Leu His Lys Ser Phe Cys Asp Leu Ala Leu His
                645                 650                 655

Arg Gly Glu Val Val Ile Glu Val Asp Pro Ala Arg Thr Ser Gln Thr
            660                 665                 670

Cys Pro Ala Cys Gly His Cys Asp Pro Lys Asn Arg Ser Ser Val Asp
            675                 680                 685

Arg Glu Val Phe Arg Cys Val Cys Gly Arg Thr Phe His Ala Asp
        690                 695                 700

Leu Glu Val Ala Thr Phe Asn Ile Glu Arg Val Ala Leu Thr Gly Glu
705                 710                 715                 720

Ser Met Pro Lys Gly Glu Glu Gly Ala Arg Glu Arg Gly Gly Gly Gly
                725                 730                 735

Lys Ser Arg Gly Gly Ala Arg Gly Arg Asn Lys Leu Lys
            740                 745
```

<210> SEQ ID NO 28
<211> LENGTH: 767
<212> TYPE: PRT
<213> ORGANISM: Unknown
<220> FEATURE:
<223> OTHER INFORMATION: Description of Unknown:
      wastewater metagenome sequence -continued

```
<400> SEQUENCE: 28

Met Ser Glu Ile Thr Asp Leu Leu Lys Ala Asn Phe Lys Gly Lys Thr
1               5                   10                  15

Phe Lys Ser Ala Asp Met Arg Met Ala Gly Arg Ile Leu Lys Lys Ser
            20                  25                  30

Gly Ala Gln Ala Val Ile Lys Tyr Leu Ser Asp Lys Gly Ala Val Asp
        35                  40                  45

Pro Pro Asp Phe Arg Pro Pro Ala Lys Cys Asn Ile Ile Ala Gln Ser
    50                  55                  60

Arg Pro Phe Asp Glu Trp Pro Ile Cys Lys Ala Ser Met Ala Ile Gln
65                  70                  75                  80

Gln His Ile Tyr Gly Leu Thr Lys Asn Glu Phe Asp Glu Ser Ser Pro
                85                  90                  95

Gly Thr Ser Ser Ala Ser His Glu Gln Trp Phe Ala Lys Thr Gly Val
            100                 105                 110

Asp Thr His Gly Phe Thr His Val Gln Gly Leu Asn Leu Ile Phe Gln
            115                 120                 125

His Ala Lys Lys Arg Tyr Glu Gly Val Ile Lys Lys Val Glu Asn Tyr
        130                 135                 140

Asn Glu Lys Glu Arg Lys Lys Phe Glu Gly Ile Asn Glu Arg Arg Ser
145                 150                 155                 160

Lys Glu Gly Met Pro Leu Leu Glu Pro Arg Leu Arg Thr Ala Phe Gly
                165                 170                 175

Asp Asp Gly Lys Phe Ala Glu Lys Pro Gly Val Asn Pro Ser Ile Tyr
            180                 185                 190

Leu Tyr Gln Gln Thr Ser Pro Arg Pro Tyr Asp Lys Thr Lys His Pro
            195                 200                 205

Tyr Val His Ala Pro Phe Glu Leu Lys Glu Ile Thr Thr Ile Pro Thr
        210                 215                 220

Gln Asp Asp Arg Leu Lys Ile Pro Phe Gly Ala Pro Gly His Val Pro
225                 230                 235                 240

Glu Lys His Arg Ser Gln Leu Ser Met Ala Lys His Lys Arg Arg Arg
                245                 250                 255

Ala Trp Tyr Ala Leu Ser Gln Asn Lys Pro Arg Pro Pro Lys Asp Gly
                260                 265                 270

Ser Lys Gly Arg Arg Ser Val Arg Asp Leu Ala Asp Leu Lys Ala Ala
            275                 280                 285

Ser Leu Ala Asp Ala Ile Pro Leu Val Ser Arg Val Gly Phe Asp Trp
        290                 295                 300

Val Val Ile Asp Gly Arg Gly Leu Leu Arg Asn Leu Arg Trp Arg Lys
305                 310                 315                 320

Leu Ala His Glu Gly Met Thr Val Glu Glu Met Leu Gly Phe Phe Ser
                325                 330                 335

Gly Asp Pro Val Ile Asp Pro Arg Arg Asn Val Ala Thr Phe Ile Tyr
            340                 345                 350

Lys Ala Glu His Ala Thr Val Lys Ser Arg Lys Pro Ile Gly Gly Ala
            355                 360                 365

Lys Arg Ala Arg Glu Glu Leu Leu Lys Ala Thr Ala Ser Ser Asp Gly
        370                 375                 380

Val Ile Arg Gln Val Gly Leu Ile Ser Val Asp Leu Gly Gln Thr Asn
385                 390                 395                 400

Pro Val Ala Tyr Glu Ile Ser Arg Met His Gln Ala Asn Gly Glu Leu
            405                 410                 415
```

-continued

```
Val Ala Glu His Leu Glu Tyr Gly Leu Leu Asn Asp Glu Gln Val Asn
            420             425             430

Ser Ile Gln Arg Tyr Arg Ala Ala Trp Asp Ser Met Asn Glu Ser Phe
            435             440             445

Arg Gln Lys Ala Ile Glu Ser Leu Ser Met Glu Ala Gln Asp Glu Ile
            450             455             460

Met Gln Ala Ser Thr Gly Ala Ala Lys Arg Thr Arg Glu Ala Val Leu
465             470             475             480

Thr Met Phe Gly Pro Asn Ala Thr Leu Pro Trp Ser Arg Met Ser Ser
            485             490             495

Asn Thr Thr Cys Ile Ser Asp Ala Leu Ile Glu Val Gly Lys Glu Glu
            500             505             510

Glu Thr Asn Phe Val Thr Ser Asn Gly Pro Arg Lys Arg Thr Asp Ala
            515             520             525

Gln Trp Ala Ala Tyr Leu Arg Pro Arg Val Asn Pro Glu Thr Arg Ala
            530             535             540

Leu Leu Asn Gln Ala Val Trp Asp Leu Met Lys Arg Ser Asp Glu Tyr
545             550             555             560

Glu Arg Leu Ser Lys Arg Lys Leu Glu Met Ala Arg Gln Cys Val Asn
            565             570             575

Phe Val Val Ala Arg Ala Glu Lys Leu Thr Gln Cys Asn Asn Ile Gly
            580             585             590

Ile Val Leu Glu Asn Leu Val Val Arg Asn Phe His Gly Ser Gly Arg
            595             600             605

Arg Glu Ser Gly Trp Glu Gly Phe Phe Glu Pro Lys Arg Glu Asn Arg
            610             615             620

Trp Phe Met Gln Val Leu His Lys Ala Phe Ser Asp Leu Ala Gln His
625             630             635             640

Arg Gly Val Met Val Phe Glu Val His Pro Ala Tyr Ser Ser Gln Thr
            645             650             655

Cys Pro Ala Cys Arg Tyr Val Asp Pro Lys Asn Arg Ser Ser Glu Asp
            660             665             670

Arg Glu Arg Phe Lys Cys Leu Lys Cys Gly Arg Ser Phe Asn Ala Asp
            675             680             685

Arg Glu Val Ala Thr Phe Asn Ile Arg Glu Ile Ala Arg Thr Gly Val
            690             695             700

Gly Leu Pro Lys Pro Asp Arg Glu Arg Ser Arg Asp Val Gln Thr Pro
705             710             715             720

Gly Thr Ala Arg Lys Ser Gly Arg Ser Leu Lys Ser Gln Asp Asn Pro
            725             730             735

Ser Glu Pro Lys Arg Val Leu Gln Ser Lys Thr Arg Lys Lys Ile Thr
            740             745             750

Ser Thr Glu Thr Gln Asn Glu Pro Leu Ala Thr Asp Leu Lys Thr
            755             760             765
```

```
<210> SEQ ID NO 29
<211> LENGTH: 749
<212> TYPE: PRT
<213> ORGANISM: Unknown
<220> FEATURE:
<223> OTHER INFORMATION: Description of Unknown:
      wastewater metagenome sequence

<400> SEQUENCE: 29

Met Pro Asp Lys Gln Thr Pro Lys Asp Thr Lys Asp Lys Pro Glu Ser
```

-continued

```
1                5                   10                  15

Pro Val Ser Ala Phe Leu Lys Lys His Phe Pro Gly Lys His Phe Phe
             20                  25                  30

Gly His Ala Gly Thr Leu Ala Arg Leu Leu Lys Thr Lys Gly Glu Glu
             35                  40                  45

Val Ala Arg Asp Tyr Ala Ala Lys Lys Val Arg Asp Glu Lys Leu Asp
    50                  55                  60

Phe Arg Pro Pro Ala Lys Cys Gln Ile Val Ala Trp Ser Arg Asp Phe
65                  70                  75                  80

Ser Glu Trp Pro Ile Ala Arg Ala Ser Ala Thr Ile Gln Gln His Val
             85                  90                  95

Ser Gly Leu Thr Lys Glu Asp Phe Glu Arg Phe Asp Pro Gly Lys Ser
             100                 105                 110

Lys Ala Ala His Asp Ala Trp Phe Gln Glu Ser Gly Val Asp Cys His
             115                 120                 125

Gly Tyr Arg His Val Gln Gly Leu Asn Leu Ile Phe Ala Asn Ala Arg
    130                 135                 140

Asp Tyr Tyr Glu Gly Val Val Lys Lys Val Glu Asn Lys Asn Ala Gln
145                 150                 155                 160

Arg Arg Arg Arg Val Glu Ala Leu Asn Ala Arg Arg Ala Glu Glu Gly
             165                 170                 175

Glu Glu Pro Ile Pro Leu Asp Val Glu Glu Ser Pro Phe Gly Glu Asp
             180                 185                 190

Gly Arg Leu Ala His Pro Pro Gly Val Asn Pro Ser Ile Tyr Val Tyr
             195                 200                 205

Gln Ala Val Ser Pro Arg Pro Leu Lys Lys Ser Asp Leu Glu Thr Val
    210                 215                 220

Val Leu Pro Pro Ala Tyr Ala Gly Tyr Asp Arg Asp Pro Ser Ala Pro
225                 230                 235                 240

Ile Pro Val Met Gly Asp Arg Leu Ser Ile Pro Glu Gly Gln Arg Gly
             245                 250                 255

His Val Pro Ala Trp Gln Arg Asp Gln Leu Ser Pro Asp Lys His Arg
             260                 265                 270

Arg Met Arg Ala Trp Tyr Ser Ala Ala Asn Thr Lys Pro Lys Pro Gly
             275                 280                 285

Arg Thr Ser Val Pro Asp Ala Ala Ala Ile Glu Arg Ala Arg Ala Glu
    290                 295                 300

Gly Ala Leu Leu Val Val Ile Arg Ile Gly Glu Asp Trp Val Val Leu
305                 310                 315                 320

Asp Ala Arg Gly Leu Leu Arg Asn Ala Arg Trp Arg Arg Ile Ala Asp
             325                 330                 335

Lys Glu Ile Ser Leu Asp Gly Leu Leu Asp Leu Phe Thr Gly Asp Pro
             340                 345                 350

Val Ile Asp Ser Lys Arg Asn Val Val Thr Phe Ile Tyr Lys Ala Glu
             355                 360                 365

His Ala Thr Ala Thr Ser Arg Lys Val Val His Arg Lys Ala Ser Arg
    370                 375                 380

Lys Ala Leu Leu Asp Met Thr Ser Pro Gly Glu Asp Gly Leu Pro Arg
385                 390                 395                 400

Glu Val Ala Leu Ala Ser Val Asp Leu Gly Gln Thr Asn Ala Ala Ala
             405                 410                 415

Val Arg Tyr Ala Arg Val His Arg Glu Gly Asp Asp Ile Thr Ser Glu
             420                 425                 430
```

```
Cys Leu Val Arg Glu Leu Leu Pro Asp Glu Ile Ser Arg Asp Ile Ala
        435               440               445

Arg Tyr Arg Ala Ala Ser Asp Arg Met Glu Ala Glu Ile Arg Glu Ala
    450               455               460

Ala Ile Ala Gly Leu Pro Glu Pro Met Gln Ala Glu Val Arg Ala Ala
465               470               475               480

Asp Ala Ser Ser Pro Glu Ala Ala Arg Ala Ala Val Val Ala Leu Val
                485               490               495

Gly Asp Gly Leu Pro Trp Glu Lys Met Ser Ser Ala Thr Tyr His Ile
            500               505               510

Ser Asp Ala Leu Val Ala Leu Gly Arg Gly Arg Glu Ala Tyr Leu Leu
        515               520               525

Ser Lys Ser Lys Asp Gly Glu Glu Lys Ser Val Gln Arg Ser Asp Tyr
    530               535               540

Gly Trp Ser Arg His Leu Arg Pro Arg Leu Ser Glu Glu Thr Arg Lys
545               550               555               560

Ala Met Asn Glu Ala Val Trp Ser Ile Lys Asp Ala His Glu Gly Tyr
                565               570               575

Gln Lys Leu Ser Arg Arg Lys Thr Glu Ile Gly Arg Arg Ala Ala Asn
            580               585               590

His Val Val Arg Arg Leu Arg Lys Leu Ala Lys Thr Asp Lys Val Ala
        595               600               605

Ile Ala Val Glu Asp Leu Asn Val Arg Met Phe His Gly Gly Gly Ser
    610               615               620

Arg Ser Thr Gly Trp Asp Asn Phe Phe Val Ala Lys Arg Glu Asn Arg
625               630               635               640

Trp Phe Val Gln Val Leu His Lys Ser Phe Cys Asp Leu Ala Leu His
                645               650               655

Arg Gly Glu Val Val Ile Glu Val Asp Pro Ala Arg Thr Ser Gln Thr
            660               665               670

Cys Pro Ala Cys Gly His Cys Asp Pro Lys Asn Arg Ser Ser Val Asp
        675               680               685

Arg Glu Val Phe Arg Cys Val Val Cys Gly Arg Thr Phe His Ala Asp
    690               695               700

Leu Glu Val Ala Thr Phe Asn Ile Glu Arg Val Ala Leu Thr Gly Glu
705               710               715               720

Ser Met Pro Lys Gly Glu Glu Gly Ala Arg Glu Arg Gly Gly Gly Gly
                725               730               735

Lys Ser Arg Gly Gly Ala Arg Gly Arg Asn Lys Leu Lys
            740               745
```

<210> SEQ ID NO 30
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
caacctaaac gatggctcga ttcgtcgaga c                                                        31

<210> SEQ ID NO 31
<211> LENGTH: 36
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 31
gtagaagacc tcgctgattg ctcggtgcgc cgagac                             36

<210> SEQ ID NO 32
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
ggttgaaccc tcaacagatt gctcggtaag ccgagac                            37

<210> SEQ ID NO 33
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
gttgaaccct caacagattg ctcggtaagc cgagac                             36

<210> SEQ ID NO 34
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
cttgaaatcc tgtcagattg ctcccttcgg ggagac                             36

<210> SEQ ID NO 35
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
gctggaagac tcaatgatgg ctccttacga ggagac                             36

<210> SEQ ID NO 36
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
cttagaatac tcaatgatgg ctccttacga ggagac                             36

<210> SEQ ID NO 37
<211> LENGTH: 22
<212> TYPE: DNA
<213> ORGANISM: Artificial Sequence
<220> FEATURE:
```

-continued

```
<223> OTHER INFORMATION: Description of Artificial Sequence: Synthetic
      oligonucleotide

<400> SEQUENCE: 37
atcggcagct ggtccacctt gg                                                    22

<210> SEQ ID NO 38
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
gtctctccgt agagagcaat cgttatccat tgagag                                     36

<210> SEQ ID NO 39
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
ctttcaagac taatagattg ctccttacga ggagac                                     36

<210> SEQ ID NO 40
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
gtagaaaggt ttactaattg ctccttacga ggagac                                     36

<210> SEQ ID NO 41
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
cccggaagac cagatgatgg ctcgatcagt cgagac                                     36

<210> SEQ ID NO 42
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
gtcgagaccg atgacgagtg cgcggtgcgc cgcgac                                     36

<210> SEQ ID NO 43
<211> LENGTH: 36
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 43
cctgcaaggg atccaaattg ctctgttcgc agagac                                    36

<210> SEQ ID NO 44
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
gcgccaacga cctctgattg tccggtacgc cggaac                                    36

<210> SEQ ID NO 45
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
gtcgagagcg atgacgagtg cgcggtgcgc cgcgac                                    36

<210> SEQ ID NO 46
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
ccatcaatgg atccaaattg ctctgtacgc agagac                                    36

<210> SEQ ID NO 47
<211> LENGTH: 1072
<212> TYPE: DNA
<213> ORGANISM: Unknown
<220> FEATURE:
<223> OTHER INFORMATION: Description of Unknown:
      plants-rhizoplane-switchgrass rhizosphere sequence

<400> SEQUENCE: 47
gaggataagc tcgcgttcgg ccgccagctc ttctgggctc atgtcggcga gcttgtgggc     60
taccacagcg aacggcttgc tcatggtctg caagtgttct ggcaggtggg cgtacgtgaa    120
aaattggagc gtgtggtttg tgtcaatcat gacgttgact acaccgacgt gacatctctg    180
tgcctttggt tttggacggg caccggtggt gtagggttgg acagcagccg tgtcgcagcg    240
ggggaggtct tggggagaat ggttctcttt ggggcctttt ctattggtgg tcttggttcg    300
ccatcctcgt ccataccaac cctccaagta tttcccgcgg aggataacac gaaatgctgc    360
gatggcgtct ctccgtagag agcaatcgtt actcgttgag atatgtacag caacttagac    420
actgggtgct gggccagctg tctccccgta gggagcaatc gtgcgcgaac acgatcactt    480
gtctcgtacg gctaccacgg ctccagcaga agctcaatca tactcaccac atacaccgca    540
gattgcgaga gggacggaag aaaaaccatg aactgtgaaa aatagtacaa agattctgtg    600
cagattaaac tactgagctt ttgatattat tggttttcga gcgggtaaca gcctttgtgc    660
acaaccaaac cactcgcatt tcaaaccttc gtatggccca ggagcggtgt aatgcagctt    720

```
cggttgccca ccgaggtggg acttcaggag caaggacatg tcgaaaacca aagaactcaa      780
tgactatcaa gaagcgctag cgcgtcgcct tcctggtgtc cgacaccaaa agtcggtacg      840
ccgagctgcg cgactcgtct acgacagaca aggggaagat gccatggtcg ccttcctcga      900
cggcaaacgt gagcgttttt gctgcaccca ctgcggagca cagcgacacg ctgacctcga      960
agtggcgaca cacaacatcg ccatggtagc caccacaggc aaatctctaa caggcaaatc     1020
gttggcgcca caacgactcc aggaagctgc agagtaacga ttgctcccta tg             1072
```

<210> SEQ ID NO 48
<211> LENGTH: 494
<212> TYPE: DNA
<213> ORGANISM: Unknown
<220> FEATURE:
<223> OTHER INFORMATION: Description of Unknown:
      aquatic-freshwater-bog forest soil sequence

<400> SEQUENCE: 48

```
cttgatgccg tcgacgacga agctcgccgg cagcgcccgg cgctcgccct cggggtacta       60
ctggctcggc cagccgcccc agaagagaac gaaattccca cggacagtga cttcgtagag      120
atcggcgtgc gtagggcctt cggcgggcat ggagaactcc ctggtgaaga cgcctttagg      180
agctaggcgg caggattgcc gctgttttca cgcttgtgcg tgacctcgac ctcgaacgcg      240
gaggacacgc taacacgtaa gaatctaact tggcaagtac aggctttctt ttcttgatcc      300
cgaattagat gcgtagtagc cgtgaaatag gagacaagat cctcatgcgt cagcccgcgg      360
agaagaccgc gttccaagtc tttcgtcagg aagtgatcgg gacacagaaa ctatcgggag      420
gcgatgccaa gactgccgga cggctctaca agcagggaaa gatggaagca gcacgtgagt      480
ggttgctcaa aggt                                                        494
```

<210> SEQ ID NO 49
<211> LENGTH: 268
<212> TYPE: DNA
<213> ORGANISM: Unknown
<220> FEATURE:
<223> OTHER INFORMATION: Description of Unknown:
      wastewater-industrial wastewater-sediment sequence

<400> SEQUENCE: 49

```
cgcatctgca acggtctact cgatgctgga ttgattcctg cggtgtagaa tagcataacc       60
agggtccgct ggactatcca gcaacgacgg ctcgatacgt cgagccgatg gagaagtcat      120
gccaaagatc aagaaaccga ctgagatttc cctgctacgc aaggaggtgt tccctgacct      180
ccactttgcc aaggaccgga tgcgtgctgc atccttggtc cttaagaatg agggccggga      240
agccgccatc gagtacctcc gggtgaat                                         268
```

<210> SEQ ID NO 50
<211> LENGTH: 544
<212> TYPE: DNA
<213> ORGANISM: Unknown
<220> FEATURE:
<223> OTHER INFORMATION: Description of Unknown:
      terrestrial-soil-forest soil sequence

<400> SEQUENCE: 50

```
ggaatgagtg gagaaggagt ggtttgtaaa ggtacttgga ataagaaaaa gaatagacca       60
aacatgttca agattaagtc taatgcttgg attggaagac ttaaagaata ctgcaacggt      120
aatatggacc taatggccag actactataa tgtttgatct taaagcagaa attgtataaa      180
```

-continued

```
taatgatatc aaaaatgatt aagcctacgg taagtcagtt tcttacgcct ggatttaagt      240
taattcggaa tcactcaaga actgctggtc taaaactaaa aaatgaaggc gaagaggctt      300
gtaagaaatt cgttcgagaa aatgaaattc ctgtcgctat aacggcccag tcgatgccga      360
aaccaacttg cgagcgctcg ggcgacgcta aaaagcctgt ccgtgctcgc aaggctaaag      420
caccggaatt tcacgataaa ttggcaccaa gctatacggt tgtgctaagg gaggctgttt      480
gaagacataa ccgctcgcaa accgaacgat aaatatgcga aatcattgaa gaatggcgag      540
gcat                                                                   544

<210> SEQ ID NO 51
<211> LENGTH: 534
<212> TYPE: DNA
<213> ORGANISM: Unknown
<220> FEATURE:
<223> OTHER INFORMATION: Description of Unknown:
      wastewater metagenome sequence

<400> SEQUENCE: 51
gtcgcgccga ggcccattgg cttttatgac tatggctctt tcgacatggc tcgatgggag       60
gacttcatcg aaaaatggat accggagcag ttgccaacgt cgtgggatca cctcatggat      120
gacttggaga tcgcggatgc cgcacgatag gtattgcgcc tccttcatga cgtttttctaa      180 gattttacgt tcggtgtaga cgtgagtatg tccgaaatca ctgatctgct caaagccaat      240
ttcaaaggga agacattcaa aagtgcagac atgaggatgg ctgggaggat cttcaagaaa      300
agcggcgcgc aggccgttat caaatacttg tcggacaagg gggcagttga tccgcctaag      360
tccggcaggt ccttgaaatc aaacaagaat ccgagcgagc ccaaacacgt tttgcggtca      420
aaaacacgta gcaacataac atctacgttg tcgcaaaatg aaccgctcgc aacggaccaa      480
aaaaccgctc caaaaacagg accttagacc ccacgccccg cggttcccgc tttt           534

<210> SEQ ID NO 52
<211> LENGTH: 1275
<212> TYPE: DNA
<213> ORGANISM: Unknown
<220> FEATURE:
<223> OTHER INFORMATION: Description of Unknown:
      wastewater metagenome sequence

<400> SEQUENCE: 52
cgccctcgcg acgcgcatcc cggggtttcg ttttccggag acgatgcagc tcacctgcgc       60
cacggagcag ccgagacggg cggcgacctt ggtcgtgccc tcggactcga cgatcttcac      120
gaacttcttg tgcgtctgtt ctggcgacat gcggggtagc ttgcgacggt ttaggtcgcc      180
tgtcaagcga gctggcgaaa agctgttgac aggagcatgg gctttggcta aggtgcgagc      240
atgcccgaca agcagacgcc caaggacacc aaggacaagc ccgagagccc cgtctccgcc      300
ttcctcaaga agcacttccc cgggaagcat ttcttcgggc atgccgggac gctcgcccgc      360
ctcctcaaga ccaagggtga ggaggttgcg ttccacgccg acctcgaagt ggcgactttc      420
aacatcgagc gggtggcgct gacgggcgag tcgatgccga aaggcgagga gggcgcacgc      480
gagcggggag gtggtgggaa gagcaggggga ggcgctcgcg ggcgaaataa attgaaatag      540
ttcgcgaaat cgggtaagct ggttggcgtc agtgaaaact gaatagacga agatacgagc      600
cgctcgcagg gtggagcgga agatctcgat ctggttccga atttctcggt ggctgtcgag      660
agcgatgacg agtgcgcggt gcgccgcgac cagctctgtg tgtagttgac ccgtagtcag      720
```

-continued

```
gacaaggaga ggtcgagagc gatgacgagt gcgcggtgcg ccgcgacgtg ctgttgatct       780
gatagacggg ggtgggcacc tgcgcggtgt cgagagcgat gacgagtgcg cggtgcgccg       840
cgactttcgt acagagcctc cggacggcgt ccggatgccg gagtcgagag cgatgacgag       900
tgcgcggtgc gccgcgacgc cgtcgcctcg aaggcgggcg cgggtgaact acttcgtcaa       960
gaccgatgac gattgcggtg cgccgcgacg gcttgcgcga ggactttttg gtcggcttct      1020
tgccgtcgtc aagaccgatg acgagtgcgc ggtgcgccgc gacgacttgg ccttcgcctc      1080
ggtcagggcg cgtcggtcga caatttcagt gcaatggctc ggtacaccgg gactatgatt      1140
gttcggtacg ccgagacacg gtcggccagc tggttatctc acgtccctca ccaccccac       1200 gtacgccatc atctccctca tcctcacctc ccacccgtgg ttctccgccg cgagcctcgc      1260 ccccgctcg gcgat                                                        1275
```

```
<210> SEQ ID NO 53
<211> LENGTH: 570
<212> TYPE: DNA
<213> ORGANISM: Unknown
<220> FEATURE:
<223> OTHER INFORMATION: Description of Unknown:
      wastewater metagenome sequence

<400> SEQUENCE: 53
gtcgcgccga ggcccattgg cttttatgac tatggctctt tcgacatggc tcgatgggag        60
gacttcatcg aaaaatgggt actggagcag ttgccaacgt cgtgggatca cctcatggat       120
gacttggaga tcgcggatgc cgcacgatag gtattgcgcc tccttcatga cgttttctaa       180
gattttacgt tcggtgtaga cgtgagtatg tccgaaatca ctgatctgct caaagccaat       240
ttcaaaggga agacattcaa aagtgcagac atgaggatgg ctgggaggat cttcaagaaa       300
agcggcgcgc aggccgttat caaatacttg tcggacaagg gggcagttga tccgcctacc       360
ccggggaccg ctcgcaagtc cggcaggtcc ttgaaatcac aagataatcc gagcgagccc       420
aaacgcgttt tgcagtcaaa aacacgtaag aaaatcacat ctacggagac acaaaacgaa       480
ccgctcgcaa cggacctaaa aacctaagtg aaaacagggg cctagacaca catccaagga       540
tgtcgcaaag ggcctcgtcg agatcccaag                                        570
```

```
<210> SEQ ID NO 54
<211> LENGTH: 703
<212> TYPE: DNA
<213> ORGANISM: Unknown
<220> FEATURE:
<223> OTHER INFORMATION: Description of Unknown:
      wastewater metagenome sequence

<400> SEQUENCE: 54
ctgctgcgcg cgtacccgct ctgggagagt cgcgactgcg gtcagcacga ctcgcgcggc        60
gagggcgtgg agggctgcta ttgcgcgcga caagatctga agcacctgat cggctggccg       120
gagccgaagc aaaaaagctc ctgcaaatga tctatctctg ttgacttcgc atcagacgat       180
cactagattg ctacaggcaa tcacaaacag cgggagacga acaatgactc tggccgagct       240
gcgcgacaaa tacttctaca agatcaagtt ccgcaagatc gatctcaggc aagccggcaa       300
gatcctcaag agagagggcg aggaagcggc tcgccgctat cttgacgagc agcgggagtc       360
gccgcccgag ggccgcggcg cggggctgcg gaaggtcgag actgaggccg aggtcgaggc       420
ggtcgacgag gcccccgcgg ccgcgagcgt ggagaagccg cgcaagcggc gcaagagcgc       480
gagcggcgag gcggcgactt cgaggccgc accgctcgcg tagtctaaga tcgcgttctc       540
```

-continued

```
gcaagagaat gcgagcaccg gccgcgaaca ccgctctagt tgtgcgaacg ttcgcggccg      600
gtgctcgcag acgagctgct aggtctttga aaattgaata gattgtaatg gtgagttgcc      660
cgagcccgca ctcgcggcgc gctacctctt cgcgccaacg acc                       703

<210> SEQ ID NO 55
<211> LENGTH: 654
<212> TYPE: DNA
<213> ORGANISM: Unknown
<220> FEATURE:
<223> OTHER INFORMATION: Description of Unknown:
      wastewater metagenome sequence

<400> SEQUENCE: 55
cgccctcgcg acgcgcatcc cggggtttcg ttttccggag acgatgcagc tcacctgcgc       60
cacggagcag ccgagacggg cggcgacctt ggtcgtgccc tcggactcga cgatcttcac      120
gaacttcttg tgcgtctgtt ctggcgacat gcggggtagc ttgcgacggt ttaggtcgcc      180
tgtcaagcga gctggcgaaa agctgttgac aggagcatgg gctttggcta aggtgcgagc      240
atgcccgaca agcagacgcc caaggacacc aaggacaagc ccgagagccc cgtctccgcc      300
ttcctcaaga agcacttccc cgggaagcat ttcttcgggc atgccgggac gctcgcccgc      360
ctcctcaaga ccaagggtga ggaggttgcg ttccacgccg acctcggggt ggcgactttc      420
aacatcgagc gggtggcgct gacgggcgag tcgatgccga aaggcgagga gggcgcacgc      480
gagcggggag gtggtgggaa gagcagggga ggcgctcgcg ggcgaaataa attgaaatag      540
ttcgcgaaat cgggtaagct ggttggcgtc agtgaaaact gaatagacga agatacgagc      600
cgctcgcagg gtggagcgga agatctcgat ctggttccga atttctcggt ggct           654

<210> SEQ ID NO 56
<211> LENGTH: 527
<212> TYPE: DNA
<213> ORGANISM: Unknown
<220> FEATURE:
<223> OTHER INFORMATION: Description of Unknown:
      wastewater metagenome sequence

<400> SEQUENCE: 56
gtcgcgccga ggcccattgg cttttatgac tatggctctt tcgacatggc tcgatgggag       60
gacttcatcg aaaaatgggt gccggagcag ttgccaacgt cgtgggatca cctcatggat      120
gacttggaga tcgcggatgc cgcacgatag gtattgcgcc tccttcatga cgttttctaa      180
gattttacgt tcggtgtaga cgtgagtatg tccgaaatca ctgatctgct caaagccaat      240
ttcaaaggga agacattcaa aagtgcagac atgaggatgg ctgggaggac cctcaagaaa      300
agcggcgcgc aggccgttat caaatacttg tcggacaagg gggcggttga tccgcctaat      360
cccggcaggt ccttgaaatc aaacaagaat ccgagcgagc ccaaacacgt tttgcggtca      420
aaaacacgta gcaacataac atctacgttg tcgcaaaatg aaccgctcgc aacggaccaa      480
aaaaccgctc caaaaacagg accttagacc ccacgccgga agtcgct                    527

<210> SEQ ID NO 57
<211> LENGTH: 147
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 57
```
tccatgtctc gttatacgct gtggttcgcc aacaaatacc ttactactcg tcacgccacg          60
ccatcgtggt gccagatctg tcacaggtaa ctgaacacct ggaaactact aatacctttt         120
gacagctagc tcagtcctag gtataat                                              147

<210> SEQ ID NO 58
<211> LENGTH: 149
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 58
tccatgtctc gttatacgct gtggttcgcc aacgcaagaa tactactact gcaacctgta          60
ctaacgtatg gtgacttaac tcgtctggat cctacaacag taacgcacta ctagaatact         120
ttgacagcta gctcagtcct aggtataat                                            149

<210> SEQ ID NO 59
<211> LENGTH: 151
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 59
tccatgtctc gttatacgct gtggttcgcc aacactctca taactactgc gtgaagtgct          60
ttccgaacgc ttcgccacgc tctcctttga tgtacagaaa actcagcgac tactctctca         120
tattgacagc tagctcagtc ctaggtataa t                                         151

<210> SEQ ID NO 60
<211> LENGTH: 153
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 60
tccatgtctc gttatacgct gtggttcgcc aacgcacccc cccgactact cggtagcgtc          60
gatgttctgc tgccgttgcc ggggcgtcac aatattgcga atgcgctggc actactcccc         120
cccgttgaca gctagctcag tcctaggtat aat                                       153

<210> SEQ ID NO 61
<211> LENGTH: 151
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 61
tccatgtctc gttatacgct gtggttcgcc aacactgcat acactactgt gaccgacggt          60
gttgtaactg acgaaattca ctacctgtct gctatcgaag aaggcaacac tactctgcat         120
acttgacagc tagctcagtc ctaggtataa t                                         151

<210> SEQ ID NO 62
<211> LENGTH: 153
<212> TYPE: DNA

```
<213> ORGANISM: Artificial Sequence
<220> FEATURE:
<223> OTHER INFORMATION: Description of Artificial Sequence: Synthetic
      polynucleotide

<400> SEQUENCE: 62
tccatgtctc gttatacgct gtggttcgcc aacgcaagaa agtcactact actgaaagcg          60
atcatctctg atgtgaacgc ttccgacgaa gatcgttgga acgctgttct actactagaa         120
agtcttgaca gctagctcag tcctaggtat aat                                       153

<210> SEQ ID NO 63
<211> LENGTH: 156
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 63
tccatgtctc gttatacgct gtggttcgcc aacatgagat ggactacttg tttggtcgtg          60
ctgcgcgtga aagccgtatt gaaagcctcc atgccgagcg tgaagtgctt tccactactt         120
gagatggttg acagctagct cagtcctagg tataat                                    156

<210> SEQ ID NO 64
<211> LENGTH: 158
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 64
tccatgtctc gttatacgct gtggttcgcc aacgcagtgg gaccactact gaaggtgatc          60
atgccgtttt cagtttcaac gtggtatgca ccaatgtgct gggtaatgcc gcccgactac         120
tgtgggacct tgacagctag ctcagtccta ggtataat                                  158

<210> SEQ ID NO 65
<211> LENGTH: 154
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 65
tccatgtctc gttatacgct gtggttcgcc aacatactgg ctactactat ggaaatacgc          60
gggtccgtac ctggaggaaa tgaagtcgcc gcatggctaa aacgaagacc gactacttac         120
tggctttgac agctagctca gtcctaggta taat                                      154

<210> SEQ ID NO 66
<211> LENGTH: 156
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 66
tccatgtctc gttatacgct gtggttcgcc aacgcacaac gctgactact ccgcgtccgg          60
cagttttgcc agccagcggc ggcccacttc atcgtcggcg ttaataatcg cctactactc         120
```
aacgctgttg acagctagct cagtcctagg tataat                                        156

<210> SEQ ID NO 67
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
agaaagagat cccgtatatc accgaactgg aaggcg                                        36

<210> SEQ ID NO 68
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
gtgtggtagg taatgtgatg ataacgcggg atatgc                                        36

<210> SEQ ID NO 69
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
aagagcgcca tgccggaagg ttatacccaa gagcgt                                        36

<210> SEQ ID NO 70
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
aagaaagacg gtcacattct gcgtaagaac gttgca                                        36

<210> SEQ ID NO 71
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
gagaaagaga tcccgtatat caccgaactg gaaggc                                        36

<210> SEQ ID NO 72
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
acggaaggtg caaaactgtt tgagaaagag atcccgtat                                     39

```
<210> SEQ ID NO 73
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
agaaagagat cccgtatatc accgaactgg aaggcgacg                        39

<210> SEQ ID NO 74
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
aatgataaat ttcatacctt cgacgtcgcc ttccagttc                        39

<210> SEQ ID NO 75
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
aagagcgcca tgccggaagg ttatacccaa gagcgtacc                        39

<210> SEQ ID NO 76
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
gagaaagaga tcccgtatat caccgaactg gaaggcgac                        39

<210> SEQ ID NO 77
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
caacctaaac gatggctcga ttcgtcgaga c                                31

<210> SEQ ID NO 78
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
ctaaacgatg gctcgattcg tcgagac                                     27
```

<210> SEQ ID NO 79
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
gtagaagacc tcgctgattg ctcggtgcgc cgagac                                    36

<210> SEQ ID NO 80
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
tgattgctcg gtgcgccgag a                                                    21

<210> SEQ ID NO 81
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
ctttcaagac taatagattg ctccttacga ggagac                                    36

<210> SEQ ID NO 82
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
ctaatagatt gctccttacg aggagac                                              27

<210> SEQ ID NO 83
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
gtcgagaccg atgacgagtg cgcggtgcgc cgcgac                                    36

<210> SEQ ID NO 84
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
tgacgagtgc gcggtgcgcc gcgac                                                25

```
<210> SEQ ID NO 85
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
cctgcaaggg atccaaattg ctctgttcgc agagac                                    36

<210> SEQ ID NO 86
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
tccaaattgc tctgttcgca gagac                                                25

<210> SEQ ID NO 87
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
cctgcaaggg atccaaattg ctctgttcgc agagac                                    36

<210> SEQ ID NO 88
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
atccaaattg ctctgttcgc agagac                                               26

<210> SEQ ID NO 89
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
gcgccaacga cctctgattg tccggtacgc cggaac                                    36

<210> SEQ ID NO 90
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
tctgattgtc cggtacgccg gaac                                                 24

<210> SEQ ID NO 91
```

-continued

```
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
ccatcaatgg atccaaattg ctctgtacgc agagac                              36

<210> SEQ ID NO 92
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
atccaaattg ctctgtacgc agagac                                        26

<210> SEQ ID NO 93
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
gtcgagagcg atgacgagtg cgcggtgcgc cgcgac                             36

<210> SEQ ID NO 94
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
tgacgagtgc gcggtgcgcc gcgac                                         25

<210> SEQ ID NO 95
<211> LENGTH: 111
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 95
gctggattga ttcctgcggt gtagaatagc ataaccaggg tccgctggac tatccagcaa    60
cgacggctcg atacgtcgag ccgatggaga agtcatgcca aagatcaaga a            111

<210> SEQ ID NO 96
<211> LENGTH: 112
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 96
tcgatgctgg attgattcct gcggtgtaga atagcataac cagggtccgc tggactatcc    60
agcaacgacg gctcgatacg tcgagccgat ggagaagtca tgccaaagat ca           112
```

<210> SEQ ID NO 97
<211> LENGTH: 98
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
attgattcct gcggtgtaga atagcataac cagggtccgc tggactatcc agcaacgacg      60
gctcgatacg tcgagccgat ggagaagtca tgccaaag                              98

<210> SEQ ID NO 98
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
atagcataac cagggtccgc tggactatcc agcaacgacg gctcgatacg tcgagccgat      60
ggagaagtca tgccaaagat                                                  80

<210> SEQ ID NO 99
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
tagcataacc agggtccgct ggactatcca gcaacgacgg ctcgatacgt cgagccgatg      60
gagaagtcat gccaaaga                                                    78

<210> SEQ ID NO 100
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
gccaaagatc aagaaaccga ctgagatttc cctgctacgc aaggaggtgt tccctga        57

<210> SEQ ID NO 101
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
attctacacc gcaggaatca atccagcatc gagtagaccg ttgc                       44

<210> SEQ ID NO 102
<211> LENGTH: 45
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 102
attctacacc gcaggaatca atccagcatc gagtagaccg ttgca                45

<210> SEQ ID NO 103
<211> LENGTH: 137
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 103
cttgtaagaa attcgttcga gaaaatgaaa ttcctgtcgc tataacggcc cagtcgatgc      60
cgaaaccaac ttgcgagcgc tcgggcgacg ctaaaaagcc tgtccgtgct cgcaaggcta     120
aagcaccgga atttcac                                                    137

<210> SEQ ID NO 104
<211> LENGTH: 136
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 104
ggcttgtaag aaattcgttc gagaaaatga aattcctgtc gctataacgg cccagtcgat      60
gccgaaacca acttgcgagc gctcgggcga cgctaaaaag cctgtccgtg ctcgcaaggc     120
taaagcaccg gaattt                                                     136

<210> SEQ ID NO 105
<211> LENGTH: 138
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 105
tgtcgagagc gatgacgagt gcgcggtgcg ccgcgaccag ctctgtgtgt agttgacccg      60
tagtcaggac aaggagaggt cgagagcgat gacgagtgcg cggtgcgccg cgacgtgctg     120
ttgatctgat agacgggg                                                   138

<210> SEQ ID NO 106
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
tcgagagcga tgacgagtgc gcggtgcgcc gcgacgtgct gttgatctga tagacg           56

<210> SEQ ID NO 107
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
ggttccgaat ttctcggtgg ctgtcgagag cgatgacgag tgcgcggtgc gccgcgacca      60
gctctgtgtg tagttgaccc g                                              81

<210> SEQ ID NO 108
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108
ggttccgaat ttctcggtgg ctgtcgagag cgatgacgag tgcgcggtgc gccgcgacca      60
gctctgtgtg tagttgacc                                                 79

<210> SEQ ID NO 109
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
tgctacaggc aatcacaaac agcgggagac gaacaatgac tctggccgag ctgcgcgaca      60
aatacttcta caagatcaa                                                 79

<210> SEQ ID NO 110
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110
ctacaggcaa tcacaaacag cgggagacga acaatgactc tggccgagct gcgcgacaaa      60
tacttctaca agatc                                                     75

<210> SEQ ID NO 111
<211> LENGTH: 93
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
gagacgaaca atgactctgg ccgagctgcg cgacaaatac ttctacaaga tcaagttccg      60
caagatcgat ctcaggcaag ccggcaagat cct                                 93

<210> SEQ ID NO 112
<211> LENGTH: 99
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112
gggagacgaa caatgactct ggccgagctg cgcgacaaat acttctacaa gatcaagttc      60

-continued

```
cgcaagatcg atctcaggca agccggcaag atcctcaag                       99

<210> SEQ ID NO 113
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113
gcggccggtg ctcgcagacg agctgctagg tctttgaaaa ttgaatagat tgtaatggtg       60
agttgc                                                                 66

<210> SEQ ID NO 114
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114
cggccggtgc tcgcagacga gctgctaggt ctttgaaaat tgaatagatt gtaatggtga       60
gttgc                                                                  65

<210> SEQ ID NO 115
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115
cgtctacacc gaacgtaaaa tcttagaaaa cgtcatgaag gaggcgcaat acctatcgtg       60
cg                                                                     62

<210> SEQ ID NO 116
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 116
ggttggcgtc agtgaaaact gaatagacga agatacgagc cgctcgcagg gtggagcgga       60
agatctcgat ctg                                                          73

<210> SEQ ID NO 117
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117
gctggttggc gtcagtgaaa actgaataga cgaagatacg agccgctcgc agggtggagc       60
ggaagatctc gatctgg                                                      77

<210> SEQ ID NO 118
```

```
<211> LENGTH: 93
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 118
cccgcatgtc gccagaacag acgcacaaga agttcgtgaa gatcgtcgag tccgagggca      60
cgaccaaggt cgccgcccgt ctcggctgct ccg                                    93

<210> SEQ ID NO 119
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 119
ccccgcatgt cgccagaaca gacgcacaag aagttcgtga agatcgtcga gtccgagggc      60
acgaccaagg tcgccgcccg tctcggctgc tccgtggcgc                            100

<210> SEQ ID NO 120
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 120
aggtgcgagc atgcccgaca agcagacgcc caaggacacc aaggacaagc ccgagagccc      60
cg                                                                     62

<210> SEQ ID NO 121
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 121
aggtgcgagc atgcccgaca agcagacgcc caaggacacc aaggacaagc ccgagagccc      60
c                                                                      61

<210> SEQ ID NO 122
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122
gtctcgacga atcgagccat cgtttaggtt g                                      31

<210> SEQ ID NO 123
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 123
gtctcggcgc accgagcaat cagcgaggtc ttctac                                          36

<210> SEQ ID NO 124
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124
gtctcggctt accgagcaat ctgttgaggg ttcaacc                                         37

<210> SEQ ID NO 125
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125
gtctcggctt accgagcaat ctgttgaggg ttcaac                                          36

<210> SEQ ID NO 126
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 126
gtctccccga agggagcaat ctgacaggat ttcaag                                          36

<210> SEQ ID NO 127
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127
gtctcctcgt aaggagccat cattgagtct tccagc                                          36

<210> SEQ ID NO 128
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 128
gtctcctcgt aaggagccat cattgagtat tctaag                                          36

<210> SEQ ID NO 129
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide -continued

```
<400> SEQUENCE: 129
ccaaggtgga ccagctgccg at                                          22

<210> SEQ ID NO 130
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 130
ctctcaatgg ataacgattg ctctctacgg agagac                          36

<210> SEQ ID NO 131
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 131
gtctcctcgt aaggagcaat ctattagtct tgaaag                          36

<210> SEQ ID NO 132
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 132
gtctcctcgt aaggagcaat tagtaaacct ttctac                          36

<210> SEQ ID NO 133
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133
gtctcgactg atcgagccat catctggtct tccggg                          36

<210> SEQ ID NO 134
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 134
gtcgcggcgc accgcgcact cgtcatcggt ctcgac                          36

<210> SEQ ID NO 135
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135
```

```
gtctctgcga acagagcaat ttggatccct tgcagg                                    36

<210> SEQ ID NO 136
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 136
gttccggcgt accggacaat cagaggtcgt tggcgc                                    36

<210> SEQ ID NO 137
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 137
gtcgcggcgc accgcgcact cgtcatcgct ctcgac                                    36

<210> SEQ ID NO 138
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 138
gtctctgcgt acagagcaat ttggatccat tgatgg                                    36

<210> SEQ ID NO 139
<211> LENGTH: 157
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 139
caacctaaac gatggctcga ttcgtcgaga caacgaaagt ggcctctggc gaagcgggcg        60
gcacaaccaa aacgatggct cgattcgtcg agacagttac ctgtgacaga tctggcacca      120
cgatggcaac caaaacgatg gctcgattcg tcgagac                                157

<210> SEQ ID NO 140
<211> LENGTH: 180
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 140
ccatcaatgg atccaaattg ctctgtacgc agagacagcg cgccgcggta catcttcttg        60
ttaacttttt gaccatcaat ggatccaaat tgctctgtac gcagagactg tacatcaaag      120
gagagcgtgg cgaagcgttc ggaaccatca atggatccaa attgctctgt acgcagagac      180

<210> SEQ ID NO 141
<211> LENGTH: 180
```

<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 141
gcgccaacga cctctgattg tccggtacgc cggaacgagg agcgcagtca ccaaaacttg      60
tcctttcagt ttgcgccaac gacctctgat tgtccggtac gccggaacga tagcagacag     120
gtagtgaatt tcgtcagtta caacgcgcca acgacctctg attgtccggt acgccggaac     180

<210> SEQ ID NO 142
<211> LENGTH: 190
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 142
gtcgagagcg atgacgagtg cgcggtgcgc cgcgacgaac cgaggtaact ggcttggagg      60
agcgcagtca ccaaaacgtc gagagcgatg acgagtgcgc ggtgcgccgc gacacgctcg     120
gcatggaggc tttcaatacg gctttcacgc gcaggtcgag agcgatgacg agtgcgcggt     180
gcgccgcgac                                                                                190

<210> SEQ ID NO 143
<211> LENGTH: 186
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 143
cctgcaaggg atccaaattg ctctgttcgc agagactggc gcgcaagccg aatgccaaag      60
tggtttatat gcactcctgc aagggatcca aattgctctg ttcgcagaga ctagccatgc     120
ggcgacttca tttcctccag gtacggaccc cctgcaaggg atccaaattg ctctgttcgc     180
agagac                                                                                    186

<210> SEQ ID NO 144
<211> LENGTH: 2774
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 144
ccccttgtat tactgtttat gtaagcagac aggatgcgtc cggcgtagag gatcgagatc      60
tccaaaaaat ggctgttttt gaaaaaaatt ctaaaggttg ttttacgaca gacgataaca     120
gggttgaaat aattttgttt aactttaaga aggagattta aatatgaaaa tcgaagaagg     180
taaaggtcac catcaccatc accacggatc catgacggca ttgacggaag gtgcaaaact     240
gtttgagaaa gagatcccgt atatcaccga actggaaggc gacgtcgaag gtatgaaatt     300
tatcattaaa ggcgagggta ccggtgacgc gaccacgggt accattaaag cgaaatacat     360
ctgcactacg ggcgacctgc cggtcccgtg ggcaaccctg gtgagcaccc tgagctacgg     420
tgttcagtgt ttcgccaagt acccgagcca catcaaggat ttctttaaga gcgccatgcc     480

-continued

```
ggaaggttat acccaagagc gtaccatcag cttcgaaggc gacggcgtgt acaagacgcg      540
tgctatggtt acctacgaac gcggttctat ctacaatcgt gtcacgctga ctggtgagaa      600
ctttaagaaa gacggtcaca ttctgcgtaa gaacgttgca ttccaatgcc cgccaagcat      660
tctgtatatt ctgcctgaca ccgttaacaa tggcatccgc gttgagttca accaggcgta      720
cgatattgaa ggtgtgaccg aaaaactggt taccaaatgc agccaaatga atcgtccgtt      780
ggcgggctcc gcggcagtgc atatcccgcg ttatcatcac attacctacc acaccaaact      840
gagcaaagac cgcgacgagc gccgtgatca catgtgtctg gtagaggtcg tgaaagcggt      900
tgatctggac acgtatcagt aataaaaagc ccgaaaggaa gctgagttgg ctgctgccac      960
cgctgagcaa taactagcat aaccccttgg ggcctctaaa cgggtcttga ggggtttttt     1020
gctgaaagga ggaactatat ccggcttcct cgctcactga ctcgctgcgc tcggtcgttc     1080
ggctgcggcg agcggtatca gctcactcaa aggcggtaat acggttatcc acagaatcag     1140
gggataacgc aggaaagaac atgtgagcaa aaggccagca aaaggccagg aaccgtaaaa     1200
aggccgcgtt gctggcgttt ttccataggc tccgccccc tgacgagcat cacaaaaatc      1260
gacgctcaag tcagaggtgg cgaaacccga caggactata aagataccag gcgtttcccc     1320
ctggaagctc cctcgtgcgc tctcctgttc cgaccctgcc gcttaccgga tacctgtccg     1380
cctttctccc ttcgggaagc gtggcgcttt ctcatagctc acgctgtagg tatctcagtt     1440
cggtgtaggt cgttcgctcc aagctgggct gtgtgcacga acccccgtt cagcccgacc      1500 gctgcgcctt atccggtaac tatcgtcttg agtccaaccc ggtaagacac gacttatcgc     1560
cactggcagc agccactggt aacaggatta gcagagcgag gtatgtaggc ggtgctacag     1620
agttcttgaa gtggtggcct aactacggct acactagaag aacagtattt ggtatctgcg     1680
ctctgctgaa gccagttacc ttcggaaaaa gagttggtag ctcttgatcc ggcaaacaaa     1740
ccaccgctgg tagcggtggt ttttttgttt gcaagcagca gattacgcgc agaaaaaaag     1800
gatctcaaga agatcctttg atcttttcta cggggtctga cgctcagtgg aacgaaaact     1860
cacgggtggc acttttcggg gaaatgtgcg cggaacccct atttgtttat ttttctaaat     1920
acattcaaat atgtatccgc tcatgaatta attcttagaa aaactcatcg agcatcaaat     1980
gaaactgcaa tttattcata tcaggattat caataccata tttttgaaaa agccgtttct     2040
gtaatgaagg agaaaactca ccgaggcagt tccataggat ggcaagatcc tggtatcggt     2100
ctgcgattcc gactcgtcca acatcaatac aacctattaa tttcccctcg tcaaaaataa     2160
ggttatcaag tgagaaatca ccatgagtga cgactgaatc cggtgagaat ggcaaaagtt     2220
tatgcatttc tttccagact tgttcaacag gccagccatt acgctcgtca tcaaaatcac     2280
tcgcatcaac caaaccgtta ttcattcgtg attgcgcctg agcgagacga atacgcgat      2340 cgctgttaaa aggacaatta caaacaggaa tcgaatgcaa ccggcgcagg aacactgcca     2400
gcgcatcaac aatattttca cctgaatcag gatattcttc taatacctgg aatgctgttt     2460
tcccggggat cgcagtggtg agtaaccatg catcatcagg agtacggata aaatgcttga     2520
tggtcggaag aggcataaat tccgtcagcc agtttagtct gaccatctca tctgtaacat     2580
cattggcaac gctacctttg ccatgtttca gaaacaactc tggcgcatcg gcttcccat      2640 acaatcgata gattgtcgca cctgattgcc cgacattatc gcgagcccat ttatacccat     2700
ataaatcagc atccatgttg gaatttaatc gcggcctaga gcaagacgtt tcccgttgaa     2760
tatggctcat aaca                                                       2774
```

-continued

```
<210> SEQ ID NO 145
<211> LENGTH: 2771
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 145
ccccttgtat tactgtttat gtaagcagac aggatgcgtc cggcgtagag gatcgagatc      60
tccaaaaaat ggctgttttt gaaaaaaatt ctaaaggttg ttttacgaca gacgataaca     120
gggttgaaat aattttgttt aactttaaga aggagattta aatatgaaaa tcgaagaagg     180
taaaggtcac catcaccatc accacggatc catggtcagc aaggggagg  aagacaatat     240 ggctattatc aaggaattca tgcgcttcaa ggtgcatatg gaaggaagcg tgaatggaca     300
cgaattcgag atcgaaggcg aggggaggg  tcgcccttat gaaggcacac aaacagctaa     360
actgaaagtg acgaagggag ggccgcttcc cttcgcttgg gacattcttt caccccagtt     420
catgtatggt tcaaaggctt atgtcaagca cccggcggac attccagact acttaaaatt     480
gtcgttcccc gaggggttta aatgggaacg cgttatgaat ttcgaggatg ggggagtcgt     540
aacggttacc caggacagta gcctgcagga tggcgagttc atctacaaag tgaaattgcg     600
cgggacgaac ttccctagcg atgggccagt catgcagaag aaaacgatgg gatgggaagc     660
gtcatccgag cgcatgtatc ctgaagatgg tgctttaaaa ggtgagatca agcagcgttt     720
gaaactgaag gacggggggcc attatgatgc tgaagttaaa acgacatata aggccaagaa     780
gccagttcaa ctgccagggg cttataatgt taatattaaa ttagacatta cgagccataa     840
tgaagattac acgattgtcg agcaatacga gcgcgcagaa ggacgccact caacgggggg     900
catggacgag ctgtacaagt aaaaagcccg aaaggaagct gagttggctg ctgccaccgc     960
tgagcaataa ctagcataac cccttggggc ctctaaacgg gtcttgaggg gttttttgct    1020
gaaaggagga actatatccg gcttcctcgc tcactgactc gctgcgctcg gtcgttcggc    1080
tgcggcgagc ggtatcagct cactcaaagg cggtaatacg gttatccaca gaatcagggg    1140
ataacgcagg aaagaacatg tgagcaaaag gccagcaaaa ggccaggaac cgtaaaaagg    1200
ccgcgttgct ggcgtttttc cataggctcc gcccccctga cgagcatcac aaaaatcgac    1260
gctcaagtca gaggtggcga aacccgacag gactataaag ataccaggcg tttccccctg    1320
gaagctccct cgtgcgctct cctgttccga ccctgccgct taccggatac ctgtccgcct    1380
ttctcccttc gggaagcgtg gcgctttctc atagctcacg ctgtaggtat ctcagttcgg    1440
tgtaggtcgt tcgctccaag ctgggctgtg tgcacgaacc ccccgttcag cccgaccgct    1500
gcgccttatc cggtaactat cgtcttgagt ccaacccggt aagacacgac ttatcgccac    1560
tggcagcagc cactggtaac aggattagca gagcgaggta tgtaggcggt gctacagagt    1620
tcttgaagtg gtggcctaac tacggctaca ctagaagaac agtatttggt atctgcgctc    1680
tgctgaagcc agttaccttc ggaaaaagag ttggtagctc ttgatccggc aaacaaacca    1740
ccgctggtag cggtggtttt tttgtttgca agcagcagat tacgcgcaga aaaaaaggat    1800
ctcaagaaga tcctttgatc ttttctacgg ggtctgacgc tcagtggaac gaaaactcac    1860
gggtggcact tttcggggaa atgtgcgcgg aaccccctatt tgtttatttt tctaaataca    1920
ttcaaatatg tatccgctca tgaattaatt cttagaaaaa ctcatcgagc atcaaatgaa    1980
actgcaattt attcatatca ggattatcaa taccatattt ttgaaaaagc cgtttctgta    2040
atgaaggaga aaactcaccg aggcagttcc ataggatggc aagatcctgg tatcggtctg    2100
```

```
cgattccgac tcgtccaaca tcaatacaac ctattaattt cccctcgtca aaaataaggt      2160
tatcaagtga gaaatcacca tgagtgacga ctgaatccgg tgagaatggc aaaagtttat      2220
gcatttcttt ccagacttgt tcaacaggcc agccattacg ctcgtcatca aaatcactcg      2280
catcaaccaa accgttattc attcgtgatt gcgcctgagc gagacgaaat acgcgatcgc      2340
tgttaaaagg acaattacaa acaggaatcg aatgcaaccg gcgcaggaac actgccagcg      2400
catcaacaat attttcacct gaatcaggat attcttctaa tacctggaat gctgttttcc      2460
cggggatcgc agtggtgagt aaccatgcat catcaggagt acggataaaa tgcttgatgg      2520
tcggaagagg cataaattcc gtcagccagt ttagtctgac catctcatct gtaacatcat      2580
tggcaacgct acctttgcca tgtttcagaa acaactctgg cgcatcgggc ttcccataca      2640
atcgatagat tgtcgcacct gattgcccga cattatcgcg agcccattta tacccatata      2700
aatcagcatc catgttggaa tttaatcgcg gcctagagca agacgtttcc cgttgaatat      2760
ggctcataac a                                                          2771

<210> SEQ ID NO 146
<211> LENGTH: 158
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 146
gaaattaata cgactcacta tagccatcaa tggatccaaa ttgctctgta cgcagagaca        60
gaaagagatc ccgtatatca ccgaactgga aggcgccatc aatggatcca aattgctctg       120
tacgcagaga cctaccccct ctctaaacgg aggggttt                              158

<210> SEQ ID NO 147
<211> LENGTH: 158
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 147
gaaattaata cgactcacta tagccatcaa tggatccaaa ttgctctgta cgcagagacg        60
tgtggtaggt aatgtgatga taacgcggga tatgcccatc aatggatcca aattgctctg       120
tacgcagaga cctaccccct ctctaaacgg aggggttt                              158

<210> SEQ ID NO 148
<211> LENGTH: 158
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 148
gaaattaata cgactcacta tagccatcaa tggatccaaa ttgctctgta cgcagagaca        60
agagcgccat gccggaaggt tatacccaag agcgtccatc aatggatcca aattgctctg       120
tacgcagaga cctaccccct ctctaaacgg aggggttt                              158

<210> SEQ ID NO 149
<211> LENGTH: 158
```

-continued

```
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 149
gaaattaata cgactcacta tagccatcaa tggatccaaa ttgctctgta cgcagagaca      60
agaaagacgg tcacattctg cgtaagaacg ttgcaccatc aatggatcca aattgctctg     120
tacgcagaga cctaacccct ctctaaacgg aggggtttt                            158

<210> SEQ ID NO 150
<211> LENGTH: 158
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 150
gaaattaata cgactcacta tagccatcaa tggatccaaa ttgctctgta cgcagagacg      60
agaaagagat cccgtatatc accgaactgg aaggcccatc aatggatcca aattgctctg     120
tacgcagaga cctaacccct ctctaaacgg aggggtttt                            158

<210> SEQ ID NO 151
<211> LENGTH: 158
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 151
gaaattaata cgactcacta taggtataac gaccctgcga agtggggtgt aacttcgacg      60
tgattgcgcc tgagcgagac gaaatacgcg atcgcgtata cgaccctgc gaagtggggt      120 gtaacttcga cctaacccct ctctaaacgg aggggtttt                            158

<210> SEQ ID NO 152
<211> LENGTH: 161
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 152
gaaattaata cgactcacta tagcctgcaa gggatccaaa ttgctctgtt cgcagagaca      60
cggaaggtgc aaaactgttt gagaaagaga tcccgtatcc tgcaagggat ccaaattgct     120
ctgttcgcag agacctaacc cctctctaaa cggaggggtt t                         161

<210> SEQ ID NO 153
<211> LENGTH: 161
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 153
gaaattaata cgactcacta tagcctgcaa gggatccaaa ttgctctgtt cgcagagaca      60
gaaagagatc ccgtatatca ccgaactgga aggcgacgcc tgcaagggat ccaaattgct     120
```

-continued

```
ctgttcgcag agacctaacc cctctctaaa cggaggggtt t                            161

<210> SEQ ID NO 154
<211> LENGTH: 161
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 154
gaaattaata cgactcacta tagcctgcaa gggatccaaa ttgctctgtt cgcagagaca      60
atgataaatt tcataccttc gacgtcgcct tccagttccc tgcaagggat ccaaattgct     120
ctgttcgcag agacctaacc cctctctaaa cggaggggtt t                          161

<210> SEQ ID NO 155
<211> LENGTH: 161
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 155
gaaattaata cgactcacta tagcctgcaa gggatccaaa ttgctctgtt cgcagagaca      60
agagcgccat gccggaaggt tatacccaag agcgtacccc tgcaagggat ccaaattgct     120
ctgttcgcag agacctaacc cctctctaaa cggaggggtt t                          161

<210> SEQ ID NO 156
<211> LENGTH: 161
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 156
gaaattaata cgactcacta tagcctgcaa gggatccaaa ttgctctgtt cgcagagacg      60
agaaagagat cccgtatatc accgaactgg aaggcgaccc tgcaagggat ccaaattgct     120
ctgttcgcag agacctaacc cctctctaaa cggaggggtt t                          161

<210> SEQ ID NO 157
<211> LENGTH: 161
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 157
gaaattaata cgactcacta taggtataac gaccctgcga agtggggtgt aacttcgacg      60
tgattgcgcc tgagcgagac gaaatacgcg atcgctgtgt ataacgaccc tgcgaagtgg     120
ggtgtaactt cgacctaacc cctctctaaa cggaggggtt t                          161

<210> SEQ ID NO 158
<211> LENGTH: 24
<212> TYPE: DNA
<213> ORGANISM: Unknown
<220> FEATURE:
<223> OTHER INFORMATION: Description of Unknown:
      AAVS1 target locus sequence
```

-continued

<400> SEQUENCE: 158
tggcctgggt cacctctacg gctg                                    24

<210> SEQ ID NO 159
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 159
cctgcaaggg atccaaattg ctctgttcgc agagactggc ctgggtcacc tctacggctg      60
cctgcaaggg atccaaattg ctctgttcgc agagac                        96

<210> SEQ ID NO 160
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 160
ccatcaatgg atccaaattg ctctgtacgc agagactggc ctgggtcacc tctacggctg      60
ccatcaatgg atccaaattg ctctgtacgc agagac                        96

<210> SEQ ID NO 161
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 161
cctgcaaggg atccaaattg ctctgttcgc agagactggc ctgggtcacc tctacggctg      60
cctgcaaggg atccaaattg ctctgttcgc agagac                        96

<210> SEQ ID NO 162
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (28)..(28)
<223> OTHER INFORMATION: a, c, t, g, unknown or other

<400> SEQUENCE: 162
gsyykmaabm ywhdhwgatk gckcbdtncg hbgagac                       37

<210> SEQ ID NO 163
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 163
cctgcgaaac cttttgattg ctcagtacgc tgagac                        36

-continued

```
<210> SEQ ID NO 164
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 164
ggatccaatc cttttgatt gcccaattcg ttgggac                                            37
```